(12) United States Patent
Brown et al.

(10) Patent No.: US 12,344,621 B2
(45) Date of Patent: Jul. 1, 2025

(54) CGRP ANTAGONIST COMPOUNDS

(71) Applicant: Nxera Pharma UK Limited, Cambridge (GB)

(72) Inventors: Giles Albert Brown, Cambridge (GB); Miles Stuart Congreve, Cambridge (GB); Stephen Paul Watson, Cambridge (GB); Julie Cansfield, Cambridge (GB); Michael Alistair O'Brien, Cambridge (GB); Francesca Deflorian, Cambridge (GB); Gregory R. Ott, North Wales, PA (US); Nigel Alan Swain, Cambridge (GB); Andrew David Cansfield, Cambridge (GB); John Andrew Christopher, Cambridge (GB); Andrea Bortolato, Cambridge (GB)

(73) Assignee: Nxera Pharma UK Limited, Cambridge (GB)

( * ) Notice: Subject to any disclaimer, the term of this patent is extended or adjusted under 35 U.S.C. 154(b) by 722 days.

(21) Appl. No.: 17/617,873

(22) PCT Filed: Jun. 12, 2020

(86) PCT No.: PCT/GB2020/051428
§ 371 (c)(1),
(2) Date: Dec. 9, 2021

(87) PCT Pub. No.: WO2020/249969
PCT Pub. Date: Dec. 17, 2020

(65) Prior Publication Data
US 2022/0306651 A1 Sep. 29, 2022

(30) Foreign Application Priority Data
Jun. 12, 2019 (GB) ...................... 1908420

(51) Int. Cl.
C07D 498/22 (2006.01)
A61K 31/438 (2006.01)
A61P 25/06 (2006.01)

(52) U.S. Cl.
CPC ................. C07D 498/22 (2013.01)

(58) Field of Classification Search
CPC ...... C07D 498/22; A61K 31/438; A61P 25/06
See application file for complete search history.

(56) References Cited

U.S. PATENT DOCUMENTS

| | | | |
|---|---|---|---|
| 2004/0229861 A1 | 11/2004 | Burgey et al. | |
| 2008/0113966 A1 | 5/2008 | Burgey et al. | |
| 2012/0196872 A1 | 8/2012 | Dreyer et al. | |
| 2013/0231358 A1 | 9/2013 | Bell et al. | |
| 2015/0005330 A1 | 1/2015 | Bell et al. | |
| 2017/0121348 A1 | 5/2017 | Christopher et al. | |
| 2018/0009808 A1 | 1/2018 | Christopher et al. | |
| 2018/0092899 A1 | 4/2018 | Liu et al. | |
| 2022/0251110 A1 | 8/2022 | Brown et al. | |

FOREIGN PATENT DOCUMENTS

| | | |
|---|---|---|
| JP | 2006-523697 A | 10/2006 |
| JP | 2008-515991 A | 5/2008 |
| JP | 2012-528827 A | 11/2012 |
| JP | 2013-542260 A | 11/2013 |
| JP | 2013-542261 A | 11/2013 |
| JP | 2018-532788 A | 11/2018 |
| JP | 2022-535994 A | 8/2022 |
| WO | 2006/044504 A1 | 4/2006 |
| WO | 2009/080682 A1 | 7/2009 |
| WO | 2010/139717 A1 | 12/2010 |
| WO | 2012/064910 A1 | 5/2012 |
| WO | 2012/064911 A1 | 5/2012 |
| WO | 2017/072721 A1 | 5/2017 |

(Continued)

OTHER PUBLICATIONS

Paone et al., Calcitonin gene-related peptide receptor antagonists for the treatment of migraine: a patent review. Expert Opin Ther Pat. Dec. 2009;19(12):1675-713.
International Search Report and Written Opinion for Application No. PCT/GB2020/051428, dated Jul. 29, 2020, 9 pages.
Yasuda et al., "Practical Asymmetric Synthesis of a Calcitonin Gene-Related Peptide (CGRP) Receptor Antagonist Ubrogepant," Organic Process Research & Development, 21(11):1851-1858 (2017).
U.S. Appl. No. 15/336,866, filed Oct. 28, 2016, U.S. Pat. No. 9,808,457, Nov. 7, 2017.
U.S. Appl. No. 15/713,775, filed Sep. 25, 2017, U.S. Pat. No. 10,300,056, May 28, 2019.

(Continued)

*Primary Examiner* — Brenda L Coleman
(74) *Attorney, Agent, or Firm* — HALEY GUILIANO LLP; Karen Mangasarian; Mihaela D. Danca

(57) ABSTRACT

The disclosures herein relate to novel compounds of Formula (1); and salts thereof, wherein $A^1$, $A^2$, Q, X, $R^1$, $R^2$ and $R^3$ are defined herein, and their use in treating, preventing, ameliorating, controlling or reducing the risk of disorders associated with CGRP receptors.

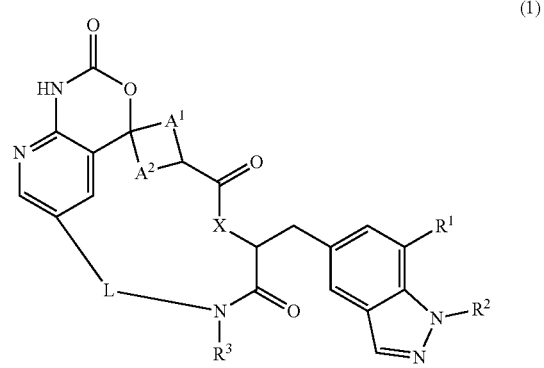

31 Claims, No Drawings

(56) References Cited

FOREIGN PATENT DOCUMENTS

WO   2018/178938 A1   10/2018
WO   2019/093284 A1   5/2019

OTHER PUBLICATIONS

U.S. Appl. No. 16/377,519, filed Apr. 8, 2019, U.S. Pat. No. 10,888,561, Jan. 12, 2021.
U.S. Appl. No. 17/139,299, filed Dec. 31, 2020.
U.S. Appl. No. 17/617,851, filed Dec. 9, 2021.

CGRP ANTAGONIST COMPOUNDS

CROSS-REFERENCE TO RELATED APPLICATIONS

This application is a 35 U.S.C. § 371 national stage filing of International Application No. PCT/GB2020/051428, filed on Jun. 12, 2020, which claims priority to United Kingdom Application No. 1908420.1, filed on Jun. 12, 2019, the entire contents of each of which are incorporated herein by reference.

This application relates to novel compounds and their use as calcitonin gene-related peptide (CGRP) receptor antagonists. Compounds described herein may be useful in the treatment or prevention of diseases in which CGRP receptors are involved. Compounds described herein may be useful in the treatment or prevention of cerebrovascular or vascular disorders such as migraine. The application is also directed to pharmaceutical compositions comprising these compounds and the manufacture and use of these compounds and compositions in the prevention or treatment of such diseases in which CGRP receptors are involved.

BACKGROUND OF THE INVENTION

Migraine is a highly disabling neurovascular disorder characterized by attacks of moderate to severe headache that are often associated with nausea, vomiting, photophobia, and phonophobia. The attacks can last from 4 to 72 h, and the average attack frequency is 1 or 2 per month. About 20-30% of migraine patients experience transient focal neurologic symptoms known as aura, which are usually visual and can precede or accompany the headache. Migraine afflicts about 11% of adults worldwide and results in a significant socioeconomic burden, in terms of both quality of life and lost productivity.

Whilst the pathomechanism of migraine is still unclear, one of the leading hypotheses is based on activation of the trigeminovascular system (TS). Several neuropeptides participate in this activation, calcitonin gene-related peptide (CGRP) playing a crucial role among them. CGRP exerts various biological effects through the peripheral and central nervous system (CNS). The functional CGRP-receptor (CGRP-R) complex has been well characterized, and novel therapeutic approaches target CGRP itself and its receptors. This invention relates to the development of CGRP receptor antagonists (CGRP-RA).

CGRP, a 37-amino acid neuropeptide derived from the gene encoding calcitonin, is formed from the alternative splicing of the calcitonin/CGRP gene located on chromosome 11. In humans, CGRP has two isoforms: α- and β-CGRP. The β-isoform differs from the α-isoform in the amino acids located at positions 3, 22 and 25. The chemical structure of CGRP involves a disulphide bridge between residues 2 and 7 and an amidated C-terminus. The cyclic cysteine2-cysteine7 motif has a basic role in receptor activation. In the human trigeminal ganglia (TRIG), CGRP-immunoreactive neurons account for up to 50% of all neurons. It has been demonstrated through an in situ hybridization technique that 40% of all nerve cell bodies contain CGRP mRNA and CGRP.

The functional CGRP-R consists of three proteins: i) Calcitonin Receptor Like Receptor (known as CRLR, CAL-CRL or CLR) is a seven-transmembrane spanning protein, which forms the ligand binding site with; ii) RAMP1, determining the specificity of the receptor; and iii) the CGRP-R component protein (RCP) couples the receptor to intracellular signal transduction pathways and to adenylyl cyclase.

Blockade of CGRP function as a treatment for migraine has been clinically validated for both antibody and small molecule agents. For example, antibody agents Erenumab (Aimovig), which targets the CGRP receptor, and Fremanezumab (Ajovy) and Galcanezumab (Emgality) which target the CGRP Protein are now approved medicines for treatment of migraine. Similarly small molecule antagonists of CGRP have also demonstrated efficacy against migraine. For example, both Ubrogepant and Rimegepant have demonstrated clinical efficacy and are now approved medicines for the treatment of migraine.

The Invention

The present invention provides compounds having activity as calcitonin gene-related peptide (CGRP) receptor antagonists. Disclosed herein are novel compounds, and the first medical use of said compounds as CGRP receptor antagonists.

Accordingly, in one embodiment the invention provides a compound of Formula (1):

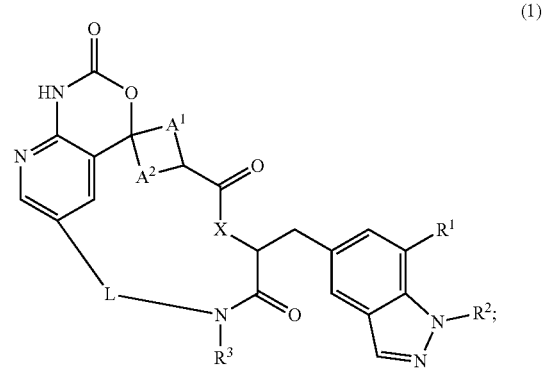

(1)

or a salt thereof, wherein;
$A^1$, $A^2$ and the atoms to which they are attached together represent an optionally substituted bicyclic or monocyclic ring system;
Q is a bond or O;
X is O or NH;
$R^1$ is H, $C_{1-3}$ alkyl or halo;
$R^2$ is H or $C_{1-3}$ alkyl;
$R^3$ is H or $C_{1-3}$ alkyl;
and L is a $C_{4-15}$ linker group optionally substituted with one or more F atoms, wherein one, two or three, but not all, of the carbon atoms of the linker group may be optionally replaced by a heteroatom selected from O and N.

The compounds may be used as CGRP receptor antagonists. The compounds may be used in the manufacture of medicaments. The compounds or medicaments may be for use in treating, preventing, ameliorating, controlling or reducing the risk of diseases or disorders in which CGRP receptors are involved including cerebrovascular or vascular disorders such as migraine.

DETAILED DESCRIPTION OF THE INVENTION

The invention relates to novel compounds. The invention also relates to the use of novel compounds as antagonists of the CGRP receptor. The invention further relates to the use of novel compounds in the manufacture of medicaments for use as CGRP receptor antagonists.

The invention further relates to compounds, compositions and medicaments for the treatment of cerebrovascular or vascular disorders including migraine (with or without aura), chronic migraine, pure menstrual migraine, frequent episodic migraine, menstrually-related migraine, migraine with aura, familial hemiplegic migraine, sporadic hemiplegic migraine, basilar-type migraine, cyclical vomiting, abdominal migraine, benign paroxysmal vertigo of childhood, retinal migraine, status migrainosus, cluster headache, dialysis headache, chronic headaches of unknown origin, tension/stress induced headaches, allergy induced headaches, paroxysmal hemicrania, osteoarthritis and associated osteoporotic fracture pain, hot flashes associated with menopause or medically induced menopause due to surgery or drug treatment, hemicrania continua, cyclic vomiting syndrome, opiate withdrawal syndrome, morphine tolerance, neurodegenerative disease, epilepsy, allergic rhinitis, rosacea, dental pain, earache, middle ear inflammation, sunburn, joint pain associated with osteoarthritis and rheumatoid arthritis and gout, cancer pain, neuropathic pain (including but not limited to cancer pain in all its various forms including of unexplained origin), dystonic pain, inflammatory pain, post-operative incision pain, sciatica, fibromyalgia, trigeminal neuralga, diabetic neuropathy, complex regional pain syndrome, Behçet's disease, endometriosis pain, back pain, phantom limb pain, menstrual period pain, pain associated with labour, pain resulting from burns to skin, or visceral pain associated with inflammatory bowel disease (including Crohn's disease, ileitis and ulcerative colitis), gastro-esophageal reflux disease, dyspepsia, irritable bowel syndrome, renal colic, cystitis, gout, pancreatitis and prostatitis.

The compounds, compositions and medicaments of the invention may also be beneficial in the treatment of inflammatory and immune associated disorders including chronic fatigue syndrome, skin diseases, neurogenic cutaneous redness, skin rosaceousness, erythema, bronchial hyperreactivity, asthma, mast cell activation syndrome, mastocytosis, mast cell degranulation disorder, vascular disorders, shock, sepsis, non-insulin dependent diabetes mellitus, and infectious diseases including those of a respiratory and gastrointestinal origin.

In one embodiment the invention provides a compound of Formula (1):

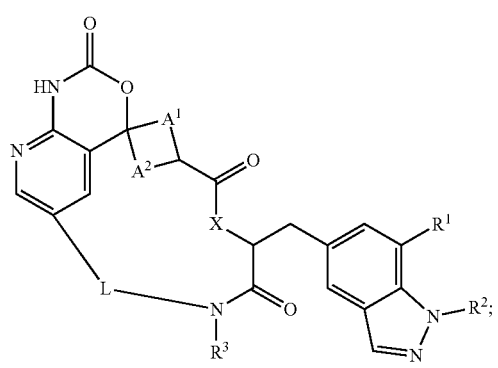

(1)

or a salt thereof, wherein;

$A^1$, $A^2$ and the atoms to which they are attached together represent an optionally substituted bicyclic or monocyclic ring system;

Q is a bond or O;

X is O or NH;

$R^1$ is H, $C_{1-3}$ alkyl or halo;

$R^2$ is H or $C_{1-3}$ alkyl;

$R^3$ is H or $C_{1-3}$ alkyl;

and L is a $C_{4-15}$ linker group optionally substituted with one or more F atoms, wherein one, two or three, but not all, of the carbon atoms of the linker group may be optionally replaced by a heteroatom selected from O and N.

Particular compounds include compounds of Formula (2a), (2b), (2c), (2d) and (2e):

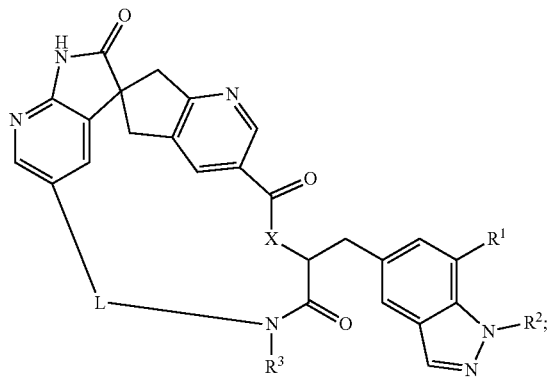

(2a)

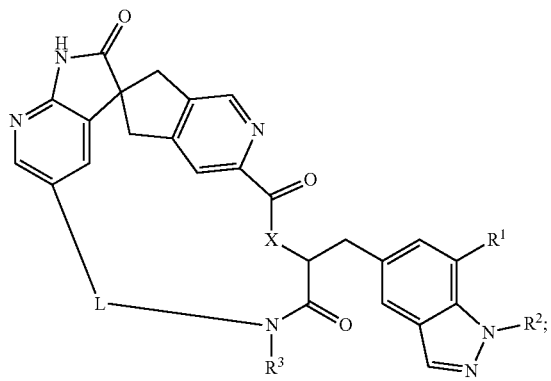

(2b)

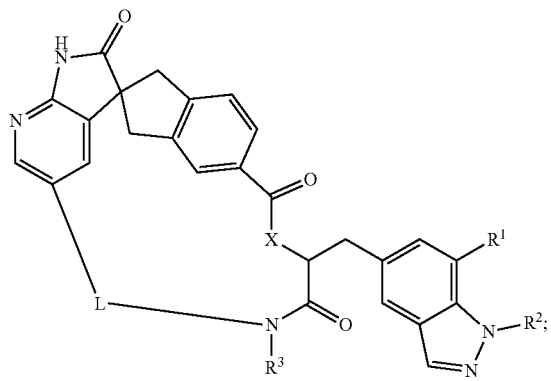

(2c)

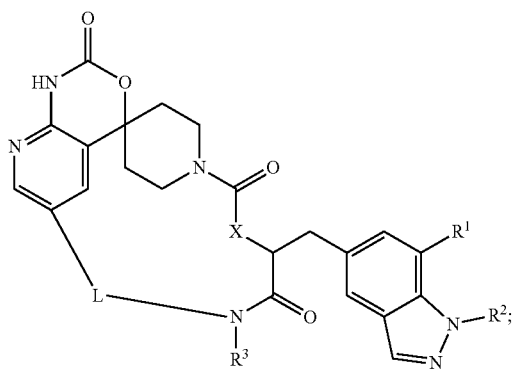
(2d)
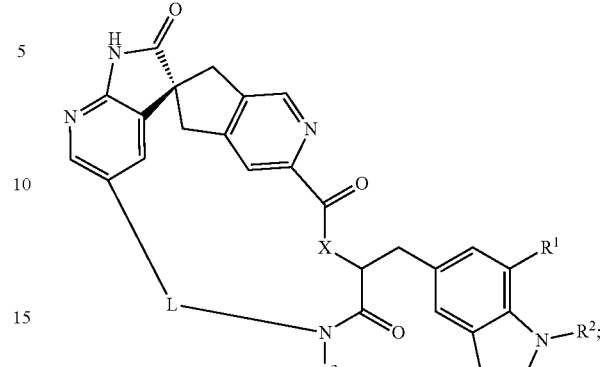
(3b)
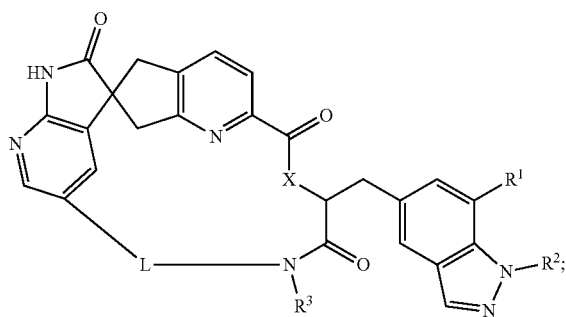
(2e)
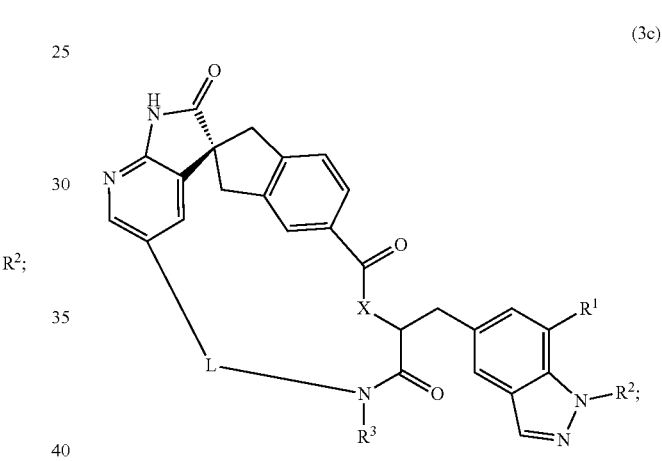
(3c)
or salts thereof, wherein X, L, R¹, R² and R³ are as defined above.
Particular compounds include compounds of Formula (3a), (3b), (3c) and (3d);
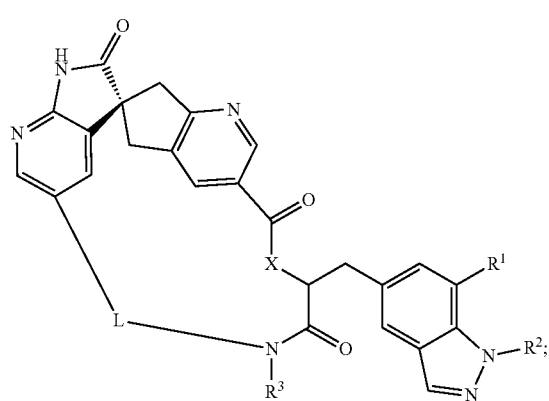
(3a)
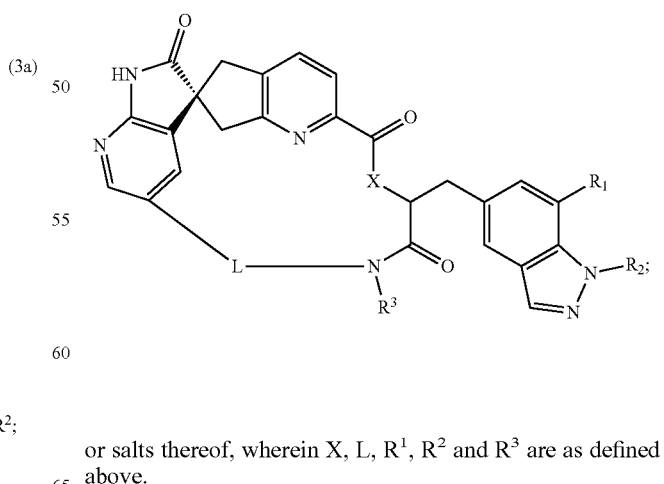
(3d)
or salts thereof, wherein X, L, R¹, R² and R³ are as defined above.
Particular compounds include compounds of Formula (4a), (4b), (4c) and (4d);

(4a)
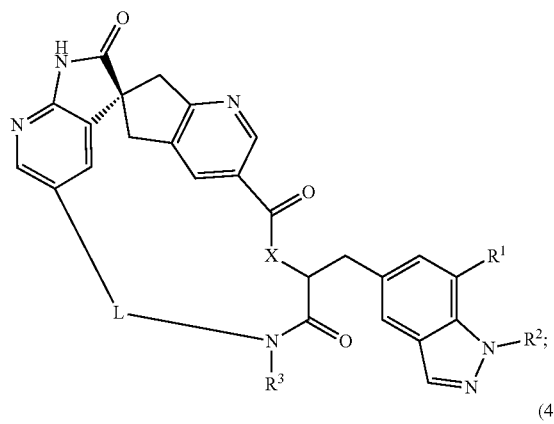
(4b)
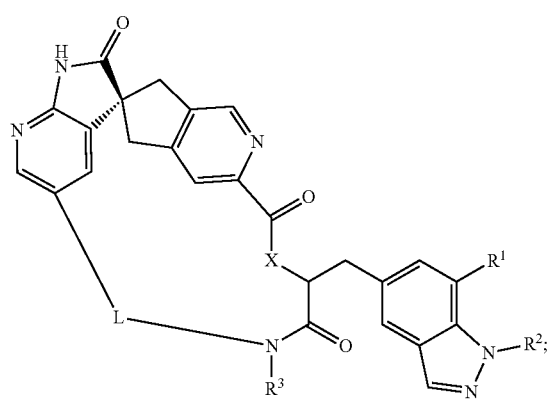
(4c)
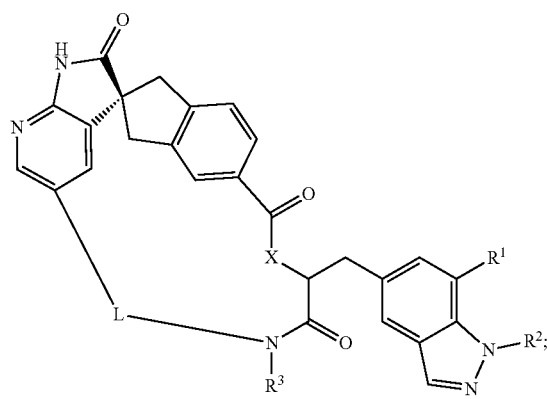
(4d)
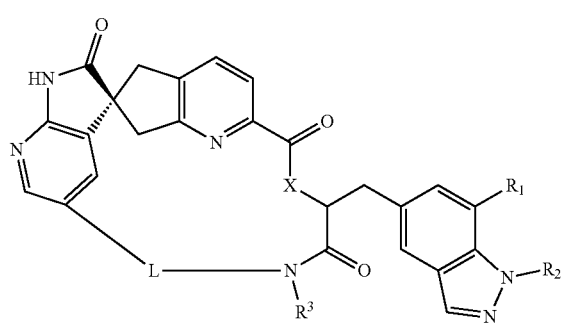
or salts thereof, wherein X, L, $R^1$, $R^2$ and $R^3$ are as defined above.
Particular compounds include compounds of Formula (5):
(5)
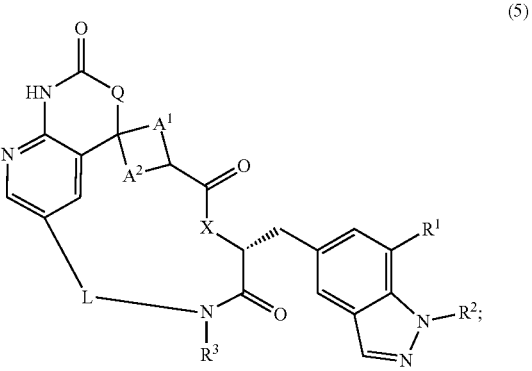
or salts thereof, wherein $A^1$, $A^2$, Q, X, L, $R^1$, $R^2$ and $R^3$ are as defined above.
Particular compounds include compounds of Formula (6a), (6b), (6c) or (6d):
(6a)
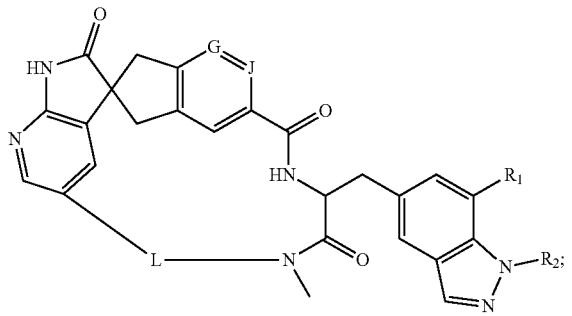
(6b)
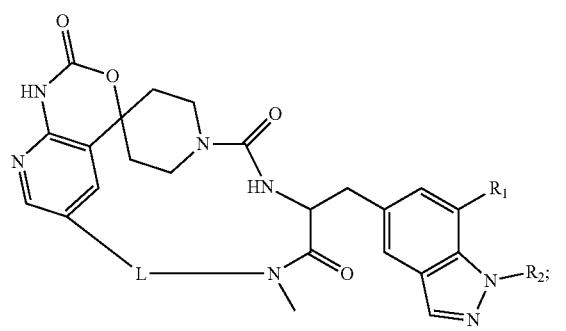
(6c)
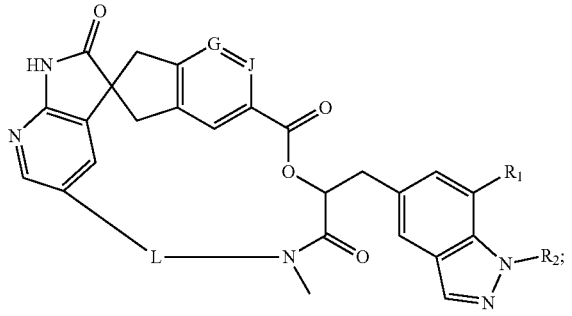

-continued

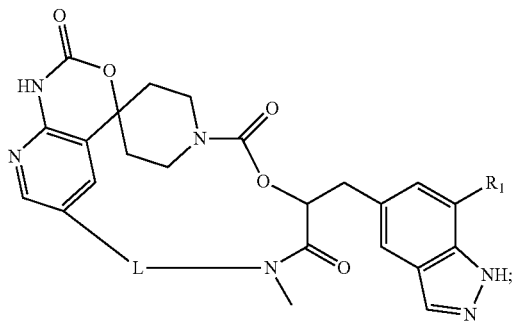
(6d)

or salts thereof, wherein G and J are independently N or CH and $R^1$ and $R^2$ are as defined above.

In the compounds herein, $A^1$, $A^2$ and the atoms to which they are attached can together represent a bicyclic or monocyclic ring system. $A^1$, $A^2$ and the atoms to which they are attached can together represent a substituted bicyclic or monocyclic ring system. $A^1$, $A^2$ and the atoms to which they are attached can together represent a bicyclic ring system. $A^1$, $A^2$ and the atoms to which they are attached can together represent a monocyclic ring system. $A^1$, $A^2$ and the atoms to which they are attached can together represent a ring system selected from the group consisting of a piperidine ring system, an indan ring system, a pyrindan, 4-azaindan, 2,3-cyclopentenopyridine or 6,7-dihydro-5H-cyclopenta[b]pyridine ring system and a 2-pyrindan, 5-azaindan or 6,7-dihydro-5H-cyclopenta[c]pyridine ring system.

$A^1$, $A^2$ and the atoms to which they are attached can together represent a ring system selected from the group consisting of:

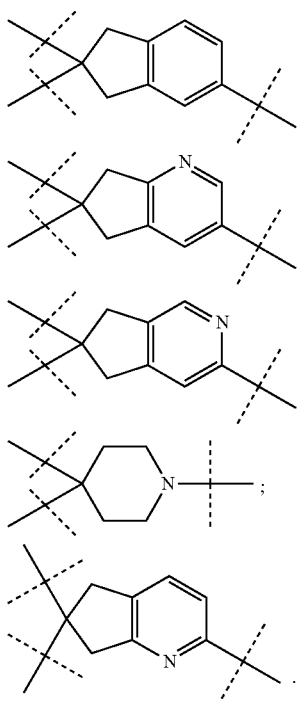

The moiety represented by:

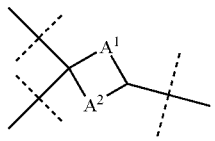

can be a ring system selected from the group consisting of:

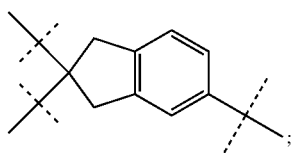

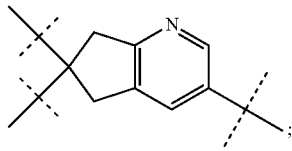

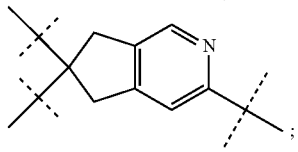

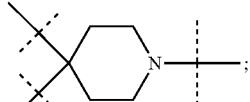

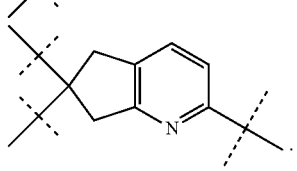

In the compounds herein, Q can be a bond. Q can be O.
In the compounds herein, X can be O. X can be NH.
In the compounds herein, $R^1$ can be H. $R^1$ can be $C_{1-3}$ alkyl. $R^1$ can be halo. $R^1$ can be methyl. $R^1$ can be Cl.
In the compounds herein, $R^2$ can be H. $R^2$ can be $C_{1-3}$ alkyl. $R^2$ can be methyl.
In the compounds herein, $R^3$ can be H. $R^3$ can be $C_{1-3}$ alkyl. $R^3$ can be methyl.
In the compounds herein, L can be a $C_{4-15}$ linker group optionally substituted with one or more F atoms. L can be a $C_{4-15}$ linker group optionally substituted with 1-3 F atoms. L can be a $C_{4-15}$ linker group substituted with 1-3 F atoms. L can be a $C_{4-15}$ linker group. L can be a $C_{4-15}$ linker group wherein one, two or three, but not all, of the carbon atoms of the linker group is replaced by a heteroatom selected from O and N. L can be a $C_{6-12}$ linker group, wherein one, two or three, but not all, of the carbon atoms of the linker group may be optionally replaced by a heteroatom selected from O and N. L can be a $C_{4-15}$ linker group, wherein one, two or three, but not all, of the carbon atoms of the linker group may be optionally replaced by O. L can be a $C_{6-12}$ linker group, wherein one, two or three, but not all, of the carbon atoms of the linker group may be optionally replaced by O. L can be partially unsaturated. L can be monounsaturated. L can be polyunsaturated. L can contain a double bond. L can be saturated. L can be substituted with one or more F atoms.

L can be a linker group of the formula:

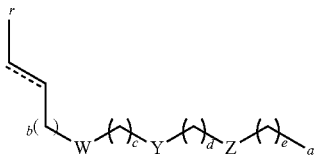

wherein "r" indicates the point of attachment to the ring and "a" indicates the point of attachment to the amide group; W, Y and Z can be independently selected from a bond, O, CH$_2$, NH and NMe; b, c, d and e are independently 1, 2 or 3 and the dotted line indicates that the bond may be a single or double bond.

L can selected from the group consisting of:
—CHCHCH$_2$OCH$_2$CH$_2$OCH$_2$CH$_2$—;
—CHCHCH$_2$OCH$_2$CH$_2$OCH$_2$CH$_2$OCH$_2$CH$_2$—;
—CH$_2$CH$_2$CH$_2$OCH$_2$CH$_2$OCH$_2$CH$_2$—;
—CHCHCH$_2$CH$_2$CH$_2$CH$_2$CH$_2$CH$_2$CH$_2$—;
—CHCHCH$_2$OCH$_2$CH$_2$CH$_2$CH$_2$CH$_2$—;
—CHCHCH$_2$OCH$_2$CH$_2$CH$_2$CH$_2$—;
—CHCHCH$_2$OCH$_2$CH$_2$CH$_2$—;
—CHCHCH$_2$OCH$_2$CH$_2$N(CH$_3$)CH$_2$CH$_2$—;
—CHCHCH$_2$OCH$_2$CH$_2$NHCH$_2$CH$_2$—;
—CHCHCH$_2$N(CH$_3$)CH$_2$CH$_2$CH$_2$CH$_2$CH$_2$—;
—CH$_2$CH$_2$CH$_2$OCH$_2$CH$_2$OCH$_2$CH$_2$OCH$_2$CH$_2$—;
—CH$_2$CH$_2$CH$_2$OCH$_2$CH$_2$CH$_2$CH$_2$CH$_2$—;
—CH$_2$CH$_2$CH$_2$OCH$_2$CH$_2$OCH$_2$CH$_2$CH$_2$—;
and
—CHCHCH$_2$OCH$_2$CH$_2$OCH$_2$CH$_2$CH$_2$—.

The compound can be selected from the group consisting of:

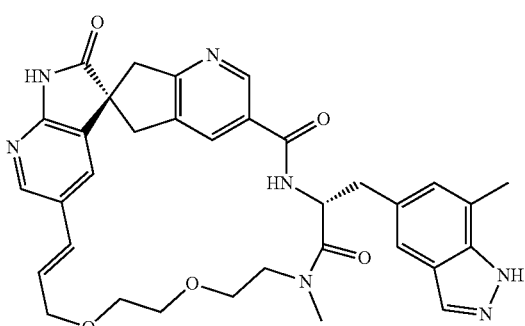

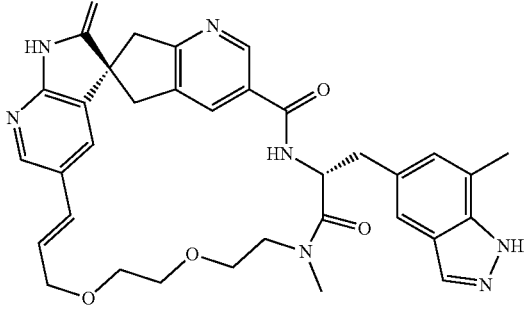

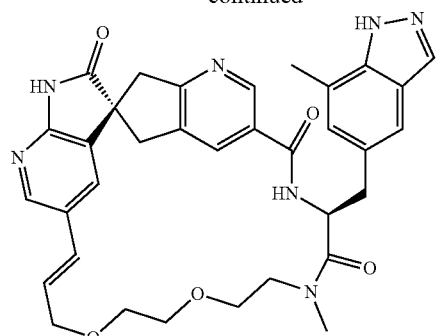

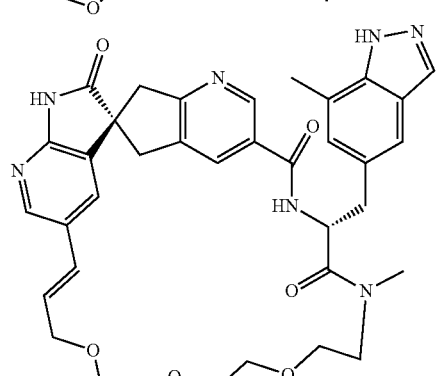

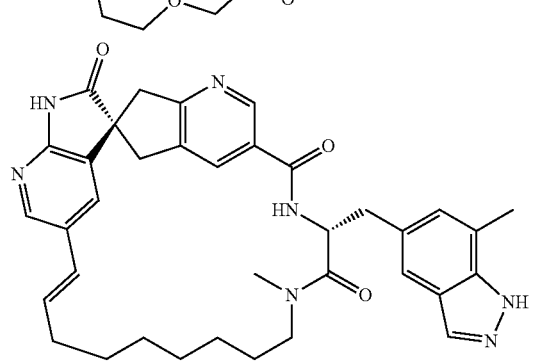

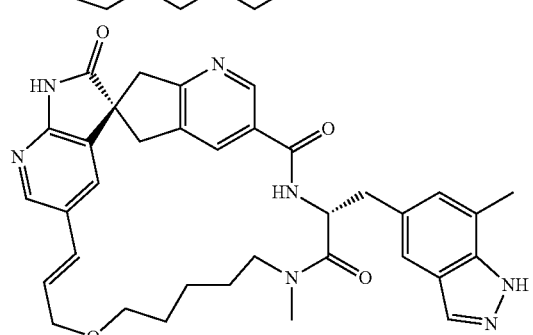

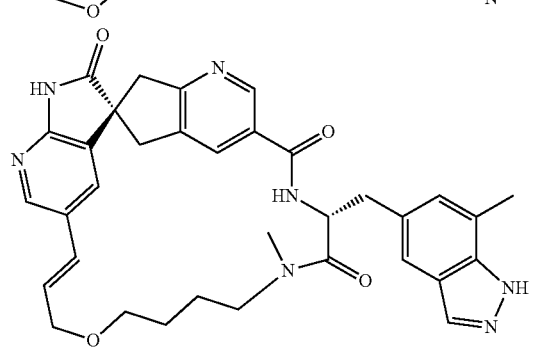

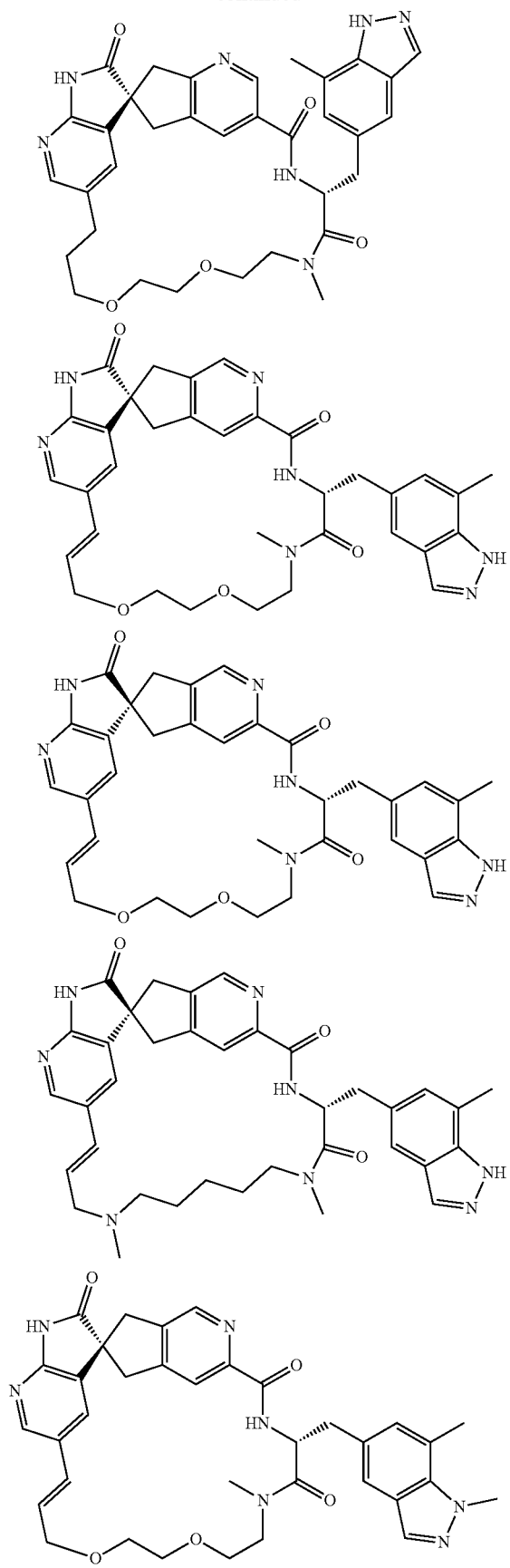
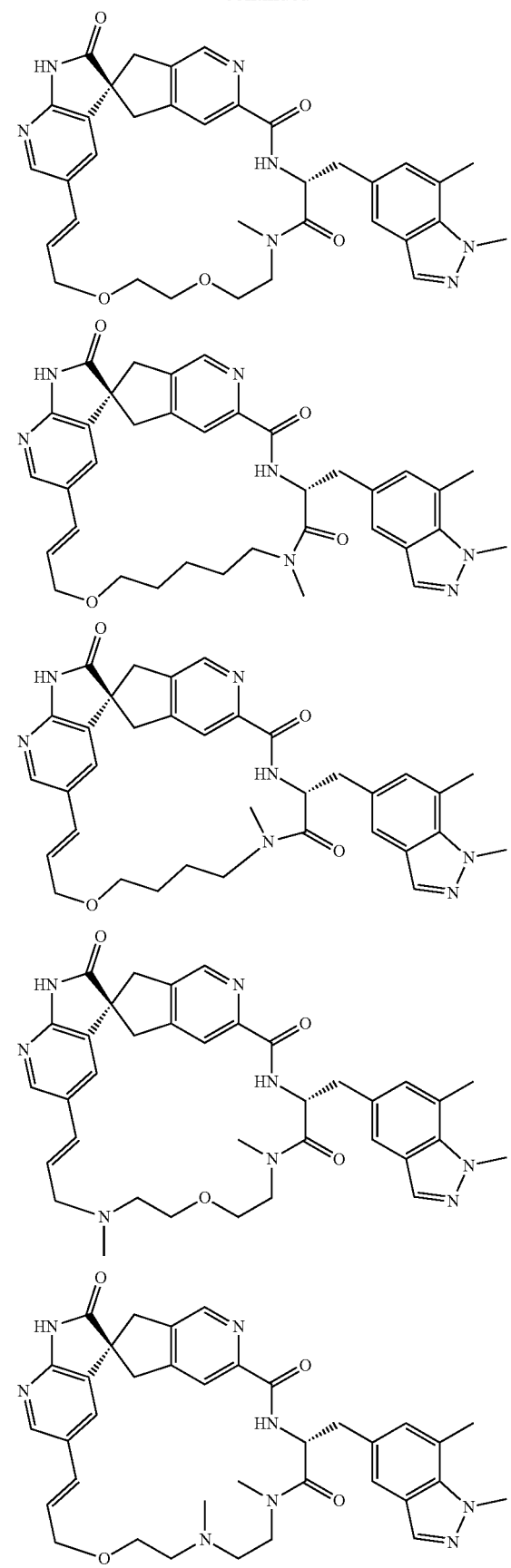

-continued
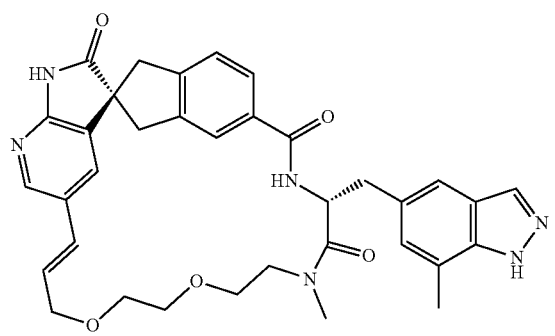
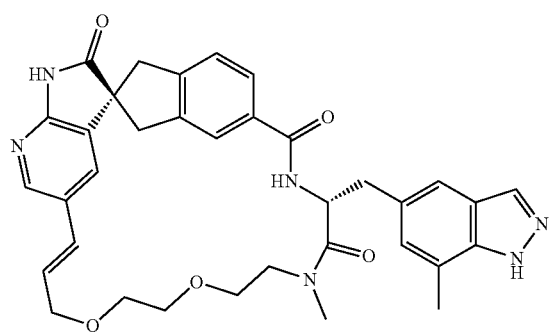
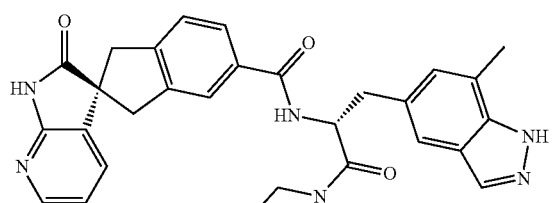
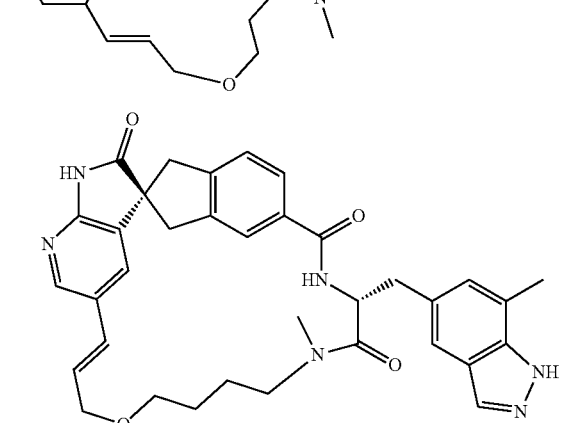
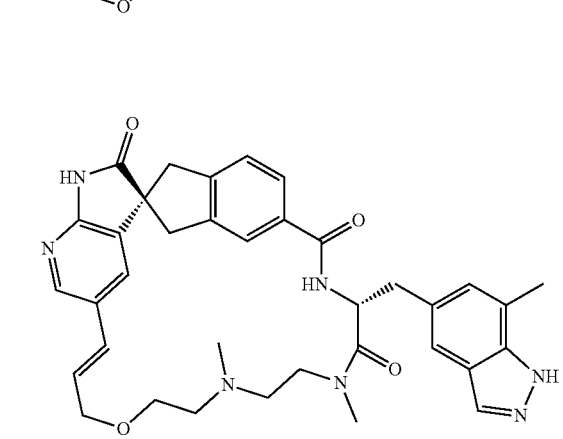
-continued
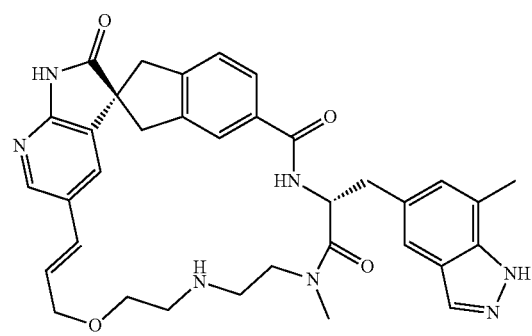
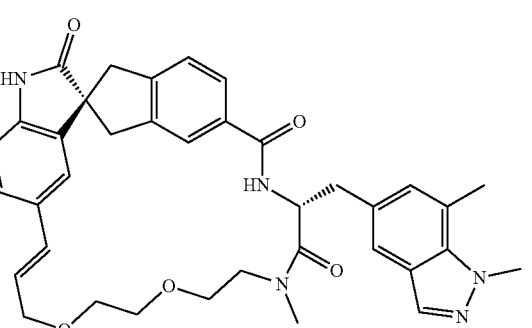
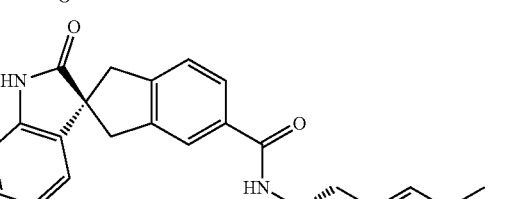
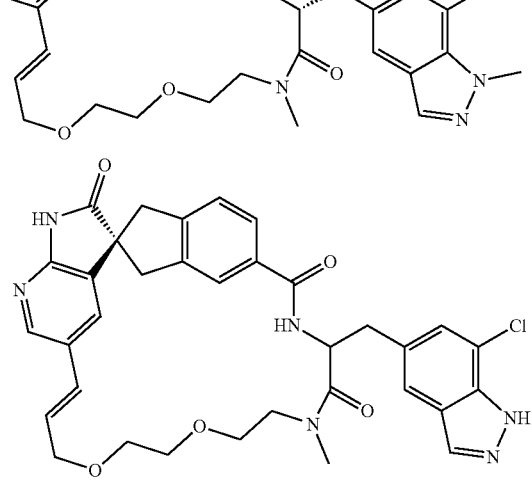
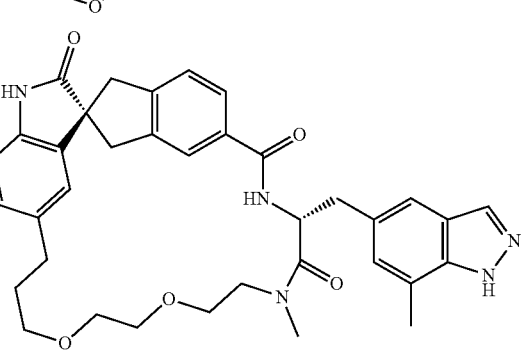

17
-continued
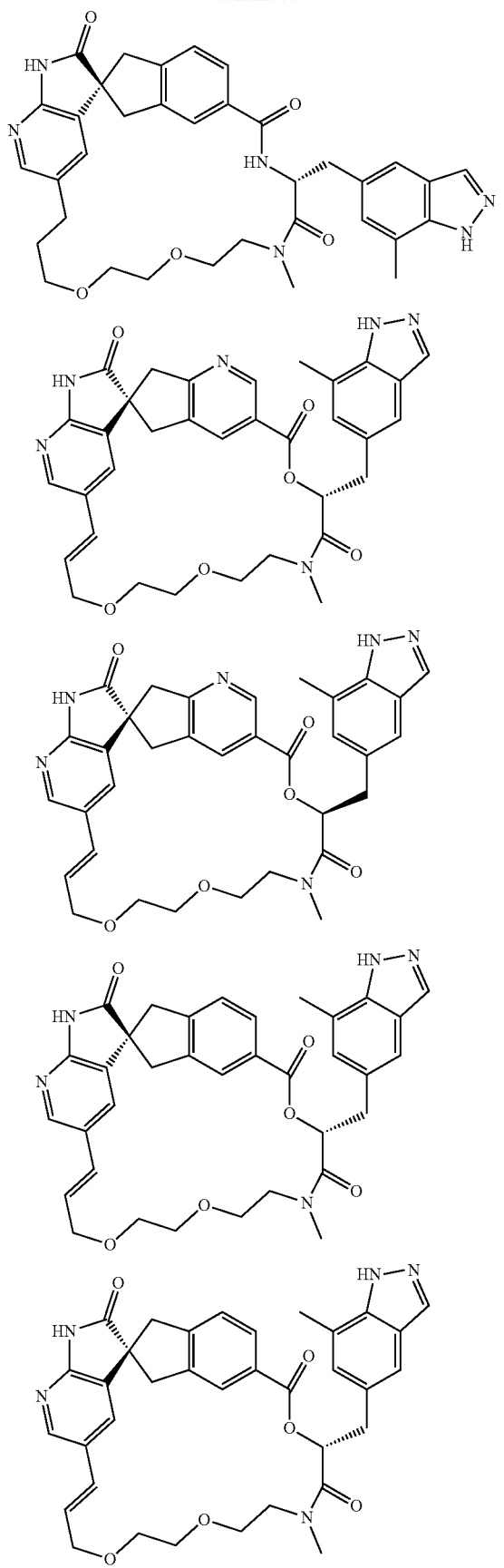
18
-continued
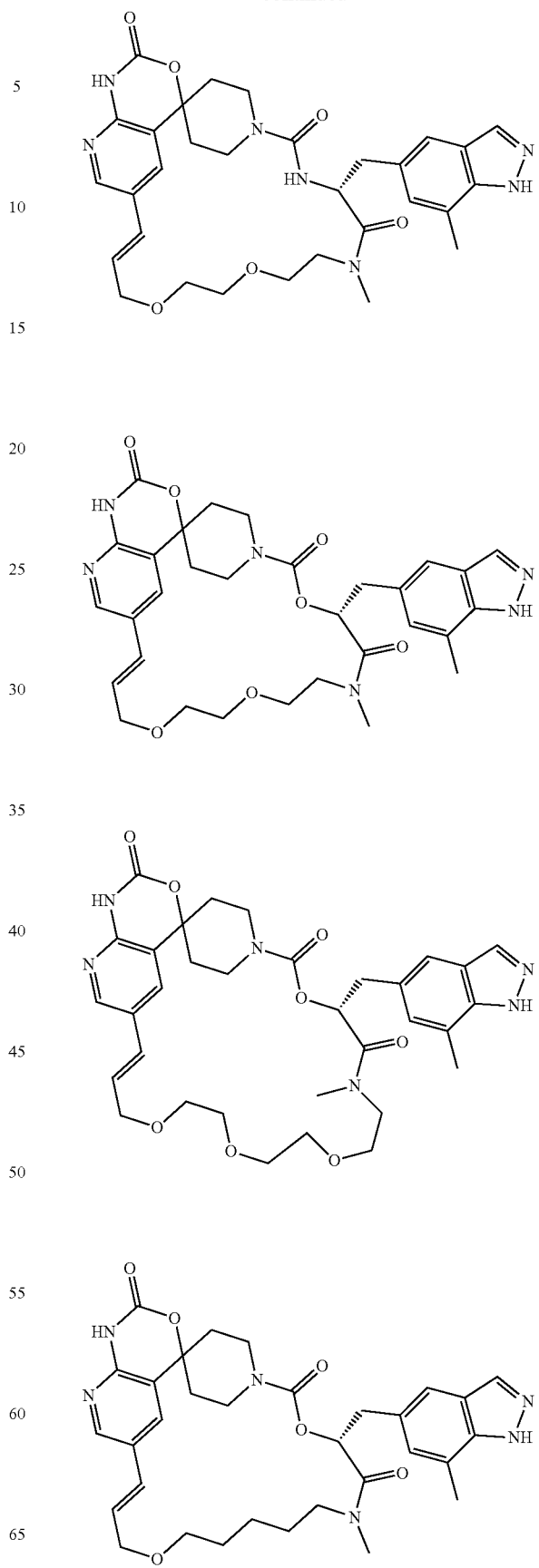

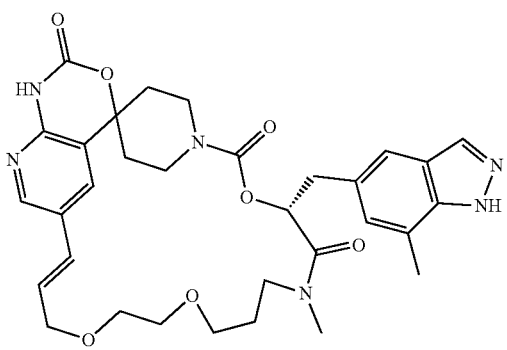
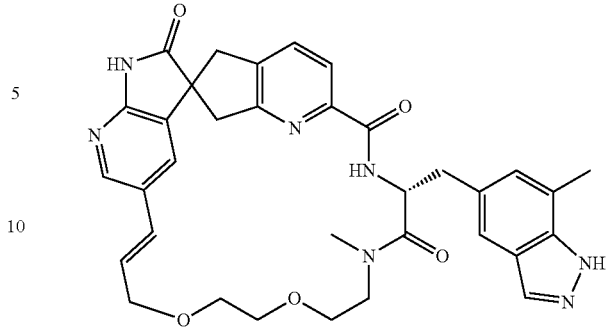

and salts thereof.

The compound can be selected from the group consisting of:

(1S,10R,20E)-12-methyl-10-[(7-methyl-1H-indazol-5-yl)methyl]-15,18-dioxa-5,9,12,24,26-pentazapentacyclo[20.5.2.1¹,⁴.1³,⁷.0²⁵,²⁸]hentriaconta-3,5,7(30),20,22(29),23,25(28)-heptaene-8,11,27-trione;

(1R,10R,20E)-12-methyl-10-[(7-methyl-1H-indazol-5-yl)methyl]-15,18-dioxa-5,9,12,24,26-pentazapentacyclo[20.5.2.1¹,⁴.1³,⁷.0²⁵,²⁸]hentriaconta-3,5,7(30),20,22(29),23,25(28)-heptaene-8,11,27-trione;

(1S,10S,20E)-12-methyl-10-[(7-methyl-1H-indazol-5-yl)methyl]-15,18-dioxa-5,9,12,24,26-pentazapentacyclo[20.5.2.1¹,⁴.1³,⁷.0²⁵,²⁸]hentriaconta-3,5,7(30),20,22(29),23,25(28)-heptaene-8,11,27-trione;

(1S,10R,23E)-12-methyl-10-[(7-methyl-1H-indazol-5-yl)methyl]-15,18,21-trioxa-5,9,12,27,29-pentazapentacyclo[23.5.2.1¹,⁴.1³,⁷.0²⁸,³¹]tetratriaconta-3,5,7(33),23,25(32),26,28(31)-heptaene-8,11,30-trione;

(1S,10R,20E)-12-methyl-10-[(7-methyl-1H-indazol-5-yl)methyl]-5,9,12,24,26-pentazapentacyclo[20.5.2.1¹,⁴.1³,⁷.0²⁵,²⁸]hentriaconta-3,5,7(30),20,22(29),23,25(28)-heptaene-8,11,27-trione;

(1S,10R,20E)-12-methyl-10-[(7-methyl-1H-indazol-5-yl)methyl]-18-oxa-5,9,12,24,26-pentazapentacyclo[20.5.2.1¹,⁴.1³,⁷.0²⁵,²⁸]hentriaconta-3,5,7(30),20,22(29),23,25(28)-heptaene-8,11,27-trione;

(1S,10R,19E)-12-methyl-10-[(7-methyl-1H-indazol-5-yl)methyl]-17-oxa-5,9,12,23,25-pentazapentacyclo[19.5.2.1¹,⁴.1³,⁷.0²⁴,²⁷]triaconta-3,5,7(29),19,21(28),22,24(27)-heptaene-8,11,26-trione;

(1S,10R)-12-methyl-10-[(7-methyl-1H-indazol-5-yl)methyl]-15,18-dioxa-5,9,12,24,26-pentazapentacyclo[20.5.2.1¹,⁴.1³,⁷.0²⁵,²⁸]hentriaconta-3,5,7(30),22(29),23,25(28)-hexaene-8,11,27-trione;

(1S,10R,20E)-12-methyl-10-[(7-methyl-1H-indazol-5-yl)methyl]-15,18-dioxa-6,9,12,24,26-pentazapentacyclo[20.5.2.1¹,⁴.1³,⁷.0²⁵,²⁸]hentriaconta-3,5,7(30),20,22(29),23,25(28)-heptaene-8,11,27-trione;

(1R,10R,20E)-12-methyl-10-[(7-methyl-1H-indazol-5-yl)methyl]-15,18-dioxa-6,9,12,24,26-pentazapentacyclo[20.5.2.1¹,⁴.1³,⁷.0²⁵,²⁸]hentriaconta-3,5,7(30),20,22(29),23,25(28)-heptaene-8,11,27-trione;

(1R,10R,20E)-12,18-dimethyl-10-[(7-methyl-1H-indazol-5-yl)methyl]-6,9,12,18,24,26-hexazapentacyclo[20.5.2.1¹,⁴.1³,⁷.0²⁵,²⁸]hentriaconta-3,5,7(30),20,22(29),23,25(28)-heptaene-8,11,27-trione;

(1S,10R,20E)-10-[(1,7-dimethylindazol-5-yl)methyl]-12-methyl-15,18-dioxa-6,9,12,24,26-pentazapentacyclo[20.5.2.1¹,⁴.1³,⁷.0²⁵,²⁸]hentriaconta-3,5,7(30),20,22(29),23,25(28)-heptaene-8,11,27-trione;

(1R,10R,20E)-10-[(1,7-dimethylindazol-5-yl)methyl]-12-methyl-15,18-dioxa-6,9,12,24,26-pentazapentacyclo[20.5.2.1¹,⁴.1³,⁷.0²⁵,²⁸]hentriaconta-3,5,7(30),20,22(29),23,25(28)-heptaene-8,11,27-trione;

(1R,10R,20E)-10-[(1,7-dimethylindazol-5-yl)methyl]-12-methyl-18-oxa-6,9,12,24,26-pentazapentacyclo[20.5.2.1¹,⁴.1³,⁷.0²⁵,²⁸]hentriaconta-3,5,7(30),20,22(29),23,25(28)-heptaene-8,11,27-trione;

(1R,10R,19E)-10-[(1,7-dimethylindazol-5-yl)methyl]-12-methyl-17-oxa-6,9,12,23,25-pentazapentacyclo[19.5.2.1¹,⁴.1³,⁷.0²⁴,²⁷]triaconta-3,5,7(29),19,21(28),22,24(27)-heptaene-8,11,26-trione;

(1R,10R,20E)-10-[(1,7-dimethylindazol-5-yl)methyl]-12,18-dimethyl-6,9,12,18,24,26-hexazapentacyclo[20.5.2.1¹,⁴.1³,⁷.0²⁵,²⁸]hentriaconta-3,5,7(30),20,22(29),23,25(28)-heptaene-8,11,27-trione;

(1R,10R,20E)-10-[(1,7-dimethylindazol-5-yl)methyl]-12,15-dimethyl-18-oxa-6,9,12,15,24,26-hexazapentacyclo[20.5.2.1¹,⁴.1³,⁷.0²⁵,²⁸]hentriaconta-3,5,7(30),20,22(29),23,25(28)-heptaene-8,11,27-trione;

(1R,10R,20E)-12-methyl-10-[(7-methyl-1H-indazol-5-yl)methyl]-15,18-dioxa-9,12,24,26-tetrazapentacyclo[20.5.2.1¹,⁴.1³,⁷.0²⁵,²⁸]hentriaconta-3,5,7(30),20,22(29),23,25(28)-heptaene-8,11,27-trione;

(1S,10R,20E)-12-methyl-10-[(7-methyl-1H-indazol-5-yl)methyl]-15,18-dioxa-9,12,24,26-tetrazapentacyclo[20.5.2.1¹,⁴.1³,⁷.0²⁵,²⁸]hentriaconta-3,5,7(30),20,22(29),23,25(28)-heptaene-8,11,27-trione;

(1S,10R,18E)-12-methyl-10-[(7-methyl-1H-indazol-5-yl)methyl]-16-oxa-9,12,22,24-tetrazapentacyclo[18.5.2.1¹,⁴.1³,⁷.0²³,²⁶]nonacosa-3,5,7(28),18,20(27),21,23(26)-heptaene-8,11,25-trione;

(1S,10R,19E)-12-methyl-10-[(7-methyl-1H-indazol-5-yl)methyl]-17-oxa-9,12,23,25-tetrazapentacyclo[19.5.2.1¹,⁴.1³,⁷.0²⁴,²⁷]triaconta-3,5,7(29),19,21(28),22,24(27)-heptaene-8,11,26-trione;

(1S,10R,20E)-12,15-dimethyl-10-[(7-methyl-1H-indazol-5-yl)methyl]-18-oxa-9,12,15,24,26-pentazapentacyclo[20.5.2.1¹,⁴.1³,⁷.0²⁵,²⁸]hentriaconta-3,5,7(30),20,22(29),23,25(28)-heptaene-8,11,27-trione;

(1S,10R,20E)-12-methyl-10-[(7-methyl-1H-indazol-5-yl)methyl]-18-oxa-9,12,15,24,26-pentazapentacyclo[20.5.2.1¹,⁴.1³,⁷.0²⁵,²⁸]hentriaconta-3,5,7(30),20,22(29),23,25(28)-heptaene-8,11,27-trione;

(1R,10R,20E)-10-[(1,7-dimethylindazol-5-yl)methyl]-12-methyl-15,18-dioxa-9,12,24,26-tetrazapentacyclo[20.5.2.1¹,⁴.1³,⁷.0²⁵,²⁸]hentriaconta-3,5,7(30),20,22(29),23,25(28)-heptaene-8,11,27-trione;

(1S,10R,20E)-10-[(1,7-dimethylindazol-5-yl)methyl]-12-methyl-15,18-dioxa-9,12,24,26-tetrazapentacyclo[20.5.2.1¹,⁴.1³,⁷.0²⁵,²⁸]hentriaconta-3,5,7(30),20,22(29),23,25(28)-heptaene-8,11,27-trione;

(1R,20E)-10-[(7-chloro-1H-indazol-5-yl)methyl]-12-methyl-15,18-dioxa-9,12,24,26-tetrazapentacyclo[20.5.2.1¹,⁴.1³,⁷.0²⁵,²⁸]hentriaconta-3,5,7(30),20,22(29),23,25(28)-heptaene-8,11,27-trione;

(1R,10R)-12-methyl-10-[(7-methyl-1H-indazol-5-yl)methyl]-15,18-dioxa-9,12,24,26-tetrazapentacyclo[20.5.2.1¹,⁴.1³,⁷.0²⁵,²⁸]hentriaconta-3,5,7(30),22(29),23,25(28)-hexaene-8,11,27-trione;

(1S,10R)-12-methyl-10-[(7-methyl-1H-indazol-5-yl)methyl]-15,18-dioxa-9,12,24,26-tetrazapentacyclo[20.5.2.1¹,⁴.1³,⁷.0²⁵,²⁸]hentriaconta-3,5,7(30),22(29),23,25(28)-hexaene-8,11,27-trione;

(1S,10R,20E)-12-methyl-10-[(7-methyl-1H-indazol-5-yl)methyl]-9,15,18-trioxa-5,12,24,26-tetrazapentacyclo[20.5.2.1¹,⁴.1³,⁷.0²⁵,²⁸]hentriaconta-3,5,7(30),20,22(29),23,25(28)-heptaene-8,11,27-trione;

(1S,10S,20E)-12-methyl-10-[(7-methyl-1H-indazol-5-yl)methyl]-9,15,18-trioxa-5,12,24,26-tetrazapentacyclo[20.5.2.1¹,⁴.1³,⁷.0²⁵,²⁸]hentriaconta-3,5,7(30),20,22(29),23,25(28)-heptaene-8,11,27-trione;

(1S,10R,20E)-12-methyl-10-[(7-methyl-1H-indazol-5-yl)methyl]-9,15,18-trioxa-12,24,26-triazapentacyclo[20.5.2.1¹,⁴.1³,⁷.0²⁵,²⁸]hentriaconta-3,5,7(30),20,22(29),23,25(28)-heptaene-8,11,27-trione;

(1R,10R,20E)-12-methyl-10-[(7-methyl-1H-indazol-5-yl)methyl]-9,15,18-trioxa-12,24,26-triazapentacyclo[20.5.2.1¹,⁴.1³,⁷.0²⁵,²⁸]hentriaconta-3,5,7(30),20,22(29),23,25(28)-heptaene-8,11,27-trione;

(7R,17E)-9-methyl-7-[(7-methyl-1H-indazol-5-yl)methyl]-12,15,25-trioxa-4,6,9,21,23-pentazatetracyclo[17.6.2.2¹,⁴.0²²,²⁶]nonacosa-17,19(27),20,22(26)-tetraene-5,8,24-trione;

(7R,17E)-9-methyl-7-[(7-methyl-1H-indazol-5-yl)methyl]-6,12,15,25-tetraoxa-4,9,21,23-tetrazatetracyclo[17.6.2.2¹,⁴.0²²,²⁶]nonacosa-17,19(27),20,22(26)-tetraene-5,8,24-trione;

(7R,20E)-9-methyl-7-[(7-methyl-1H-indazol-5-yl)methyl]-6,12,15,18,28-pentaoxa-4,9,24,26-tetrazatetracyclo[20.6.2.2¹,⁴.0²⁵,²⁹]dotriaconta-20,22(30),23,25(29)-tetraene-5,8,27-trione;

(7R,17E)-9-methyl-7-[(7-methyl-1H-indazol-5-yl)methyl]-6,15,25-trioxa-4,9,21,23-tetrazatetracyclo[17.6.2.2¹,⁴.0²²,²⁶]nonacosa-17,19(27),20,22(26)-tetraene-5,8,24-trione;

(7R,18E)-9-methyl-7-[(7-methyl-1H-indazol-5-yl)methyl]-6,13,16,26-tetraoxa-4,9,22,24-tetrazatetracyclo[18.6.2.2¹,⁴.0²³,²⁷]triaconta-18,20(28),21,23(27)-tetraene-5,8,25-trione;

(7R)-9-methyl-7-[(7-methyl-1H-indazol-5-yl)methyl]-6,12,15,18,28-pentaoxa-4,9,24,26-tetrazatetracyclo[20.6.2.2¹,⁴.0²⁵,²⁹]dotriaconta-22(30),23,25(29)-triene-5,8,27-trione;

(7R)-9-methyl-7-[(7-methyl-1H-indazol-5-yl)methyl]-6,15,25-trioxa-4,9,21,23-tetrazatetracyclo[17.6.2.2¹,⁴.0²²,²⁶]nonacosa-19(27),20,22(26)-triene-5,8,24-trione;

(7R)-9-methyl-7-[(7-methyl-1H-indazol-5-yl)methyl]-6,13,16,26-tetraoxa-4,9,22,24-tetrazatetracyclo[18.6.2.2¹,⁴.0²³,²⁷]triaconta-20(28),21,23(27)-triene-5,8,25-trione;

(10R,20E)-12-methyl-10-[(7-methyl-1H-indazol-5-yl)methyl]-15,18-dioxa-9,12,24,26,30-pentazapentacyclo[20.5.2.1¹,⁴.1³,⁷.0²⁵,²⁸]hentriaconta-3,5,7(30),20,22,24,28-heptaene-8,11,27-trione;

and salts thereof.

Further embodiments of the invention include methods of treatment comprising administering an effective therapeutic amount of a compound of Formula (1), (2a), (2b), (2c), (2d), (2e), (3a), (3b), (3c), (3d), (4a), (4b), (4c), (4d), (5), (6a), (6b), (6c) or (6d) as a CGRP receptor antagonist. The treatment using a compound of Formula (1), (2a), (2b), (2c), (2d), (2e), (3a), (3b), (3c), (3d), (4a), (4b), (4c), (4d), (5), (6a), (6b), (6c) or (6d) may be in the treatment of cerebrovascular or vascular disorders including migraine (with or without aura), chronic migraine, pure menstrual migraine, frequent episodic migraine, menstrually-related migraine, migraine with aura, familial hemiplegic migraine, sporadic hemiplegic migraine, basilar-type migraine, cyclical vomiting, abdominal migraine, benign paroxysmal vertigo of childhood, retinal migraine, status migrainosus, cluster headache, dialysis headache, chronic headaches of unknown origin, tension/stress induced headaches, allergy induced headaches, paroxysmal hemicrania, osteoarthritis and associated osteoporotic fracture pain, hot flashes associated with menopause or medically induced menopause due to surgery or drug treatment, hemicrania continua, cyclic vomiting syndrome, opiate withdrawal syndrome, morphine tolerance, neurodegenerative disease, epilepsy, allergic rhinitis, rosacea, dental pain, earache, middle ear inflammation, sunburn, joint pain associated with osteoarthritis and rheumatoid arthritis and gout, cancer pain, neuropathic pain (including but not limited to cancer pain in all its various forms including of unexplained origin), dystonic pain, inflammatory pain, post-operative incision pain, sciatica, fibromyalgia, trigeminal neuralga, diabetic neuropathy, complex regional pain syndrome, Behget's disease, endometriosis pain, back pain, phantom limb pain, menstrual period pain, pain associated with labour, pain resulting from burns to skin, or visceral pain associated with inflammatory bowel disease (including Crohn's disease, ileitis and ulcerative colitis), gastro-esophageal reflux disease, dyspepsia, irritable bowel syndrome, renal colic, cystitis, gout, pancreatitis and prostatitis.

The compounds of Formula (1), (2a), (2b), (2c), (2d), (2e), (3a), (3b), (3c), (3d), (4a), (4b), (4c), (4d), (5), (6a), (6b), (6c) or (6d) may also be used in the treatment of inflammatory and immune associated disorders including chronic fatigue syndrome, skin diseases, neurogenic cutaneous redness, skin rosaceousness, erythema, bronchial hyperreactivity, asthma, mast cell activation syndrome, mastocytosis, mast cell degranulation disorder, vascular disorders, shock, sepsis, non-insulin dependent diabetes mellitus, and infectious diseases including those of a respiratory and gastrointestinal origin.

The compounds of the invention may be used alone or in combination with any other therapy or standard of care for any of the above indications.

Certain novel compounds of the invention show particularly high activities as CGRP receptor antagonists.

Definitions

In this application, the following definitions apply, unless indicated otherwise.

The term "treatment", in relation to the uses of any of the compounds described herein, including those of Formula (1), (2a), (2b), (2c), (2d), (2e), (3a), (3b), (3c), (3d), (4a), (4b), (4c), (4d), (5), (6a), (6b), (6c) or (6d) is used to describe any form of intervention where a compound is administered to a subject suffering from, or at risk of suffering from, or potentially at risk of suffering from the disease or disorder in question. Thus, the term "treatment" covers both preventative (prophylactic) treatment and treatment where measurable or detectable symptoms of the disease or disorder are being displayed.

The term "effective therapeutic amount" (for example in relation to methods of treatment of a disease or condition) refers to an amount of the compound which is effective to produce a desired therapeutic effect. For example, if the condition is pain, then the effective therapeutic amount is an amount sufficient to provide a desired level of pain relief. The desired level of pain relief may be, for example, complete removal of the pain or a reduction in the severity of the pain.

The terms "alkyl" as in "$C_{1-3}$ alkyl", "halo", "monocyclic" and "bicyclic" are all used in their conventional sense (e.g. as defined in the IUPAC Gold Book), unless indicated otherwise. "Optionally substituted" as applied to any group means that the said group may if desired be substituted with one or more substituents, which may be the same or different.

To the extent that any of the compounds described have chiral centres, the present invention extends to all optical isomers of such compounds, whether in the form of racemates or resolved enantiomers. The invention described herein relates to all crystal forms, solvates and hydrates of any of the disclosed compounds however so prepared. To the extent that any of the compounds disclosed herein have acid or basic centres such as carboxylates or amino groups, then all salt forms of said compounds are included herein. In the case of pharmaceutical uses, the salt should be seen as being a pharmaceutically acceptable salt.

Salts or pharmaceutically acceptable salts that may be mentioned include acid addition salts and base addition salts. Such salts may be formed by conventional means, for example by reaction of a free acid or a free base form of a compound with one or more equivalents of an appropriate acid or base, optionally in a solvent, or in a medium in which the salt is insoluble, followed by removal of said solvent, or said medium, using standard techniques (e.g. in vacuo, by freeze-drying or by filtration). Salts may also be prepared by exchanging a counter-ion of a compound in the form of a salt with another counter-ion, for example using a suitable ion exchange resin.

Examples of pharmaceutically acceptable salts include acid addition salts derived from mineral acids and organic acids, and salts derived from metals such as sodium, magnesium, potassium and calcium.

Examples of acid addition salts include acid addition salts formed with acetic, 2,2-dichloroacetic, adipic, alginic, aryl sulfonic acids (e.g. benzenesulfonic, naphthalene-2-sulfonic, naphthalene-1,5-disulfonic and p-toluenesulfonic), ascorbic (e.g. L-ascorbic), L-aspartic, benzoic, 4-acetamidobenzoic, butanoic, (+) camphoric, camphor-sulfonic, (+)-(1S)-camphor-10-sulfonic, capric, caproic, caprylic, cinnamic, citric, cyclamic, dodecylsulfuric, ethane-1,2-disulfonic, ethanesulfonic, 2-hydroxyethanesulfonic, formic, fumaric, galactaric, gentisic, glucoheptonic, gluconic (e.g. D-gluconic), glucuronic (e.g. D-glucuronic), glutamic (e.g. L-glutamic), α-oxoglutaric, glycolic, hippuric, hydrobromic, hydrochloric, hydriodic, isethionic, lactic (e.g. (+)-L-lactic and (±)-DL-lactic), lactobionic, maleic, malic (e.g. (−)-L-malic), malonic, (±)-DL-mandelic, metaphosphoric, methanesulfonic, 1-hydroxy-2-naphthoic, nicotinic, nitric, oleic, orotic, oxalic, palmitic, pamoic, phosphoric, propionic, L-pyroglutamic, salicylic, 4-amino-salicylic, sebacic, stearic, succinic, sulfuric, tannic, tartaric (e.g.(+)-L-tartaric), thiocyanic, undecylenic and valeric acids.

Also encompassed are any solvates of the compounds and their salts. Preferred solvates are solvates formed by the incorporation into the solid state structure (e.g. crystal structure) of the compounds of the invention of molecules of a non-toxic pharmaceutically acceptable solvent (referred to below as the solvating solvent). Examples of such solvents include water, alcohols (such as ethanol, isopropanol and butanol) and dimethylsulfoxide. Solvates can be prepared by recrystallising the compounds of the invention with a solvent or mixture of solvents containing the solvating solvent. Whether or not a solvate has been formed in any given instance can be determined by subjecting crystals of the compound to analysis using well known and standard techniques such as thermogravimetric analysis (TGA), differential scanning calorimetry (DSC) and X-ray crystallography.

The solvates can be stoichiometric or non-stoichiometric solvates. Particular solvates may be hydrates, and examples of hydrates include hemihydrates, monohydrates and dihydrates. For a more detailed discussion of solvates and the methods used to make and characterise them, see Bryn et al, Solid-State Chemistry of Drugs, Second Edition, published by SSCI, Inc of West Lafayette, IN, USA, 1999, ISBN 0-967-06710-3.

The term "pharmaceutical composition" in the context of this invention means a composition comprising an active agent and comprising additionally one or more pharmaceutically acceptable carriers. The composition may further contain ingredients selected from, for example, diluents, adjuvants, excipients, vehicles, preserving agents, fillers, disintegrating agents, wetting agents, emulsifying agents, suspending agents, sweetening agents, flavouring agents, perfuming agents, antibacterial agents, antifungal agents, lubricating agents and dispersing agents, depending on the nature of the mode of administration and dosage forms. The compositions may take the form, for example, of tablets, dragees, powders, elixirs, syrups, liquid preparations including suspensions, sprays, inhalants, tablets, lozenges, emulsions, solutions, cachets, granules, capsules and suppositories, as well as liquid preparations for injections, including liposome preparations.

The compounds of the invention may contain one or more isotopic substitutions, and a reference to a particular element includes within its scope all isotopes of the element. For example, a reference to hydrogen includes within its scope $^1H$, $^2H$ (D), and $^3H$ (T). Similarly, references to carbon and oxygen include within their scope respectively $^{12}C$, 13C and $^{14}C$ and $^{16}O$ and 18O. In an analogous manner, a reference to a particular functional group also includes within its scope isotopic variations, unless the context indicates otherwise. For example, a reference to an alkyl group such as an ethyl group or an alkoxy group such as a methoxy group also covers variations in which one or more of the hydrogen atoms in the group is in the form of a deuterium or tritium isotope, e.g. as in an ethyl group in which all five hydrogen atoms are in the deuterium isotopic form (a perdeuteroethyl group) or a methoxy group in which all three hydrogen atoms are in the deuterium isotopic form (a trideuteromethoxy group). The isotopes may be radioactive or non-radioactive.

Therapeutic dosages may be varied depending upon the requirements of the patient, the severity of the condition being treated, and the compound being employed. Determination of the proper dosage for a particular situation is within the skill of the art. Generally, treatment is initiated with the smaller dosages which are less than the optimum dose of the compound. Thereafter the dosage is increased by small increments until the optimum effect under the circumstances is reached. For convenience, the total daily dosage may be divided and administered in portions during the day if desired.

The magnitude of an effective dose of a compound will, of course, vary with the nature of the severity of the condition to be treated and with the particular compound and its route of administration. The selection of appropriate dosages is within the ability of one of ordinary skill in this art, without undue burden. In general, the daily dose range may be from about 10 µg to about 30 mg per kg body weight of a human and non-human animal, preferably from about 50 µg to about 30 mg per kg of body weight of a human and non-human animal, for example from about 50 µg to about 10 mg per kg of body weight of a human and non-human animal, for example from about 100 µg to about 30 mg per kg of body weight of a human and non-human animal, for example from about 100 µg to about 10 mg per kg of body weight of a human and non-human animal and most preferably from about 100 µg to about 1 mg per kg of body weight of a human and non-human animal.

Pharmaceutical Formulations

While it is possible for the active compound to be administered alone, it is preferable to present it as a pharmaceutical composition (e.g. formulation).

Accordingly, in another embodiment of the invention, there is provided a pharmaceutical composition comprising at least one compound of Formula (1) as defined above together with at least one pharmaceutically acceptable excipient.

The composition may be a tablet composition.

The composition may be a capsule composition.

The pharmaceutically acceptable excipient(s) can be selected from, for example, carriers (e.g. a solid, liquid or semi-solid carrier), adjuvants, diluents (e.g. solid diluents such as fillers or bulking agents; and liquid diluents such as solvents and co-solvents), granulating agents, binders, flow aids, coating agents, release-controlling agents (e.g. release retarding or delaying polymers or waxes), binding agents, disintegrants, buffering agents, lubricants, preservatives, anti-fungal and antibacterial agents, antioxidants, buffering agents, tonicity-adjusting agents, thickening agents, flavouring agents, sweeteners, pigments, plasticizers, taste masking agents, stabilisers or any other excipients conventionally used in pharmaceutical compositions.

The term "pharmaceutically acceptable" as used herein means compounds, materials, compositions, and/or dosage forms which are, within the scope of sound medical judgment, suitable for use in contact with the tissues of a subject (e.g. a human subject) without excessive toxicity, irritation, allergic response, or other problem or complication, commensurate with a reasonable benefit/risk ratio. Each excipient must also be "acceptable" in the sense of being compatible with the other ingredients of the formulation.

Pharmaceutical compositions containing compounds of the Formula (1) can be formulated in accordance with known techniques, see for example, Remington's Pharmaceutical Sciences, Mack Publishing Company, Easton, PA, USA.

The pharmaceutical compositions can be in any form suitable for oral, parenteral, topical, intranasal, intrabronchial, sublingual, ophthalmic, otic, rectal, intra-vaginal, or transdermal administration.

Pharmaceutical dosage forms suitable for oral administration include tablets (coated or uncoated), capsules (hard or soft shell), caplets, pills, lozenges, syrups, solutions, powders, granules, elixirs and suspensions, sublingual tablets, wafers or patches such as buccal patches.

Tablet compositions can contain a unit dosage of active compound together with an inert diluent or carrier such as a sugar or sugar alcohol, eg; lactose, sucrose, sorbitol or mannitol; and/or a non-sugar derived diluent such as sodium carbonate, calcium phosphate, calcium carbonate, or a cellulose or derivative thereof such as microcrystalline cellulose (MCC), methyl cellulose, ethyl cellulose, hydroxypropyl methyl cellulose, and starches such as corn starch. Tablets may also contain such standard ingredients as binding and granulating agents such as polyvinylpyrrolidone, disintegrants (e.g. swellable crosslinked polymers such as crosslinked carboxymethylcellulose), lubricating agents (e.g. stearates), preservatives (e.g. parabens), antioxidants (e.g. BHT), buffering agents (for example phosphate or citrate buffers), and effervescent agents such as citrate/ bicarbonate mixtures. Such excipients are well known and do not need to be discussed in detail here.

Tablets may be designed to release the drug either upon contact with stomach fluids (immediate release tablets) or to release in a controlled manner (controlled release tablets) over a prolonged period of time or with a specific region of the GI tract.

The pharmaceutical compositions typically comprise from approximately 1% (w/w) to approximately 95%, preferably % (w/w) active ingredient and from 99% (w/w) to 5% (w/w) of a pharmaceutically acceptable excipient (for example as defined above) or combination of such excipients. Preferably, the compositions comprise from approximately 20% (w/w) to approximately 90% (w/w) active ingredient and from 80% (w/w) to 10% of a pharmaceutically excipient or combination of excipients. The pharmaceutical compositions comprise from approximately 1% to approximately 95%, preferably from approximately 20% to approximately 90%, active ingredient. Pharmaceutical compositions according to the invention may be, for example, in unit dose form, such as in the form of ampoules, vials, suppositories, pre-filled syringes, dragées, powders, tablets or capsules.

Tablets and capsules may contain, for example, 0-20% disintegrants, 0-5% lubricants, 0-5% flow aids and/or 0-99% (w/w) fillers/or bulking agents (depending on drug dose). They may also contain 0-10% (w/w) polymer binders, 0-5% (w/w) antioxidants, 0-5% (w/w) pigments. Slow release tablets would in addition typically contain 0-99% (w/w) release-controlling (e.g. delaying) polymers (depending on dose). The film coats of the tablet or capsule typically contain 0-10% (w/w) polymers, 0-3% (w/w) pigments, and/or 0-2% (w/w) plasticizers.

Parenteral formulations typically contain 0-20% (w/w) buffers, 0-50% (w/w) cosolvents, and/or 0-99% (w/w) Water for Injection (WFI) (depending on dose and if freeze dried). Formulations for intramuscular depots may also contain 0-99% (w/w) oils.

The pharmaceutical formulations may be presented to a patient in "patient packs" containing an entire course of treatment in a single package, usually a blister pack.

The compounds of the Formula (1) will generally be presented in unit dosage form and, as such, will typically contain sufficient compound to provide a desired level of biological activity. For example, a formulation may contain from 1 nanogram to 2 grams of active ingredient, e.g. from 1 nanogram to 2 milligrams of active ingredient. Within these ranges, particular sub-ranges of compound are 0.1 milligrams to 2 grams of active ingredient (more usually from 10 milligrams to 1 gram, e.g. 50 milligrams to 500 milligrams), or 1 microgram to 20 milligrams (for example 1 microgram to 10 milligrams, e.g. 0.1 milligrams to 2 milligrams of active ingredient).

For oral compositions, a unit dosage form may contain from 1 milligram to 2 grams, more typically 10 milligrams to 1 gram, for example 50 milligrams to 1 gram, e.g. 100 milligrams to 1 gram, of active compound.

The active compound will be administered to a patient in need thereof (for example a human or animal patient) in an amount sufficient to achieve the desired therapeutic effect (effective amount). The precise amounts of compound administered may be determined by a supervising physician in accordance with standard procedures.

Methods for the Preparation of Compounds of the Formula (1)

Compounds of Formula (1) can be prepared in accordance with synthetic methods well known to the skilled person and as described herein. The invention provides a process for the preparation of a compound as defined in Formula (1) above, which process comprises any one of the steps represented by general methods A, B, C, and D (wherein G, J, $R^1$, $R^2$ and the compounds of Formula (6a), (6b), (6c) and (6d) are as defined above) Compounds of Formula (1) may also be prepared by chemical transformation of other compounds of Formula (1).

General Method A to make compounds of type (6a):

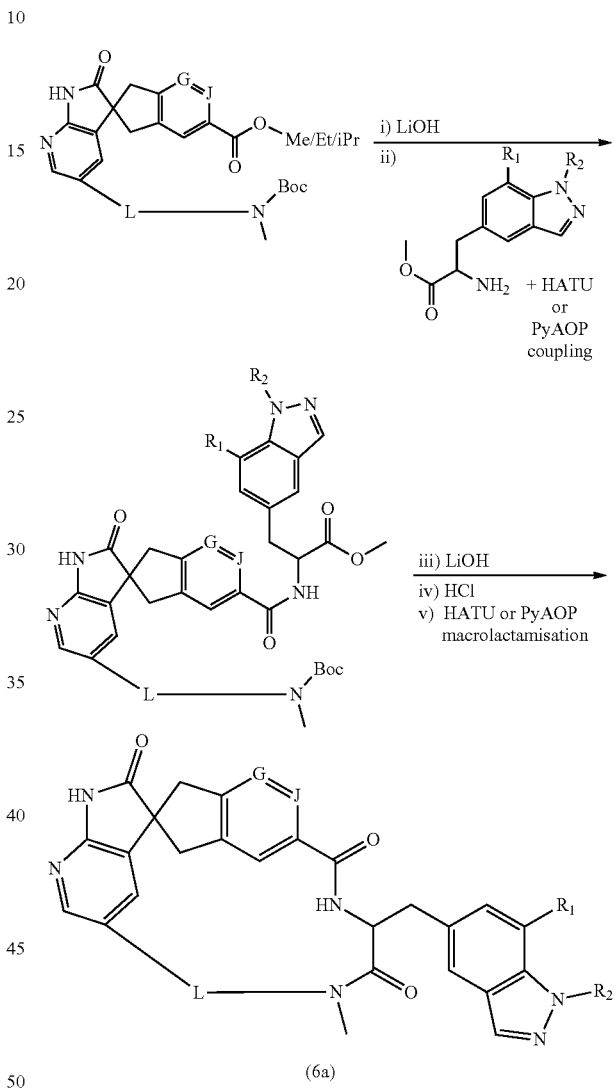

General method B to make compounds of type (6b):

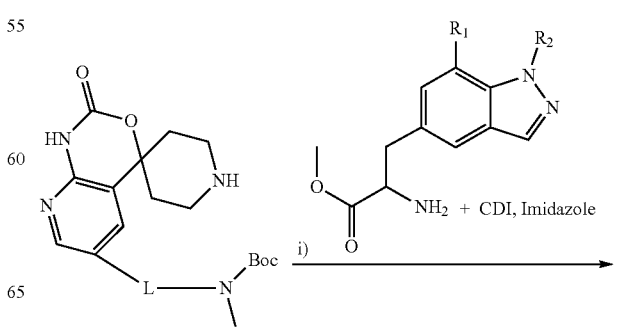

29
-continued
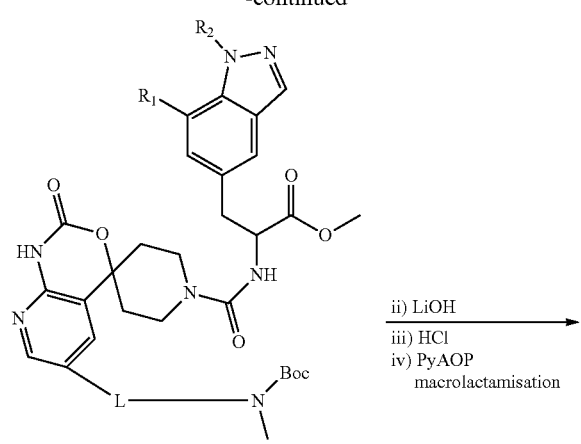
(6b)
General Method C to make compounds of type (6c):
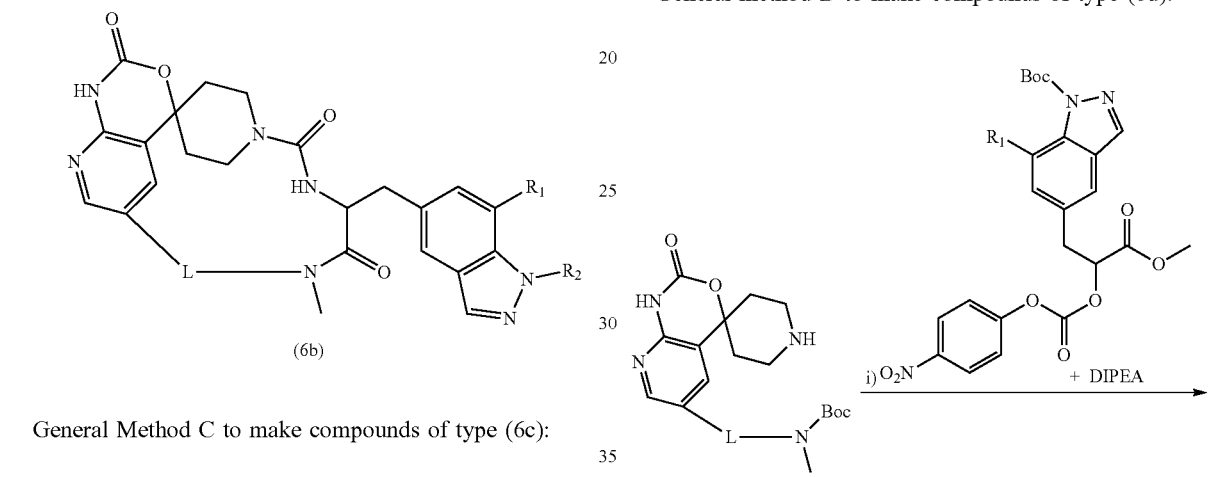
30
-continued
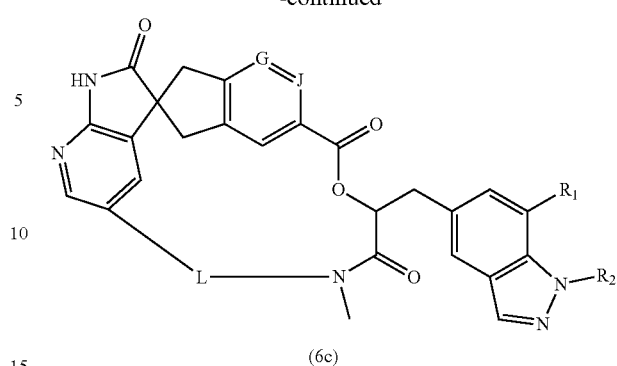
(6c)
General method D to make compounds of type (6d):
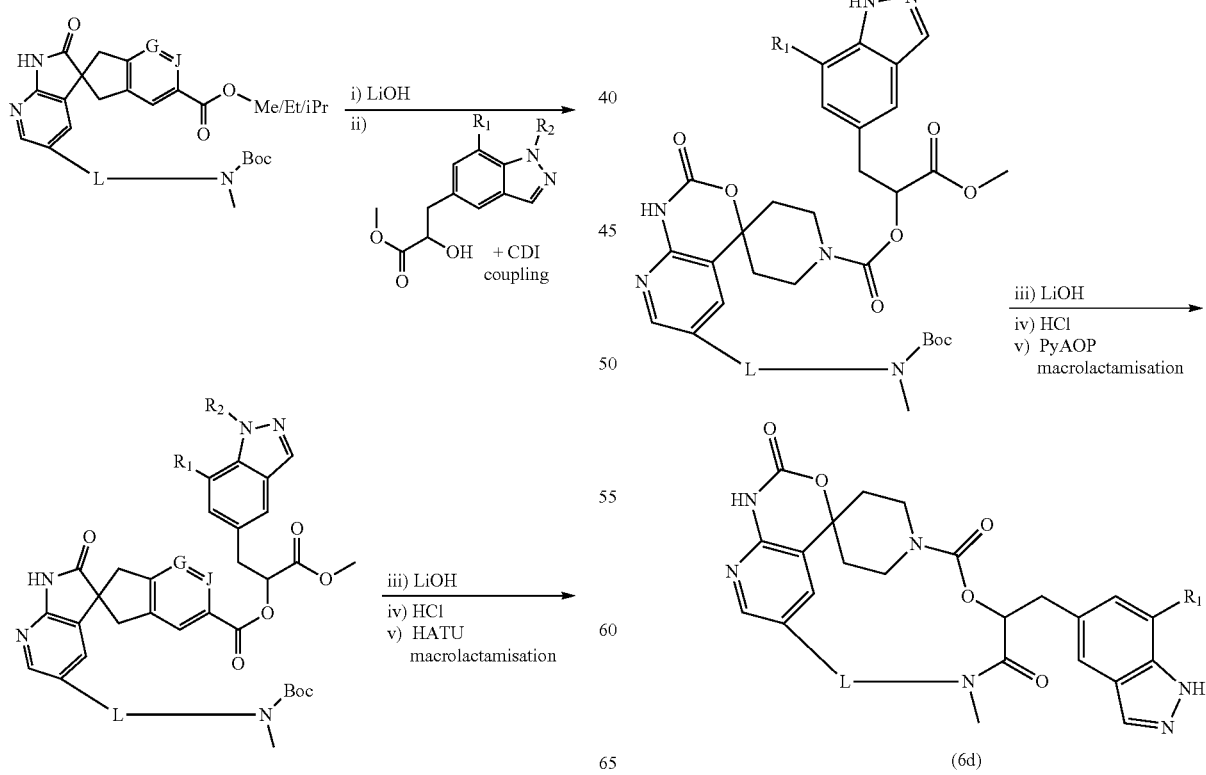
(6d)

EXAMPLES

The invention will now be illustrated, but not limited, by reference to the following examples.

Examples 1-1 to 8-2

The compounds of Examples 1-1 to 8-2 shown in Table 1 below have been prepared. Their NMR and LCMS properties and the methods used to prepare them are set out in Table 3. The starting materials for each of the Examples are listed in Table 2.

TABLE 1

Example compounds

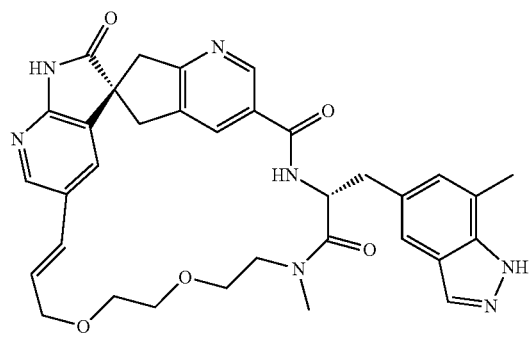 [SMILES: Cc1cc(C[C@H]2NC(=O)c3cnc4c(c3)C[C@@]3(C4)C(=O)Nc4ncc(cc43)/C=C/COCCOCCN(C)C2=O)cc2cn[nH]c12]

Example 1-1

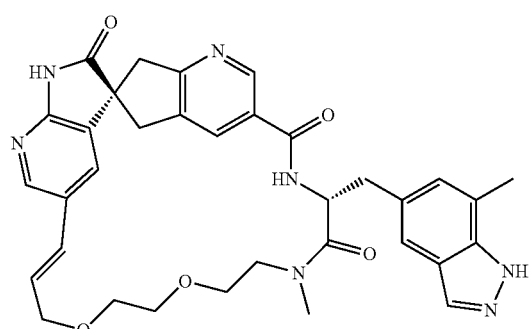

Example 1-2

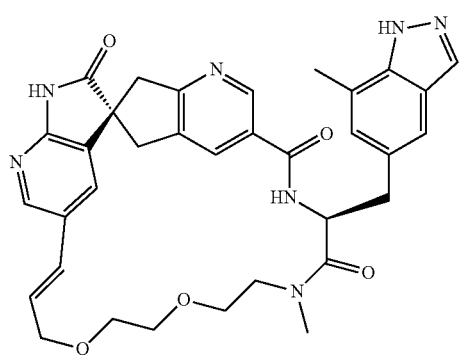 [SMILES: Cc1cc(C[C@@H]2NC(=O)c3cnc4c(c3)C[C@@]3(C4)C(=O)Nc4ncc(cc43)/C=C/COCCOCCN(C)C2=O)cc2cn[nH]c12]

Example 1-3

TABLE 1-continued

Example compounds

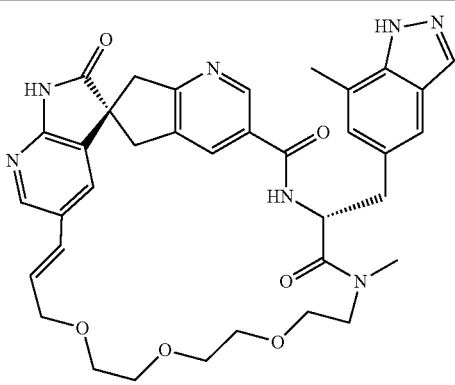 [SMILES: Cc1cc(C[C@H]2NC(=O)c3cnc4c(c3)C[C@@]3(C4)C(=O)Nc4ncc(cc43)/C=C/COCCOCCOCCN(C)C2=O)cc2cn[nH]c12]

Example 1-4

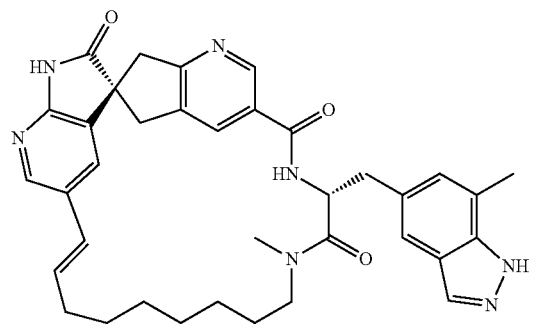 [SMILES: Cc1cc(C[C@H]2NC(=O)c3cnc4c(c3)C[C@@]3(C4)C(=O)Nc4ncc(cc43)/C=C/CCCCCCCN(C)C2=O)cc2cn[nH]c12]

Example 1-5

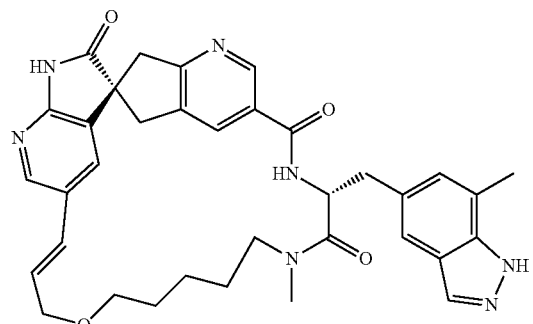

Example 1-6

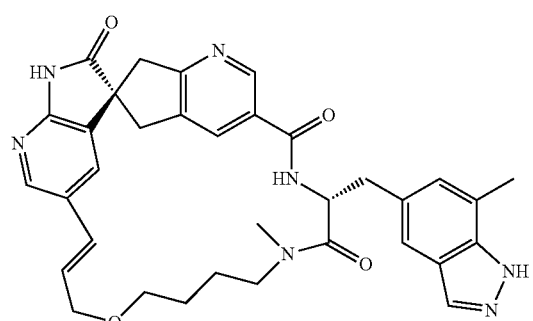

Example 1-7

TABLE 1-continued
Example compounds
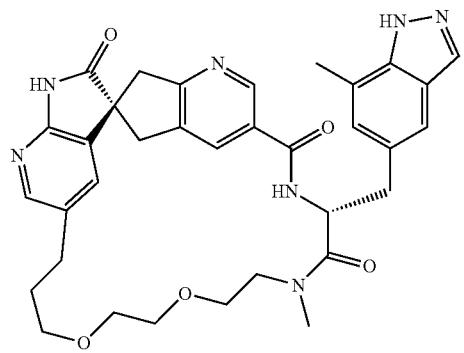 [SMILES: Cc1cc(C[C@H]2NC(=O)c3cnc4c(c3)C[C@@]3(C4)C(=O)Nc4ncc(cc43)CCCOCCOCCN(C)C2=O)cc2cn[nH]c12]
Example 1-8
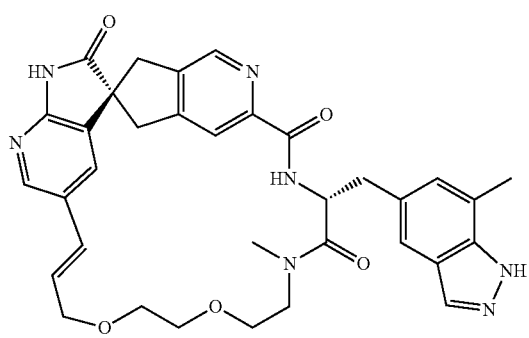 [SMILES: Cc1cc(C[C@H]2NC(=O)c3cc4c(cn3)C[C@]3(C4)C(=O)Nc4ncc(cc43)/C=C/COCCOCCN(C)C2=O)cc2cn[nH]c12]
Example 2-1
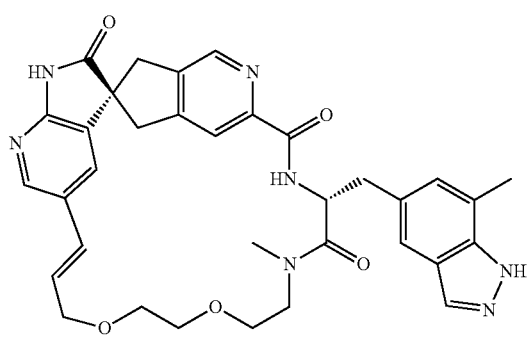 [SMILES: Cc1cc(C[C@H]2NC(=O)c3cc4c(cn3)C[C@@]3(C4)C(=O)Nc4ncc(cc43)/C=C/COCCOCCN(C)C2=O)cc2cn[nH]c12]
Example 2-2
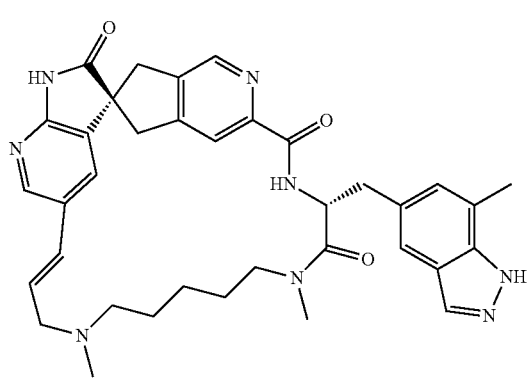 [SMILES: Cc1cc(C[C@H]2NC(=O)c3cc4c(cn3)C[C@@]3(C4)C(=O)Nc4ncc(cc43)/C=C/CN(C)CCCCCN(C)C2=O)cc2cn[nH]c12]
Example 2-3
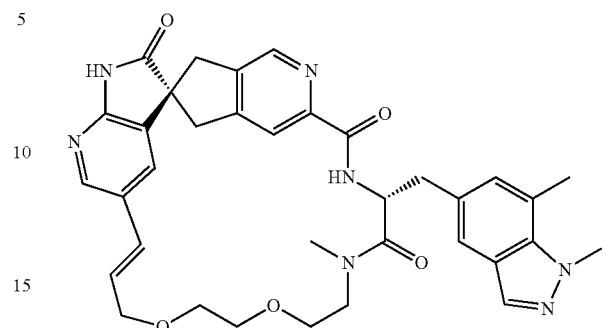
Example 2-4
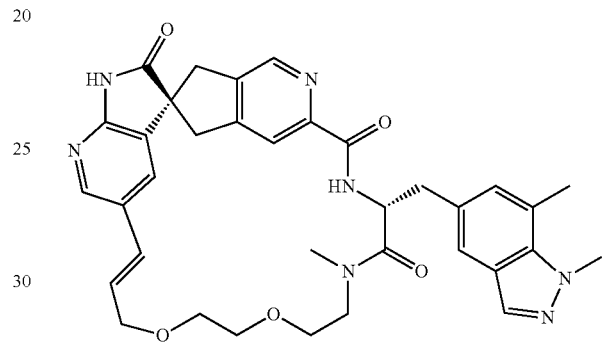
Example 2-5
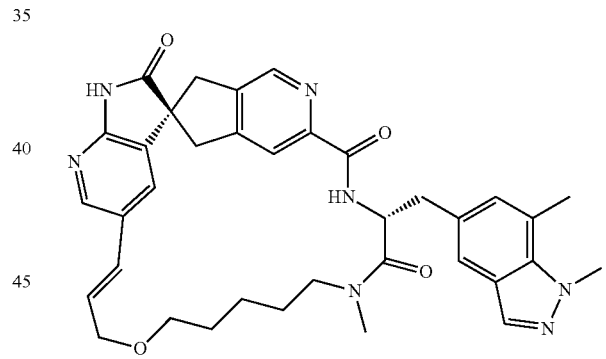
Example 2-6
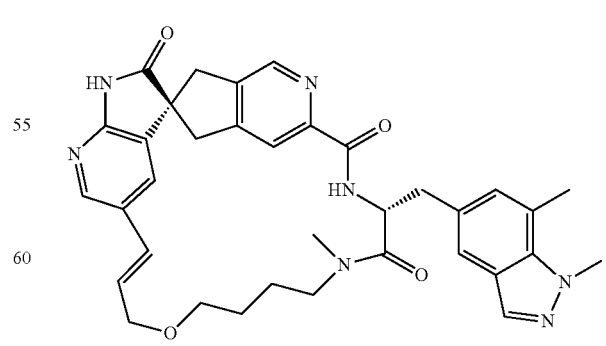
Example 2-7

TABLE 1-continued
Example compounds
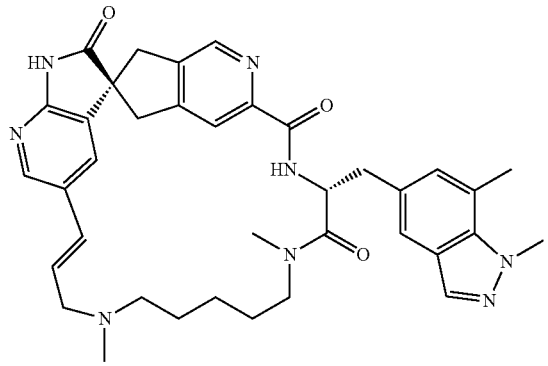
Example 2-8
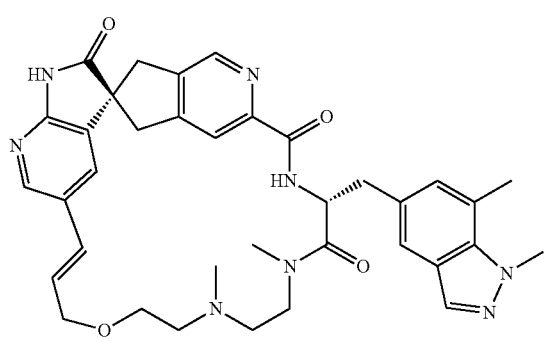 [SMILES: Cc1cc(C[C@H]2NC(=O)c3cc4c(cn3)C[C@@]3(C4)C(=O)Nc4ncc(cc43)/C=C/COCCOCCN(C)C2=O)cc2cnn(C)c12]
Example 2-9
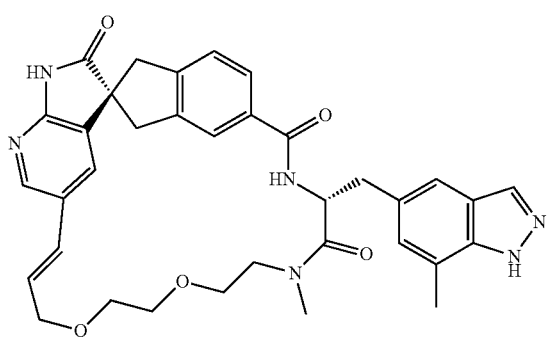 [SMILES: Cc1cc(C[C@H]2NC(=O)c3ccc4c(c3)C[C@@]3(C4)C(=O)Nc4ncc(cc43)/C=C/COCCOCCN(C)C2=O)cc2cn[nH]c12]
Example 3-1
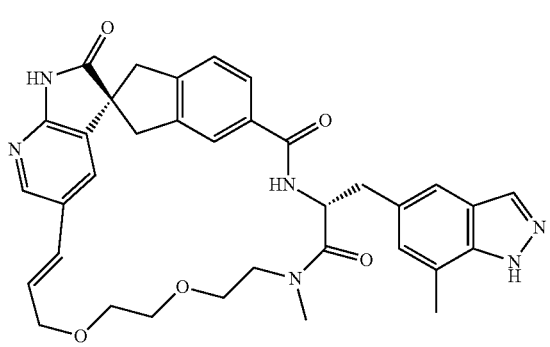 [SMILES: Cc1cc(C[C@H]2NC(=O)c3ccc4c(c3)C[C@]3(C4)C(=O)Nc4ncc(cc43)/C=C/COCCOCCN(C)C2=O)cc2cn[nH]c12]
Example 3-2
TABLE 1-continued
Example compounds
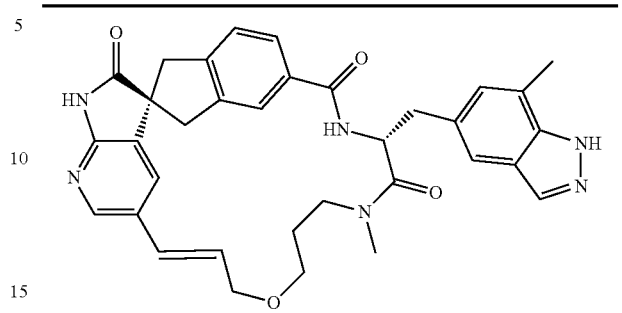
Example 3-3
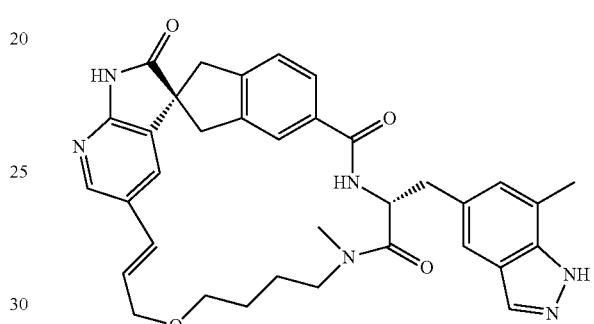
Example 3-4
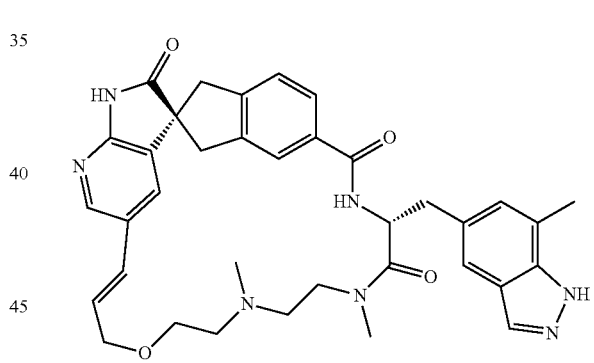
Example 3-5
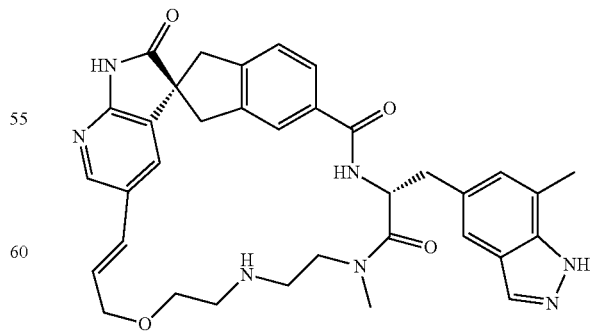
Example 3-6

TABLE 1-continued
Example compounds
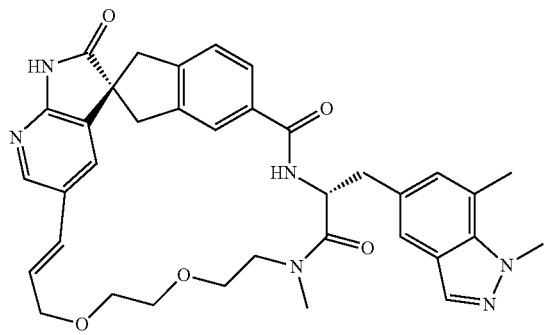 [SMILES: Cc1cc(C[C@H]2NC(=O)c3ccc4c(c3)C[C@@]3(C4)C(=O)Nc4ncc(cc43)/C=C/COCCOCCN(C)C2=O)cc2cnn(C)c12]
Example 3-7
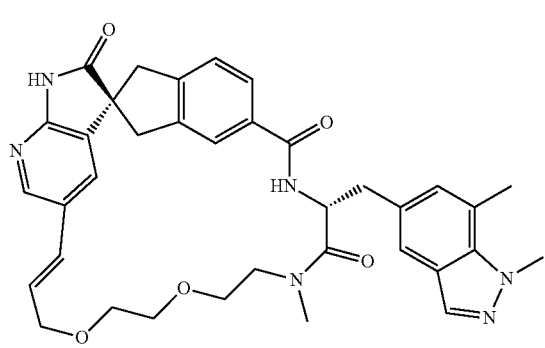
Example 3-8
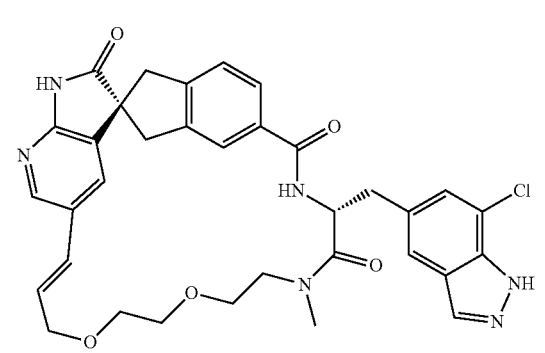 [SMILES: CN1CCOCCOC/C=C/c2cnc3c(c2)[C@]2(Cc4ccc(cc4C2)C(=O)N[C@H](Cc2cc(Cl)c4[nH]ncc4c2)C1=O)C(=O)N3]
Example 3-9
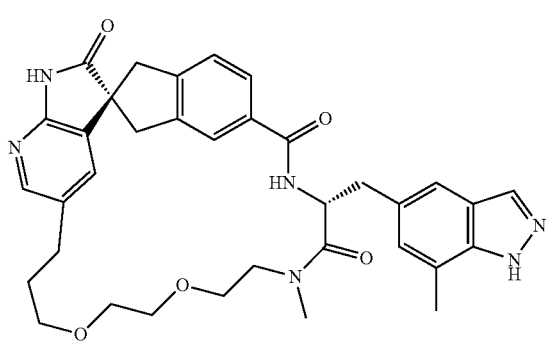 [SMILES: Cc1cc(C[C@H]2NC(=O)c3ccc4c(c3)C[C@@]3(C4)C(=O)Nc4ncc(cc43)CCCOCCOCCN(C)C2=O)cc2cn[nH]c12]
Example 3-10
TABLE 1-continued
Example compounds
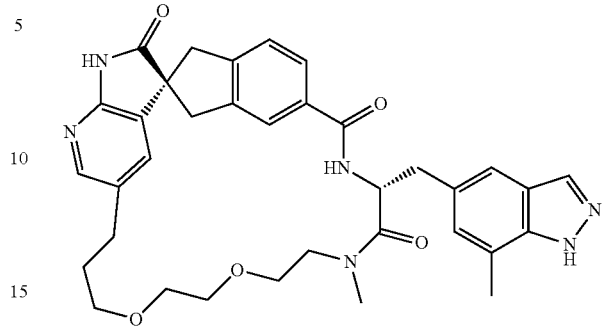
Example 3-11
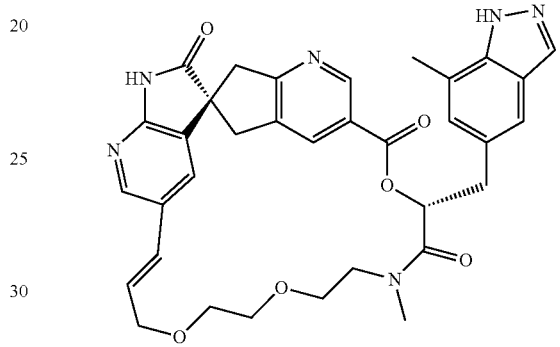
Example 4-1
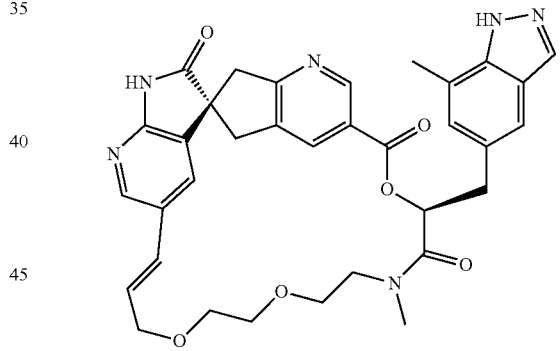
Example 4-2
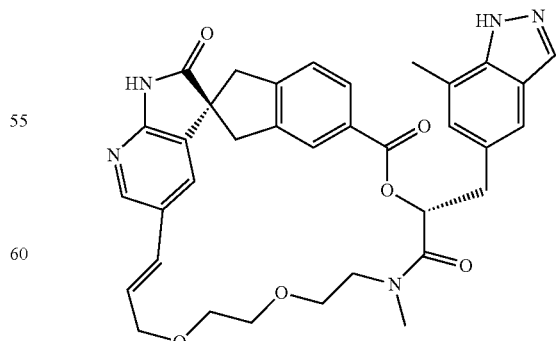
Example 5-1

TABLE 1-continued
Example compounds
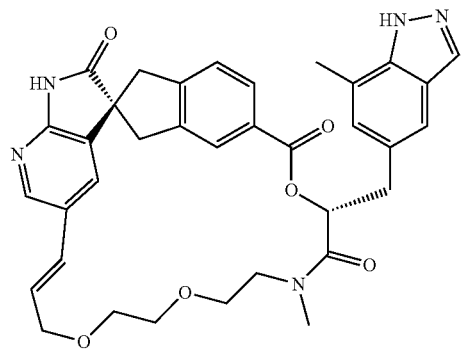 [SMILES: Cc1cc(C[C@H]2OC(=O)c3ccc4c(c3)C[C@@]3(C4)C(=O)Nc4ncc(cc43)/C=C/COCCOCCN(C)C2=O)cc2cn[nH]c12]
Example 5-2
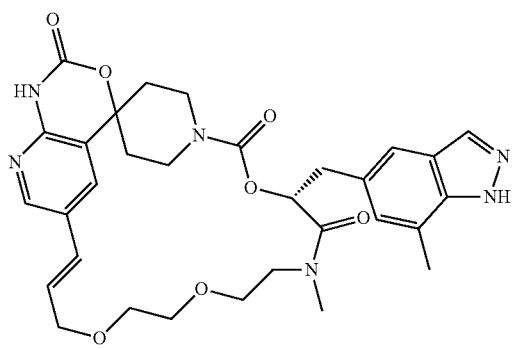 [SMILES: Cc1cc(C[C@H]2OC(=O)N3CCC4(CC3)OC(=O)Nc3ncc(cc34)/C=C/COCCOCCN(C)C2=O)cc2cn[nH]c12]
Example 6-1
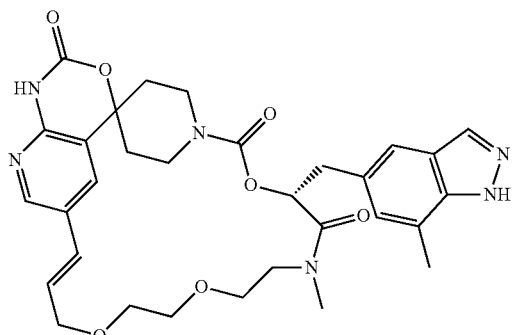
Example 7-1
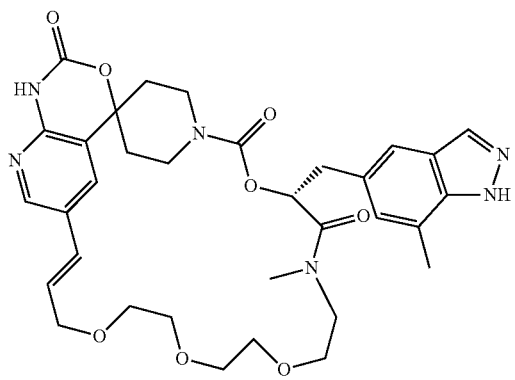 [SMILES: Cc1cc(C[C@H]2OC(=O)N3CCC4(CC3)OC(=O)Nc3ncc(cc34)/C=C/COCCOCCOCCN(C)C2=O)cc2cn[nH]c12]
Example 7-2
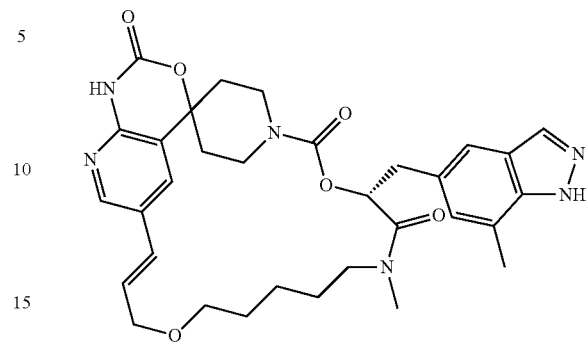
Example 7-3
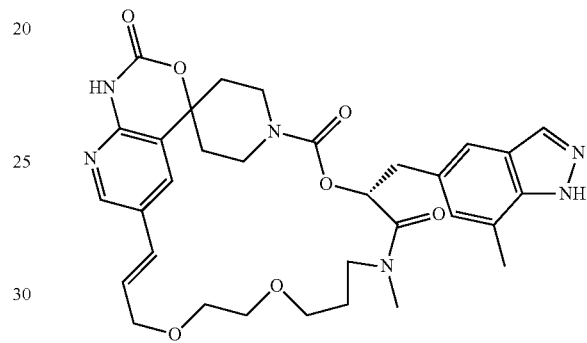
Example 7-4
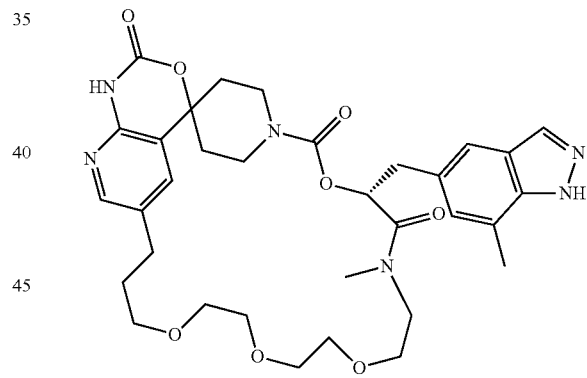
Example 7-5
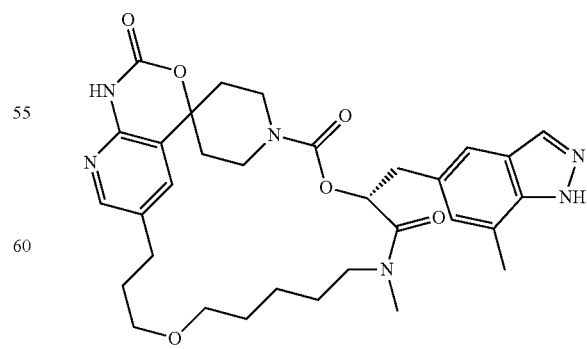
Example 7-6

TABLE 1-continued

Example compounds

Example 7-7

Example 8-1

Example 8-2

General Procedures

NMR spectra were recorded on a Bruker DPX 300 MHz equipped with a 5 mm BBI probe, Bruker AV400 MHz equipped with a 5 mm PABBO probe, Bruker DRX 500 MHz equipped with a 5 mm PABBI probe or a Bruker Avance III 600 spectrometer equipped with a 5 mm RT BBI probe. The samples were recorded at 25° C. using DMSO-$d_6$, $CD_3OD$ or $CDCl_3$ as a solvent and TMS as the internal standard.

For chiral HPLC analysis, instrument Agilent HP1100 was used. The system is composed of a binary pump, an autosampler, a mobile phase degasser and a diode array detector. Sample was dissolved in mixture of IPA and hexane to the final concentration of 1 mg/ml. 5.0 μL of clear solution was injected. Analyses were performed at 25° C.

For preparative purification, HPLC Waters Mass Directed Autopurification System was used. The system is composed of Waters Sample Manager 2767, Waters System Fluid Organizer, Waters Binary Gradient Module 2545, Waters 515 HPLC Pump, Waters Photodiode Array Detector 2998 and Waters Micromass ZQ MS detector. Software used: FractionLynx and MassLynx v4.1.

For chiral SFC purification, PIC 400 instrument was used. Column: YMC Cellulose-SC or YMC Amylose-C, mobile phase: $CO_2$/MeOH or $CO_2$/IPA.

General HPLC analytical method parameters: gradient mobile phase of 0.1% formic acid in $H_2O$ and MeCN or 10 mM $NH_4HCO_3$ (aq.) pH 10 and MeCN. Column XBridge 30×150 mm, 5 μm.

Photodiode Array Detector settings: wavelength: 210-400 nm, resolution: 1.2 nm, sampling rate: 1.0 points/sec, filter response: 1

MS detector settings: MS scan: centroid, ionization mode: ES+ and ES−, mass range: 105-1500, scan time: 1.0 s, inter-scan delay: 0.1 s, capillary: 3.00 kV, cone: 30 V, extractor: 3.00 V, RF Lens: 0.2 V, source temp.: 150° C., desolvation temp.: 350° C., cone gas flow: 50 L/h, desolvation gas flow: 700 L/h, LM 1 resolution: 15.0, HM 1 resolution: 15.0, ion energy 1:1.0 and multiplier: 650 V.

Analytical LCMS/UPLC Instruments and Methods

Method 01_A Acquity UPLC coupled with SQD mass spectrometer, PDA detector, SQD mass spectrometer, Acquity UPLC BEH C18 (50 mm×2.1 mm i.d., 1.7 μm packing diameter), A: 0.1% v/v solution of Formic Acid in $H_2O$, B: 0.1% v/v solution of Formic Acid in Acetonitrile. Method length: 12 mins Method 01_B Acquity UPLC coupled with SQD mass spectrometer, PDA detector, SQD mass spectrometer, Acquity UPLC BEH C18 (50 mm×2.1 mm i.d., 1.7 μm packing diameter), A: 0.1% v/v solution of Formic Acid in $H_2O$, B: 0.1% v/v solution of Formic Acid in Acetonitrile. Method length: 4 mins Method 01_C Acquity UPLC coupled with SQD mass spectrometer, PDA detector, SQD mass spectrometer, Acquity UPLC BEH C18 (50 mm×2.1 mm i.d., 1.7 μm packing diameter), A: 0.1% v/v solution of Formic Acid in $H_2O$, B: 0.1% v/v solution of Formic Acid in Acetonitrile. Method length: 2 mins Method 02_A Acquity UPLC coupled with SQD mass spectrometer, PDA detector, SQD mass spectrometer, Acquity UPLC BEH C18 (50 mm×2.1 mm i.d., 1.7 μm packing diameter), A: 10 mM aqueous solution of $NH_4HCO_3$ (adjusted to pH 10 with ammonia), B: Acetonitrile. Method length: 12 mins Method 03_A HP 1100 with G1315A DAD coupled with Micromass ZQ mass spectrometer, Phenomenex Gemini-NX C18 (30 mm×2.0 mm I.D, 5 μm packing diameter), A: 0.1% v/v 28% ammonia in $H_2O$ solution in $H_2O$, B: 0.1% v/v 28% ammonia in $H_2O$ solution in acetonitrile. Method length: 12 mins Purification Methods Flash Chromatography Purification Methods
Purification Method A Normal phase ($SiO_2$), Interchim Puriflash Silica HC 15 μm 4 g flash column, gradient DCM-DCM/MeOH (10/1)
Purification Method B Normal phase ($SiO_2$), Interchim Puriflash Silica HC 25 μm 12 g flash column, gradient DCM-DCM/MeOH/$NH_4OH$ (90/10/0.1)

Purification Method C Normal phase (SiO$_2$), Interchim Puriflash Silica HC 25 µm 12 g flash column, gradient DCM-DCM/MeOH (9/1)

Purification Method D Normal phase (SiO$_2$), Interchim Puriflash Silica HC 25 µm 4 g flash column, gradient DCM-DCM/MeOH (9/1)

Purification Method E Normal phase (SiO$_2$), Interchim Puriflash Silica HC 25 µm 25 g flash column, gradient DCM-DCM/MeOH (9/1)

Purification Method F Normal phase (SiO$_2$), Interchim Puriflash Silica HC 15 µm 4 g flash column, gradient DCM-DCM/MeOH (9/1)

Purification Method G Normal phase (SiO$_2$), Interchim Puriflash Silica HC 15 µm 25 g flash column, gradient DCM-DCM/MeOH (10/1)

Purification Method H Normal phase (SiO$_2$), Interchim Puriflash Silica HC 15 µm 2 g flash column, gradient DCM-DCM/MeOH (10/1)

Purification Method I Normal phase (SiO$_2$), Interchim Puriflash Silica HC 15 µm 4 g flash column, gradient DCM-DCM/MeOH (95/5)

Purification Method J Normal phase (SiO$_2$), Interchim Puriflash Silica HC 25 µm 25 g flash column, gradient DCM-DCM/MeOH (10/1)

Purification Method K Normal phase (SiO$_2$), Interchim Puriflash Silica HC 25 µm 25 g flash column, gradient DCM-DCM/MeOH/NH$_4$OH (90/15/1.5)

Purification Method M Normal phase (SiO$_2$), Interchim Puriflash Silica HC 25 µm 25 g flash column, gradient DCM-DCM/MeOH (15/1)

Purification Method N Normal phase (SiO$_2$), Interchim Puriflash Silica HC 15 µm 12 g flash column, gradient DCM-DCM/MeOH (10/1)

Purification Method O Normal phase (SiO$_2$), Interchim Puriflash Silica HC 25 µm 25 g flash column, gradient EtOAc-EtOAc/MeOH (9/1)

Purification Method P Normal phase (SiO$_2$), Interchim Puriflash Silica HC 15 µm 80 g flash column, gradient DCM-DCM/MeOH (10/1)

HPLC Chromatography Purification Methods

Purification Method L Waters Mass Directed Autopurification System, column XBridge 19×100 mm 5 mL (preparative), A: 10 mM aqueous solution of NH$_4$HCO$_3$ (adjusted to pH 10 with ammonia), B: Acetonitrile Abbreviations AcCl=acetyl chloride
aq.=aqueous
BBI=double resonance broadband probe
BBO=broadband observe probe
Boc$_2$O=di-tert-butyl dicarbonate
Cbz-Cl=benzyl chloroformate
CDI=1,1'-carbonyldiimidazole
CV(s)=column volume(s)
DCE=1,2-dichloroethane
DCM=dichloromethane
PDA=photodiode array
Pd$_2$(dba)$_3$=tris(dibenzylideneacetone)dipalladium(0)
Pd(dppf)Cl$_2$=[1,1'-bis(diphenylphosphino)ferrocene]dichloropalladium(II)
DEAD=diethyl azodicarboxylate
DIPEA=N, N-diisopropylethylamine
DMA=dimethylacetamide
DMAP=4-dimethylaminopyridine
DMF=dimethylformamide
ES(I)=electro spray ionisation
EtOAc=ethyl acetate
h(s)=hour(s)
HATU=(1-[Bis(dimethylamino)methylene]-1H-1,2,3-triazolo[4,5-b]pyridinium 3-oxid hexafluorophosphate
HPLC=high performance liquid chromatography
IPA=propan-2-ol
LC=liquid chromatography
MeOH=methanol
min(s)=minute(s)
MS=mass spectrometry
N/A=not applicable
NBS=N-bromosuccinimide
nm=nanometre(s)
NMR=nuclear magnetic resonance
PyAOP=7-Azabenzotriazol-1-yloxy)tripyrrolidinophosphonium hexafluorophosphate
SEM=[2-(trimethylsilyl)ethoxy]methyl acetal
SFC=supercritical fluid chromatography
SPhos=2-Dicyclohexylphosphino-2',6'-dimethoxybiphenyl
TBAF=tetra-n-butylammonium fluoride
TBDMSiCl=tert-butyldimethylsilyl chloride
TEA=triethylamine
THF=tetrahydrofuran
TFA=trifluoroacetic acid
TFAA=trifluoroacetic anhydride
TMS=tetramethylsilane
XPhos=2-dicyclohexylphosphino-2',4',6'-triisopropylbiphenyl
XphosPdG2=2nd Generation XPhos Precatalyst Prefixes n-, s-, i-, t- and tert- have their usual meanings: normal, secondary, iso, and tertiary.

Synthesis of Intermediates

Route 1

Typical procedure for the preparation of macrocycle precursors, as exemplified by the preparation of Intermediate 1, Ethyl (S,E)-2'-oxo-5'-(2,2,5-trimethyl-4-oxo-3,8,11-trioxa-5-azatetradec-13-en-14-yl)-1',2',5,7-tetrahydrospiro[cyclopenta[b]pyridine-6,3'-pyrrolo[2,3-b]pyridine]-3-carboxylate.

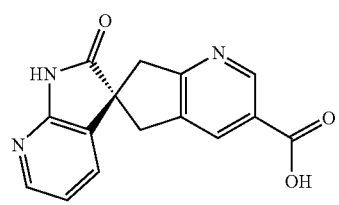

Intermediate 32

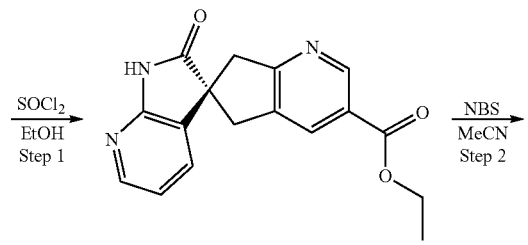

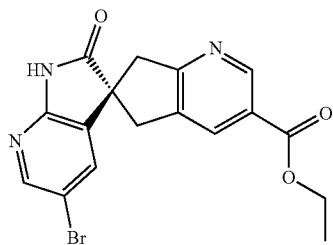

-continued

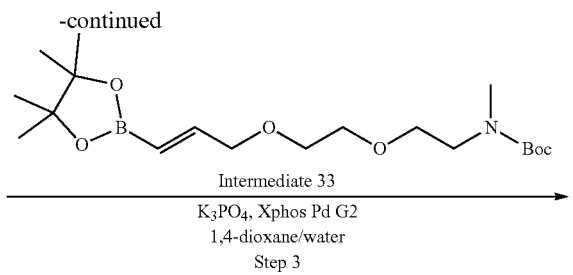

Intermediate 33

K₃PO₄, Xphos Pd G2
1,4-dioxane/water
Step 3

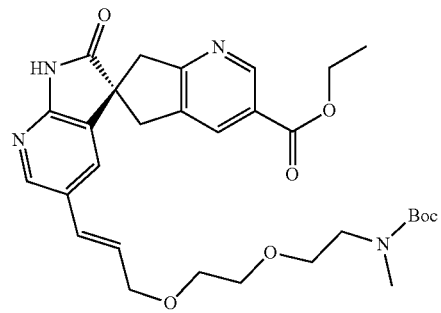

Intermediate 1

Route 1_Step 1

To a solution of (S)-2'-oxo-1',2',5,7-tetrahydrospiro[cyclopenta[b]pyridine-6,3'-pyrrolo[2,3-b]pyridine]-3-carboxylic acid (Intermediate 32) (1.02 g, 3.63 mmol) in dry EtOH (50 ml) at 0° C. was added dropwise SOCl₂ (1.06 mL, 14.5 mmol). The mixture was stirred at 75° C. for 5 h. The reaction mixture was concentrated in vacuo to give ethyl (S)-2'-oxo-1',2',5,7-tetrahydrospiro[cyclopenta[b]pyridine-6,3'-pyrrolo[2,3-b]pyridine]-3-carboxylate (1.12 g, 100%).

LC-MS (ESI+): 310.13 [M+H].

Route 1_Step 2

To a suspension of ethyl (S)-2'-oxo-1',2',5,7-tetrahydrospiro[cyclopenta[b]pyridine-6,3'-pyrrolo[2,3-b]pyridine]-3-carboxylate (1.12 g, 3.63 mmol) in the dry MeCN (20 ml) at 0° C. was added NBS(1.29 g, 7.26 mmol). The reaction mixture was stirred at room temperature overnight. The reaction mixture was then added dropwise into H₂O (300 mL). The resulting precipitate was collected by filtration, washed with H₂O (50 mL-) and dried in vacuo at 45° C. to give ethyl (S)-5'-bromo-2'-oxo-1',2',5,7-tetrahydrospiro[cyclopenta[b]pyridine-6,3'-pyrrolo[2,3-b]pyridine]-3-carboxylate (1.4 g, 100%).

LC-MS (ESI+): 388/390 [M+H].

Route 1_Step 3

To a mixture of tert-butyl (E)-methyl(2-(2-((3-(4,4,5,5-tetramethyl-1,3,2-dioxaborolan-2-yl)allyl)oxy)ethoxy)ethyl)carbamate (Intermediate 33) (0.30 g, 0.77 mmol) and ethyl (S)-5'-bromo-2'-oxo-1',2',5,7-tetrahydrospiro[cyclopenta[b]pyridine-6,3'-pyrrolo[2,3-b]pyridine]-3-carboxylate (0.2 g, 0.52 mmol) in 1,4-dioxane (2.0 ml) was added a solution of K₃PO₄ (0.22 g, 1.04 mmol) in H₂O (0.5 mL). The reaction mixture was purged with argon for 5 mins after which XphosPdG2 (0.041 g, 0.052 mmol) was added and purged again for additional 5 mins. The reaction mixture was sealed and heated at 100° C. for 4.5 h. The reaction mixture was then partitioned between DCM (20 ml) and saturated aqueous NaHCO₃ (10 mL). The organic layer was washed with further saturated aqueous NaHCO₃ (2×10 mL), dried (Na₂SO₄), and concentrated in vacuo to give the crude product. This was then purified by flash chromatography (SiO₂, DCM-EtOAc) to give ethyl (S,E)-2'-oxo-5'-(2,2,5-trimethyl-4-oxo-3,8,11-trioxa-5-azatetradec-13-en-14-yl)-1',2',5,7-tetrahydrospiro[cyclopenta[b]pyridine-6,3'-pyrrolo[2,3-b]pyridine]-3-carboxylate (Intermediate 1) (114 mg, 39%).

The characterisation for Intermediate 1 are in Table 2.

Route 2

Preparation of Intermediate 3, Methyl (S)-2-amino-3-(7-methyl-1H-indazol-5-yl)propanoate dihydrochloride

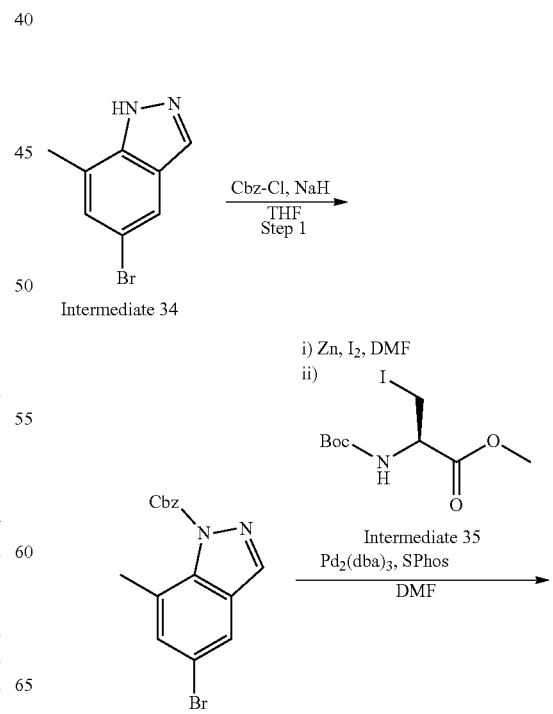

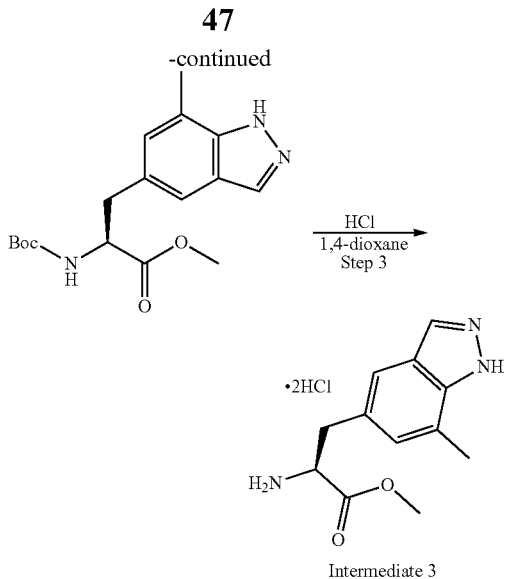

Intermediate 3

Route 2_Step 1

To a stirred solution of 5-bromo-7-methyl-1H-indazole (Intermediate 34) (10 g, 47.37 mmol) in THF (150 mL) at 0° C., were added sodium hydride (60% in mineral oil) (2.89 g, 71.05 mmol) and 50% Cbz-Cl in toluene (19.34 mL, 56.84 mmol). The reaction mixture was stirred at 0° C. for 2 h. The reaction mixture was then quenched with H₂O and extracted with EtOAc (2×200 mL). The combined organic layers were washed with saturated aqueous NaHCO₃ (100 mL) and brine (100 mL), dried (Na₂SO₄) and concentrated in vacuo to give crude product. The residue was purified by flash chromatography (SiO₂, petroleum ether-EtOAc) to give benzyl 5-bromo-7-methyl-1H-indazole-1-carboxylate (10 g, 61%).

LC-MS (ESI+): 345.0 [M+H].

Route 2_Step 2

The reaction was implemented on 10×1 g batches of benzyl 5-bromo-7-methyl-1H-indazole-1-carboxylate and combined for purification.

To a stirred suspension of activated zinc powder (944 mg, 14.45 mmol) in dry DMF (3 mL), was added iodine (75 mg, 0.28 mmol). The reaction mixture was heated at 50° C., followed by the addition of methyl (R)-2-((tert-butoxycarbonyl)amino)-3-iodopropanoate (Intermediate 35) (1.9 g, 5.79 mmol) with continued heating for 1 h to obtain the organo zinc reagent. Then to a degassed solution of benzyl 5-bromo-7-methyl-1H-indazole-1-carboxylate (1 g, 2.89 mmol) and SPhos (35.5 mg, 0.08 mmol) in DMF (2 mL), the organo zinc reagent and Pd₂(dba)₃ were added. The resultant reaction mixture was heated at 70° C. for 16 h. The reaction mixture was quenched with H₂O and extracted with EtOAc (2×20 mL). The combined organic layers were washed with brine (100 mL), dried (Na₂SO₄) and concentrated in vacuo to give the crude product. The residue was purified by flash chromatography (SiO₂, petroleum ether-EtOAc) to give methyl (S)-2-((tert-butoxycarbonyl)amino)-3-(7-methyl-1H-indazol-5-yl)propanoate (2.2 g, 21%).

LC-MS (ESI+): 334.2 [M+H].

Route 2_Step 3

To a solution of methyl (S)-2-((tert-butoxycarbonyl)amino)-3-(7-methyl-1H-indazol-5-yl)propanoate (150 mg, 0.45 mmol) in dry 1,4-dioxane (10 mL) was added 4M HCl in 1,4-dioxane (4.5 mL, 18.00 mmol) and the reaction mixture was stirred at room temperature overnight. The reaction mixture was concentrated in vacuo to give methyl (S)-2-amino-3-(7-methyl-1H-indazol-5-yl)propanoate dihydrochloride (Intermediate 3) (137 mg, 99%).

The characterisation for Intermediate 3 are in Table 2.

Route 3

Typical Procedure for the Preparation of Vinyl Boronates, as Exemplified by the Preparation of Intermediate 33, Tert-butyl (E)-methyl(2-(2-((3-(4,4,5,5-tetramethyl-1,3,2-dioxaborolan-2-yl)allyl)oxy)ethoxy)ethyl)carbamate

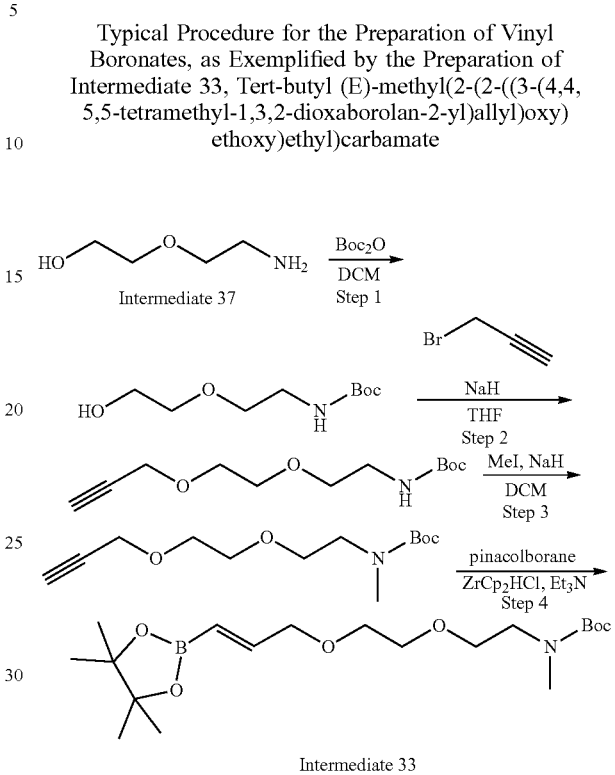

Intermediate 33

Route 3_Step 1

To a solution of 2-(2-aminoethoxy)ethan-1-ol (Intermediate 37) (2 g, 19.0 mmol) in dry DCM (50 mL) at 0° C. was added then Boc₂O (4.98 mmol, 22.8 mmol) and the reaction mixture was stirred at room temperature overnight. The reaction mixture was then concentrated in vacuo and the resulting residue was purified by flash chromatography (SiO₂, DCM-MeOH) to give tert-butyl (2-(2-hydroxyethoxy)ethyl)carbamate (3.8 g, 97%).

LC-MS (ESI+): 106.36 [M+H−Boc], 228.52 [M+Na].

Route 3_Step 2

To a solution of tert-butyl (2-(2-hydroxyethoxy)ethyl)carbamate (2.62 g, 12.75 mmol) in THF (70 mL) at 0° C. was added portion wise sodium hydride (60% in mineral oil) (561 mg, 14.02 mmol). The reaction mixture was stirred at 0° C. for 30 min, before 3-bromoprop-1-yne (80% in toluene, 1.56 mL, 14.02 mmol) was added dropwise. Stirring was continued at 0° C., warming slowly to room temperature overnight. Saturated aqueous NH₄Cl (100 mL) was added and the reaction mixture was extracted with diethyl ether (150 mL), dried (Na₂SO₄) and concentrated in vacuo. The resulting residue was purified by flash chromatography (SiO₂, cyclohexane-EtOAc) to give tert-butyl (2-(2-(prop-2-yn-1-yloxy)ethoxy)ethyl)carbamate (2.13 g, 72%).

Route 3_Step 3

Into a cooled solution of tert-butyl (2-(2-(prop-2-yn-1-yloxy)ethoxy)ethyl)carbamate (0.5 g, 2.05 mmol) in dry DMF (5 mL) at 0° C. was added portion wise sodium hydride (60% in mineral oil) (165 mg, 4.11 mmol). The mixture was stirred at 0° C. for 5 mins after which methyliodide (154 µL, 2.47 mmol) was added dropwise. The reaction mixture was stirred at 0° C. for 10 mins and after that at room temperature for 2 h. The reaction mixture was diluted with EtOAc (5 mL) and H₂O (20 mL). The organic layer was washed with saturated aqueous NaHCO₃ (3×10 mL), dried (Na₂SO₄) and concentrated in vacuo. The resulting residue was purified by flash chromatography (SiO₂, cyclohexane-EtOAc) to give tert-butyl methyl(2-(2-(prop-2-yn-1-yloxy)ethoxy)ethyl)carbamate (438 mg, 83%).

LC-MS (ESI+): 202.11 [M+H-ᵗBu], 158.03 [M+H-Boc].

Route 3_Step 4

Into neat tert-butyl methyl(2-(2-(prop-2-yn-1-yloxy)ethoxy)ethyl)carbamate (0.44 g, 1.70 mmol) were added pinacolborane (269 µL, 1.87 mmol), Et₃N (23.7 µL, 0.170 mmol), and ZrCp₂HCl (43.9 mg, 0.170 mmol). The suspension was stirred at 70° C. overnight. The reaction mixture was quenched with saturated aqueous NH₄Cl (5 mL) and EtOAc (20 mL). The aqueous layer was further extracted with EtOAc (2×5 mL). The combined organic layers were washed with saturated aqueous NaHCO₃ (2×10 mL), dried (Na₂SO₄) and concentrated in vacuo to give tert-butyl (E)-methyl(2-(2-((3-(4,4,5,5-tetramethyl-1,3,2-dioxaborolan-2-yl)allyl)oxy)ethoxy)ethyl)carbamate (Intermediate 33) (538 mg) which was used without further purification.

The characterisation for Intermediate 33 are in Table 2.

Route 4

Alternative Procedure for the Preparation of Vinyl Boronates, as Exemplified by the Preparation of Intermediate 39, Tert-butyl (E)-methyl(9-(4,4,5,5-tetramethyl-1,3,2-dioxaborolan-2-yl)non-8-en-1-yl)carbamate

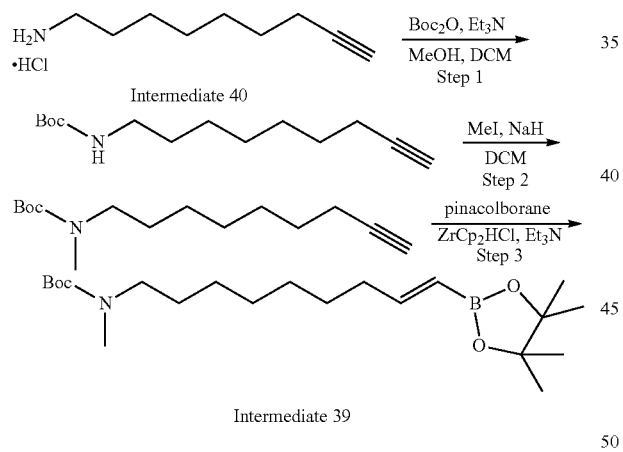

Route 4_Step 1

To a solution of non-8-yn-1-amine hydrochloride (Intermediate 40) (600 mg, 3.42 mmol) in DCM (4 mL) and MeOH (0.5 mL) were added Et₃N (522 µL, 3.75 mmol) and Boc₂O (819 mg, 3.75 mmol). The reaction mixture was stirred at room temperature for 3 h. The reaction mixture was concentrated in vacuo and the resulting residue was partitioned between DCM (10 mL) and saturated aqueous NaHCO₃ (50 mL). The aqueous layer was further extracted with DCM (3×10 mL). The combined organic layers were dried (Na₂SO₄) and concentrated in vacuo to give tert-butyl non-8-yn-1-ylcarbamate (826 mg, 63%).

LC-MS (ESI+): 140.53 [M+H–Boc].

Route 4_Step 2

To an ice cooled solution of tert-butyl non-8-yn-1-ylcarbamate (817 mg, 3.42 mmol) in dry DMF (12 mL) was added portion wise sodium hydride (60% in mineral oil) (205 mg, 5.12 mmol). The reaction mixture was stirred at 0° C. for 5 mins after which methyliodide (233 µL, 3.76 mmol) was added. Stirring was continued at 0° C. for 10 mins and then at room temperature overnight. The reaction mixture was quenched with saturated aqueous NaHCO₃/H₂O (1:1) (25 mL) and DCM (20 mL). The organic layer was washed with saturated aqueous NaHCO₃ (3×10 mL) and 5% LiOH (3×10 mL), dried (Na₂SO₄) and concentrated in vacuo. The resulting residue was purified by flash chromatography (SiO₂, cyclohexane-EtOAc) to give tert-butyl methyl(non-8-yn-1-yl)carbamate (655 mg, 76%).

LC-MS (ESI+): 154.59 [M+H–Boc].

Route 4_Step 3

Into neat tert-butyl methyl(non-8-yn-1-yl)carbamate (150 mg, 0.592 mmol) were added pinacolborane (97 µL, 0.651 mmol), Et₃N (8.2 µL, 0.059 mmol) and ZrCp₂HCl (15.9 mg, 0.059 mmol). The vial was sealed and the suspension was stirred at 70° C. for 2 h. The reaction mixture was quenched with saturated aqueous NH₄Cl (25 mL) and extracted with EtOAc (2×15 mL). The combined organic layers were washed with saturated aqueous NaHCO₃ (3×10 mL), dried (Na₂SO₄) and concentrated in vacuo to give tert-butyl (E)-methyl(9-(4,4,5,5-tetramethyl-1,3,2-dioxaborolan-2-yl)non-8-en-1-yl)carbamate (Intermediate 39) (213 mg, 94%) which was used without further purification.

The characterisation for Intermediate 39 are in Table 2.

Route 5

Alternative Procedure for the Preparation of Macrocycle Precursors, as Exemplified by the Preparation of Intermediate 6, Methyl (S,E)-5'-(3-(4-((tert-butoxycarbonyl)(methyl)amino)butoxy)prop-1-en-1-yl)-2'-oxo-1',2',5,7-tetrahydrospiro[cyclopenta[b]pyridine-6,3'-pyrrolo[2,3-b]pyridine]-3-carboxylate

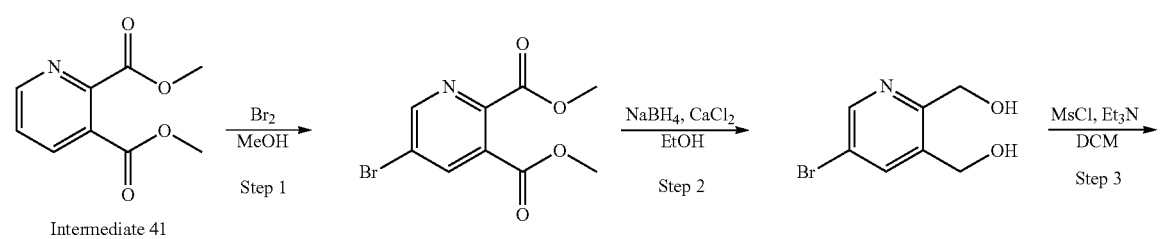

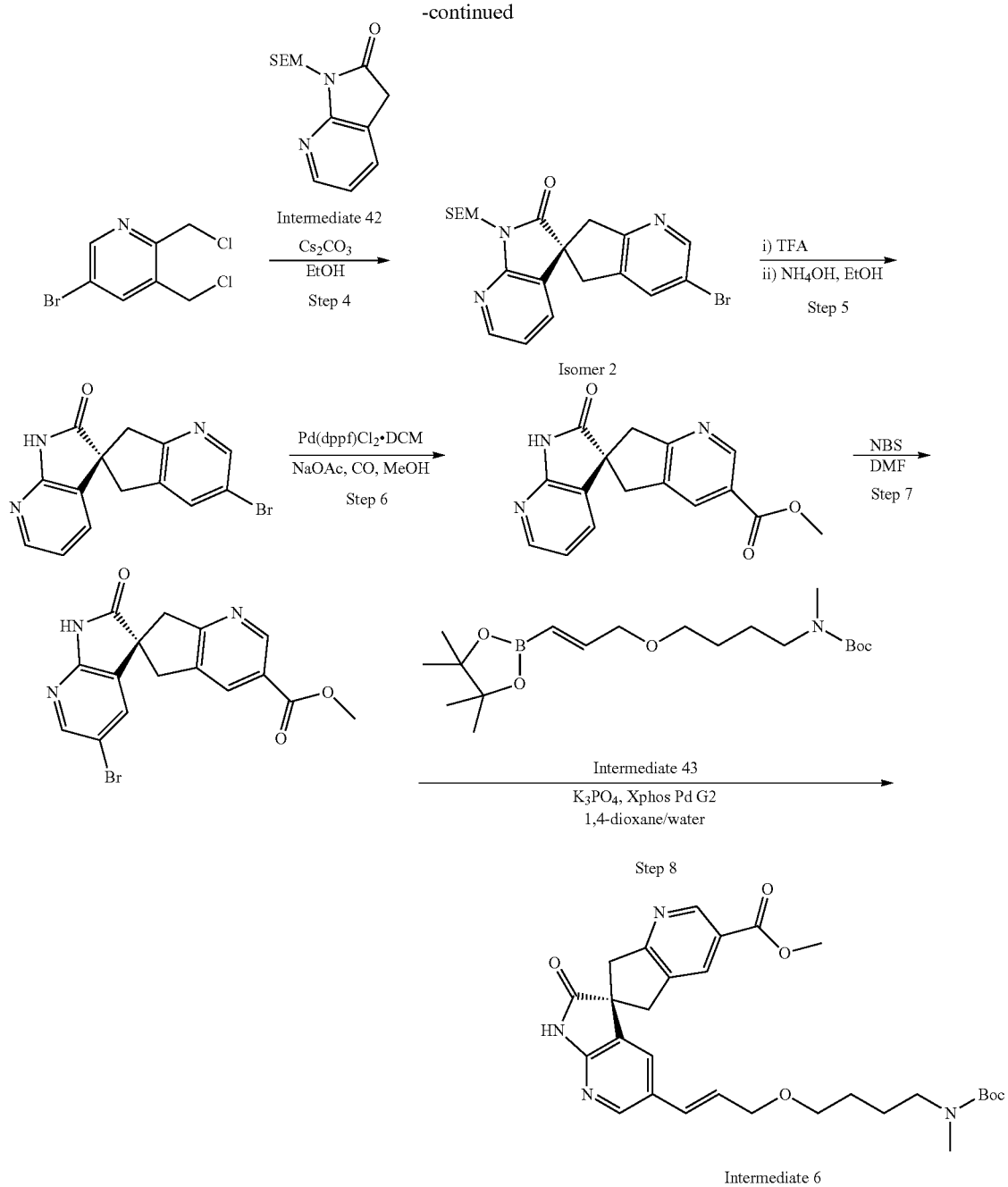

Intermediate 6

Route 5_Step 1

To stirred solution of dimethyl pyridine-2,3-dicarboxylate (Intermediate 41) (100 g, 0.510 mol) in MeOH (500 mL) at 0° C. was added dropwise bromine (52.48 mL, 1.22 mol). The reaction mixture was then stirred at 55° C. overnight. The reaction mixture was quenched with ice cold $H_2O$ and extracted with EtOAc (2×1 L). The combined organic layers were washed with brine (500 mL) and concentrated in vacuo. The resulting residue was purified by flash chromatography ($SiO_2$, petroleum ether-EtOAc) to give dimethyl 5-bromopyridine-2,3-dicarboxylate (135 g, 96%).

LC-MS (ESI+): 274.0 [M+H].

Route 5_Step 2

To a stirred solution dimethyl 5-bromopyridine-2,3-dicarboxylate (135 g, 0.492 mol) in EtOH (2.5 L) at 0° C. was added portion wise sodium borohydride (112 g, 2.96 mol), followed by the dropwise addition of a solution of $CaCl_2$ (164 g, 1.48 mol) in EtOH (1.5 L) over a period of 40 mins. The temperature was maintained at 0° C. throughout the addition (exothermic reaction—efficient cooling was needed). The reaction mixture was then stirred at room temperature for 20 h and then re-cooled to 0° C. The reaction mixture was quenched with 2M HCl solution over a period of 30 mins to obtain a clear solution and was then allowed to warm to room temperature and stirred for 1 h. The reaction mixture was washed with EtOAc (1 L) and the organic layer was washed with further 1M HCL (0.2 L). The pH of the combined aqueous layers was adjusted to pH 7 using saturated aqueous $NaHCO_3$ and then extracted with EtOAc (2×1 L). The combined organic layers were washed with brine (500 mL) and concentrated in vacuo. The crude residue was triturated with MeOH to obtain a solid. The solid was collected by filtration to give (5-bromopyridine-2,3-diyl)dimethanol (48 g, 45%).

LC-MS (ESI+): 218.0 [M+H].

Route 5_Step 3

To a solution of (5-bromopyridine-2,3-diyl)dimethanol (35 g, 0.160 mol) and $Et_3N$ (67 mL, 0.401 mol) in dry DCM (850 mL) at 0° C. was added methanesulfonyl chloride (31 mL, 0.481 mol). The reaction mixture was stirred at room temperature for 16 h and was then quenched with saturated aqueous $NH_4Cl$ (500 mL) and extracted with DCM (500 mL). The organic layer was washed with brine (150 mL), dried ($Na_2SO_4$) and concentrated in vacuo to give 5-bromo-2,3-bis(chloromethyl)pyridine (31.5 g, 77%).

LC-MS (ESI+): 253.9 [M+H].

Route 5_Step 4

To a suspension of 1-((2-(trimethylsilyl)ethoxy)methyl)-1,3-dihydro-2H-pyrrolo[2,3-b]pyridin-2-one (Intermediate 42, CAS 879132-48-6) (33 g, 0.125 mmol) and 5-bromo-2,3-bis(chloromethyl)pyridine (44.6 g, 0.175 mol) in EtOH (900 mL) was added $Cs_2CO_3$ (113.75 g, 0.35 mol). The reaction mixture was stirred at room temperature for 16 h and was then quenched with ice cold $H_2O$ (1 L) and extracted with EtOAc (2×1 L). The combined organic layers were washed with sat. NaCl (aq) (500 mL), dried ($Na_2SO_4$) and concentrated in vacuo. The resulting residue was purified by flash chromatography ($SiO_2$, petroleum ether-EtOAc) to give 3-bromo-1'-((2-(trimethylsilyl)ethoxy)methyl)-5,7-dihydrospiro[cyclopenta[b]pyridine-6,3'-pyrrolo[2,3-b]pyridin]-2'(1'H)-one.

Purification by Chiral SFC:
  Instrument: PICLab PREP 400
  Solvents: Primary mobile phase=$CO_2$ Modifier: 35% MeOH
  Column: YMC Cellulose-SC 5 µm, 250×30 mm, at 35° C.
  UV monitoring: 210 nm
  Flow: 120 g/min..
  (S)-3-bromo-1'-((2-(trimethylsilyl)ethoxy)methyl)-5,7-dihydrospiro[cyclopenta[b]pyridine-6,3'-pyrrolo[2,3-b]pyridin]-2'(1'H)-one isomer 2 (4.0 g). and
  (R)-3-bromo-1'-((2-(trimethylsilyl)ethoxy)methyl)-5,7-dihydrospiro[cyclopenta[b]pyridine-6,3'-pyrrolo[2,3-b]pyridin]-2'(1'H)-one (3.5 g) isomer 1

LC-MS (ESI+): 446.2 [M+H]$^+$.

Chiral SFC analytical Isomer 1 2.34 min; Isomer 2 3.25 min (YMC Cellulose-SC, 250×4.6 mm 5µ at 35° C., 3 ml/min, 40% Methanol 35° C.)

Route 5_Step 5

A suspension of (S)-3-bromo-1'-((2-(trimethylsilyl)ethoxy)methyl)-5,7-dihydrospiro[cyclopenta[b]pyridine-6,3'-pyrrolo[2,3-b]pyridin]-2'(1'H)-one (19 g, 42.6 mmol) in TFA (100 mL) was heated at 60° C. for 3 h and then concentrated in vacuo. The resulting residue was dissolved in EtOH (100 mL) and to this was then added $NH_4OH$ (100 ml). The reaction mixture was stirred at room temperature for 2 h. The resulting precipitate was collected by filtration to give (S)-3-bromo-5,7-dihydrospiro[cyclopenta[b]pyridine-6,3'-pyrrolo[2,3-b]pyridin]-2'(1'H)-one (10.2 g, 76%).

LC-MS (ESI+): 446.2 [M+H].

Route 5_Step 6

A stirred solution of (S)-3-bromo-5,7-dihydrospiro[cyclopenta[b]pyridine-6,3'-pyrrolo[2,3-b]pyridin]-2'(1'H)-one (10 g, 31.62 mmol) and sodium acetate (5.24 g, 63.3 mmol) in MeOH (150 mL) in a mini clave vessel was degassed with argon, followed by the addition of Pd(dppf)$Cl_2$·DCM (3.87 g, 4.74 mmol). The reaction mixture was heated at 100° C. for 16 h under 5 Kg/cm² pressure of CO gas. The reaction mixture was partitioned between EtOAc (600 mL) and $H_2O$ (200 mL). The organic layer was washed with brine (200 mL), dried ($Na_2SO_4$) and concentrated in vacuo. The resulting residue was purified by flash chromatography ($SiO_2$, petroleum ether-EtOAc) to give methyl (S)-2'-oxo-1',2',5,7-tetrahydrospiro[cyclopenta[b]pyridine-6,3'-pyrrolo[2,3-b]pyridine]-3-carboxylate (5 g, 54%).

LC-MS (ESI+): 296.1 [M+H].

Route 5_Step 7

To a stirred solution of methyl (S)-2'-oxo-1',2',5,7-tetrahydrospiro[cyclopenta[b]pyridine-6,3'-pyrrolo[2,3-b]pyridine]-3-carboxylate (5.0 g, 16.9 mmol) in DMF (50 mL) at 0° C. was added NBS (9.04 g, 50.8 mmol). The reaction mixture was stirred at room temperature for 3 h and was then quenched by ice cold $H_2O$. The resulting precipitate was collected by filtration, washed with cold $H_2O$, dried over high vacuum for 3 h to give methyl (S)-5'-bromo-2'-oxo-1',2',5,7-tetrahydrospiro[cyclopenta[b]pyridine-6,3'-pyrrolo[2,3-b]pyridine]-3-carboxylate (4.7 g, 74%).

LC-MS (ESI+): 374.0 [M+H].

Route 5_Step 8

To a suspension of methyl (S)-5'-bromo-2'-oxo-1',2',5,7-tetrahydrospiro[cyclopenta[b]pyridine-6,3'-pyrrolo[2,3-b]pyridine]-3-carboxylate (160.0 mg, 0.428 mmol) and tert-butyl (E)-methyl(4-((3-(4,4,5,5-tetramethyl-1,3,2-dioxaborolan-2-yl)allyl)oxy)butyl)carbamate (Intermediate 43) (332 mg, 0.759 mmol) in degassed 1,4-dioxane (1.6 mL) was added a solution of $K_3PO_4$ (185 mg, 0.855 mmol) in degassed $H_2O$ (400 µL). XphosPdG2 (34 mg, 0.043 mmol) was added and the reaction mixture degassed for additional 5 mins, sealed and heated at 100° C. for 1.5 h. The reaction mixture was diluted with EtOAc (50 mL) and washed with $H_2O$ (3×15 mL), saturated aqueous $NaHCO_3$ (2×10 mL), dried ($Na_2SO_4$) and concentrated in vacuo. The resulting residue was purified by flash chromatography ($SiO_2$, DCM-MeOH) to give methyl (S,E)-5'-(3-(4-((tert-butoxycarbonyl)(methyl)amino)butoxy)prop-1-en-1-yl)-2'-oxo-1',2',5,7-tetrahydrospiro[cyclopenta[b]pyridine-6,3'-pyrrolo[2,3-b]pyridine]-3-carboxylate (Intermediate 6) (104 mg, 45%).

The characterisation for Intermediate 6 are in Table 2.

Route 6

Alternative Procedure for the Preparation of Vinyl Boronates, as Exemplified by the Preparation of Intermediate 43, Tert-butyl (E)-methyl(4-((3-(4,4,5,5-tetramethyl-1,3,2-dioxaborolan-2-yl)allyl)oxy)butyl)carbamate

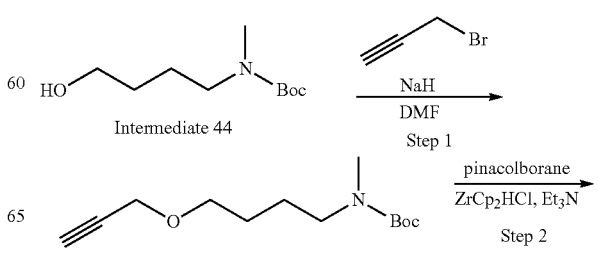

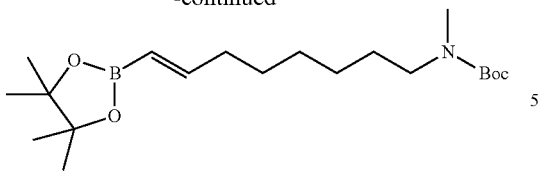

Intermediate 43

Route 6_Step 1

To an ice cooled solution of tert-butyl (4-hydroxybutyl)(methyl)carbamate (Intermediate 44) (500 mg, 2.46 mmol) in dry DMF (6.2 mL) was added portion wise sodium hydride (60% in mineral oil) (118 mg, 2.95 mmol). The reaction mixture was stirred at 0° C. for 30 mins after which 3-bromoprop-1-yne (318 µL, 2.95 mmol) was added dropwise. Stirring was continued, allowing the temperature to slowly raise from 0° C. to room temperature and stirred for 13 h. Further sodium hydride (60% in mineral oil) (118 mg, 2.95 mmol) and 3-bromoprop-1-yne (318 µL, 2.95 mmol) were added and the reaction mixture was stirred at room temperature for 3 h. Further sodium hydride (60% in mineral oil) (118.0 mg, 2.952 mmol) and 3-bromoprop-1-yne (318 µL, 2.95 mmol) were added and the reaction mixture was stirred at room temperature for 18 h. The reaction mixture was quenched with saturated aqueous NH$_4$Cl (50 mL) and extracted with diethyl ether (3×25 mL). The combined organic layers were washed with saturated aqueous NaHCO$_3$ (2×25 mL) and LiCl (5% aq, 25 mL), dried (Na$_2$SO$_4$) and concentrated in vacuo. The resulting residue was purified by flash chromatography (SiO$_2$.DCM-EtOAc) to give tert-butyl methyl(4-(prop-2-yn-1-yloxy)butyl)carbamate (487 mg, 82%).

LC-MS (ESI+): 142.50 [M+H−Boc].

Route 6_Step 2

Into neat tert-butyl methyl(4-(prop-2-yn-1-yloxy)butyl)carbamate (183 mg, 0.758 mmol) were added pinacolborane (169 µL, 1.14 mmol), Et$_3$N (11 µL, 0.076 mmol) and ZrCp$_2$HCl (20 mg, 0.076 mmol). The reaction vial was sealed and the suspension was heated at 70° C. for 2 h. To this was then added further pinacolborane (75 µL, 0.506 mmol) and heating continued for 1 h. The reaction mixture was quenched with saturated aqueous NH$_4$Cl (30 mL) and extracted with EtOAc (2×15 mL). The combined organic layers were washed with saturated aqueous NaHCO$_3$ (2×10 mL), dried (Na$_2$SO$_4$) and concentrated in vacuo to give tert-butyl (E)-methyl(4-((3-(4,4,5,5-tetramethyl-1,3,2-dioxaborolan-2-yl)allyl)oxy)butyl)carbamate (Intermediate 43) (332 mg, 119%) which was used without further purification.

The characterisation for Intermediate 43 are in Table 2.

Route 7

Preparation of Intermediate 12, Methyl (R)-2-amino-3-(1,7-dimethyl-1H-indazol-5-yl)propanoate dihydrochloride

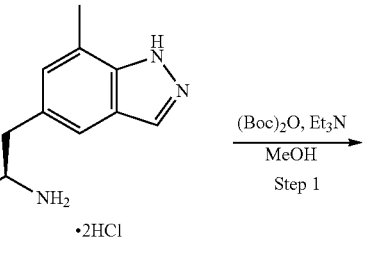

Intermediate 2

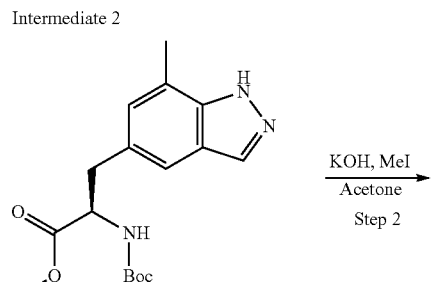

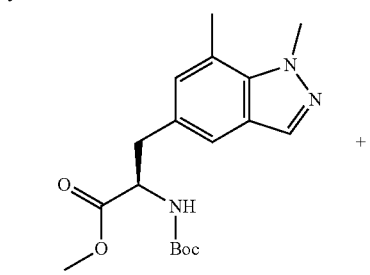

+

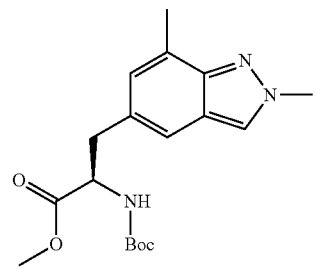

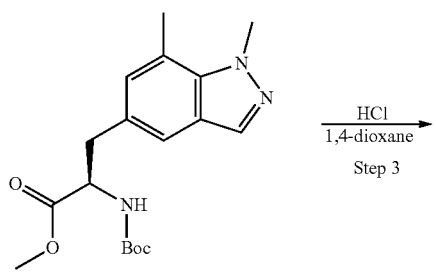

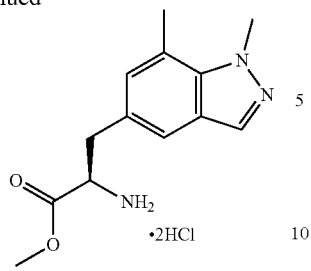

Intermediate 12

Route 7_Step 1

To a solution of methyl (R)-2-amino-3-(7-methyl-1H-indazol-5-yl)propanoate dihydrochloride (Intermediate 2) (500 mg, 1.63 mmol) in MeOH (2 mL) were added Et₃N (0.34 mL, 2.45 mmol) and Boc₂O (0.56 mL, 2.45 mmol). The solution was stirred at room temperature for 1 day. To this was then added further Et₃N (0.34 mL, 2.45 mmol) and stirring was continued at room temperature for 4 h. The reaction mixture was concentrated in vacuo and the resulting residue was dissolved with DCM (30 mL), washed with H₂O (3×10 mL) and brine (10 mL), dried (Na₂SO₄) and concentrated in vacuo to give methyl (R)-2-((tert-butoxycarbonyl)amino)-3-(7-methyl-1H-indazol-5-yl)propanoate (545 mg, 100%).

LC-MS (ESI+): 334.71 [M+H].

Route 7_Step 2

To a solution of methyl (R)-2-((tert-butoxycarbonyl)amino)-3-(7-methyl-1H-indazol-5-yl)propanoate (227 mg, 0.680 mmol) in dry acetone (5 mL) at 0° C. was added KOH (46 mg, 0.816 mmol). The reaction mixture was stirred at 0° C. for 10 mins and to this was then added dropwise a solution of methyliodide (47 μL, 0.748 mmol) in dry acetone (340.0 μL). The reaction mixture was stirred at room temperature for 4 h and was then concentrated in vacuo. The resulting residue was dissolved in EtOAc (30 mL), washed with H₂O (3×10 mL) and brine (15 mL), dried (Na₂SO₄) and concentrated in vacuo. This was then purified by flash chromatography (SiO₂, cyclohexane-EtOAc) to give methyl (R)-2-((tert-butoxycarbonyl)amino)-3-(1,7-dimethyl-1H-indazol-5-yl)propanoate (107 mg, 46%) and by-product, methyl (R)-2-((tert-butoxycarbonyl)amino)-3-(2,7-dimethyl-2H-indazol-5-yl)propanoate (50 mg, 21%).

LC-MS (ESI+): 348.23 [M+H].

Route 7_Step 3

To the solution of methyl (R)-2-((tert-butoxycarbonyl)amino)-3-(1,7-dimethyl-1H-indazol-5-yl)propanoate (106 mg, 0.304 mmol) in 1,4-dioxane (7.8 mL) was added 4M HCl in 1,4-dioxane (3.0 mL, 12.1 mmol). The reaction mixture was stirred at room temperature for 16 h. To this was then added further 4M HCl in 1,4-dioxane (1.0 mL, 4.01 mmol) and stirring was continued at room temperature for 25 h. The reaction mixture was concentrated in vacuo to give methyl (R)-2-amino-3-(1,7-dimethyl-1H-indazol-5-yl)propanoate dihydrochloride (Intermediate 12) (95 mg, 97%).

The characterisation for Intermediate 12 is in Table 2.

Route 8

Preparation of Intermediate 49, (S)-3-chloro-1'-((2-(trimethylsilyl)ethoxy)methyl)-5,7-dihydrospiro[cyclopenta[c]pyridine-6,3'-pyrrolo[2,3-b]pyridin]-2'(1'H)-one and Intermediate 50, (R)-3-chloro-1'-((2-(trimethylsilyl)ethoxy)methyl)-5,7-dihydrospiro[cyclopenta[c]pyridine-6,3'-pyrrolo[2,3-b]pyridin]-2'(1'H)-one

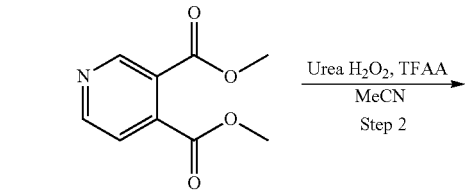

Intermediate 51

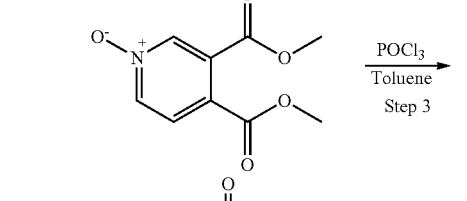

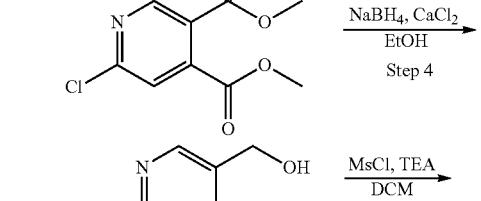

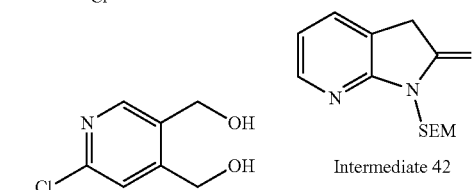

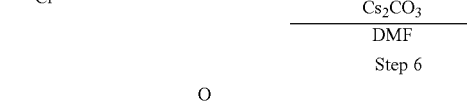

Intermediate 42

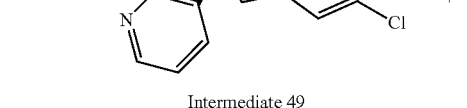

Intermediate 49

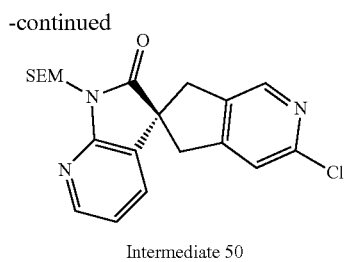

Intermediate 50

Route 8_Step 1

To stirred solution of pyridine-3,4-dicarboxylic acid (Intermediate 51) (500 g, 2.99 mol) in MeOH (4 L) at 0° C. was added dropwise SOCl₂ (1.1 L, 15.0 mol). The reaction mixture was stirred at 70° C. for 16 h. The reaction mixture was then concentrated in vacuo and the resulting residue was quenched with saturated aqueous NaHCO₃ (2 L) and extracted with EtOAc (2×2 L). The combined organic layers were washed with brine (1 L), dried (Na₂SO₄) and concentrated in vacuo to give dimethyl pyridine-3,4-dicarboxylate (380 g, 65%).

LC-MS (ESI+): 196.1 [M+H].

Route 8_Step 2

To a stirred solution of dimethyl pyridine-3,4-dicarboxylate (380 g, 1.94 mol) and urea hydrogen peroxide (366 g, 3.89 mol) in MeCN (3.5 L) at 0° C. was added dropwise TFAA (548 mL, 3.89 mol). The reaction mixture was stirred at 0° C. for 2 h and was then quenched with saturated aqueous NaHCO₃ (1 L) (cautiously) and extracted with DCM (2×2 L). The combined organic layers were washed with brine (1 L), dried (Na₂SO₄) and concentrated in vacuo to give 3,4-bis(methoxycarbonyl)pyridine 1-oxide (390 g, 95%).

LC-MS (ESI+): 212.0 [M+H].

Route 8_Step 3

To a suspension of 3,4-bis(methoxycarbonyl)pyridine 1-oxide (390 g, 1.84 mol) in toluene (3.5 L) at 0° C. was added POCl₃ (1.7 L, 18.4 mol) and the reaction mixture was then heated at 110° C. for 12 h. The reaction mixture was concentrated in vacuo and the resulting residue was poured into ice cold H₂O (1 L), neutralised by the addition of saturated aqueous NaHCO₃ (~3.0 L) and extracted with EtOAc (2×2 L). The combined organic layers were washed with brine (2 L), dried (Na₂SO₄) and concentrated in vacuo. The crude was purified by flash chromatography (SiO₂, hexane-EtOAc) to give dimethyl 6-chloropyridine-3,4-dicarboxylate (113 g, 27%).

LC-MS (ESI+): 230.0 [M+H].

Route 8_Step 4

To a stirred solution of dimethyl 6-chloropyridine-3,4-dicarboxylate (113 g, 0.49 mol) in EtOH (2.5 L) at 0° C. was added portion wise sodium borohydride (112 g, 2.95 mol), followed by the slow addition of a solution of CaCl₂ (164 g, 1.47 mmol) in EtOH (2.0 L) at 0° C. (over a period of 1.5 h, exothermic reaction-efficient cooling was needed). The reaction mixture was stirred at room temperature for 20 h and was then quenched by the addition of 4M HCl solution, over a period of 30 mins at 0° C., to obtain a clear solution. The reaction mixture was then stirred at room temperature for 1 h. The reaction mixture was washed with EtOAc (3 L) and the organic layer was washed with further 1M HCL (2.0 L). The pH of the combined aqueous layers was adjusted to pH 7 using saturated aqueous NaHCO₃ and then extracted with EtOAc (2×5 L). The combined organic layers were washed with brine (3.0 L), dried (Na₂SO₄) and concentrated in vacuo to give (6-chloropyridine-3,4-diyl)dimethanol (90 g, crude).

LC-MS (ESI+): 174.0 [M+H].

Route 8_Step 5

To a solution of (6-chloropyridine-3,4-diyl)dimethanol (90 g, 0.518 mol) and Et₃N (216 mL, 1.56 mol) in dry DCM (1.8 L) at 0° C. was added slowly methanesulfonyl chloride (80 mL, 1.04 mol). The reaction mixture was stirred at room temperature for 2 h and was then quenched with saturated aqueous NaHCO₃ (1 L) and extracted with DCM (1.0 L). The organic layer was washed with brine (1.5 L), dried (Na₂SO₄) and concentrated in vacuo to give 2-chloro-4,5-bis(chloromethyl)pyridine (105 g, crude).

LC-MS (ESI+): 209.9 [M+H].

Route 8_Step 6

To a suspension of 1-((2-(trimethylsilyl)ethoxy)methyl)-1,3-dihydro-2H-pyrrolo[2,3-b]pyridin-2-one (Intermediate 42) (132 g, 0.498 mol) and 2-chloro-4,5-bis(chloromethyl)pyridine (105 g, 0.498 mol) in DMF (1.5 L) at room temperature was added CS₂CO₃ (485 g, 1.49 mol). The reaction mixture was stirred for 16 h and was then quenched with ice cold H₂O (2.0 L) and extracted with EtOAC (2×2 L). The combined organic layers were washed with brine (2×2 L), dried (Na₂SO₄) and concentrated in vacuo. This was then purified by flash chromatography (SiO₂, petroleum ether-EtOAc) to give 3-chloro-1'-((2-(trimethylsilyl)ethoxy)methyl)-5,7-dihydrospiro[cyclopenta[c]pyridine-6,3'-pyrrolo[2,3-b]pyridin]-2'(1'H)-one (60 g).

Purified by Chiral SFC

Instrument: PICLab PREP 150

Solvents: Primary mobile phase=CO₂ Modifier: 25% MeOH

Column: YMC Cellulose-SC 5 μm, 250×30 mm, at 35° C. UV monitoring: 210 nm

Flow: 100 g/min..

To give (S)-3-chloro-1'-((2-(trimethylsilyl)ethoxy)methyl)-5,7-dihydrospiro[cyclopenta[c]pyridine-6,3'-pyrrolo[2,3-b]pyridin]-2'(1'H)-one isomer 1 (Intermediate 49) (20 g). LC-MS (ESI+): 402.1 [M+H]⁺ SFC 3.14 min. and (R)-3-chloro-1'-((2-(trimethylsilyl)ethoxy)methyl)-5,7-dihydrospiro[cyclopenta[c]pyridine-6,3'-pyrrolo[2,3-b]pyridin]-2'(1'H)-one isomer 2 (Intermediate 50) (19 g). LC-MS (ESI+): 402.1 [M+H]⁺. SFC 3.73 min.

Chiral SFC analytical YMC Cellulose-SC, 250×4.6 mm 5 μ at 35° C., 3 ml/min, 40% Methanol 35° C.

The characterisation for Intermediate 49 and Intermediate 50 are in Table 2.

Route 9

Alternative Procedure for the Preparation of Macrocycle Precursors, as Exemplified by the Preparation of Intermediate 9, Isopropyl (S,E)-2'-oxo-5'-(2,2,5-trimethyl-4-oxo-3,8,11-trioxa-5-azatetradec-13-en-14-yl)-1',2',5,7-tetrahydrospiro[cyclopenta[c]pyridine-6,3'-pyrrolo[2,3-b]pyridine]-3-carboxylate
Route analogously utilised for Intermediate 50 (the opposite enantiomer to Intermediate 49)

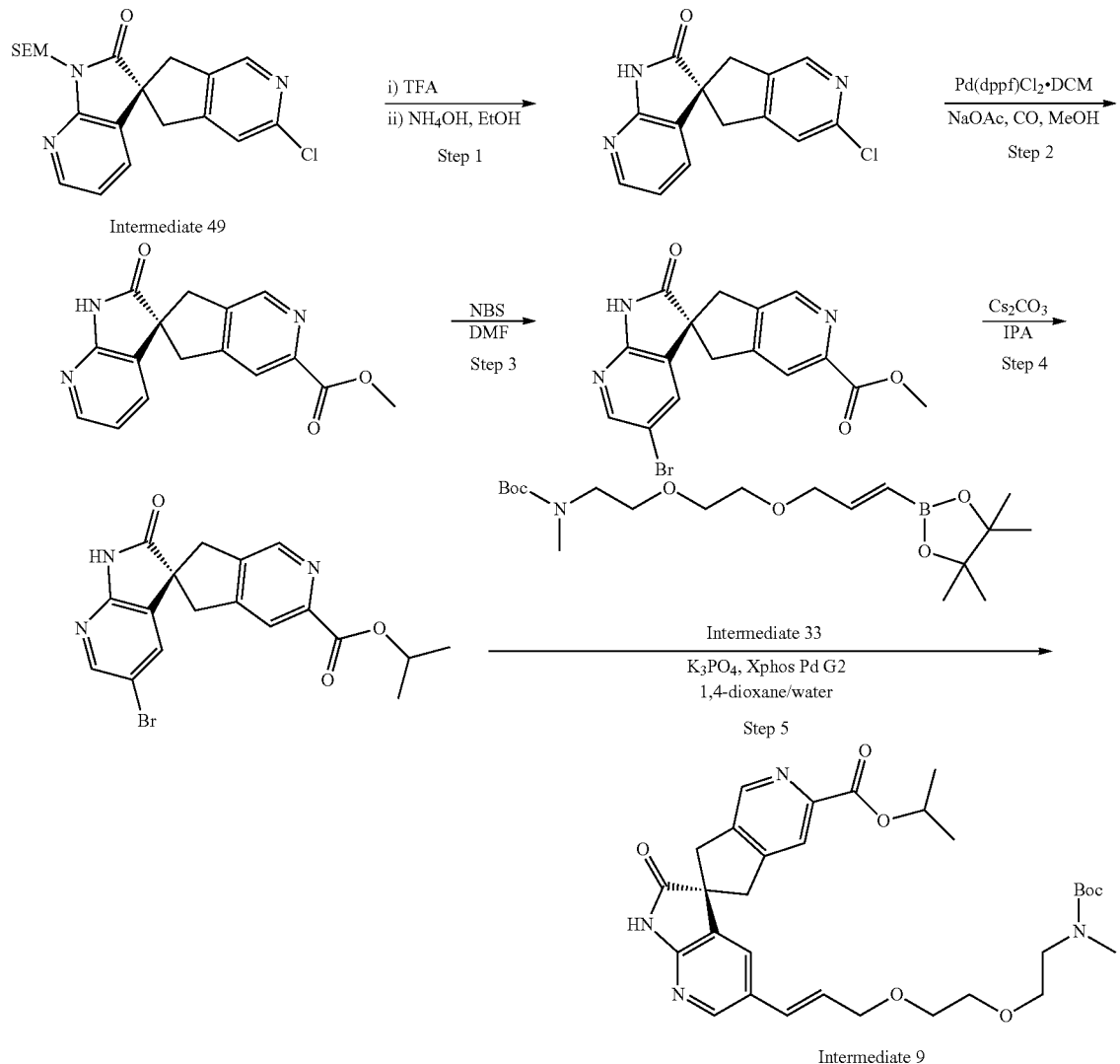

Route 9_Step 1

A suspension of (S)-3-chloro-1'-((2-(trimethylsilyl)ethoxy)methyl)-5,7-dihydrospiro[cyclopenta[c]pyridine-6,3'-pyrrolo[2,3-b]pyridin]-2'(1'H)-one (Intermediate 49) (10 g, 0.024 mol) in TFA (70 mL) was heated at 60° C. for 1 h. The reaction mixture was concentrated in vacuo and dried under high vacuum. The resulting residue was dissolved in EtOH (70 mL) and to this was then added NH₄OH (50 ml). The reaction mixture was stirred at 60° C. for 2 h. The resulting precipitate was collected by filtration, washed with H₂O (100 mL) and dried under high vacuum to give (S)-3-chloro-5,7-dihydrospiro[cyclopenta[c]pyridine-6,3'-pyrrolo[2,3-b]pyridin]-2'(1'H)-one (6.2 g, 82%).

LC-MS (ESI+): 272.0 [M+H].

Route 9_Step 2

A stirred solution of (S)-3-chloro-5,7-dihydrospiro[cyclopenta[c]pyridine-6,3'-pyrrolo[2,3-b]pyridin]-2'(1'H)-one (6.2 g, 0.0228 mol) and sodium acetate (3.79 g, 0.457 mol) in MeOH (120 mL) was degassed with argon and to this was added Pd(dppf)Cl₂·DCM (2.8 g, 0.0034 mol). The reaction mixture was heated at 100° C. for 16 h in a mini clave vessel under 5 Kg/cm² pressure of CO gas. The reaction mixture was concentrated in vacuo and the resulting residue was purified by flash chromatography (SiO$_2$, petroleum ether-EtOAc). The solid obtained was triturated with MeOH (20 mL) and the solids were collected by filtration to give methyl (S)-2'-oxo-1',2',5,7-tetrahydrospiro[cyclopenta[c]pyridine-6,3'-pyrrolo[2,3-b]pyridine]-3-carboxylate (3.2 g, 48%).

LC-MS (ESI+): 296.2 [M+H].

Route 9_Step 3

To a stirred solution of methyl (S)-2'-oxo-1',2',5,7-tetrahydrospiro[cyclopenta[c]pyridine-6,3'-pyrrolo[2,3-b]pyridine]-3-carboxylate (2.4 g, 8.1 mmol) in DMF (25 mL) at 0° C. was added NBS (1.9 g, 10.5 mmol). The reaction mixture was stirred at room temperature for 5 h and was then quenched by the addition of ice cold H$_2$O (100 mL). The resulting precipitate was collected by filtration, washed with cold H$_2$O and dried under high vacuum to give methyl (S)-5'-bromo-2'-oxo-1',2',5,7-tetrahydrospiro[cyclopenta[c]pyridine-6,3'-pyrrolo[2,3-b]pyridine]-3-carboxylate (1.33 g, 44%).

LC-MS (ESI+): 374.0 [M+H].

Route 9_Step 4

To a suspension of methyl (S)-5'-bromo-2'-oxo-1',2',5,7-tetrahydrospiro[cyclopenta[c]pyridine-6,3'-pyrrolo[2,3-b]pyridine]-3-carboxylate (1.18 g, 3.14 mmol) in a dry IPA (78 mL) was added Cs$_2$CO$_3$ (414 mg, 1.26 mmol). The reaction mixture was stirred at 50° C. for 13 h. The reaction mixture was concentrated in vacuo and to this was added H$_2$O (50 mL) and extracted with EtOAc (3×25 mL). The combined organic layers were washed with brine (50 mL), dried (Na$_2$SO$_4$) and concentrated in vacuo. This was purified by flash chromatography (SiO$_2$, DCM-MeOH) to give isopropyl (S)-5'-bromo-2'-oxo-1',2',5,7-tetrahydrospiro[cyclopenta[c]pyridine-6,3'-pyrrolo[2,3-b]pyridine]-3-carboxylate (1.07 g, 85%).

LC-MS (ESI+): 402.10, 404.10 [M+H].

Route 9_Step 5

To a suspension of isopropyl (S)-5'-bromo-2'-oxo-1',2',5,7-tetrahydrospiro[cyclopenta[c]pyridine-6,3'-pyrrolo[2,3-b]pyridine]-3-carboxylate (85 mg, 0.211 mmol) and tert-butyl (E)-methyl(2-(2-((3-(4,4,5,5-tetramethyl-1,3,2-dioxaborolan-2-yl)allyl)oxy)ethoxy)ethyl)carbamate (Intermediate 33) (129 mg, 0.330 mmol) in degassed 1,4-dioxane (790 µL) was added a solution of K$_3$PO$_4$ (91 mg, 0.422 mmol) in degassed H$_2$O (200 µL). To this was then added XphosPdG2 (17 mg, 0.021 mmol) and the reaction mixture degassed for additional 5 mins, sealed and heated at 100° C. for 20 h. The reaction mixture was diluted with EtOAc (50 mL) and washed with H$_2$O (2×15 mL), saturated aqueous NaHCO$_3$ (10 mL), dried (Na$_2$SO$_4$) and concentrated in vacuo. The resulting residue was purified by flash chromatography (SiO$_2$, DCM-MeOH) to give isopropyl (S,E)-2'-oxo-5'-(2,2,5-trimethyl-4-oxo-3,8,11-trioxa-5-azatetradec-13-en-14-yl)-1',2',5,7-tetrahydrospiro[cyclopenta[c]pyridine-6,3'-pyrrolo[2,3-b]pyridine]-3-carboxylate (Intermediate 9) (45 mg, 37%).

The characterisation for Intermediate 9 is in Table 2.

Route 10

Alternative Procedure for the Preparation of Macrocycle Precursors, as Exemplified by the Preparation of Intermediate 11, Isopropyl (R,E)-5'-(3-((5-((tert-butoxycarbonyl)(methyl)amino)pentyl)(methyl)amino)prop-1-en-1-yl)-2'-oxo-1',2',5,7-tetrahydrospiro[cyclopenta[c]pyridine-6,3'-pyrrolo[2,3-b]pyridine]-3-carboxylate

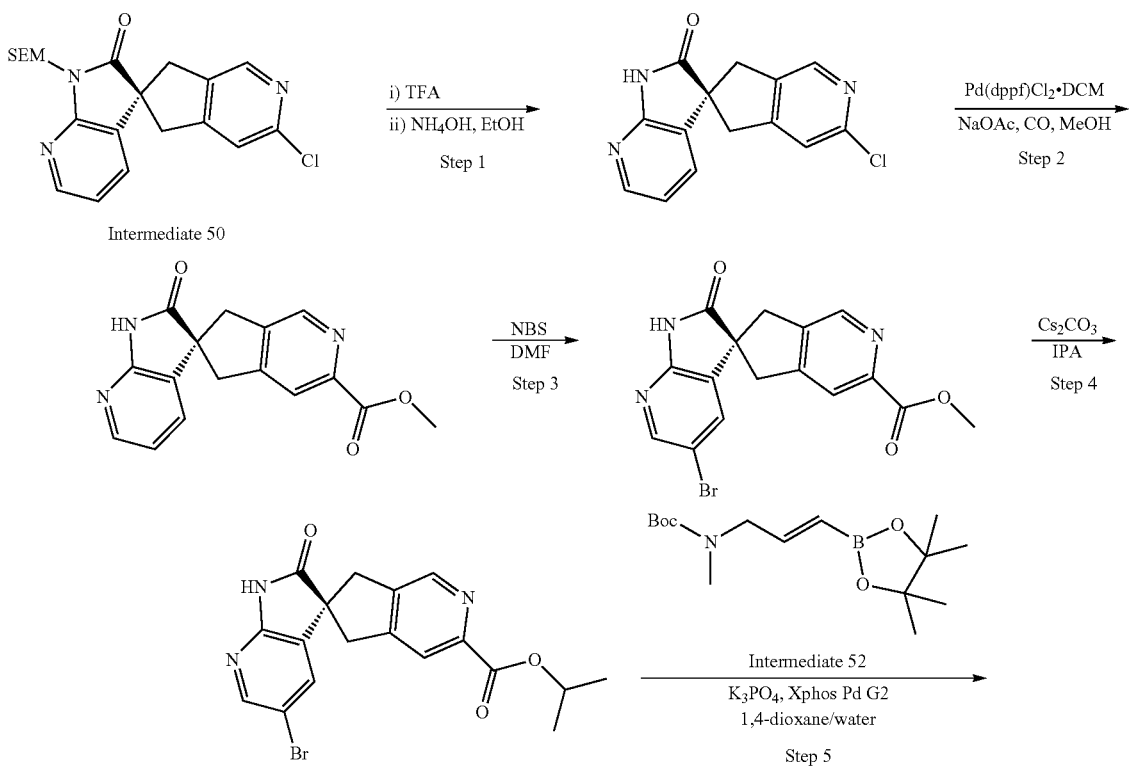

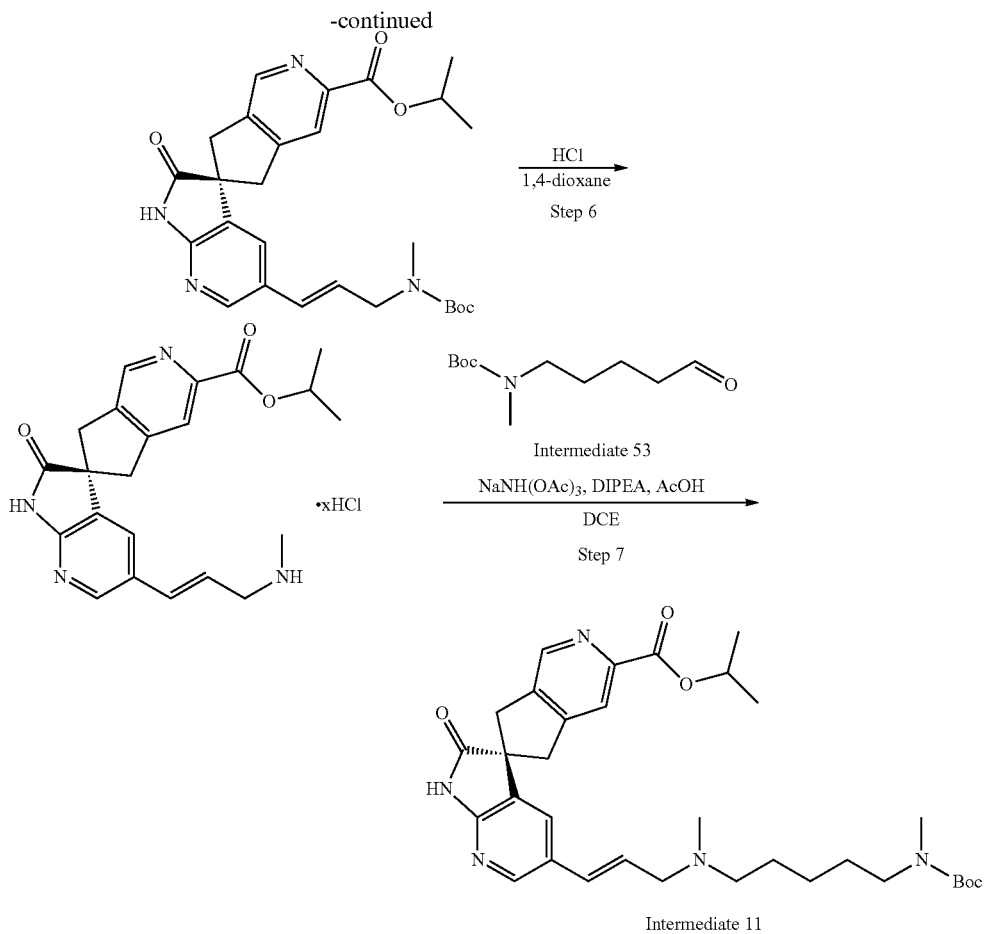

Intermediate 11

Route 10_Step 1

A suspension of (R)-3-chloro-1'-((2-(trimethylsilyl)ethoxy)methyl)-5,7-dihydrospiro[cyclopenta[c]pyridine-6,3'-pyrrolo[2,3-b]pyridin]-2'(1'H)-one (Intermediate 50) (9 g, 0.022 mol) in TFA (70 mL) was heated at 60° C. for 1 h. The reaction mixture was concentrated in vacuo and dried under high vacuum. The resulting residue was dissolved in EtOH (70 mL) and to this was then added NH₄OH (50 ml). The reaction mixture was heated at 60° C. for 2 h. The resulting precipitate was collected by filtration, washed with H₂O (100 mL) and dried under high vacuum to give (R)-3-chloro-5,7-dihydrospiro[cyclopenta[c]pyridine-6,3'-pyrrolo[2,3-b]pyridin]-2'(1'H)-one (4.5 g, 75%).

LC-MS (ESI+): 271.9 [M+H].

Route 10_Step 2

A stirred solution of (R)-3-chloro-5,7-dihydrospiro[cyclopenta[c]pyridine-6,3'-pyrrolo[2,3-b]pyridin]-2'(1'H)-one (4.5 g, 0.016 mol) and sodium acetate (5.8 g, 0.032 mol) in MeOH (100 mL) was degassed with argon. To this was then added Pd(dppf)Cl₂·DCM (2.7 g, 0.003 mol) and the reaction mixture was heated at 100° C. for 16 h in a mini clave vessel under 5 Kg/cm² pressure of CO gas. The reaction mixture was concentrated in vacuo, purified by flash chromatography (SiO₂, petroleum ether-EtOAc) and triturated with MeOH (20 mL). The solid obtained was collected by filtration to give methyl (R)-2'-oxo-1',2',5,7-tetrahydrospiro[cyclopenta[c]pyridine-6,3'-pyrrolo[2,3-b]pyridine]-3-carboxylate (2.4 g, 45%).

LC-MS (ESI+): 296.0 [M+H].

Route 10_Step 3

To a stirred solution of methyl (R)-2'-oxo-1',2',5,7-tetrahydrospiro[cyclopenta[c]pyridine-6,3'-pyrrolo[2,3-b]pyridine]-3-carboxylate (3.3 g, 11.2 mmol) in DMF (30 mL) at 0° C. was added NBS (2.38 g, 13.4 mmol). The reaction mixture was stirred at room temperature for 5 h and was then quenched by the addition of ice cold H₂O (100 mL). This was stirred for 15 min and then resulting precipitate was collected by filtration, washed with cold H₂O and dried over high vacuum to give methyl (R)-5'-bromo-2'-oxo-1',2',5,7-tetrahydrospiro[cyclopenta[c]pyridine-6,3'-pyrrolo[2,3-b]pyridine]-3-carboxylate (3.07 g, 73%).

LC-MS (ESI+): 373.9 [M+H].

Route 10_Step 4

To a suspension of methyl (R)-5'-bromo-2'-oxo-1',2',5,7-tetrahydrospiro[cyclopenta[c]pyridine-6,3'-pyrrolo[2,3-b]pyridine]-3-carboxylate (3.07 g, 8.20 mmol) in IPA (200 mL) was added Cs₂CO₃ (1.08 g, 3.28 mmol). The reaction mixture was stirred at 50° C. for 15 days and was then filtered to remove the Cs₂CO₃, washing with EtOAc. The filtrate was concentrated in vacuo and the resulting residue was purified by flash chromatography (SiO₂, DCM-MeOH) to give isopropyl (R)-5'-bromo-2'-oxo-1',2',5,7-tetrahydrospiro[cyclopenta[c]pyridine-6,3'-pyrrolo[2,3-b]pyridine]-3-carboxylate (2.6 g, 79%).

LC-MS (ESI+): 402.07, 404.07 [M+H].

Route 10_Step 5

To a suspension of isopropyl (R)-5'-bromo-2'-oxo-1',2',5,7-tetrahydrospiro[cyclopenta[c]pyridine-6,3'-pyrrolo[2,3-b]

pyridine]-3-carboxylate (300 mg, 0.746 mmol) and tert-butyl (E)-methyl(3-(4,4,5,5-tetramethyl-1,3,2-dioxaborolan-2-yl)allyl)carbamate (Intermediate 52) (433 mg, 1.33 mmol) in degassed 1,4-dioxane (2.8 mL) was added a solution of K$_3$PO$_4$ (323 mg, 1.49 mmol) in degassed H$_2$O (0.7 mL). To this was then added XphosPdG2 (120 mg, 0.149 mmol) and the reaction mixture degassed for 5 mins and then heated at 100° C. for 2 h. The reaction mixture was diluted with H$_2$O (50 mL) and extracted with EtOAc (3×15 mL). The combined organic layers were washed with saturated aqueous NaHCO$_3$ (2×15 mL), dried (Na$_2$SO$_4$) and concentrated in vacuo. The resulting residue was purified by flash chromatography (SiO$_2$, DCM-MeOH) to give isopropyl (R,E)-5'-(3-((tert-butoxycarbonyl)(methyl)amino)prop-1-en-1-yl)-2'-oxo-1',2',5,7-tetrahydrospiro[cyclopenta[c]pyridine-6,3'-pyrrolo[2,3-b]pyridine]-3-carboxylate (223 mg, 61

LC-MS (ESI+): 493.12 [M+H].

Route 10_Step 6

To a solution of isopropyl (R,E)-5'-(3-((tert-butoxycarbonyl)(methyl)amino)prop-1-en-1-yl)-2'-oxo-1',2',5,7-tetrahydrospiro[cyclopenta[c]pyridine-6,3'-pyrrolo[2,3-b]pyridine]-3-carboxylate (223 mg, 0.452 mmol) in 1,4-dioxane (11.6 mL) was added 4M HCl in 1,4-dioxane (4.5 mL, 18.1 mmol). The reaction mixture was stirred at room temperature for 2 h and was then concentrated to give isopropyl (R,E)-5'-(3-(methylamino)prop-1-en-1-yl)-2'-oxo-1',2',5,7-tetrahydrospiro[cyclopenta[c]pyridine-6,3'-pyrrolo[2,3-b]pyridine]-3-carboxylate hydrochloride salt (233 mg, 100%).

LC-MS (ESI+): 393.18 [M+H].

Route 10_Step 7

To a suspension of isopropyl (R,E)-5'-(3-(methylamino)prop-1-en-1-yl)-2'-oxo-1',2',5,7-tetrahydrospiro[cyclopenta[c]pyridine-6,3'-pyrrolo[2,3-b]pyridine]-3-carboxylate hydrochloride salt (186 mg, 0.345 mmol), DIPEA (245 µL, 1.38 mmol) and 4 Å molecular sieves in DCE (8.8 mL) was added a solution of tert-butyl methyl(5-oxopentyl)carbamate (Intermediate 53) (149 mg, 0.690 mmol) in DCE (5.80 mL), followed by AcOH (79 µL, 1.38 mmol) and sodium triacetoxyborohydride (293 mg, 1.38 mmol). The reaction mixture was stirred at room temperature 2 h and was then quenched with saturated aqueous NaHCO$_3$ (50 mL) and extracted with DCM (3×15 mL). The combined organic layers were washed with brine (30 mL), dried (Na$_2$SO$_4$) and concentrated in vacuo. The resulting residue was purified by flash chromatography (SiO$_2$, DCM-MeOH) to give isopropyl (R,E)-5'-(3-((5-((tert-butoxycarbonyl)(methyl)amino)pentyl)(methyl)amino)prop-1-en-1-yl)-2'-oxo-1',2',5,7-tetrahydrospiro[cyclopenta[c]pyridine-6,3'-pyrrolo[2,3-b]pyridine]-3-carboxylate (Intermediate 11) (140 mg, 69%).

The characterisation for Intermediate 11 is in Table 2.

Route 11

Alternative Procedure for the Preparation of Vinyl Boronates, as Exemplified by the Preparation of Intermediate 52, Tert-butyl (E)-methyl(3-(4,4,5,5-tetramethyl-1,3,2-dioxaborolan-2-yl)allyl)carbamate

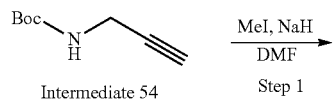

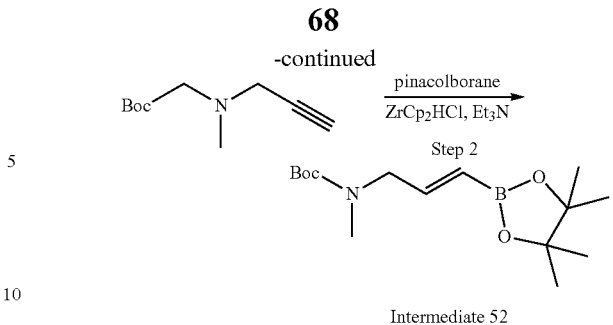

Intermediate 52

Route 11_Step 1

To a cooled solution of tert-butyl prop-2-yn-1-ylcarbamate (Intermediate 54) (2.0 g, 12.6 mmol) in dry DMF (30 mL) at 0° C. was added portion wise sodium hydride (60% in mineral oil) (606 mg, 15.2 mmol). The reaction mixture was stirred at 0° C. for 30 mins after which methyliodide (942 µL, 15.2 mmol) was added. Stirring was continued at room temperature for 1 h. The reaction mixture was quenched with H$_2$O (60 mL) and extracted with EtOAc (3×20 mL). The combined organic layers were washed with saturated aqueous NaHCO$_3$ (2×25 mL) and LiCl (5% aq, 20 mL), dried (Na$_2$SO$_4$) and concentrated in vacuo. The resulting residue was purified by flash chromatography (SiO$_2$, cyclohexane-EtOAc) to give tert-butyl methyl(prop-2-yn-1-yl)carbamate (1.6 g, 75%).

Route 11_Step 2

Into neat tert-butyl methyl(prop-2-yn-1-yl)carbamate (240 mg, 1.42 mmol) were added pinacolborane (315 µL, 2.13 mmol), Et$_3$N (20 µL, 0.142 mmol) and ZrCp$_2$HCl (38 mg, 0.142 mmol). The suspension was stirred at 70° C. for 2 h. Further pinacolborane (95 µL, 0.638 mmol) was added and stirring was continued at 70° C. for 1 h. The reaction mixture was quenched with saturated aqueous NH$_4$Cl (50 mL) and extracted with EtOAc (2×15 mL). The combined organic layers were washed with saturated aqueous NaHCO$_3$ (2×15 mL), dried (Na$_2$SO$_4$) and concentrated in vacuo to give tert-butyl (E)-methyl(3-(4,4,5,5-tetramethyl-1,3,2-dioxaborolan-2-yl)allyl)carbamate (Intermediate 52) (433 mg, 100%) which was used without further purification.

The characterisation for Intermediate 52 are in Table 2.

Route 12

Preparation of Intermediate 53, Tert-butyl methyl(5-oxopentyl)carbamate

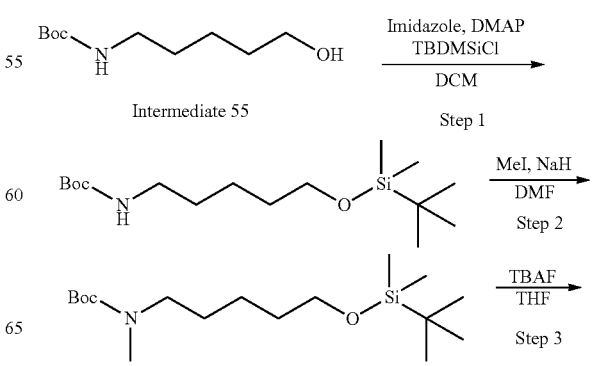

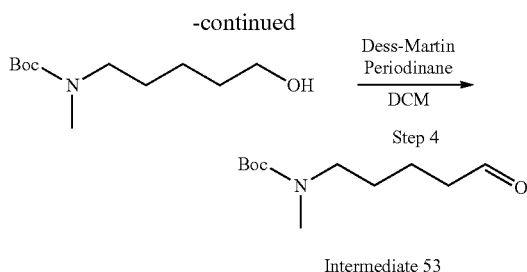

Intermediate 53

Route 12_Step 1

To a solution of tert-butyl (5-hydroxypentyl)carbamate (Intermediate 55) (1.0 g, 4.92 mmol) in dry DCM (11 mL) were added imidazole (0.57 g, 8.38 mmol), DMAP (0.095 g, 0.139 mmol) and TBDMSiCl (0.926 g, 6.14 mmol). The reaction mixture was stirred at room temperature for 5 h and was then quenched with $H_2O$ (15 mL) and DCM (10 mL). The organic layer was washed with $H_2O$ (4×15 mL), dried ($Na_2SO_4$) and concentrated in vacuo. The resulting residue was purified by flash chromatography ($SiO_2$, cyclohexane-EtOAc) to give tert-butyl (5-((tert-butyldimethylsilyl)oxy)pentyl)carbamate (1.65 g, 93%).

LC-MS (ESI+): 218.23 [M+H−Boc].

Route 12_Step 2

To a cooled solution of tert-butyl (5-((tert-butyldimethylsilyl)oxy)pentyl)carbamate (500 mg, 1.58 mmol) in dry DMF (4.0 mL) at 0° C. was added portion wise sodium hydride (60% in mineral oil) (76 mg, 1.89 mmol). The reaction mixture was stirred at 0° C. for 30 mins after which methyliodide (118 µL, 1.89 mmol). Stirring was continued at room temperature for 3 h. The reaction mixture was quenched with saturated aqueous $NH_4Cl$ (30 mL) and extracted with EtOAc (3×15 mL). The combined organic layers were washed with saturated aqueous $NaHCO_3$ (3×15 mL) and LiCl (5% aq, 20 mL), dried ($Na_2SO_4$) and concentrated in vacuo to give tert-butyl (5-((tert-butyldimethylsilyl)oxy)pentyl)(methyl)carbamate (498 mg, 95%).

LC-MS (ESI+): 232.20 [M+H−Boc].

Route 12_Step 3

A solution of tert-butyl (5-((tert-butyldimethylsilyl)oxy)pentyl)(methyl)carbamate (498 mg, 1.50 mmol) in dry THF (5 mL) was purged with argon for 5 mins. To this was then added 1M TBAF in THF (1.50 ml, 1.50 mmol). The reaction mixture was stirred at room temperature for 3 h. Further 1M TBAF in THF (150 µL, 0.150 mmol) was then added and stirring was continued for 2 h. The reaction mixture was diluted between EtOAc (30 mL) and washed with saturated aqueous $NH_4Cl$ (3×15 mL). The organic layer was dried ($Na_2SO_4$) and concentrated in vacuo. The resulting residue was purified by flash chromatography ($SiO_2$, cyclohexane-EtOAc) to give tert-butyl (5-hydroxypentyl)(methyl)carbamate (269 mg, 82%).

LC-MS (ESI+): 240.09 [M+Na].

Route 12 Step 4

To a solution of tert-butyl (5-hydroxypentyl)(methyl)carbamate (150 mg, 0.690 mmol) in DCM (9.3 mL) at 0° C. was added Dess-Martin Periodinane (462 mg, 1.04 mmol) and the reaction mixture stirred at room temperature for 1 h. The reaction mixture was quenched by the addition of saturated aqueous $NaHCO_3$ and saturated aqueous $Na_2S_2O_3$ (1:1) (18.5 ml). The mixture was stirred for 10 mins and then filtered through a phase separator. The organic layer was concentrated in vacuo to give tert-butyl methyl(5-oxopentyl)carbamate (Intermediate 53) and used without further purification in the next step.

Route 13

Alternative Procedure for the Preparation of Macrocycle Precursors, as Exemplified by the Preparation of Intermediate 15, Isopropyl (R,E)-2'-oxo-5'-(2,2,5,8-tetramethyl-4-oxo-3,11-dioxa-5,8-diazatetradec-13-en-14-yl)-1',2',5,7-tetrahydrospiro[cyclopenta[c]pyridine-6,3'-pyrrolo[2,3-b]pyridine]-3-carboxylate

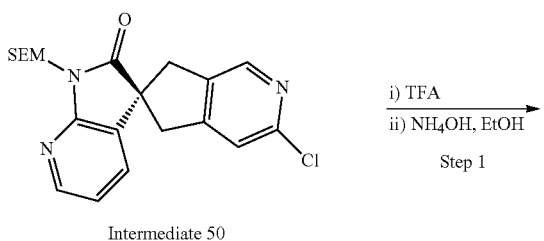

Intermediate 50

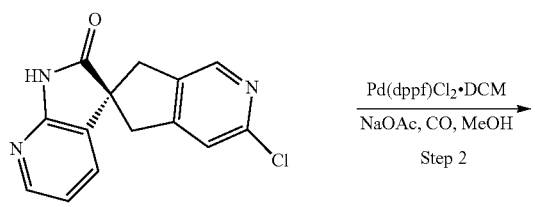

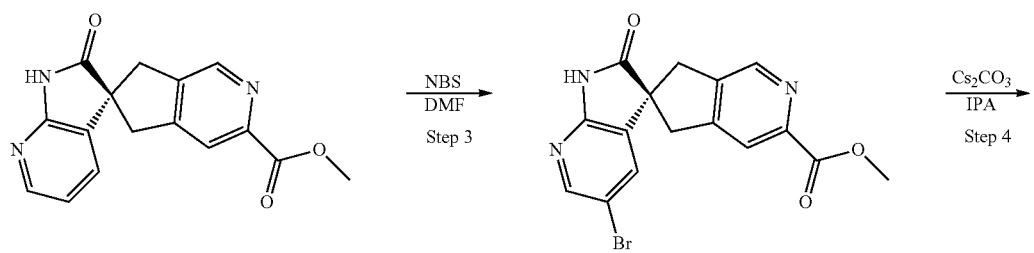

-continued

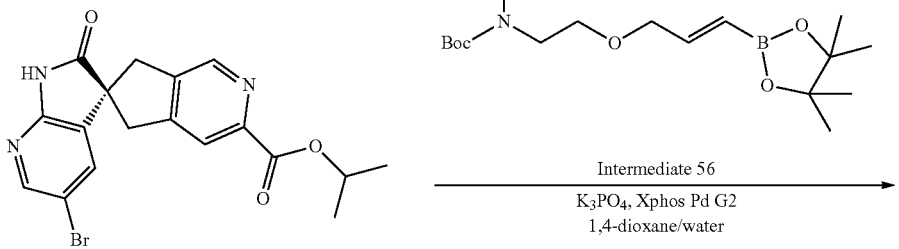

Intermediate 56
———————————→
K₃PO₄, Xphos Pd G2
1,4-dioxane/water

Step 5

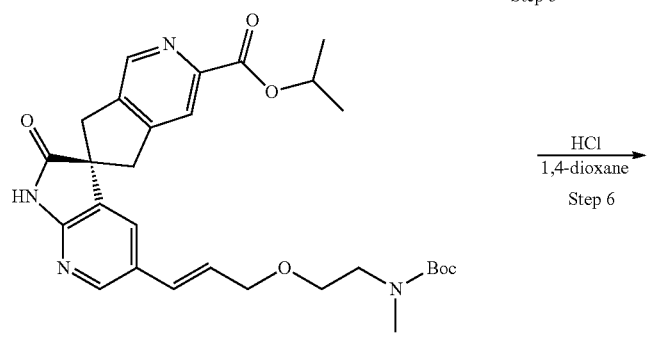

HCl
———————→
1,4-dioxane

Step 6

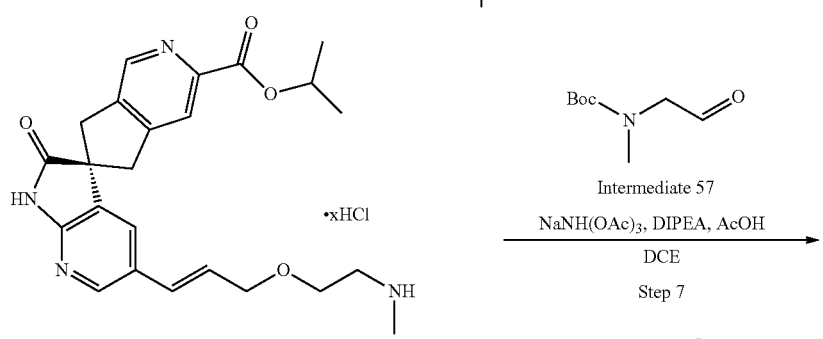
•xHCl

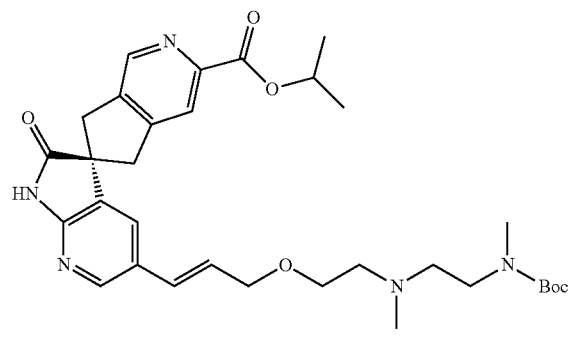

Intermediate 57
———————————→
NaNH(OAc)₃, DIPEA, AcOH

DCE

Step 7

[Final structure shown as Intermediate 15]

Intermediate 15

Route 13_Step 1

A suspension of (R)-3-chloro-1'-((2-(trimethylsilyl)ethoxy)methyl)-5,7-dihydrospiro[cyclopenta[c]pyridine-6,3'-pyrrolo[2,3-b]pyridin]-2'(1'H)-one (Intermediate 50) (9 g, 0.022 mol) in TFA (70 mL) was heated at 60° C. for 1 h. The reaction mixture was concentrated in vacuo and dried under high vacuum. The resulting residue was dissolved in EtOH (70 mL) and to this was then added NH₄OH (50 ml). The reaction mixture was heated at 60° C. for 2 h. The resulting precipitate was collected by filtration, washed with H₂O (100 mL) and dried under high vacuum to give (R)-3-chloro-5,7-dihydrospiro[cyclopenta[c]pyridine-6,3'-pyrrolo[2,3-b]pyridin]-2'(1'H)-one (4.5 g, 75%).

LC-MS (ESI+): 271.9 [M+H].

Route 13_Step 2

A stirred solution of (R)-3-chloro-5,7-dihydrospiro[cyclopenta[c]pyridine-6,3'-pyrrolo[2,3-b]pyridin]-2'(1'H)-one (4.5 g, 0.016 mol) and sodium acetate (5.8 g, 0.032 mol) in MeOH (100 mL) was degassed with argon. To this was then added Pd(dppf)Cl₂·DCM (2.7 g, 0.003 mol) and the resultant reaction mixture was heated at 100° C. for 16 h in a mini clave vessel under Kg/cm² pressure of CO gas. The reaction mixture was concentrated in vacuo, purified by flash chromatography (SiO₂, petroleum ether-EtOAc) and triturated with MeOH (20 mL). The solid obtained was collected by filtration to give methyl (R)-2'-oxo-1',2',5,7-tetrahydrospiro[cyclopenta[c]pyridine-6,3'-pyrrolo[2,3-b]pyridine]-3-carboxylate (2.4 g, 45%).

LC-MS (ESI+): 296.0 [M+H].

Route 13_Step 3

To a stirred solution of methyl (R)-2'-oxo-1',2',5,7-tetrahydrospiro[cyclopenta[c]pyridine-6,3'-pyrrolo[2,3-b]pyridine]-3-carboxylate (3.3 g, 11.2 mmol) in DMF (30 mL) at 0° C. was added NBS (2.38 g, 13.4 mmol). The reaction mixture was stirred at room temperature for 5 h and was then quenched by the addition of ice cold $H_2O$ (100 mL). This was stirred 15 mins and then the resulting precipitate was collected by filtration, washed with cold $H_2O$ and dried over high vacuum to give methyl (R)-5'-bromo-2'-oxo-1',2',5,7-tetrahydrospiro[cyclopenta[c]pyridine-6,3'-pyrrolo[2,3-b]pyridine]-3-carboxylate (3.07 g, 73

LC-MS (ESI+): 373.9 [M+H].

Route 13_Step 4

To a suspension of methyl (R)-5'-bromo-2'-oxo-1',2',5,7-tetrahydrospiro[cyclopenta[c]pyridine-6,3'-pyrrolo[2,3-b]pyridine]-3-carboxylate (3.07 g, 8.20 mmol) in IPA (200 mL) was added $Cs_2CO_3$ (1.08 g, 3.28 mmol). The reaction mixture was stirred at 50° C. for 15 days and was then filtered to remove the $Cs_2CO_3$, washing with EtOAc. The filtrate was concentrated in vacuo and the resulting residue was purified by flash chromatography ($SiO_2$, DCM-MeOH) to give isopropyl (R)-5'-bromo-2'-oxo-1',2',5,7-tetrahydrospiro[cyclopenta[c]pyridine-6,3'-pyrrolo[2,3-b]pyridine]-3-carboxylate (2.6 g, 79%).

LC-MS (ESI+): 402.07, 404.07 [M+H].

Route 13_Step 5

To a suspension of isopropyl (R)-5'-bromo-2'-oxo-1',2',5,7-tetrahydrospiro[cyclopenta[c]pyridine-6,3'-pyrrolo[2,3-b]pyridine]-3-carboxylate (400 mg, 0.994 mmol) and tert-butyl (E)-methyl(2-((3-(4,4,5,5-tetramethyl-1,3,2-dioxaborolan-2-yl)allyl)oxy)ethyl)carbamate (Intermediate 56) (526 mg, 1.39 mmol) in degassed 1,4-dioxane (3.8 mL) was added a solution of $K_3PO_4$ (431 mg, 1.99 mmol) in degassed $H_2O$ (950 µL). To this was then added XphosPdG2 (160 mg, 0.199 mmol) and the reaction mixture was degassed for additional 5 mins, sealed and heated at 100° C. for 2 h. The reaction mixture was diluted with $H_2O$ (100 mL) and extracted with EtOAc (3×30 mL). The combined organic layers were washed with saturated aqueous $NaHCO_3$ (2×50 mL), dried ($Na_2SO_4$) and concentrated in vacuo. The resulting residue was purified by flash chromatography ($SiO_2$, DCM-MeOH) to give isopropyl (R,E)-5'-(3-(2-((tert-butoxycarbonyl)(methyl)amino)ethoxy)prop-1-en-1-yl)-2'-oxo-1',2',5,7-tetrahydrospiro[cyclopenta[c]pyridine-6,3'-pyrrolo[2,3-b]pyridine]-3-carboxylate (265 mg, 50%).

LC-MS (ESI+): 537.17 [M+H].

Route 13_Step 6

To the solution of isopropyl (R,E)-5'-(3-(2-((tert-butoxycarbonyl)(methyl)amino)ethoxy)prop-1-en-1-yl)-2'-oxo-1',2',5,7-tetrahydrospiro[cyclopenta[c]pyridine-6,3'-pyrrolo[2,3-b]pyridine]-3-carboxylate (264 mg, 0.492 mmol) in 1,4-dioxane (12.6 mL) was added 4M HCl in 1,4-dioxane (4.92 mL, 19.7 mmol). The reaction mixture was stirred at room temperature for 2 h and was then concentrated in vacuo to give isopropyl (R,E)-5'-(3-(2-(methylamino)ethoxy)prop-1-en-1-yl)-2'-oxo-1',2',5,7-tetrahydrospiro[cyclopenta[c]pyridine-6,3'-pyrrolo[2,3-b]pyridine]-3-carboxylate hydrochloride salt (322 mg).

LC-MS (ESI+): 437.14 [M+H].

Route 13_Step 7

To a suspension of isopropyl (R,E)-5'-(3-(2-(methylamino)ethoxy)prop-1-en-1-yl)-2'-oxo-1',2',5,7-tetrahydrospiro[cyclopenta[c]pyridine-6,3'-pyrrolo[2,3-b]pyridine]-3-carboxylate hydrochloride salt (322 mg, 0.492 mmol), DIPEA (350 µL, 1.97 mmol) and 4 Å molecular sieves in DCE (11.6 mL) was added a solution of tert-butyl methyl(2-oxoethyl)carbamate (Intermediate 57) (171 mg, 0.985 mmol) in DCE (8.3 mL) followed by AcOH (113 µL, 1.97 mmol) and sodium triacetoxyborohydride (417 mg, 1.97 mmol). The reaction mixture was stirred at room temperature for 90 mins. The reaction mixture was filtered through a celite pad, quenched with saturated aqueous $NaHCO_3$ (50 mL) and the aqueous layer extracted with EtOAc (3×15 mL). The combined organic layers were washed with brine (50 mL), dried ($Na_2SO_4$) and concentrated in vacuo. The resulting residue was purified by flash chromatography ($SiO_2$, DCM-MeOH/$NH_4OH$) to give isopropyl (R,E)-2'-oxo-5'-(2,2,5,8-tetramethyl-4-oxo-3,11-dioxa-5,8-diazatetradec-13-en-14-yl)-1',2',5,7-tetrahydrospiro[cyclopenta[c]pyridine-6,3'-pyrrolo[2,3-b]pyridine]-3-carboxylate (Intermediate 15) (253 mg, 86%).

The characterisation for Intermediate 15 is in Table 2.

Route 14

Alternative Procedure for the Preparation of Vinyl Boronates, as Exemplified by the Preparation of Intermediate 56, Tert-butyl (E)-methyl(2-((3-(4,4,5,5-tetramethyl-1,3,2-dioxaborolan-2-yl)allyl)oxy)ethyl)carbamate

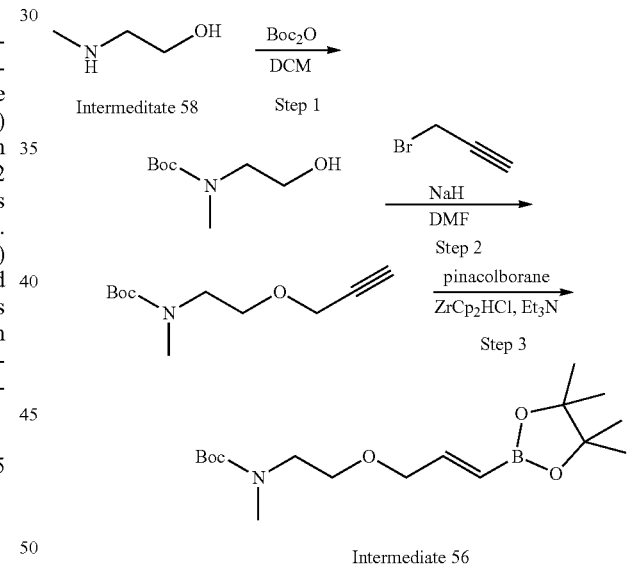

Route 14_Step 1

To a solution of 2-(methylamino)ethan-1-ol (Intermediate 58) (5 g, 53.3 mmol) dry in DCM (100 mL) was added $Boc_2O$ (8.4 g, 47.7 mmol). The reaction mixture was stirred at room temperature for 2 h and was then concentrated in vacuo. The resulting residue was purified by flash chromatography ($SiO_2$, cyclohexane-EtOAc) to give tert-butyl (2-hydroxyethyl)(methyl)carbamate (8.4 g, 90%).

LC-MS (ESI+): 120.05 [M+H-'Bu].

Route 14_Step 2

To an ice cooled solution of tert-butyl (2-hydroxyethyl)(methyl)carbamate (8.4 g, 47.7 mmol) in dry DMF (120 mL) was added portion wise sodium hydride (60% in mineral oil) (2.3 g, 57.2 mmol). The reaction mixture was stirred at 0° C. for 30 mins after which 3-bromoprop-1-yne (6.37 mL, 57.2 mmol) was added dropwise. The temperature was slowly raised from 0° C. to room temperature overnight. The reaction mixture was quenched with saturated aqueous NH$_4$Cl (500 mL) and extracted with EtOAc (3×250 mL). The combined organic layers were washed with saturated aqueous NaHCO$_3$ (3×250 mL) and LiCl (5% aq, 250 mL), dried (Na$_2$SO$_4$) and concentrated in vacuo. The resulting residue was purified by flash chromatography (SiO$_2$, DCM-cyclohexane/EtOAc) to give tert-butyl methyl(2-(prop-2-yn-1-yloxy)ethyl)carbamate (7.17 g, 71%).

LC-MS (ESI+): 236.21 [M+Na].

Route 14_Step 3

Into neat tert-butyl methyl(2-(prop-2-yn-1-yloxy)ethyl) carbamate (320 mg, 1.50 mmol) were added pinacolborane (334 µL, 2.25 mmol), Et$_3$N (21 µL, 0.150 mmol) and ZrCp$_2$HCl (40 mg, 0.150 mmol). The vial was sealed and the suspension was stirred at 70° C. for 2 h. The reaction mixture was quenched with saturated aqueous NH$_4$Cl (50 mL) and extracted with EtOAc (2×15 mL). The combined organic layers were washed with saturated aqueous NaHCO$_3$ (2×15 mL), dried (Na$_2$SO$_4$) and concentrated in vacuo to give tert-butyl (E)-methyl(2-((3-(4,4,5,5-tetramethyl-1,3,2-dioxaborolan-2-yl)allyl)oxy)ethyl)carbamate (Intermediate 56) (526 mg, 103%) which was used without further purification.

The characterisation for Intermediate 56 is in Table 2.

Route 15

Preparation of Intermediate 59, Methyl (S)-2'-oxo-1'-((2-(trimethylsilyl)ethoxy)methyl)-1,1',2',3-tetrahydrospiro[indene-2,3'-pyrrolo[2,3-b]pyridine]-5-carboxylate and Intermediate 60, Methyl (R)-2'-oxo-1'-((2-(trimethylsilyl)ethoxy)methyl)-1,1',2',3-tetrahydrospiro[indene-2,3'-pyrrolo[2,3-b]pyridine]-5-carboxylate

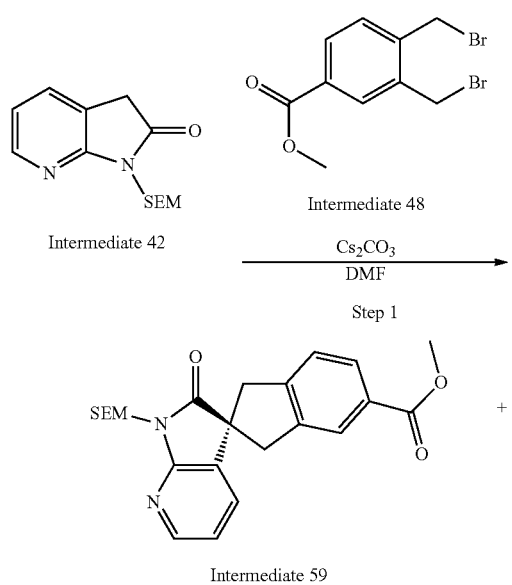

Intermediate 59

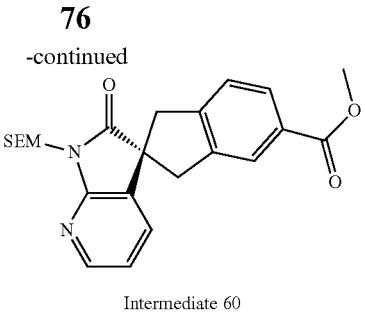

Intermediate 60

Route 15_Step 1

To a suspension of 1-((2-(trimethylsilyl)ethoxy)methyl)-1,3-dihydro-2H-pyrrolo[2,3-b]pyridin-2-one (Intermediate 42) (60 g, 0.22 mol) and methyl 3,4-bis(bromomethyl) benzoate (Intermediate 48) (87.2 g, 0.27 mol) in DMF (1.5 L) was added Cs$_2$CO$_3$ (222 g, 0.68 mol). The reaction mixture was stirred at room temperature for 16 h and was then quenched with ice cold H$_2$O (5 L) and extracted with EtOAc (2×3 L). The combined organic layers were washed with brine (3 L), dried (Na$_2$SO$_4$) and concentrated in vacuo. The resulting residue was purified by flash chromatography (SiO$_2$, petroleum ether-EtOAc) to give methyl 2'-oxo-1'-((2-(trimethylsilyl)ethoxy)methyl)-1,1',2',3-tetrahydrospiro[indene-2,3'-pyrrolo[2,3-b]pyridine]-5-carboxylate.

Purified by Chiral SFC
  Instrument: PICLab PREP 400
  Solvents: Primary mobile phase=CO$_2$ Modifier: 25% MeOH
  Column: YMC Amylose-C 5 µm, 250×30 mm, at 35° C.
  UV monitoring: 210 nm
  Flow: 100 g/min..
  To give
  Methyl (S)-2'-oxo-1'-((2-(trimethylsilyl)ethoxy)methyl)-1,1',2',3-tetrahydrospiro[indene-2,3'-pyrrolo[2,3-b]pyridine]-5-carboxylate isomer 1 (Intermediate 59) (11.5 g) LC-MS (ESI+): 425.1 [M+H]$^+$ SFC 1.52 min.
  and
  Methyl (R)-2'-oxo-1'-((2-(trimethylsilyl)ethoxy)methyl)-1,1',2',3-tetrahydrospiro[indene-2,3'-pyrrolo[2,3-b] pyridine]-5-carboxylate isomer 2 (Intermediate 60) (9.8 g) LC-MS (ESI+): 425.1 [M+H]$^+$ SFC 2.02 min.
Chiral SFC analytical YMC Amylose-C, 250×4.6 mm 5p at 35° C., 3 ml/min, 40% Methanol 35° C.

The characterisation for Intermediate 59 and Intermediate 60 are in Table 2.

Route 16

Alternative Procedure for the Preparation of Macrocycle Precursors, as Exemplified by the Preparation of Intermediate 17, Methyl (S,E)-2'-oxo-5'-(2,2,5-trimethyl-4-oxo-3,8,11-trioxa-5-azatetradec-13-en-14-yl)-1,1',2',3-tetrahydrospiro[indene-2,3'-pyrrolo[2,3-b]pyridine]-5-carboxylate. Route analogously utilised for Intermediate 60 (the opposite enantiomer to Intermediate 59)

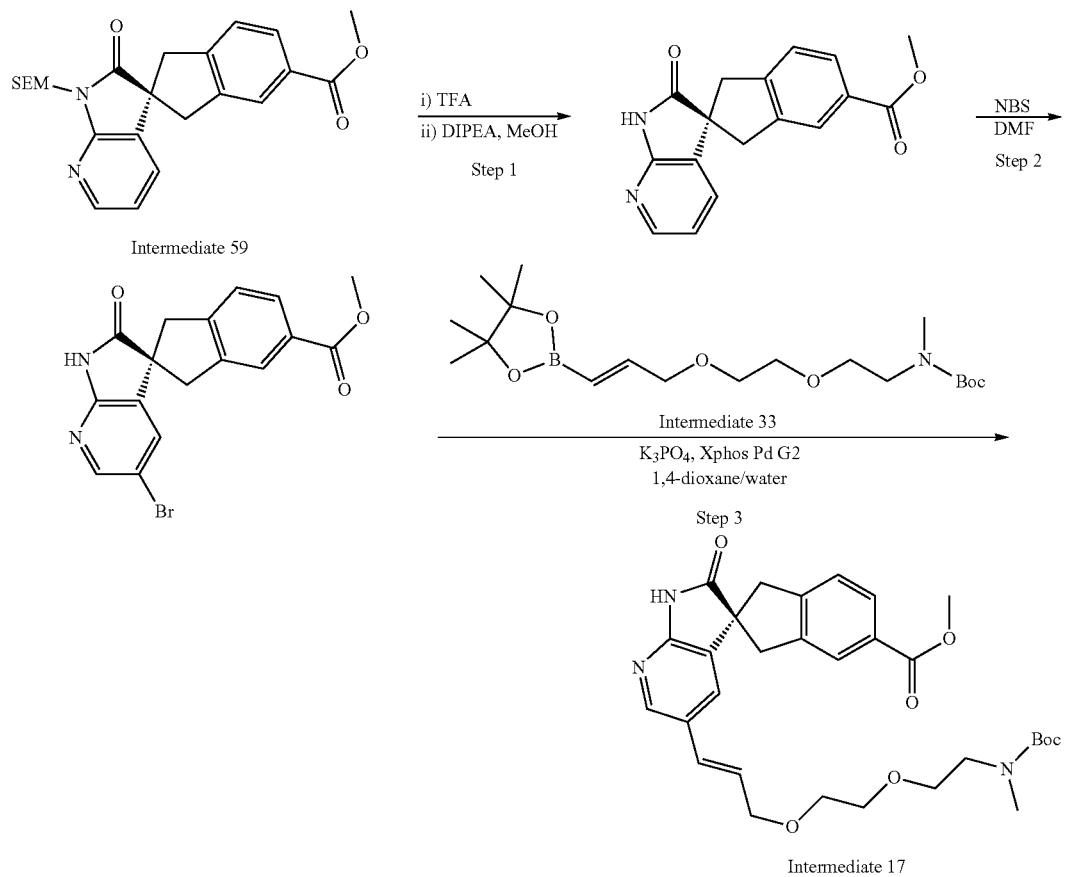

Route 16_Step 1

A suspension of methyl (S)-2'-oxo-1'-((2-(trimethylsilyl)ethoxy)methyl)-1,1',2',3-tetrahydrospiro[indene-2,3'-pyrrolo[2,3-b]pyridine]-5-carboxylate (Intermediate 59) (11.5 g, 27.12 mmol) in TFA (100 mL) was heated at 60° C. for 2 h. The reaction mixture was concentrated in vacuo and dried over high vacuum. The crude mass was dissolved in MeOH (100 mL) and to this was then added DIPEA (18.6 ml, 108.3 mmol). The reaction mixture was heated at 60° C. for 2 h. The resulting precipitate was collected by filtration and dried to give methyl (S)-2'-oxo-1,1',2',3-tetrahydrospiro[indene-2,3'-pyrrolo[2,3-b]pyridine]-5-carboxylate (6.7 g, 84%).

LC-MS (ESI+): 295.1 [M+H].

Route 16_Step 2

To a stirred solution of methyl (S)-2'-oxo-1,1',2',3-tetrahydrospiro[indene-2,3'-pyrrolo[2,3-b]pyridine]-5-carboxylate (6.7 g, 22.7 mmol) in DMF (65 mL) at 0° C. was added NBS (12.2 g, 68.5 mmol). The reaction mixture was stirred at room temperature for 5 h and was then quenched with ice cold $H_2O$. The reaction mixture was stirred for 1 h and the resulting precipitate was collected by filtration, washed with ice cold $H_2O$ and dried under high vacuum. The solid was triturated with MeOH to give methyl (S)-5'-bromo-2'-oxo-1,1',2',3-tetrahydrospiro[indene-2,3'-pyrrolo[2,3-b]pyridine]-5-carboxylate (7.0 g, 82%).

LC-MS (ESI+): 373.0 [M+H].

Route 16_Step 3

A mixture of methyl (S)-5'-bromo-2'-oxo-1,1',2',3-tetrahydrospiro[indene-2,3'-pyrrolo[2,3-b]pyridine]-5-carboxylate (291 mg, 0.78 mmol) and tert-butyl (E)-methyl(2-(2-((3-(4,4,5,5-tetramethyl-1,3,2-dioxaborolan-2-yl)allyl)oxy)ethoxy)ethyl)carbamate (Intermediate 33) (450 mg, 1.17 mmol) was evacuated and backfilled with argon. To this was then added degassed 1,4-dioxane (4 mL) followed by a solution of $K_3PO_4$ (331 mg, 1.56 mmol) in degassed $H_2O$ (1 mL) and XphosPdG2 (61 mg, 0.078 mmol). The reaction mixture was degassed with argon for 5 mins and was then heated at 100° C. for 3 h. The reaction mixture was diluted with H₂O (30 mL) and extracted with EtOAc (3×10 mL). The combined organic layers were washed with saturated aqueous NaHCO₃ (2×10 mL) and brine (10 mL), dried (Na₂SO₄) and concentrated in vacuo. The resulting residue was purified by flash chromatography (SiO₂, DCM-EtOAc) to give methyl (S,E)-2'-oxo-5'-(2,2,5-trimethyl-4-oxo-3,8, 11-trioxa-5-azatetradec-13-en-14-yl)-1,1',2',3-tetrahydrospiro[indene-2,3'-pyrrolo[2,3-b]pyridine]-5-carboxylate (Intermediate 17) (208 mg, 48%).

The characterisation for Intermediate 17 is in Table 2.

Route 17

Alternative Procedure for the Preparation of Macrocycle Precursors, as Exemplified by the Preparation of Intermediate 20, Methyl (S,E)-2'-oxo-5'-(2,2,5,8-tetramethyl-4-oxo-3,11-dioxa-5,8-diazatetradec-13-en-14-yl)-1,1',2',3-tetrahydrospiro[indene-2,3'-pyrrolo[2,3-b]pyridine]-5-carboxylate for 2 h. The resulting precipitate was collected by filtration and dried to give methyl (S)-2'-oxo-1,1',2',3-tetrahydrospiro [indene-2,3'-pyrrolo[2,3-b]pyridine]-5-carboxylate (6.7 g, 84%).

LC-MS (ESI+): 295.1 [M+H].

Route 17_Step 2

To a stirred solution of methyl (S)-2'-oxo-1,1',2',3-tetrahydrospiro[indene-2,3'-pyrrolo[2,3-b]pyridine]-5-carboxylate (6.7 g, 22.7 mmol) in DMF (65 mL) at 0° C. was added NBS (12.2 g, 68.5 mmol). The reaction mixture was stirred at room temperature for 5 h and was then quenched with ice cold H₂O. The reaction mixture was stirred for 1 h and the resulting precipitate was collected by filtration, washed with ice cold H₂O and dried under high vacuum. The solid was triturated with MeOH to give methyl (S)-5'-bromo-2'-oxo-1,1',2',3-tetrahydrospiro[indene-2,3'-pyrrolo[2,3-b]pyridine]-5-carboxylate (7.0 g, 82%).

LC-MS (ESI+): 373.0 [M+H].

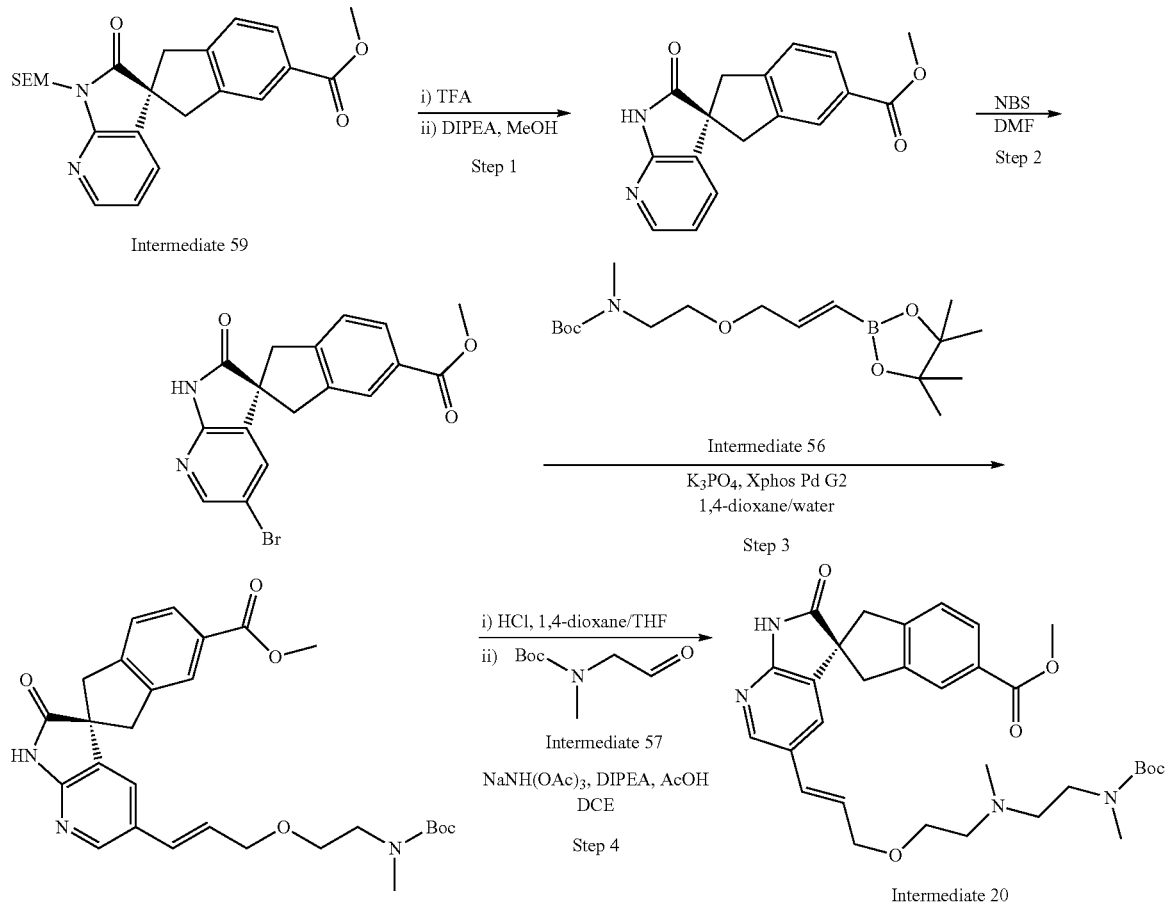

Route 17_Step 1

A suspension of methyl (S)-2'-oxo-1'-((2-(trimethylsilyl) ethoxy)methyl)-1,1',2',3-tetrahydrospiro[indene-2,3'-pyrrolo[2,3-b]pyridine]-5-carboxylate (Intermediate 59) (11.5 g, 27.12 mmol) in TFA (100 mL) was heated at 60° C. for 2 h. The reaction mixture was concentrated in vacuo and dried over high vacuum. The crude mass was dissolved in MeOH (100 mL) and to this was then added DIPEA (18.6 ml, 108.3 mmol). The reaction mixture was heated at 60° C.

Route 17_Step 3

To a mixture of methyl (S)-5'-bromo-2'-oxo-1,1',2',3-tetrahydrospiro[indene-2,3'-pyrrolo[2,3-b]pyridine]-5-carboxylate (300 mg, 0.84 mmol) and tert-butyl (E)-methyl(2-((3-(4,4,5,5-tetramethyl-1,3,2-dioxaborolan-2-yl)allyl)oxy) ethyl)carbamate (Intermediate 56) (411 mg, 1.21 mmol) in 1,4-dioxane (3 mL) was added H₂O (0.7 mL), followed by K₃PO₄ (341 mg, 1.61 mmol). The reaction mixture was degassed with argon for 5 mins and to this was then added XphosPdG2 (79 mg, 0.088 mmol) and degassed for an additional 5 mins. The reaction vial was sealed and heated at 100° C. for 2 h. The reaction mixture was diluted with DCM. The aqueous layer was further extracted with DCM (2×30 mL). The combined organic layers were dried (Na$_2$SO$_4$) and concentrated in vacuo. The resulting residue was purified by flash chromatography (SiO$_2$, DCM-MeOH) to give methyl (S,E)-5'-(3-(2-((tert-butoxycarbonyl)(methyl)amino)ethoxy)prop-1-en-1-yl)-2'-oxo-1,1',2',3-tetrahydrospiro[indene-2,3'-pyrrolo[2,3-b]pyridine]-5-carboxylate (270 mg, 66%).

LC-MS (ESI+): 508.30 [M+H].

Route 17_Step 4

To a solution of methyl (S,E)-5'-(3-(2-((tert-butoxycarbonyl)(methyl)amino)ethoxy)prop-1-en-1-yl)-2'-oxo-1,1',2',3-tetrahydrospiro[indene-2,3'-pyrrolo[2,3-b]pyridine]-5-carboxylate (270 mg, 0.53 mmol) in THF (10 mL) at 0° C. was added 4M HCl in 1,4-dioxane (10 mL). The reaction mixture was stirred at room temperature until complete and was then concentrated in vacuo. The resulting residue was suspended in DCE (20 mL) and DIPEA (364 µL, 2.13 mmol) was added followed by tert-butyl methyl(2-oxoethyl)carbamate (Intermediate 57) (184 mg, 1.06 mmol) as a solution in DCE (5 mL), AcOH (122 µL, 2.13 mmol) and sodium triacetoxyborohydride (450 mg, 2.13 mmol). The reaction mixture was stirred at room temperature for 2 h and was then quenched with H$_2$O and DCM. The organic layer was dried (Na$_2$SO$_4$) and concentrated in vacuo. The resulting residue was purified by flash chromatography (SiO$_2$, DCM-MeOH) to give methyl (S,E)-2'-oxo-5'-(2,2,5,8-tetramethyl-4-oxo-3,11-dioxa-5,8-diazatetradec-13-en-14-yl)-1,1',2',3-tetrahydrospiro[indene-2,3'-pyrrolo[2,3-b]pyridine]-5-carboxylate (Intermediate 20) (200 mg, 67%).

The characterisation for Intermediate 20 is in Table 2.

Route 18

Typical Procedure for the Preparation of Chiral Alcohols as Exemplified by the Preparation of Intermediate 22, Tert-butyl (R)-2-hydroxy-3-(7-methyl-1H-indazol-5-yl)propanoate

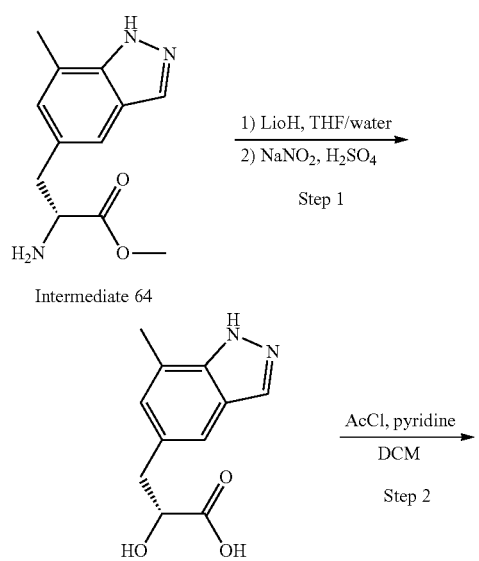

Intermediate 64

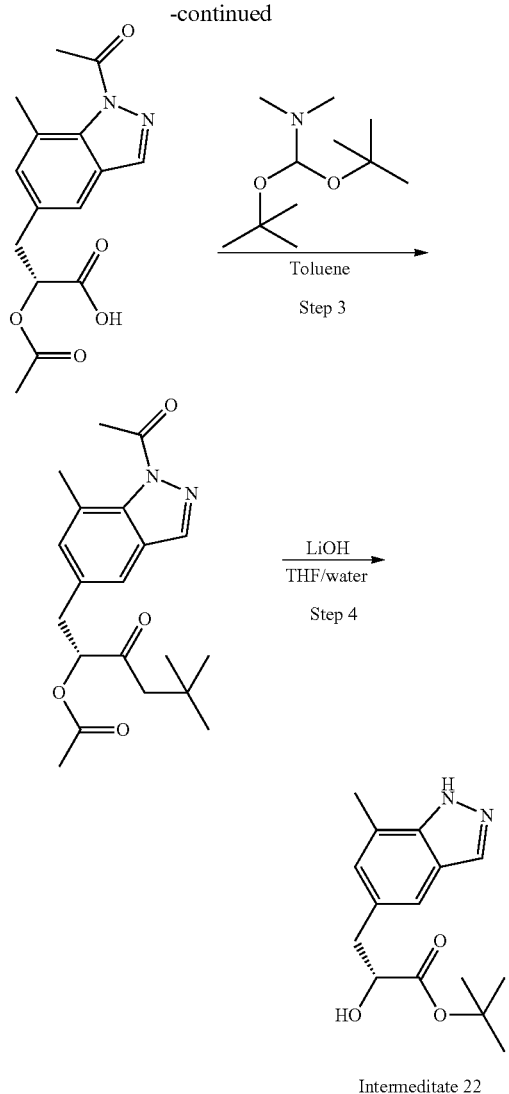

Intermeditate 22

Route 18_Step 1

To a solution of methyl (R)-2-amino-3-(7-methyl-1H-indazol-5-yl)propanoate (Intermediate 64) (627 mg, 2.7 mmol) THF (4 mL) and H$_2$O (2 mL) was added LiOH (129 mg, 5.4 mmol). The reaction mixture was stirred at room temperature for 1 h and was then concentrated in vacuo. The resulting residue was diluted with H$_2$O (15 mL), cooled to 0° C., then concentrated H$_2$SO$_4$ (0.891 mL, 16.4 mmol) was added, followed by the dropwise addition of NaNO$_2$ (1.1 g, 16.4 mmol) as a solution in H$_2$O (3 mL). The reaction mixture was stirred at 0° C. for 20 mins then at room temperature overnight. The pH was adjusted to pH 4 by the addition of 20% aqueous NaOH and extracted with EtOAc. The organic layer was dried (Na$_2$SO$_4$) and concentrated in vacuo to give (R)-2-hydroxy-3-(7-methyl-1H-indazol-5-yl)propanoic acid (550 mg, 87%).

LC-MS (ESI+): 221.50 [M+H].

Route 18_Step 2

To a suspension of (R)-2-hydroxy-3-(7-methyl-1H-indazol-5-yl)propanoic acid (276 mg, 1.25 mmol) in DCM (15 mL) was added pyridine (0.202 mL, 2.5 mmol), followed by AcCl (0.187 mL, 2.5 mmol). The reaction mixture was stirred at room temperature for 2 h and was then diluted with H$_2$O (5 mL). The organic layer was dried (Na$_2$SO$_4$) and concentrated in vacuo, azeotroping twice with toluene to give (R)-2-acetoxy-3-(1-acetyl-7-methyl-1H-indazol-5-yl)propanoic acid (380 mg, 100%).

LC-MS (ESI+): 305.7 [M+H]

Route 18_Step 3

To a solution of (R)-2-acetoxy-3-(1-acetyl-7-methyl-1H-indazol-5-yl)propanoic acid (380 mg, 1.25 mmol) in toluene (5 mL) was added 1,1-di-tert-butoxy-N,N-dimethylmethanamine (1.2 mL, 5 mmol). The reaction mixture was heated at 95° C. for 2 h and was then concentrated in vacuo to give tert-butyl (R)-2-acetoxy-3-(1-acetyl-7-methyl-1H-indazol-5-yl)propanoate (398 mg, 100%)

LC-MS (ESI+): 361.62 [M+H].

Route 18_Step 4

To a solution of tert-butyl (R)-2-acetoxy-3-(1-acetyl-7-methyl-1H-indazol-5-yl)propanoate (398 mg, 1.11 mmol) in THF (4 mL) and H$_2$O (1 mL) was added LiOH (60 mg, 2.5 mmol) and the reaction mixture was stirred at room temperature for 2 h. The reaction mixture was then extracted with EtOAc (2×20 mL), dried (Na$_2$SO$_4$) and concentrated in vacuo. The resulting residue was purified by flash chromatography (SiO$_2$, cyclohexane-EtOAc) to give tert-butyl (R)-2-hydroxy-3-(7-methyl-1H-indazol-5-yl)propanoate (Intermediate 22) (97 mg, 28%).

The characterisation for Intermediate 22 is in Table 2.

Route 19

Preparation of Intermediate 65, Methyl (S)-2-amino-3-(7-methyl-1H-indazol-5-yl)propanoate

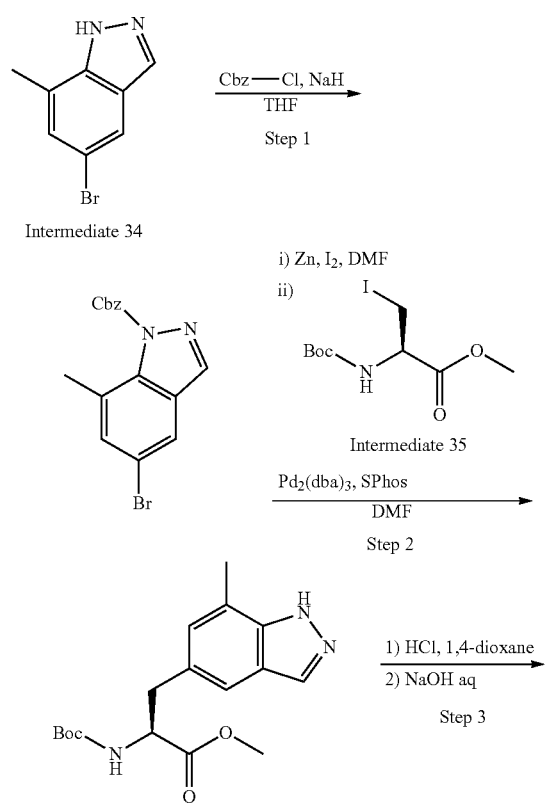

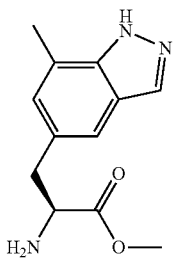

Intermediate 65

Route 19_Step 1

To a stirred solution of 5-bromo-7-methyl-1H-indazole (Intermediate 34) (10 g, 47.37 mmol) in THF (150 mL) at 0° C., were added sodium hydride (60% in mineral oil) (2.89 g, 71.05 mmol) and 50% Cbz-Cl in toluene (19.34 mL, 56.84 mmol). The reaction mixture was stirred at 0° C. for 2 h. The reaction mixture was then quenched with H$_2$O and extracted with EtOAc (2×200 mL). The combined organic layers were washed with saturated aqueous NaHCO$_3$ (100 mL) and brine (100 mL), dried (Na$_2$SO$_4$) and concentrated in vacuo. The residue was purified by flash chromatography (SiO$_2$, petroleum ether-EtOAc) to give benzyl 5-bromo-7-methyl-1H-indazole-1-carboxylate (10 g, 61%).

LC-MS (ESI+): 345.0 [M+H].

Route 19_Step 2

The reaction was implemented on 10×1 g batches of benzyl 5-bromo-7-methyl-1H-indazole-1-carboxylate and combined for purification.

To a stirred suspension of activated zinc powder (944 mg, 14.45 mmol) in dry DMF (3 mL), was added iodine (75 mg, 0.28 mmol). The reaction mixture was heated at 50° C., followed by the addition of methyl (R)-2-((tert-butoxycarbonyl)amino)-3-iodopropanoate (Intermediate 35) (1.9 g, 5.79 mmol) with continued heating for 1 h to obtain the organo zinc reagent. Then to a degassed solution of benzyl 5-bromo-7-methyl-1H-indazole-1-carboxylate (1 g, 2.89 mmol) and SPhos (35.5 mg, 0.08 mmol) in DMF (2 mL), the organo zinc reagent and Pd$_2$(dba)$_3$ were added. The resultant reaction mixture was heated at 70° C. for 16 h. The reaction mixture was quenched with H$_2$O and extracted with EtOAc (2×20 mL). The combined organic layers were washed with brine (100 mL), dried (Na$_2$SO$_4$) and concentrated in vacuo. The residue was purified by flash chromatography (SiO$_2$, petroleum ether-EtOAc) to give methyl (S)-2-((tert-butoxycarbonyl)amino)-3-(7-methyl-1H-indazol-5-yl)propanoate (2.2 g, 21%).

LC-MS (ESI+): 334.2 [M+H].

Route 19_Step 3

To a solution of methyl (S)-2-((tert-butoxycarbonyl)amino)-3-(7-methyl-1H-indazol-5-yl)propanoate (1 g, 3 mmol) in 1,4-dioxane (20 mL) was added 4M HCl in 1,4-dioxane (5 mL). The reaction mixture was stirred at room temperature until complete and was then concentrated in vacuo. The resulting residue was dissolved in H$_2$O (50 mL) and basified to pH 8 by the addition aqueous 2M NaOH, then extracted with EtOAc. The organic layer was dried (Na$_2$SO$_4$) and concentrated in vacuo to give methyl (S)-2-amino-3-(7-methyl-1H-indazol-5-yl)propanoate (Intermediate 65) (699 mg, 100%).

The characterisation for Intermediate 65 is in Table 2.

Route 20

Alternative Procedure for the Preparation of Macrocycle Precursors, as Exemplified by the Preparation of Intermediate 26, Tert-butyl (E)-methyl(2-(2-((3-(2'-oxo-1',2'-dihydrospiro[piperidine-4,4'-pyrido[2,3-d][1,3]oxazin]-6'-yl)allyl)oxy)ethoxy)ethyl)carbamate Route 21

Preparation of Intermediate 27, Tert-Butyl (R)-5-(3-Methoxy-2-(((4-nitrophenoxy)carbonyl)oxy)-3-oxo-propyl)-7-methyl-1H-indazole-1-carboxylate

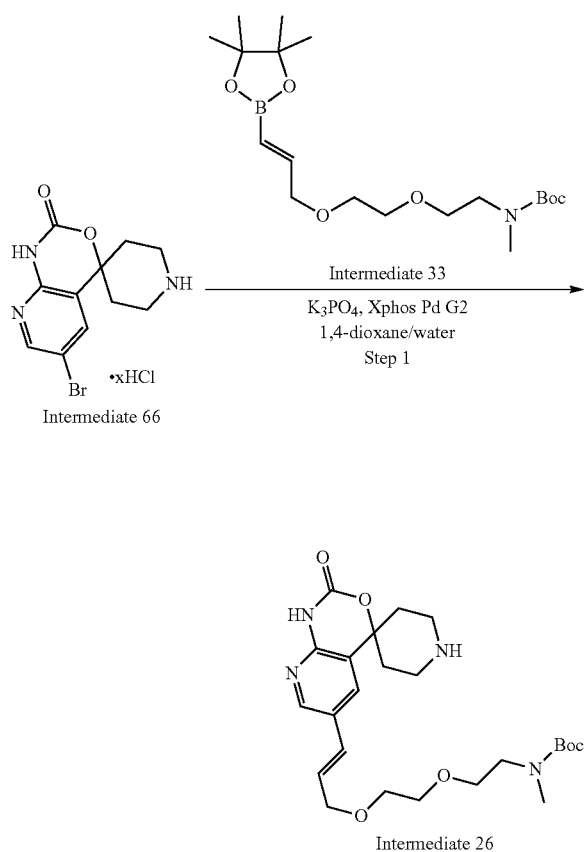

Route 20_Step 1

To a suspension of 6'-bromospiro[piperidine-4,4'-pyrido[2,3-d][1,3]oxazin]-2'(1'H)-one hydrochloride salt (Intermediate 66) (153 mg, 0.375 mmol) and tert-butyl (E)-methyl(2-(2-((3-(4,4,5,5-tetramethyl-1,3,2-dioxaborolan-2-yl)allyl)oxy)ethoxy)ethyl)carbamate (Intermediate 33) (217 mg, 0.563 mmol) in 1,4-dioxane (2 mL) was added $H_2O$ (0.4 mL) followed by $K_3PO_4$ (159 mg, 0.751 mmol). The reaction mixture was degassed with argon for 5 mins and to this was then added XPhosPdG2 (35.4 mg, 0.0451 mmol) and the mixture was degassed for an additional 5 mins. The vial was sealed and was heated at 105° C. for 1.5 h. The reaction mixture was diluted with DCM and the aqueous layer was further extracted with DCM (2×10 mL). The combined organic layers were dried ($Na_2SO_4$) and concentrated in vacuo. The resulting residue was purified by flash chromatography ($SiO_2$, DCM-MeOH/$NH_4OH$) to give tert-butyl (E)-methyl(2-(2-((3-(2'-oxo-1',2'-dihydrospiro[piperidine-4,4'-pyrido[2,3-d][1,3]oxazin]-6'-yl)allyl)oxy)ethoxy)ethyl)carbamate (Intermediate 26) (110 mg, 56%).

The characterisation for Intermediate 26 is in Table 2.

Route 21_Step 1

To a solution of methyl (R)-2-hydroxy-3-(7-methyl-1H-indazol-5-yl)propanoate (Intermediate 67) (250 mg, 1.07 mmol) in DCM (10 mL) was added DMAP (6 mg, 0.05 mmol), followed by $Boc_2O$ (233 mg, 1.28 mmol). The reaction mixture was stirred at room temperature until the starting alcohol had disappeared. To this was then added 4-nitrophenyl chloroformate (264 mg, 1.28 mmol), $Et_3N$ (570 µL, 3.21 mmol). The reaction mixture was stirred at room temperature for 1 h and was then washed with saturated aqueous $KHSO_4$ (5 mL) and then with saturated aqueous $NaHCO_3$ (5×5 mL). The organic layer was dried ($Na_2SO_4$) and concentrated in vacuo. The resulting residue was purified by flash chromatography ($SiO_2$, cyclohexane-EtOAc) to give tert-butyl (R)-5-(3-methoxy-2-(((4-nitrophenoxy)carbonyl)oxy)-3-oxopropyl)-7-methyl-1H-indazole-1-carboxylate (Intermediate 27) (270 mg, 50%).

The characterisation for Intermediate 27 is in Table 2.

Route 22

Alternative Procedure for the Preparation of Vinyl Boronates, as Exemplified by the Preparation of Intermediate 68, Tert-butyl (E)-methyl(3-(2-((3-(4,4,5,5-tetramethyl-1,3,2-dioxaborolan-2-yl)allyl)oxy)ethoxy)propyl)carbamate

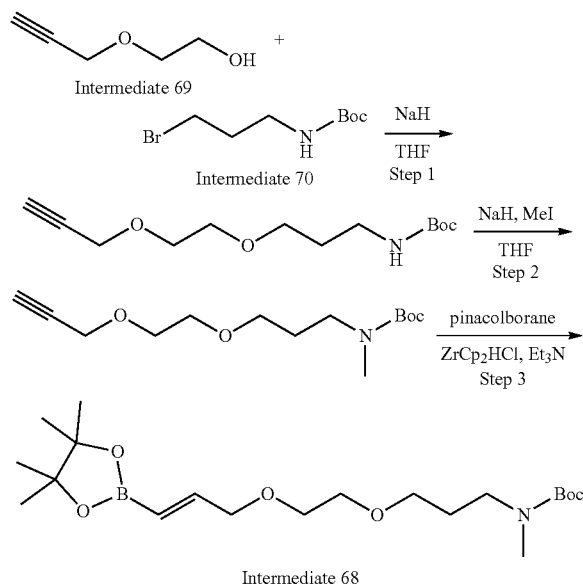

Route 22_Step 1

Into a suspension of sodium hydride (60% in mineral oil) (256 mg, 6.39 mmol) in dry THF (4.65 mL) at 0° C. was added a solution of 2-(prop-2-yn-1-yloxy)ethan-1-ol (Intermediate 69) (160 mg, 1.60 mmol) in dry THF (9.28 mL) over 10 mins. After stirring the resulting reaction mixture for 10 mins at 0° C., s solution of tert-butyl (3-bromopropyl) carbamate (951 mg, 3.20 mmol) (Intermediate 70) in dry THF (3.48 mL) was added over 10 mins. The reaction mixture was stirred at room temperature overnight and was then diluted with saturated aqueous NaHCO$_3$/H$_2$O (1:1, 30 mL) and EtOAc (10 mL). The aqueous layer was further extracted with EtOAc (3×10 mL). The combined organic layers were washed with saturated aqueous NaHCO$_3$ (10 mL), dried (Na$_2$SO$_4$) and concentrated in vacuo. The resulting residue was purified by flash chromatography (SiO$_2$, cyclohexane-EtOAc) to give tert-butyl (3-(2-(prop-2-yn-1-yloxy)ethoxy)propyl)carbamate (184 mg, 45%).

LC-MS (ESI+): 158.04 [M+H−Boc].

Route 22_Step 2

To an argon purged solution of tert-butyl (3-(2-(prop-2-yn-1-yloxy)ethoxy)propyl)carbamate (322 mg, 1.25 mmol) in DMF (3.0 mL) at 0° C. was added portion wise sodium hydride (60% in mineral oil) (60.0%, 75.1 mg, 1.88 mmol). The reaction mixture was stirred at 0° C. for 5 mins and to this was then added methyliodide (213 mg, 1.50 mmol). The reaction mixture was stirred at room temperature for 3 h and was then diluted with saturated aqueous NH$_4$Cl (10 mL) and EtOAc (15 mL). The aqueous layer was further extracted with EtOAc (2×10 mL). The combined organic layers were washed saturated aqueous NH$_4$CO$_3$ (×2), dried (Na$_2$SO$_4$) and concentrated in vacuo. The resulting residue was purified by flash chromatography (SiO$_2$, cyclohexane-EtOAc) to give tert-butyl methyl(3-(2-(prop-2-yn-1-yloxy)ethoxy)propyl)carbamate (270 mg, 78%).

LC-MS (ESI+): 172.07 [M+H−Boc].

Route 22_Step 3

Into neat tert-butyl methyl(3-(2-(prop-2-yn-1-yloxy)ethoxy)propyl)carbamate (160 mg, 0.590 mmol) were added pinacolborane (113 mg, 0.884 mmol), Et$_3$N (6.0 mg, 0.059 mmol) and ZrCp$_2$HCl (15 mg, 0.059 mmol). The suspension was stirred at 65° C. for 2 h. and was then diluted with saturated aqueous NH$_4$Cl (5 mL) and EtOAc (10 mL). The aqueous layer was further extracted with EtOAc (2×5 mL). The combined organics were washed with saturated aqueous NaHCO$_3$, dried (Na$_2$SO$_4$) and concentrated in vacuo to give tert-butyl (E)-methyl(3-(2-((3-(4,4,5,5-tetramethyl-1,3,2-dioxaborolan-2-yl)allyl)oxy)ethoxy)propyl)carbamate (Intermediate 68) (235 mg, 100%) which was used without further purification.

The characterisation for Intermediate 68 is in Table 2.

Route 23

Preparation of Intermediate 24, Isomer 1: 2-chloro-1'-((2-(trimethylsilyl)ethoxy)methyl)-5,7-dihydrospiro[cyclopenta[b]pyridine-6,3'-pyrrolo[2,3-b]pyridin]-2'(1'H)-one and Intermediate 25, Isomer 2: 2-chloro-1'-((2-(trimethylsilyl)ethoxy)methyl)-5,7-dihydrospiro[cyclopenta[b]pyridine-6,3'-pyrrolo[2,3-b]pyridin]-2'(1'H)-one

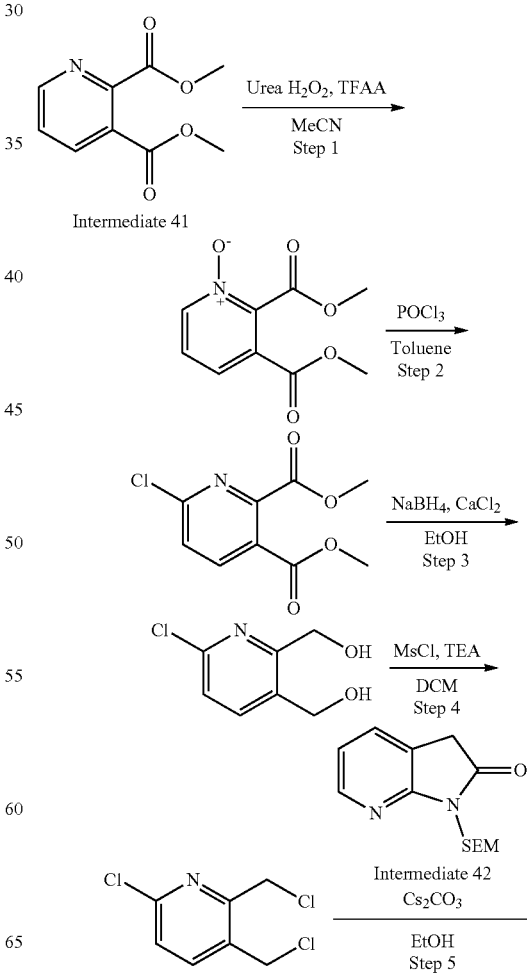

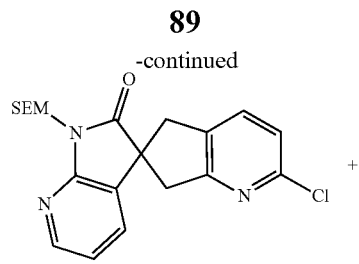

Intermediate 24

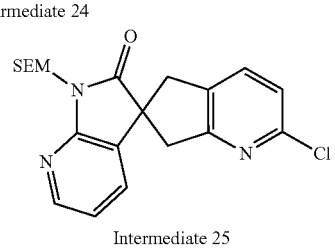

Intermediate 25

Route 23_Step 1

To a suspension of dimethyl pyridine-2,3-dicarboxylate (Intermediate 41) (500 g, 2.56 mol) in MeCN (5 L) at 0° C. was added portion wise urea hydrogen peroxide (482 g, 5.12 mol) followed by the drop wise addition of TFAA (722 mL, 5.12 mol). The reaction mixture was stirred at room temperature for 3 h and was then partitioned between saturated aqueous $Na_2CO_3$ (3 L) and EtOAc (2×4 L). The combined organic layers were washed with brine (2.5 L), dried ($Na_2SO_4$) and concentrated in vacuo to give 2,3-bis(methoxycarbonyl)pyridine 1-oxide (510 g, 94%).

LC-MS (ESI+): 212.0 [M+H].

Route 23_Step 2

To a suspension of 2,3-bis(methoxycarbonyl)pyridine 1-oxide (510 g, 2.41 mol) in toluene (2.5 L) at 0° C. was added $POCl_3$ (1.5 L, 19.3 mol). The reaction mixture was heated at 120° C. for 12 h and was then concentrated in vacuo. The resulting residue was poured into ice cold $H_2O$ (5 L), neutralised to pH 8 by the addition of solid $NaHCO_3$ and extracted with EtOAc (5 L). The organic layer was washed with brine (2.5 L), dried ($Na_2SO_4$) and concentrated in vacuo to give dimethyl 6-chloropyridine-2,3-dicarboxylate (320 g, 58%).

LC-MS (ESI+): 230.0 [M+H].

Route 23_Step 3

To a stirred solution of dimethyl 6-chloropyridine-2,3-dicarboxylate (320 g, 1.39 mol) in EtOH (3 L) at 0° C. was added portion wise sodium borohydride (316 g, 8.36 mol) followed by the drop wise addition of $CaCl_2$ (685 g, 4.18 mol) as a solution in EtOH (2 L) over a period of 1.5 h (exothermic reaction—efficient cooling was needed). The reaction mixture was stirred at room temperature for 20 h and was then quenched at 0° C. by the addition of 2M HCl solution, until a clear solution was observed. The reaction mixture was stirred at room temperature for 1 h and was then diluted with EtOAc (3 L). The organic layer was washed with 1M HCL (2 L). The pH of the combined aqueous layers was adjusted to pH 7 by the drop wise addition of saturated aqueous $NaHCO_3$ and the resultant aqueous layer was extracted with EtOAc (2×5 L). The combined organic layers were washed with brine (5 L), dried ($Na_2SO_4$) and concentrated in vacuo. The crude mass obtained was triturated with MeOH (1 L) and the solid was collected by filtration, washed with MeOH (200 mL) and dried to give (6-chloropyridine-2,3-diyl)dimethanol (130 g, 53%).

LC-MS (ESI+): 174.1 [M+H].

Route 23_Step 4

To a solution of (6-chloropyridine-2,3-diyl)dimethanol (120 g, 0.691 mol) and $Et_3N$ (480 mL, 2.73 mol) in dry DCM (1.8 L) at 0° C. was added methanesulfonyl chloride (160 mL, 7.16 mol). The reaction mixture was stirred at room temperature for 16 h and was then partitioned between saturated aqueous $NH_4Cl$ solution (2 L) and extracted with DCM (1 L). The organic layer was washed with brine (1.5 L), dried ($Na_2SO_4$) and concentrated in vacuo to give 6-chloro-2,3-bis(chloromethyl)pyridine (120 g, 82%).

LC-MS (ESI+): 209.9 [M+H].

Route 23_Step 5

To a suspension of 1-((2-(trimethylsilyl)ethoxy)methyl)-1,3-dihydro-2H-pyrrolo[2,3-b]pyridin-2-one (Intermediate 42) (120 g, 0.453 mol) and 6-chloro-2,3-bis(chloromethyl)pyridine (120 g, 0.543 mol) in EtOH (1.8 L) was added $Cs_2CO_3$ (368.7 g, 1.13 mol). The reaction mixture was stirred at room temperature for 16 h and was then quenched by the addition of ice cold $H_2O$ (2 L) and extracted with EtOAC (2×3 L). The combined organic layers were washed with brine (3.5 L), dried ($Na_2SO_4$) and concentrated in vacuo. The crude mass was purified by flash chromatography ($SiO_2$, petroleum ether-EtOAc) to give 2-chloro-1'-((2-(trimethylsilyl)ethoxy)methyl)-5,7-dihydrospiro[cyclopenta[b]pyridine-6,3'-pyrrolo[2,3-b]pyridin]-2'(1'H)-one (54 g, 30%). The racemic compound was further purified by Chiral SFC (flow rate: 3 ml/min, column: YMC Cellulose SC, co-solvent: 30%, IPA, outlet pressure: 100 bar, temperature: 35° C.) to give Isomer 1,2-chloro-1'-((2-(trimethylsilyl)ethoxy)methyl)-5,7-dihydrospiro[cyclopenta[b]pyridine-6,3'-pyrrolo[2,3-b]pyridin]-2'(1'H)-one and (Intermediate 24) (19 g) (retention time 2.96 min) and Isomer 2,2-chloro-1'-((2-(trimethylsilyl)ethoxy)methyl)-5,7-dihydrospiro[cyclopenta[b]pyridine-6,3'-pyrrolo[2,3-b]pyridin]-2'(1'H)-one (Intermediate 25) (22 g) (retention time 3.55 min).

The characterisation for Intermediate 24 and Intermediate 25 are in Table 2.

Route 24

Preparation of Intermediate 66, 6'-Bromospiro[piperidine-4,4'-pyrido[2,3-d][1,3]oxazin]-2'(1'H)-one hydrochloride salt

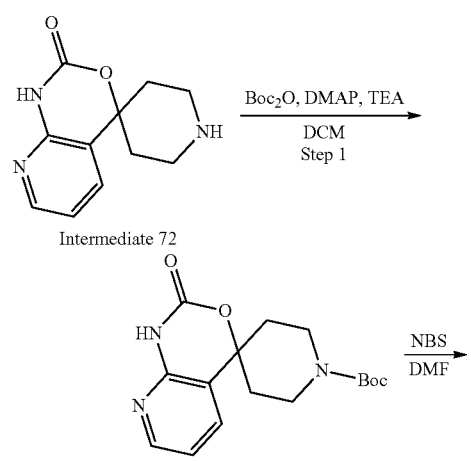

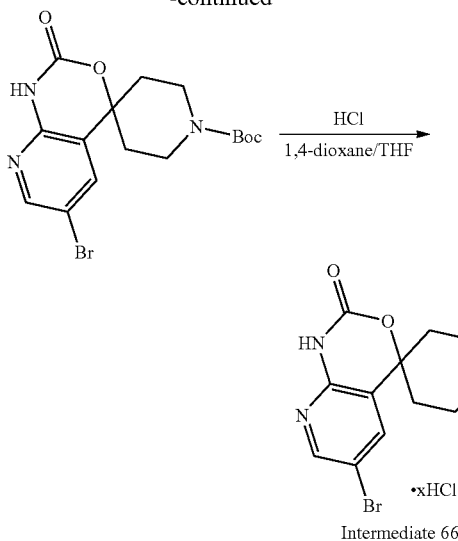

Intermediate 66

Route 24_Step 1

To a solution of spiro[piperidine-4,4'-pyrido[2,3-d][1,3]oxazin]-2'(1'H)-one (Intermediate 72) (900 mg, 4.11 mmol) in dry DCM (36 ml) were added Et₃N (1.14 ml, 8.21 mmol) and DMAP (30 mg, 0.246 mmol), followed by the portion wise addition of Boc₂O (1.08 g, 4.93 mmol). The reaction mixture was stirred at room temperature overnight and was then diluted with DCM (30 ml) and saturated aqueous NH₄Cl/H₂O (1:1; 50 ml). The organic layer was washed with saturated aqueous NaHCO₃ (50 ml), dried (MgSO₄) and concentrated in vacuo to give tert-butyl 2'-oxo-1',2'-dihydrospiro[piperidine-4,4'-pyrido[2,3-d][1,3]oxazine]-1-carboxylate (1.05 g, 80%).

LC-MS (ESI+): 320.14 [M+H].

Route 24_Step 2

A suspension of give tert-butyl 2'-oxo-1',2'-dihydrospiro[piperidine-4,4'-pyrido[2,3-d][1,3]oxazine]-1-carboxylate (1.05 g, 3.29 mmol) in the dry DMF (10 ml) at 0° C. was added NBS (1.17 g, 6.58 mmol). The reaction mixture was stirred at room temperature overnight and was then poured into the ice cold H₂O (200 ml). The resulting precipitate was collected by filtration, washed with H₂O (3×30 mL) and diethyl ether (2×30 mL). The solid was dried in a vacuum oven at 40° C. for 7 h to give tert-butyl 6'-bromo-2'-oxo-1',2'-dihydrospiro[piperidine-4,4'-pyrido[2,3-d][1,3]oxazine]-1-carboxylate (759 mg, 58%).

LC-MS (ESI+): 343.94 [M+H−ᵗBu]

Route 24_Step 3

To a solution of tert-butyl 6'-bromo-2'-oxo-1',2'-dihydrospiro[piperidine-4,4'-pyrido[2,3-d][1,3]oxazine]-1-carboxylate (150 mg, 0.377 mmol) in THF (4.6 mL) at 0° C. was added 4M HCl in 1,4-dioxane (2.31 mL) and the reaction mixture was stirred at room temperature for 2 h. Further 4M HCl in 1,4-dioxane (1 mL) was added and the reaction mixture was stirred at room temperature overnight. The reaction mixture was concentrated in vacuo to give 6'-bromospiro[piperidine-4,4'-pyrido[2,3-d][1,3]oxazin]-2'(1'H)-one hydrochloride salt (139 mg, 91%) which was used without further purification.

The characterisation for Intermediate 66 is in Table 2.

Route 25

Preparation of Intermediate 67, Methyl (R)-2-hydroxy-3-(7-methyl-1H-indazol-5-yl)propanoate

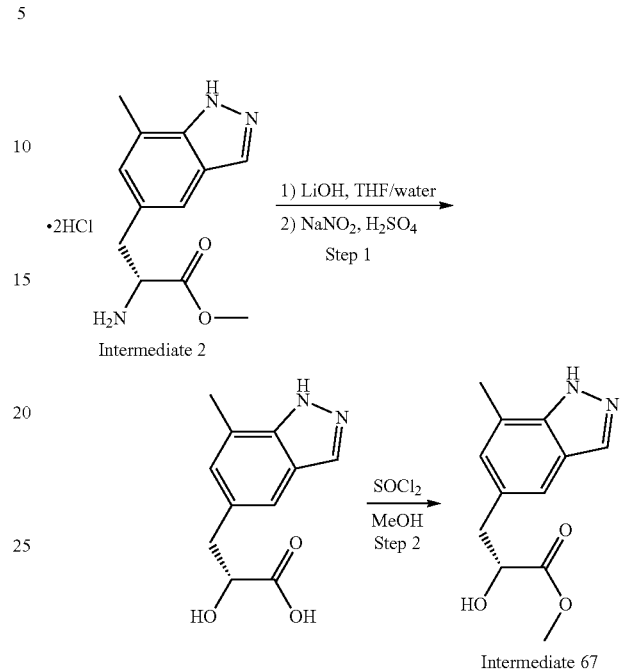

Intermediate 67

Route 25_Step 1

A solution of methyl (R)-2-amino-3-(7-methyl-1H-indazol-5-yl)propanoate dihydrochloride (Intermediate 2) (2 g, 6.7 mmol) in H₂O (100 mL) at 0° C. was basified to pH 8 using saturated aqueous NaHCO₃. The free base was extracted with EtOAc and the organic layer was dried (Na₂SO₄) and concentrated in vacuo to give crude methyl (R)-2-amino-3-(7-methyl-1H-indazol-5-yl)propanoate (1.5 g). This was then dissolved in THF (20 mL) and H₂O (10 mL) and to this was added LiOH (309 mg, 12.9 mmol). The reaction mixture was stirred at room temperature for 1 h. The reaction mixture was concentrated in vacuo to remove the THF and the resulting residue was diluted with H₂O (50 mL) cooled to 0° C. and to this was then added concentrated H₂SO₄ (1.05 mL, 38.6 mmol), followed by the dropwise addition of NaNO₂ (2.66 g, 38.6 mmol) as a solution in H₂O (20 mL). The reaction mixture was stirred at 0° C. for 20 mins then at room temperature overnight. To this was added further NaNO₂ (1 g) and stirring was continued for 4 h. The pH was adjusted to pH 4 using 20% aqueous NaOH and the product was extracted with EtOAc. The organic layer was dried (Na₂SO₄) and concentrated in vacuo to give (R)-2-hydroxy-3-(7-methyl-1H-indazol-5-yl)propanoic acid (1.5 g, crude).

LC-MS (ESI+): 221.50 [M+H]

Route 25_Step 2

To a solution of (R)-2-hydroxy-3-(7-methyl-1H-indazol-5-yl)propanoic acid (1.5 g, 6.6 mmol) in dry MeOH (40 mL) at 0° C. was added SOCl₂ (741 µL, 10.2 mmol). The reaction mixture was stirred for 0.5 h and then allowed to warm to room temperature and stirring was continued overnight. The reaction mixture was concentrated in vacuo and the resulting residue was dissolved in saturated aqueous NaHCO₃ (100 mL) and extracted with DCM (3×30 mL). The combined organic layers were dried (Na₂SO₄) and concentrated in vacuo. This was then purified by flash chromatography (SiO$_2$, DCM-MeOH) to give methyl (R)-2-hydroxy-3-(7-methyl-1H-indazol-5-yl)propanoate (Intermediate 67) (570 mg, 33%).

The characterisation for Intermediate 67 is in Table 2.

Synthesis of Examples

The examples of the invention may be prepared according to one of the following synthetic procedures, Routes A, B, C or D or modifications thereof. Each of these routes is exemplified by the synthesis of at least one example of the invention.

In addition, examples of the invention may be prepared by transformation of other examples of the invention, for example according to the procedures of Routes E, F or G, each of which is also exemplified below.

Note from NMR characterisation the presence of two distinct solution conformers was often evident for examples of the invention General Synthetic Procedures:
Route A Exemplified by the synthesis of Example 1-1, (1S,10R,20E)-12-methyl-10-[(7-methyl-1H-indazol-5-yl)methyl]-15,18-dioxa-5,9,12,24,26-pentazapentacyclo[20.5.2.11,4.13,7.025,28]hentriaconta-3,5,7(30),20,22(29),23,25(28)-heptaene-8,11,27-trione (1S,10R,20E)-12-methyl-10-[(7-methyl-1H-indazol-5-yl)methyl]-5,9,12,24,26-pentazapentacyclo[20.5.2.11,4.13,7.025,28]hentriaconta-3,5,7(30),20,22(29),23,25(28)-heptaene-8,11,27-trione

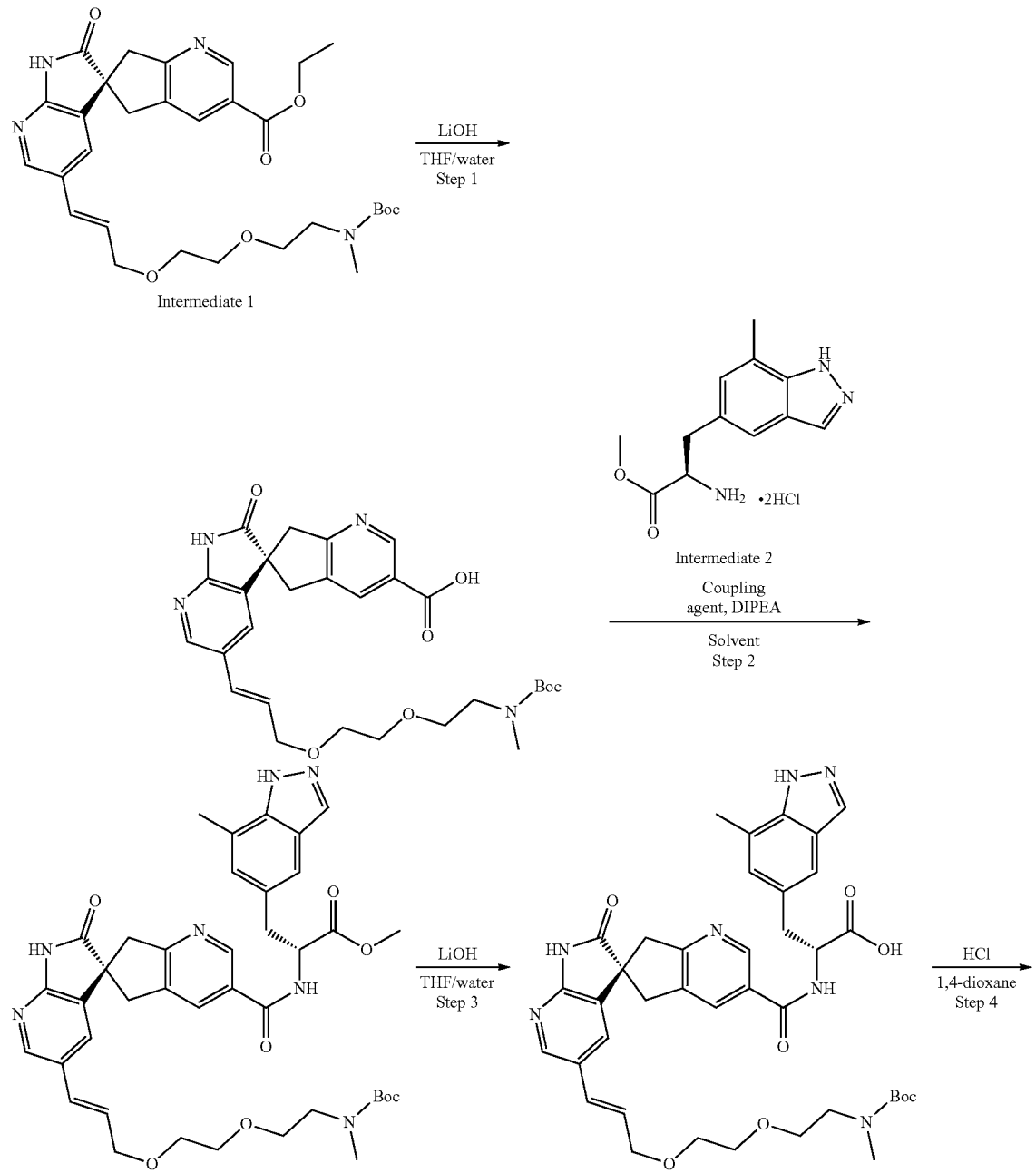

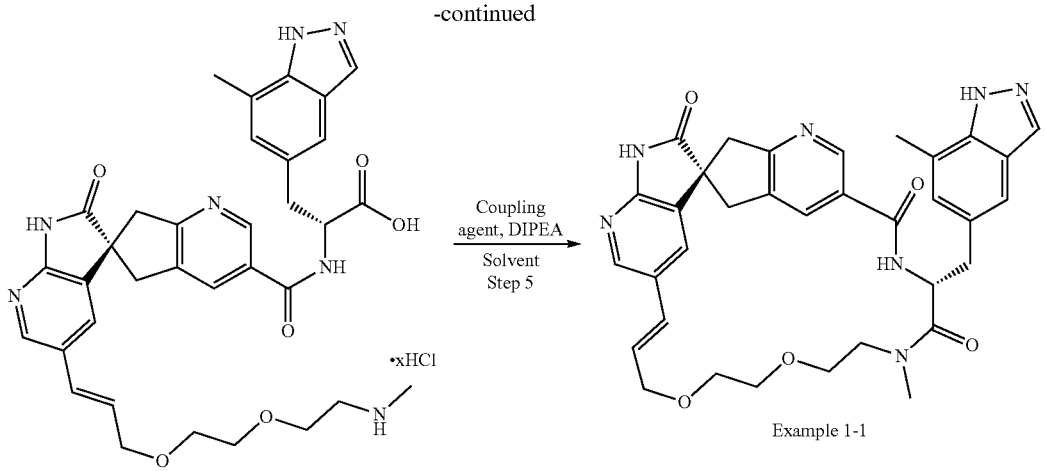

Example 1-1

Route A_Step 1

To a solution of ethyl (S,E)-2'-oxo-5'-(2,2,5-trimethyl-4-oxo-3,8,11-trioxa-5-azatetradec-13-en-14-yl)-1',2',5,7-tetrahydrospiro[cyclopenta[b]pyridine-6,3'-pyrrolo[2,3-b]pyridine]-3-carboxylate (Intermediate 1) (390 mg, 0.688 mmol) in THF (10 mL) was added 1M LiOH (2.75 mL, 2.75 mmol). The reaction mixture was stirred at room temperature for 2 h. The solvent was concentrated in vacuo and the residue was partitioned between H$_2$O (30 mL) and EtOAc (15 mL). The pH of the mixture was adjusted to pH 4 using a 1M HCl solution. The aqueous layer was further extracted with EtOAc (3×10 mL) and the combined organic layers were dried (Na$_2$SO$_4$), filtered and concentrated in vacuo to give (S,E)-2'-oxo-5'-(2,2,5-trimethyl-4-oxo-3,8,11-trioxa-5-azatetradec-13-en-14-yl)-1',2',5,7-tetrahydrospiro[cyclopenta[b]pyridine-6,3'-pyrrolo[2,3-b]pyridine]-3-carboxylic acid (288 mg, 78%).

LC-MS (ESI+): 539.20 [M+H].

Route A_Step 2

To a solution of (S,E)-2'-oxo-5'-(2,2,5-trimethyl-4-oxo-3,8,11-trioxa-5-azatetradec-13-en-14-yl)-1',2',5,7-tetrahydrospiro[cyclopenta[b]pyridine-6,3'-pyrrolo[2,3-b]pyridine]-3-carboxylic acid (250 mg, 0.464 mmol) in DMA (8 mL), at 0° C. was added DIPEA (283 µL, 1.62 mmol) followed by the appropriate coupling reagent for example HATU (194 mg, 0.510 mmol). The reaction mixture was stirred at 0° C. for 1 h. To this was then added methyl (R)-2-amino-3-(7-methyl-1H-indazol-5-yl)propanoate dihydrochloride (Intermediate 2) (163 mg, 0.533 mmol) and the mixture was stirred at room temperature for 90 mins. The mixture was partitioned between EtOAc (30 mL) and saturated aqueous NaHCO$_3$/H$_2$O (3:1) (30 mL). The organic layer was washed with further saturated aqueous NaHCO$_3$ (3×15 mL), dried (Na$_2$SO$_4$), filtered and concentrated in vacuo to give methyl (R)-3-(7-methyl-1H-indazol-5-yl)-2-((S)-2'-oxo-5'-((E)-2,2,5-trimethyl-4-oxo-3,8,11-trioxa-5-azatetradec-13-en-14-yl)-1',2',5,7-tetrahydrospiro[cyclopenta[b]pyridine-6,3'-pyrrolo[2,3-b]pyridine]-3-carboxamido)propanoate (351 mg, 99%).

LC-MS (ESI+): 754.20 [M+H].

Route A_Step 3

To a solution of methyl (R)-3-(7-methyl-1H-indazol-5-yl)-2-((S)-2'-oxo-5'-((E)-2,2,5-trimethyl-4-oxo-3,8,11-trioxa-5-azatetradec-13-en-14-yl)-1',2',5,7-tetrahydrospiro[cyclopenta[b]pyridine-6,3'-pyrrolo[2,3-b]pyridine]-3-carboxamido)propanoate (351 mg, 0.462 mmol) in THF (9 mL) was added 1 M LiOH (1.86 mL, 1.86 mmol). The reaction mixture was stirred at room temperature for 1 h. The solvent was concentrated in vacuo and the residue was partitioned between H$_2$O (30 mL) and EtOAc (15 mL). The pH of the mixture was adjusted to pH 4 using a 1M HCl solution. The aqueous layer was further extracted with EtOAc (3×10 mL) and the combined organic layers were dried (Na$_2$SO$_4$), filtered and concentrated in vacuo to give (R)-3-(7-methyl-1H-indazol-5-yl)-2-((S)-2'-oxo-5'-((E)-2,2,5-trimethyl-4-oxo-3,8,11-trioxa-5-azatetradec-13-en-14-yl)-1',2',5,7-tetrahydrospiro[cyclopenta[b]pyridine-6,3'-pyrrolo[2,3-b]pyridine]-3-carboxamido)propanoic acid (297 mg, 86%).

LC-MS (ESI+): 740.38 [M+H].

Route A_Step 4

(R)-3-(7-methyl-1H-indazol-5-yl)-2-((S)-2'-oxo-5'-((E)-2,2,5-trimethyl-4-oxo-3,8,11-trioxa-5-azatetradec-13-en-14-yl)-1',2',5,7-tetrahydrospiro[cyclopenta[b]pyridine-6,3'-pyrrolo[2,3-b]pyridine]-3-carboxamido)propanoic acid (297 mg, 0.401 mmol) was dissolved in dry 1,4-dioxane (12 mL) and cooled to 0° C. To this was added 4M HCl in 1,4-dioxane (4.0 mL) and the reaction mixture stirred at room temperature for 1 h. The reaction mixture was 50 concentrated in vacuo to give (R)-3-(7-methyl-1H-indazol-5-yl)-2-((S)-5'-((E)-3-(2-(2-(methylamino)ethoxy)ethoxy)prop-1-en-1-yl)-2'-oxo-1',2',5,7-tetrahydrospiro[cyclopenta[b]pyridine-6,3'-pyrrolo[2,3-b]pyridine]-3-carboxamido)propanoic acid hydrochloride salt (311 mg, 100%).

LC-MS (ESI+): 640.39 [M+H].

Route A_Step 5

To a solution of DIPEA (414 µL, 2.38 mmol) and the appropriate coupling reagent for example HATU (301 mg, 0.792 mmol) in the appropriate dry solvent for example DMA (40 mL) was added a solution of (R)-3-(7-methyl-1H-indazol-5-yl)-2-((S)-5'-((E)-3-(2-(2-(methylamino)ethoxy)ethoxy)prop-1-en-1-yl)-2'-oxo-1',2',5,7-tetrahydrospiro[cyclopenta[b]pyridine-6,3'-pyrrolo[2,3-b]pyridine]-3-carboxamido)propanoic acid hydrochloride salt (311 mg, 0.396 mmol) in dry DMA (20 mL) dropwise over 15 mins. The reaction mixture was partitioned between EtOAc (50 mL) and saturated aqueous NaHCO$_3$/H$_2$O (1:1) (300 mL). The aqueous layer was further extracted with DCM/IPA (3:1) (10×15 mL). The combined organic layers were dried (Na$_2$SO$_4$), filtered and concentrated in vacuo to afford the crude product (551 mg). The residue was purified using purification method A to give (1S,10R,20E)-12-methyl-10-

[(7-methyl-1H-indazol-5-yl)methyl]-15,18-dioxa-5,9,12,24,26-pentazapentacyclo[20.5.2.1¹,⁴.1³,⁷.0²⁵,²⁸]hentria-conta-3,5,7(30),20,22(29),23,25(28)-heptaene-8,11,27-trione (Example 1-1) (127 mg, 51%).

LC-MS (ESI+): 622.17 [M+H].

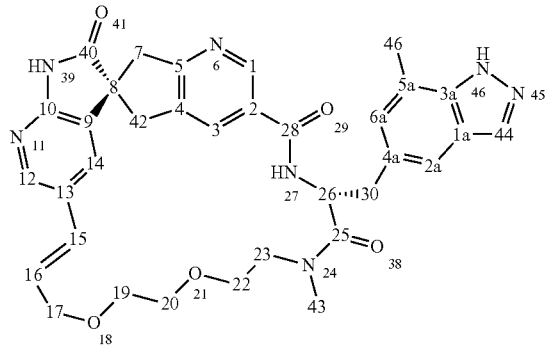

¹H NMR (500 MHz, CD₃OD): δ ppm 2.55 (s, 6H, 46), 2.68-2.77 (m, 2H, 23<">), 2.94 (s, 3H, 43), 2.98 (s, 3H, 43), 3.07 (d, J=16.5 Hz, 2H, 42<">), 3.14 (d, J=15.6 Hz, 2H, 7<">), 3.14-3.20 (m, 2H, 30<">), 3.30 (d, J=7.6 Hz, 2H, 30<'>), 3.44-3.56 (m, 4H, 19), 3.56-3.63 (m, 4H, 20), 3.65 (t, J=6.0 Hz, 4H, 22), 3.68 (d, J=16.0 Hz, 2H, 42<'>), 3.80 (d, J=15.0 Hz, 2H, 7<'>), 3.94-4.06 (m, 2H, 17<">), 4.06-4.14 (m, 2H, 17<'>), 4.33 (dt, J=14.2, 5.4 Hz, 2H, 23<'>), 5.38 (d, J=7.5 Hz, 1H, 26), 5.42 (t, J=7.5 Hz, 1H, 26), 5.68-5.76 (m, 1H, 16), 5.77-5.86 (m, 1H, 16), 6.44 (d, J=16.0 Hz, 1H, 15), 6.47 (d, J=16.2 Hz, 1H, 15), 6.59 (d, J=1.5 Hz, 1H, 14), 6.83 (d, J=1.8 Hz, 1H, 14), 7.17 (s, 1H, 6a), 7.20 (s, 1H, 6a), 7.50 (s, 1H, 2a), 7.54 (s, 1H, 2a), 7.94 (d, J=1.8 Hz, 1H, 12), 7.96 (d, J=1.8 Hz, 1H, 12), 7.97 (s, 2H, 44), 8.18 (s, 1H, 3), 8.23 (s, 1H, 3), 8.83 (s, 1H, 1), 8.86 (s, 1H, 1)

¹³C NMR (126 MHz, CD₃OD): δ ppm 17.1 (46), 36.5 (43), 39.3 (30), 41.9 (42), 44.7 (7), 49.0 (23), 52.9 (26), 55.8 (8), 69.5 (22), 70.9 (19), 71.5 (20), 72.5 (17), 119.6 (2a), 121.7 (5a), 124.6 (1a), 125.4 (14), 128.1 (16), 128.8 (15), 129.0 (13), 130.0 (6a), 130.2 (2), 131.5 (4a), 131.8 (9), 132.4 (3), 135.4 (44), 136.7 (4), 141.2 (3a), 147.7 (12), 149.8 (1), 156.2 (10), 167.2 (5), 167.9 (28), 173.1 (25), 180.7 (40)

Characterisation data for Example 1-1 is also shown in Table 3.

Route A_1

Exemplification of Route A by the synthesis of Example 1-6, (1S,10R,20E)-12-methyl-10-[(7-methyl-1H-indazol-5-yl)methyl]-18-oxa-5,9,12,24,26-pentazapentacyclo[20.5.2.1¹,⁴.1³,⁷.0²⁵,²⁸]hen-triaconta-3,5,7(30),20,22(29),23,25(28)-heptaene-8,11,27-trione

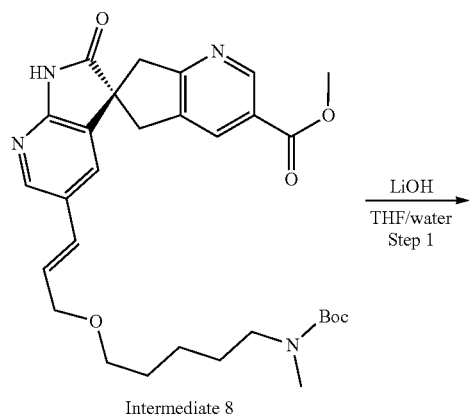

Intermediate 8

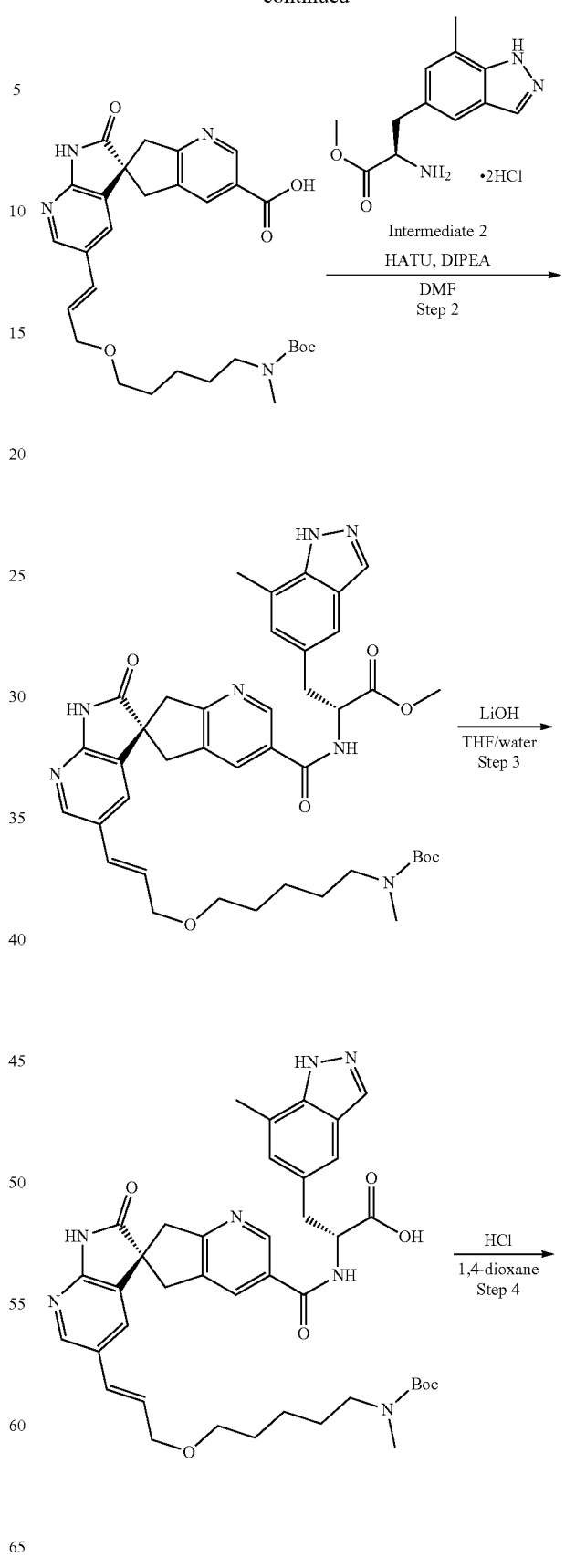

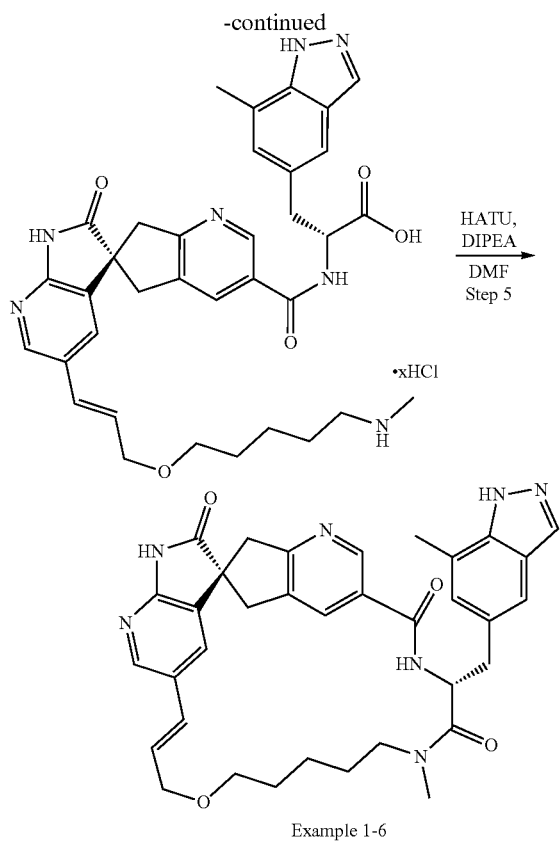

Example 1-6

Route A_1_Step 1

To a solution of methyl (S,E)-5'-(3-((5-((tert-butoxycarbonyl)(methyl)amino)pentyl)oxy)prop-1-en-1-yl)-2'-oxo-1',2',5,7-tetrahydrospiro[cyclopenta[b]pyridine-6,3'-pyrrolo[2,3-b]pyridine]-3-carboxylate (Intermediate 8) (157 mg, 0.272 mmol) in THF (3.6 mL) was added a 1M LiOH (1.09 mL, 1.09 mmol). The reaction mixture was stirred at room temperature for 2 h and was then concentrated in vacuo. The resulting residue was dissolved in H₂O (30 mL) and washed with diethyl ether (2×10 mL). The pH of the aqueous layer was adjusted to pH 4.1 using a 1M HCl solution. The aqueous layer was extracted with DCM/IPA (1:1) (3×20 mL). The combined organic layers were dried (Na₂SO₄) and concentrated in vacuo to give (S,E)-5'-(3-((5-((tert-butoxycarbonyl)(methyl)amino)pentyl)oxy)prop-1-en-1-yl)-2'-oxo-1',2',5,7-tetrahydrospiro[cyclopenta[b]pyridine-6,3'-pyrrolo[2,3-b]pyridine]-3-carboxylic acid (125 mg, 86%).

LC-MS (ESI+): 537.45 [M+H].

Route A_1_Step 2

To a solution of (S,E)-5'-(3-((5-((tert-butoxycarbonyl)(methyl)amino)pentyl)oxy)prop-1-en-1-yl)-2'-oxo-1',2',5,7-tetrahydrospiro[cyclopenta[b]pyridine-6,3'-pyrrolo[2,3-b]pyridine]-3-carboxylic acid (1.10 g, 2.05 mmol) and methyl (R)-2-amino-3-(7-methyl-1H-indazol-5-yl)propanoate dihydrochloride (Intermediate 2) (755 mg, 2.46 mmol) in DMF (25 mL) was added DIPEA (2.19 mL, 12.2 mmol) followed by HATU (857 mg, 2.26 mmol). The reaction mixture was stirred at room temperature for 5 mins and was then diluted with saturated aqueous NaHCO₃/H₂O (1:1) (150 mL) and extracted with EtOAc (4×25 mL). The combined organic layers were washed with saturated aqueous NaHCO₃ (3×25 mL) and LiCl (5% aq, 2×20 mL), dried (Na₂SO₄) and concentrated in vacuo to give methyl (R)-2-((S)-5'-((E)-3-((5-(((tert-butoxycarbonyl)(methyl)amino)pentyl)oxy)prop-1-en-1-yl)-2'-oxo-1',2',5,7-tetrahydrospiro[cyclopenta[b]pyridine-6,3'-pyrrolo[2,3-b]pyridine]-3-carboxamido)-3-(7-methyl-1H-indazol-5-yl)propanoate (1.59 g).

LC-MS (ESI+): 752.75 [M+H].

Route A_1_Step 3

To a solution of methyl (R)-2-((S)-5'-((E)-3-((5-((tert-butoxycarbonyl)(methyl)amino)pentyl)oxy)prop-1-en-1-yl)-2'-oxo-1',2',5,7-tetrahydrospiro[cyclopenta[b]pyridine-6,3'-pyrrolo[2,3-b]pyridine]-3-carboxamido)-3-(7-methyl-1H-indazol-5-yl)propanoate (1.59 g, 2.13 mmol) in THF (41 mL) was added 1M LiOH (8.50 mL, 8.50 mmol) and the reaction mixture was stirred at room temperature for 1 h. The reaction mixture was then concentrated in vacuo and the resulting residue was dissolved in H₂O (150 mL). The pH of the mixture was adjusted to pH 3.6 using a 1M HCl solution and the aqueous layer was extracted with DCM/IPA (2:1) (4×20 mL). The combined organic layers were dried (Na₂SO₄) and concentrated in vacuo to give (R)-2-((S)-5'-((E)-3-((5-((tert-butoxycarbonyl)(methyl)amino)pentyl)oxy)prop-1-en-1-yl)-2'-oxo-1',2',5,7-tetrahydrospiro[cyclopenta[b]pyridine-6,3'-pyrrolo[2,3-b]pyridine]-3-carboxamido)-3-(7-methyl-1H-indazol-5-yl)propanoic acid (1.44 g, 92%).

LC-MS (ESI+): 738.17 [M+H].

Route A_1_Step 4

To a solution of (R)-2-((S)-5'-((E)-3-((5-((tert-butoxycarbonyl)(methyl)amino)pentyl)oxy)prop-1-en-1-yl)-2'-oxo-1',2',5,7-tetrahydrospiro[cyclopenta[b]pyridine-6,3'-pyrrolo[2,3-b]pyridine]-3-carboxamido)-3-(7-methyl-1H-indazol-5-yl)propanoic acid (1.44 g, 1.95 mmol) in dry 1,4-dioxane (25 mL) was added 4M HCl in 1,4-dioxane (19.5 mL, 77.8 mmol) and the reaction mixture was stirred at room temperature for 3 h. This was then concentrated in vacuo to give (R)-3-(7-methyl-1H-indazol-5-yl)-2-((S)-5'-((E)-3-((5-(methylamino)pentyl)oxy)prop-1-en-1-yl)-2'-oxo-1',2',5,7-tetrahydrospiro[cyclopenta[b]pyridine-6,3'-pyrrolo[2,3-b]pyridine]-3-carboxamido)propanoic acid (1.56 g).

LC-MS (ESI+): 638.72 [M+H].

Route A_1_Step 5

To a solution of DIPEA (670 µL, 3.85 mmol) and HATU (1.09 g, 2.882 mmol) in dry DMF (350 mL) was added dropwise a solution of (R)-3-(7-methyl-1H-indazol-5-yl)-2-((S)-5'-((E)-3-((5-(methylamino)pentyl)oxy)prop-1-en-1-yl)-2'-oxo-1',2',5,7-tetrahydrospiro[cyclopenta[b]pyridine-6,3'-pyrrolo[2,3-b]pyridine]-3-carboxamido)propanoic acid (1.51 g, 1.93 mmol) and DIPEA (1.34 mL, 7.69 mmol) in dry DMF (175 mL) over a period of 2 mins. The reaction mixture was then diluted with DCM (100 mL) and saturated aqueous NaHCO₃/H₂O (1:1) (900 mL). The aqueous layer was further extracted with DCM (3×10 mL) and the combined organic layers were dried (Na₂SO₄) and concentrated in vacuo. The resulting solid was dissolved in EtOAc (700 mL) and washed with saturated aqueous NaHCO₃ (3×100 mL), dried (Na₂SO₄) and concentrated in vacuo. The crude material was purified by purification method P to give (1S,10R,20E)-12-methyl-10-[(7-methyl-1H-indazol-5-yl)methyl]-18-oxa-5,9,12,24,26-pentazapentacyclo[20.5.2.11,4.13,7.025,28]hentriaconta-3,5,7(30),20,22(29),23,25(28)-heptaene-8,11,27-trione (Example 1-6) (638 mg, 58.9%)

LC-MS (ESI+): 620.54 [M+H].

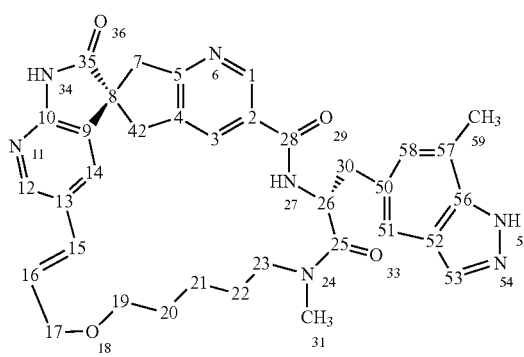

<sup>1</sup>H NMR (600 MHz, DMSO-d<sub>6</sub>): δ ppm 0.85 (br. s., 1H, 21<''>), 0.94-1.01 (m, 1H, 21<'>), 1.06-1.14 (m, 1H, 21<''>), 1.16-1.22 (m, 1H, 21<'>), 1.23-1.33 (m, 2H, 20<''>, 20<'>), 1.39 (br. s., 3H, 20<'', 22<''>), 1.44-1.56 (m, 3H, 22<'>, 20<'>), 2.40-2.44 (m, 1H, 23<''>), 2.45 (br. s., 3H, 59), 2.46 (s, 3H, 59), 2.76 (s, 3H, 31), 2.80-2.87 (m, 1H, 23<''>), 2.93 (s, 3H, 31), 2.95-2.97 (m, 1H, 30<''>), 2.99 (d, J=16.1 Hz, 2H, 7<''>), 3.02-3.05 (m, 1H, 30<''>), 3.09 (d, J=15.6 Hz, 2H, 42<''>), 3.11-3.16 (m, 1H, 30<'>), 3.18-3.28 (m, 5H, 30<'>, 19), 3.45-3.49 (m, 1H, 23<'>), 3.50 (d, J=15.0 Hz, 2H, 42<'>), 3.58 (d, J=16.0 Hz, 1H, 7<'>), 3.57-3.64 (m, 1H, 7<'>), 3.86-3.96 (m, 2H, 17<''>), 3.96-4.03 (m, 2H, 17<'>), 4.04-4.15 (m, 1H, 23<'>), 5.16 (q, J=7.9 Hz, 1H, 26), 5.20 (q, J=8.4 Hz, 1H, 26), 5.58-5.66 (m, 1H, 16), 5.67-5.81 (m, 1H, 16), 6.41 (d, J=15.6 Hz, 1H, 15), 6.43 (d, J=16.0 Hz, 1H, 15), 6.48 (br. s., 1H, 14), 6.60 (s, 1H, 14), 7.03 (s, 1H, 58), 7.10 (s, 1H, 58), 7.38 (s, 1H, 51), 7.46 (s, 1H, 51), 7.89-8.04 (m, 4H, 53, 12), 8.23 (br. s., 1H, 3), 8.30 (s, 1H, 3), 8.70 (s, 2H, 1), 8.95 (d, J=8.6 Hz, 1H, 27), 9.09 (d, J=9.0 Hz, 1H, 27), 11.39 (br. s., 2H, 34), 13.00 (br. s., 2H, 55)

<sup>13</sup>C NMR (151 MHz, DMSO-d<sub>6</sub>): δ ppm 17.3 (59), 23.5 (21), 23.8 (21), 27.2 (22), 28.3 (22), 29.9 (20), 30.7 (20), 33.3 (31), 34.9 (31), 37.9 (30), 38.5 (30), 40.6 (42), 40.8 (42), 43.8 (7), 47.1 (23), 48.8 (23), 51.4 (26), 51.7 (26), 54.4 (8), 54.5 (8), 69.7 (19), 70.2 (19), 70.5 (17), 70.8 (17), 118.2 (51), 118.3 (51), 119.7 (57), 123.2 (52), 123.4 (14, 52), 123.5 ( ), 126.8 (13), 126.9 (16), 127.5 (15), 127.6 (16), 127.7 (15), 128.1 (2), 128.3 (58), 130.4 (9), 130.4 (50), 131.0 (3), 131.1 (3), 133.8 (53), 134.3 (4), 139.6 (56), 146.6 (12), 146.9 (12), 149.1 (1), 155.8 (10), 164.4 (28), 165.0 (28), 165.6 (5), 170.0 (25), 171.0 (25), 178.5 (35), 178.7 (35)

Characterisation data for Example 1-6 is also shown in Table 3.

Route A_2

Exemplification of Route A by the Synthesis of (1S,10R,20E)-12-methyl-10-[(7-methyl-1H-indazol-5-yl)methyl]-5,9,12,24,26-pentazapentacyclo[20.5.2.11,4.13,7.025,28]hentriaconta-3,5,7(30),20,22(29),23,25(28)-heptaene-8,11,27-trione

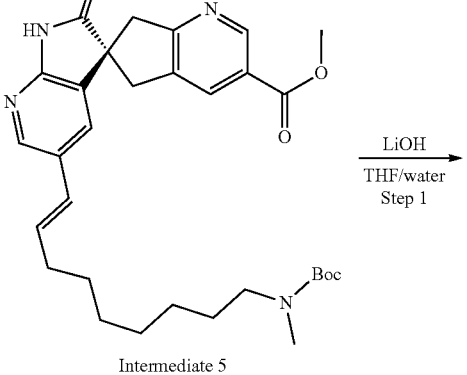

Intermediate 5

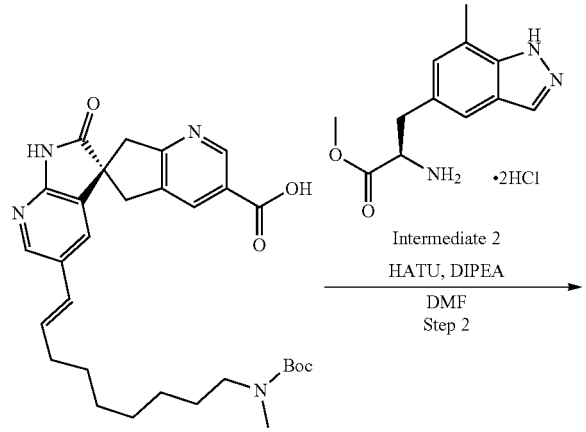

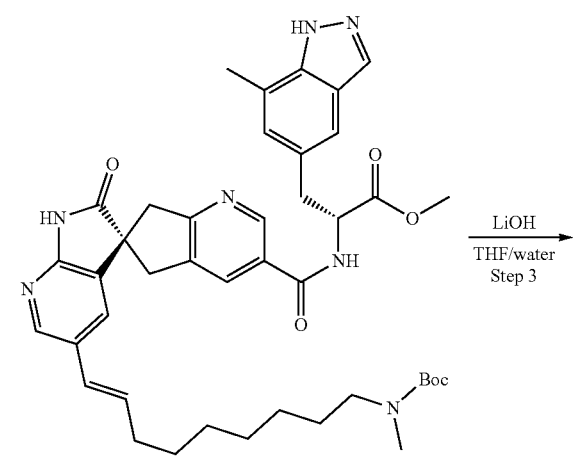

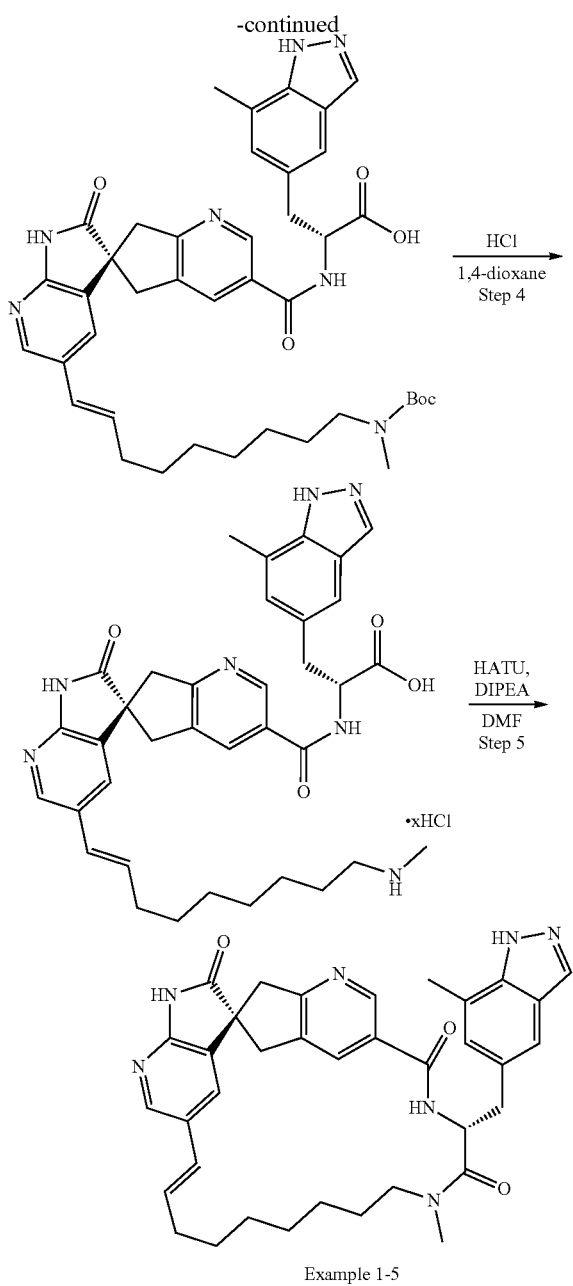

Example 1-5

Route A_2_Step 1

To the solution of intermediate 5 (2.11 g, 3.81 mmol) in THF (55 mL), LiOH (1.0 N in H₂O, 7.61 mL, 7.61 mmol) was added. The reaction mixture was stirred at room temperature for 4 hours, diluted with water (4 mL) and THF evaporated. The aqueous layer was washed with diethyl ether (2×10 mL) and the pH value of cooled aqueous layer was adjusted to 3.6 using 6 N and 1 N HCl solutions. Formed precipitate was filtered off, washed with cold water (2×5 ml) and dried in a vacuum oven to afford (3S)-5-[(E)-9-[tert-butoxycarbonyl(methyl)amino]non-1-enyl]-2-oxo-spiro[1H-pyrrolo[2,3-b]pyridine-3,6'-5,7-dihydrocyclopenta[b]pyridine]-3'-carboxylic acid (1.74 g, 82.9%) as a beige solid which was used as is in the next reaction step.

LC-MS (ES+): 535.37 [M+H].

Route A_2_Step 2

To a solution of (3S)-5-[(E)-9-[tert-butoxycarbonyl(methyl)amino]non-1-enyl]-2-oxo-spiro[1H-pyrrolo[2,3-b]pyridine-3,6'-5,7-dihydrocyclopenta[b]pyridine]-3'-carboxylic acid (1.74 g, 3.16 mmol), Intermediate 2 (846 mg, 3.63 mmol) and DIPEA (1.46 mL, 8.20 mmol) in dry DMF (32.6 mL) was added HATU (1.32 g, 3.48 mmol). The reaction mixture was left to stir at room temperature for 5 minutes, diluted with EtOAc (230 mL), washed with a mixture of sat NaHCO₃/H₂O 1:1 (220 mL), sat NaHCO₃ (2×150 mL), and LiCl (5% aq, 200 mL), dried over MgSO₄, filtered and concentrated under reduced pressure to afford methyl (2R)-2-[[(3S)-5-[(E)-9-[tert-butoxycarbonyl(methyl)amino]non-1-enyl]-2-oxo-spiro[1H-pyrrolo[2,3-b]pyridine-3,6'-5,7-dihydrocyclopenta[b]pyridine]-3'-carbonyl]amino]-3-(7-methyl-1H-indazol-5-yl)propanoate (2.2 g, 83.6%) which was used as is in the next reaction step.

LC-MS (ES+): 750.52 [M+H].

Route A_2_Step 3

To the solution methyl (2R)-2-[[(3S)-5-[(E)-9-[tert-butoxycarbonyl(methyl)amino]non-1-enyl]-2-oxo-spiro[1H-pyrrolo[2,3-b]pyridine-3,6'-5,7-dihydrocyclopenta[b]pyridine]-3'-carbonyl]amino]-3-(7-methyl-1H-indazol-5-yl)propanoate (2.2 g, 2.64 mmol) in THF (38.2 mL), a LiOH (1.0 N in H₂O, 10.6 mL, 10.6 mmol) was added. The reaction mixture was stirred at room temperature for 1 hour, diluted with water (4 ml) and THF evaporated. The aqueous layer was washed with diethyl ether (2×10 mL) and the pH value of cooled aqueous layer was adjusted to 3.6 using a 6 N and 2 N HCl solutions. Formed precipitate was filtered off, washed with cold water (2×5 ml) and dried in a vacuum oven to afford the (2R)-2-[[(3S)-5-[(E)-9-[tert-butoxycarbonyl(methyl)amino]non-1-enyl]-2-oxo-spiro[1H-pyrrolo[2,3-b]pyridine-3,6'-5,7-dihydrocyclopenta[b]pyridine]-3'-carbonyl]amino]-3-(7-methyl-1H-indazol-5-yl)propanoic acid (1.85 g, 78.1%) as a beige solid. This product was used as is in the next reaction step.

LC-MS (ES+): 736.48 [M+H].

Route A_2_Step 4

To the solution of (2R)-2-[[(3S)-5-[(E)-9-[tert-butoxycarbonyl(methyl)amino]non-1-enyl]-2-oxo-spiro[1H-pyrrolo[2,3-b]pyridine-3,6'-5,7-dihydrocyclopenta[b]pyridine]-3'-carbonyl]amino]-3-(7-methyl-1H-indazol-5-yl)propanoic acid (1.85 g, 2.29 mmol) in dioxane (50 mL) and THF (35 ml), HCl (4.0 M in dioxane, 22.9 mL, 91.5 mmol) was added. The reaction mixture was stirred at room temperature for 1 hour. The reaction mixture was concentrated to yield (2R)-2-[[(3S)-5-[(E)-9-(methylamino)non-1-enyl]-2-oxo-spiro[1H-pyrrolo[2,3-b]pyridine-3,6'-5,7-dihydrocyclopenta[b]pyridine]-3'-carbonyl]amino]-3-(7-methyl-1H-indazol-5-yl)propanoic acid hydrochloride (2.12 g) which was used in the next reaction step as is.

LC-MS (ES*): 636.48 [M+H].

Route A_2_Step 5

To a solution of DIPEA (784 μL, 4.502 mmol) and HATU (1.28 g, 3.379 mmol) in dry DMF (495 mL) a solution of (2R)-2-[[(3S)-5-[(E)-9-(methylamino)non-1-enyl]-2-oxo-spiro[1H-pyrrolo[2,3-b]pyridine-3,6'-5,7-dihydrocyclopenta[b]pyridine]-3'-carbonyl]amino]-3-(7-methyl-1H-indazol-5-yl)propanoic acid hydrochloride (2.12 g, 2.256 mmol) and DIPEA (1.57 ml, 9.005 mmol) in dry DMF (248 mL) was added dropwise. The reaction was stopped by adding DCM (120 mL) and a mixture sat. NaHCO₃/water (1 L). The layers were separated and the aqueous layer washed with DCM (3×100 mL). The combined organic layers were concentrated under reduced pressure to afford the crude product (2.5 g). The raw material was dissolved in EtOAc (1 L) and washed with sat NaHCO₃ (3×100 mL). The organic layer was dried over Na₂SO₄ and concentrated under reduced pressure to afford the crude 50 product (1.32 g). The crude material was loaded and purified on silica column (Interchim 80 g, 15 µm, SiO₂) using Interchim PuriFlash 450 instrument with a flow of 40 mL/min starting with DCM (100%) and going to 50% [DCM/MeOH (9:1)] in 20 CVs. Go to 80% [DCM/MeOH (9:1)] in 20 CVs. The appropriate fractions have been combined, concentrated and then triturated with acetone/EtOAc (5 ml/2 ml) to yield (1S,10R,20E)-12-methyl-10-[(7-methyl-1 H-indazol-5-yl)methyl]-5,9,12,24,26-pentazapentacyclo[20.5.2.11,4.13,7.025,28]hentriaconta-3,5,7(30),20,22(29),23,25(28)-heptaene-8,11,27-trione (Example 1-5) (490 mg, 34.8%).

LC-MS (ESI+): 618.3 [M+H].

¹H NMR (500 MHz, DMSO-d₆): δ=0.97-1.14 (m, 12H), 1.15-1.27 (m, 3H), 1.30-1.39 (m, 4H), 1.49-1.55 (m, 2H), 2.03-2.18 (m, 4H), 2.44 (s, 3H), 2.44-2.49 (m, 1H), 2.46 (s, 3H), 2.75 (s, 3H), 2.76-2.80 (m, 1H), 2.95 (s, 3H), 2.96-3.02 (m, 3H), 3.02-3.07 (m, 1H), 3.08-3.18 (m, 4H), 3.49 (d, J=15.8 Hz, 2H), 3.56 (d, J=16.0 Hz, 2H), 3.55-3.63 (m, 1H), 4.08-4.16 (m, 1H), 5.14-5.22 (m, 1H), 5.24-5.30 (m, 1H), 5.56-5.62 (m, 1H), 5.62-5.68 (m, 1H), 6.29 (d, J=15.6 Hz, 1H), 6.30 (d, J=16.0 Hz, 1H), 6.51 (d, J=2.0 Hz, 1H), 6.62 (d, J=1.8 Hz, 1H), 7.01 (s, 1H), 7.10 (s, 1H), 7.37 (s, 1H), 7.46 (s, 1H), 7.90 (d, J=2.0 Hz, 1H), 7.93 (d, J=2.0 Hz, 1H), 7.94 (s, 1H), 7.96 (s, 1H), 8.26 (s, 1H), 8.36 (s, 1H), 8.73 (br. s., 1H), 8.74 (s, 1H), 8.94 (d, J=8.6 Hz, 1H), 9.01 (d, J=9.0 Hz, 1H), 11.33 (br. s., 1H), 12.99 (br. s., 1H), 13.00 (s, 1H) ppm.

Route B

Exemplified by the Synthesis of Example 6-1, (7R,17E)-9-methyl-7-[(7-methyl-1H-indazol-5-yl)methyl]-12,15,25-trioxa-4,6,9,21,23-pentazatetracyclo[17.6.2.21,4.022,26]nonacosa-17,19(27),20,22(26)-tetraene-5,8,24-trione

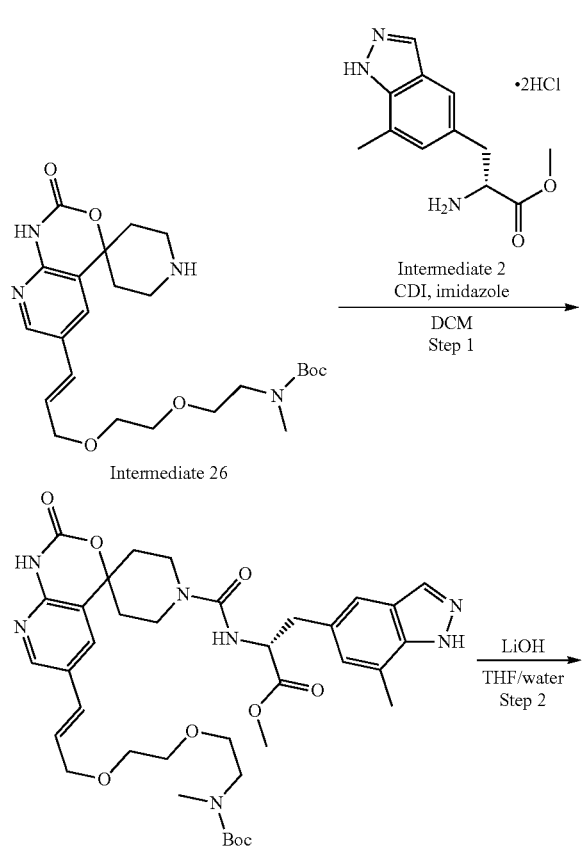

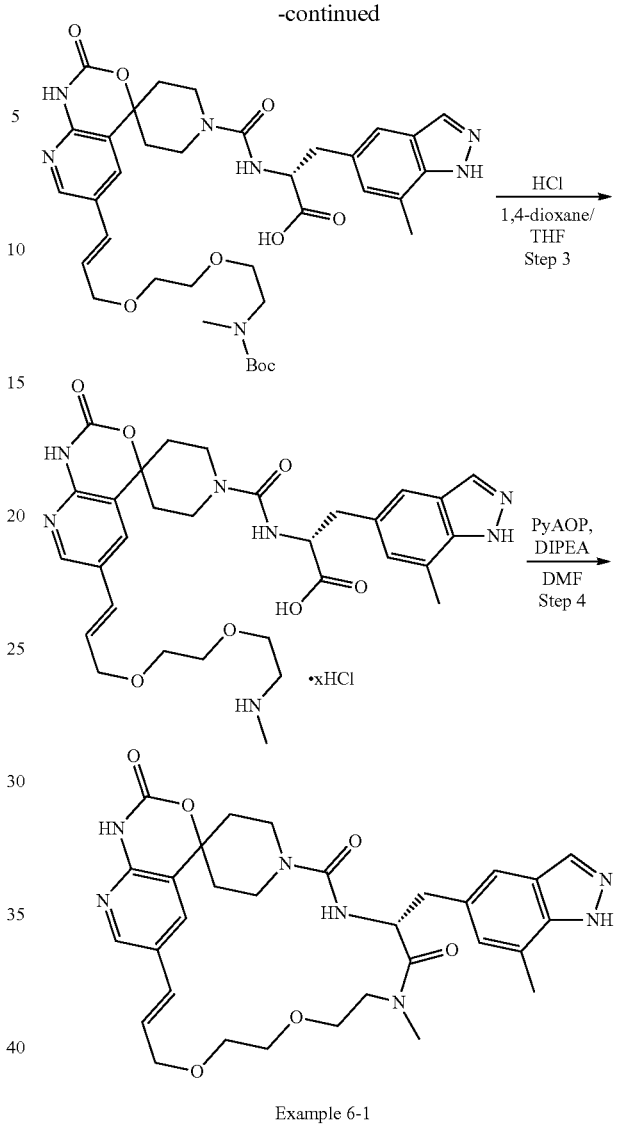

Example 6-1

Route B_Step 1

To a suspension of methyl (R)-2-amino-3-(7-methyl-1H-indazol-5-yl)propanoate dihydrochloride (Intermediate 2) (12.8 mg, 0.042 mmol) in DCM (1 mL) was added CDI (7.49 mg, 0.046 mmol) followed by imidazole (6.29 mg, 0.092 mmol). The reaction mixture was stirred at room temperature for 1 h. To this was then added tert-butyl (E)-methyl(2-(2-((3-(2'-oxo-1',2'-dihydrospiro[piperidine-4,4'-pyrido[2,3-d][1,3]oxazin]-6'-yl)allyl)oxy)ethoxy)ethyl)carbamate (Intermediate 26) (20.0 mg, 0.042 mmol) and the reaction mixture was stirred at room temperature overnight. The reaction mixture was quenched with saturated aqueous NH₄Cl (5 mL). The organics were washed with saturated aqueous NaHCO₃, dried (Na₂SO₄) and concentrated in vacuo to give methyl (R,E)-3-(7-methyl-1H-indazol-5-yl)-2-(2'-oxo-6'-(2,2,5-trimethyl-4-oxo-3,8,11-trioxa-5-azatetradec-13-en-14-yl)-1',2'-dihydrospiro[piperidine-4,4'-pyrido[2,3-d][1,3]oxazine]-1-carboxamido)propanoate (31 mg, 100%).

LC-MS (ESI+): 736.21 [M+H].

Route B_Step 2

To a solution of methyl (R,E)-3-(7-methyl-1H-indazol-5-yl)-2-(2'-oxo-6'-(2,2,5-trimethyl-4-oxo-3,8,11-trioxa-5-azatetradec-13-en-14-yl)-1',2'-dihydrospiro[piperidine-4,4'-pyrido[2,3-d][1,3]oxazine]-1-carboxamido)propanoate (31 mg, 0.037 mmol) in THF (4 mL) and H$_2$O (1 mL) was added LiOH (6 mg, 0.250 mmol). The reaction mixture was stirred at room temperature for 1 h. The reaction mixture was concentrated in vacuo and the resulting residue was diluted with H$_2$O (1 mL) and acidified to pH 4 by dropwise addition of 0.2 M HCl. The product was extracted with EtOAc/IPA (3:1), dried (Na$_2$SO$_4$) and concentrated in vacuo to give (R,E)-3-(7-methyl-1H-indazol-5-yl)-2-(2'-oxo-6'-(2,2,5-trimethyl-4-oxo-3,8,11-trioxa-5-azatetradec-13-en-14-yl)-1',2'-dihydrospiro[piperidine-4,4'-pyrido[2,3-d][1,3]oxazine]-1-carboxamido)propanoic acid (27 mg, 100%).

LC-MS (ESI+): 722.17 [M+H].

Route B_Step 3

A solution of (R,E)-3-(7-methyl-1H-indazol-5-yl)-2-(2'-oxo-6'-(2,2,5-trimethyl-4-oxo-3,8,11-trioxa-5-azatetradec-13-en-14-yl)-1',2'-dihydrospiro[piperidine-4,4'-pyrido[2,3-d][1,3]oxazine]-1-carboxamido)propanoic acid (27 mg, 0.037 mmol) in THF (1 mL) was cooled to 0° C. To this was then added 4M HCl in 1,4-dioxane (1 mL) and the reaction mixture was stirred at room temperature for 3 h. The reaction mixture was then concentrated in vacuo to give (R,E)-3-(7-methyl-1H-indazol-5-yl)-2-(6'-(3-(2-(2-(methylamino)ethoxy)ethoxy)prop-1-en-1-yl)-2'-oxo-1',2'-dihydrospiro[piperidine-4,4'-pyrido[2,3-d][1,3]oxazine]-1-carboxamido) propanoic acid hydrochloride salt (28 mg, 100%).

LC-MS (ESI+): 622.24 [M+H].

Route B_Step 4

To a solution of PyAOP (29 mg, 0.055 mmol) and DIPEA (0.013 mL, 0.072 mmol) in DMF (8 mL) was added dropwise a solution of (R,E)-3-(7-methyl-1H-indazol-5-yl)-2-(6'-(3-(2-(2-(methylamino)ethoxy)ethoxy)prop-1-en-1-yl)-2'-oxo-1',2'-dihydrospiro[piperidine-4,4'-pyrido[2,3-d][1,3]oxazine]-1-carboxamido)propanoic acid hydrochloride salt and DIPEA (0.027 mL, 0.147 mmol) in DMF (4 mL) over 10 mins. The reaction mixture was stirred at room temperature for 20 min and was then quenched with H$_2$O (120 mL) and EtOAc (30 mL). The aqueous layer was further extracted with EtOAc (3×15 mL). The combined organic layers were washed with saturated aqueous NaHCO$_3$ (×2), dried (Na$_2$SO$_4$) and concentrated in vacuo. This was then purified using purification method D to give (7R,17E)-9-methyl-7-[(7-methyl-1H-indazol-5-yl)methyl]-12,15,25-trioxa-4,6,9,21,23-pentazatetracyclo[17.6.2.2$^{1,4}$.0$^{22,26}$]nonacosa-17,19(27),20,22(26)-tetraene-5,8,24-trione (Example 6-1) (10 mg, 45%).

Characterisation data for Example 6-1 is shown in Table 3.

Route C

Exemplified by the Synthesis of Example 4-1, (1S, 10R,20E)-12-methyl-10-[(7-methyl-1H-indazol-5-yl)methyl]-9,15,18-trioxa-5,12,24,26-tetrazapentacyclo[20.5.2.1$^{1,4}$.1$^{3,7}$.0$^{25,28}$]hentriaconta-3,5,7(30),20,22(29),23,25(28)-heptaene-8,11,27-trione

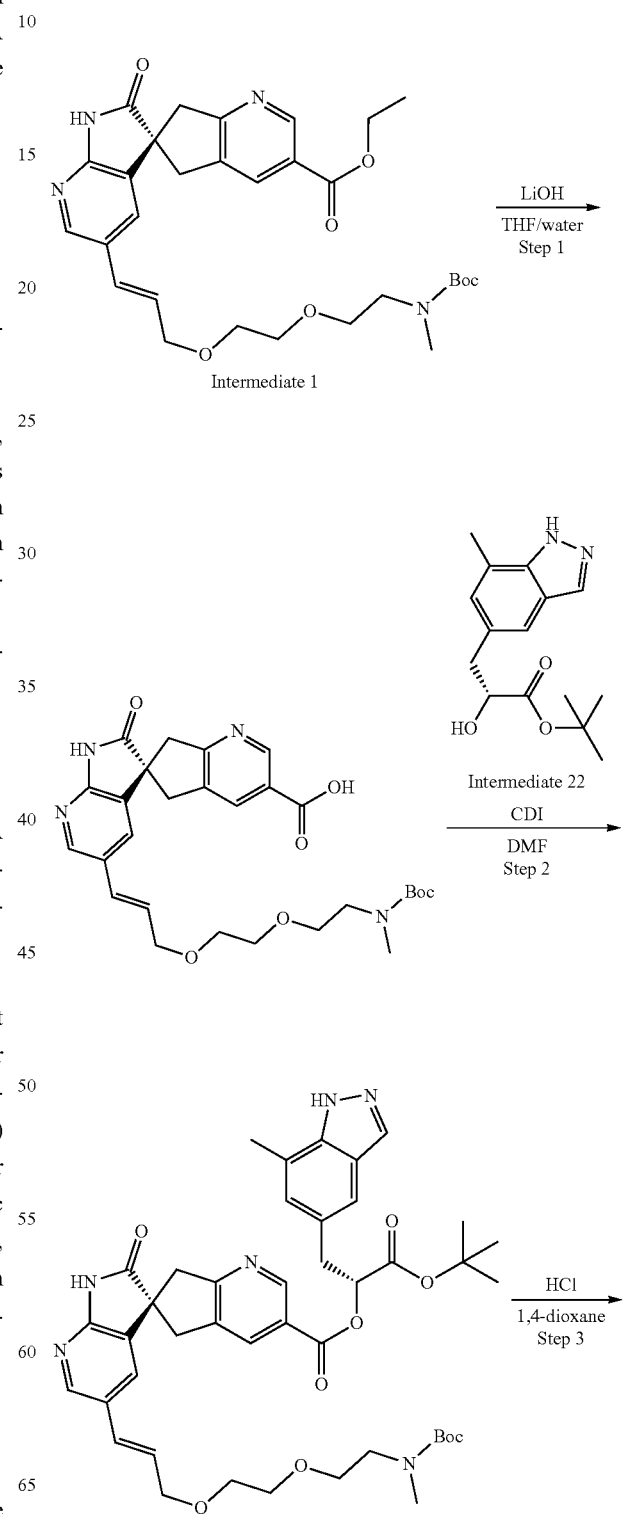

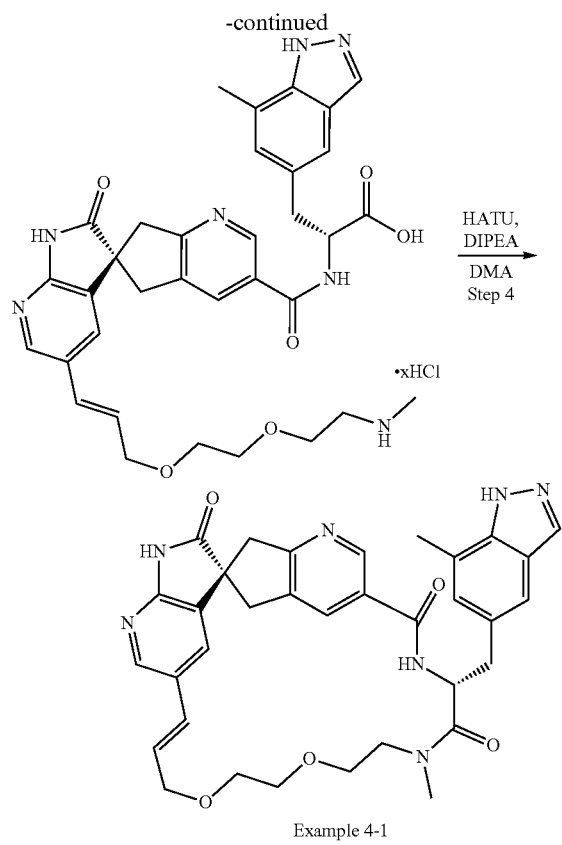

Example 4-1

Route C_Step 1

To a solution of ethyl (S,E)-2'-oxo-5'-(2,2,5-trimethyl-4-oxo-3,8,11-trioxa-5-azatetradec-13-en-14-yl)-1',2',5,7-tetrahydrospiro[cyclopenta[b]pyridine-6,3'-pyrrolo[2,3-b]pyridine]-3-carboxylate (Intermediate 1) (107 mg, 0.189 mmol) in THF (4 mL) and H$_2$O (1 mL) was added LiOH (10 mg, 0.378 mmol). The reaction mixture was stirred at room temperature for 1 h. The solvent was concentrated in vacuo and to this was then added H$_2$O (2 mL). The pH of the mixture was adjusted to pH 5 using a 0.2M HCl solution and the aqueous layer extracted with EtOAc. The organics were dried (Na$_2$SO$_4$) and concentrated in vacuo to give (S,E)-2'-oxo-5'-(2,2,5-trimethyl-4-oxo-3,8,11-trioxa-5-azatetradec-13-en-14-yl)-1',2',5,7-tetrahydrospiro[cyclopenta[b]pyridine-6,3'-pyrrolo[2,3-b]pyridine]-3-carboxylic acid (93 mg, 92%).

LC-MS (ESI+): 539.75 [M+H].

Route C_Step 2

To a solution of (S,E)-2'-oxo-5'-(2,2,5-trimethyl-4-oxo-3,8,11-trioxa-5-azatetradec-13-en-14-yl)-1',2',5,7-tetrahydrospiro[cyclopenta[b]pyridine-6,3'-pyrrolo[2,3-b]pyridine]-3-carboxylic acid (96 mg, 0.170 mmol) in DMF (2 mL) was added CDI (41 mg, 0.255 mmol) and the reaction mixture was stirred at room temperature for 20 mins. To this was then added tert-butyl (R)-2-hydroxy-3-(7-methyl-1H-indazol-5-yl)propanoate (Intermediate 22) (56 mg, 0.205 mmol) and DMAP (10 mg, 0.085 mmol) and then stirred at 90° C. for 2 h. Heating was continued at 100° C. until the reaction was complete. The reaction mixture was then poured into H$_2$O and extracted with DCM (2×15 mL) and then with EtOAc/IPA (2:1) (2×20 mL). The combined organic layers were dried (Na$_2$SO$_4$) and concentrated in vacuo. The residue was purified using purification method C to give (R)-1-(tert-butoxy)-3-(7-methyl-1H-indazol-5-yl)-1-oxopropan-2-yl (S)-2'-oxo-5'-((E)-2,2,5-trimethyl-4-oxo-3,8,11-trioxa-5-azatetradec-13-en-14-yl)-1',2',5,7-tetrahydrospiro[cyclopenta[b]pyridine-6,3'-pyrrolo[2,3-b]pyridine]-3-carboxylate (47 mg, 35%).

LC-MS (ESI+): 797.90 [M+H].

Route C_Step 3

To a solution of (R)-1-(tert-butoxy)-3-(7-methyl-1H-indazol-5-yl)-1-oxopropan-2-yl (S)-2'-oxo-5'-((E)-2,2,5-trimethyl-4-oxo-3,8,11-trioxa-5-azatetradec-13-en-14-yl)-1',2',5,7-tetrahydrospiro[cyclopenta[b]pyridine-6,3'-pyrrolo[2,3-b]pyridine]-3-carboxylate (47 mg, 0.06 mmol) in 1,4-dioxane (7 mL) was added 4M HCl in 1,4-dioxane (1.5 mL) and the reaction mixture stirred at room temperature until the reaction was complete. The reaction mixture was then concentrated in vacuo to give (R)-3-(7-methyl-1H-indazol-5-yl)-2-(((S)-5'-((E)-3-(2-(2-(methylamino)ethoxy)ethoxy)prop-1-en-1-yl)-2'-oxo-1',2',5,7-tetrahydrospiro[cyclopenta[b]pyridine-6,3'-pyrrolo[2,3-b]pyridine]-3-carbonyl)oxy)propanoic acid hydrochloride salt (47 mg, 100%).

LC-MS (ESI+): 641.78 [M+H].

Route C_Step 4

To a solution of HATU (46 mg, 0.12 mmol) and DIPEA (0.063 mL, 0.36 mmol) in DMA (8 mL) was added dropwise a solution of (R)-3-(7-methyl-1H-indazol-5-yl)-2-(((S)-5'-((E)-3-(2-(2-(methylamino)ethoxy)ethoxy)prop-1-en-1-yl)-2'-oxo-1',2',5,7-tetrahydrospiro[cyclopenta[b]pyridine-6,3'-pyrrolo[2,3-b]pyridine]-3-carbonyl)oxy)propanoic acid hydrochloride salt (47 mg, 0.06 mmol) in DMA (4 mL) over 5 mins. The reaction mixture was immediately quenched with H$_2$O and EtOAc. The aqueous layer was further extracted with EtOAc (2×10 mL) and then with DCM (2×10 mL). The combined organic layers were dried (Na$_2$SO$_4$) and concentrated in vacuo. The residue was then purified using purification method C to give (1S,10R,20E)-12-methyl-10-[(7-methyl-1H-indazol-5-yl)methyl]-9,15,18-trioxa-5,12,24,26-tetrazapentacyclo[20.5.2.1¹,⁴.1³,⁷.0²⁵,²⁸]hentriaconta-3,5,7(30),20,22(29),23,25(28)-heptaene-8,11,27-trione (Example 4-1) (23 mg, 62%).

LC-MS (ESI+): 623.78 [M+H].

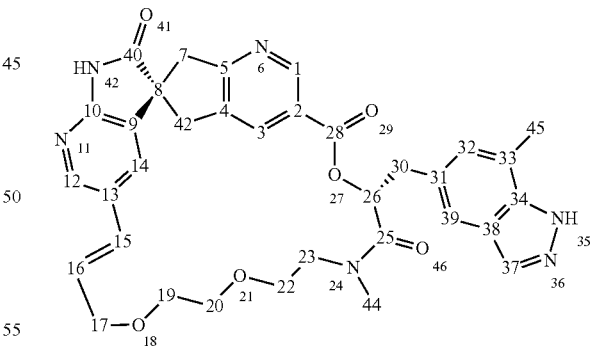

$^1$H NMR (600 MHz, DMSO-d6): δ ppm 2.42 (s, 3H, 45), 2.44 (s, 3H, 45), 2.86 (s, 3H, 44), 2.95 (s, 3H, 44), 2.96-3.01 (m, 2H, 23<"), 3.04 (d, J=16.7 Hz, 1H, 7<">), 3.06 (d, J=16.5 Hz, 1H, 7<">), 3.19 (d, J=15.4 Hz, 2H, 43<">), 3.22-3.29 (m, 4H, 30), 3.34-3.40 (m, 4H, 19), 3.43-3.45 (m, 2H, 20<">), 3.47 (d, J=5.0 Hz, 4H, 22), 3.49 (s, 2H, 43<">), 3.50-3.53 (m, 2H, 20<'>), 3.62 (d, J=16.1 Hz, 1H, 7<'>), 3.63 (d, J=16.3 Hz, 1H, 7<'>), 3.78-3.85 (m, 2H, 23<'>), 3.89 (dd, J=13.4, 8.3 Hz, 1H, 17<">), 3.92 (dd, J=13.9, 7.3 Hz, 1H, 17<">), 4.01 (ddd, J=12.4, 4.5, 1.6 Hz, 1H, 17<'>), 4.05 (ddd, J=13.6, 5.1, 1.5 Hz, 1H, 17<'>), 5.62 (ddd, J=16.1, 8.2, 4.7 Hz, 1H, 16), 5.71 (dd, J=16.0, 7.5, 5.0 Hz, 1H, 16), 5.86 (dd, J=8.3, 5.8 Hz, 1H, 26), 5.89 (t, J=7.0 Hz, 1H, 26), 6.41 (d, J=16.3 Hz, 1H, 15), 6.43 (d, J=16.1 Hz, 1H, 15), 6.53 (d, J=2.0 Hz, 1H, 14), 6.57 (d, J=2.0 Hz, 1H, 14), 7.08 (s, 1H, 32), 7.12 (s, 1H, 32), 7.44 (s, 1H, 39), 7.49 (s, 1H, 39), 7.94 (s, 1H, 37), 7.95 (s, 1H, 37), 7.98 (d, J=2.0 Hz, 1H, 12), 7.99 (d, J=2.0 Hz, 1H, 12), 8.21-8.27 (m, 1H, 3), 8.32 (s, 1H, 3), 8.85 (s, 2H, 1), 11.38 (br. s., 1H, 42), 11.40 (s, 1H, 42), 13.02 (br. s., 2H, 35)

$^{13}$C NMR (151 MHz, DMSO-d6): δ ppm 16.7 (45), 36.7 (30), 40.3 (43), 43.5 (7), 47.2 (23), 47.7 (23), 53.9 (8), 67.9 (20), 68.8 (22), 69.0 (22), 69.3 (19), 70.4 (17), 70.6 (17), 73.0 (26), 118.1 (39), 119.6 (33), 122.8 (38), 123.0 (14), 123.4 (2), 125.9 (16), 126.1 (13), 127.2 (16), 127.5 (15), 127.8 (32), 128.2 (31), 129.6 (9), 132.4 (3), 133.4 (37), 135.2 (4), 139.2 (34), 146.6 (12), 149.9 (1), 155.4 (10), 164.0 (28), 167.7 (25), 167.9 (5), 178.0 (40)

Characterisation data for Example 4-1 is also shown in Table 3.

Route D

Exemplified by the Synthesis of Example 7-1, (7R, 17E)-9-methyl-7-[(7-methyl-1H-indazol-5-yl)methyl]-6,12,15,25-tetraoxa-4,9,21,23-tetrazatetracyclo[17.6.2.2¹,⁴.0²²,²⁶]nonacosa-17,19(27),20,22(26)-tetraene-5,8,24-trione

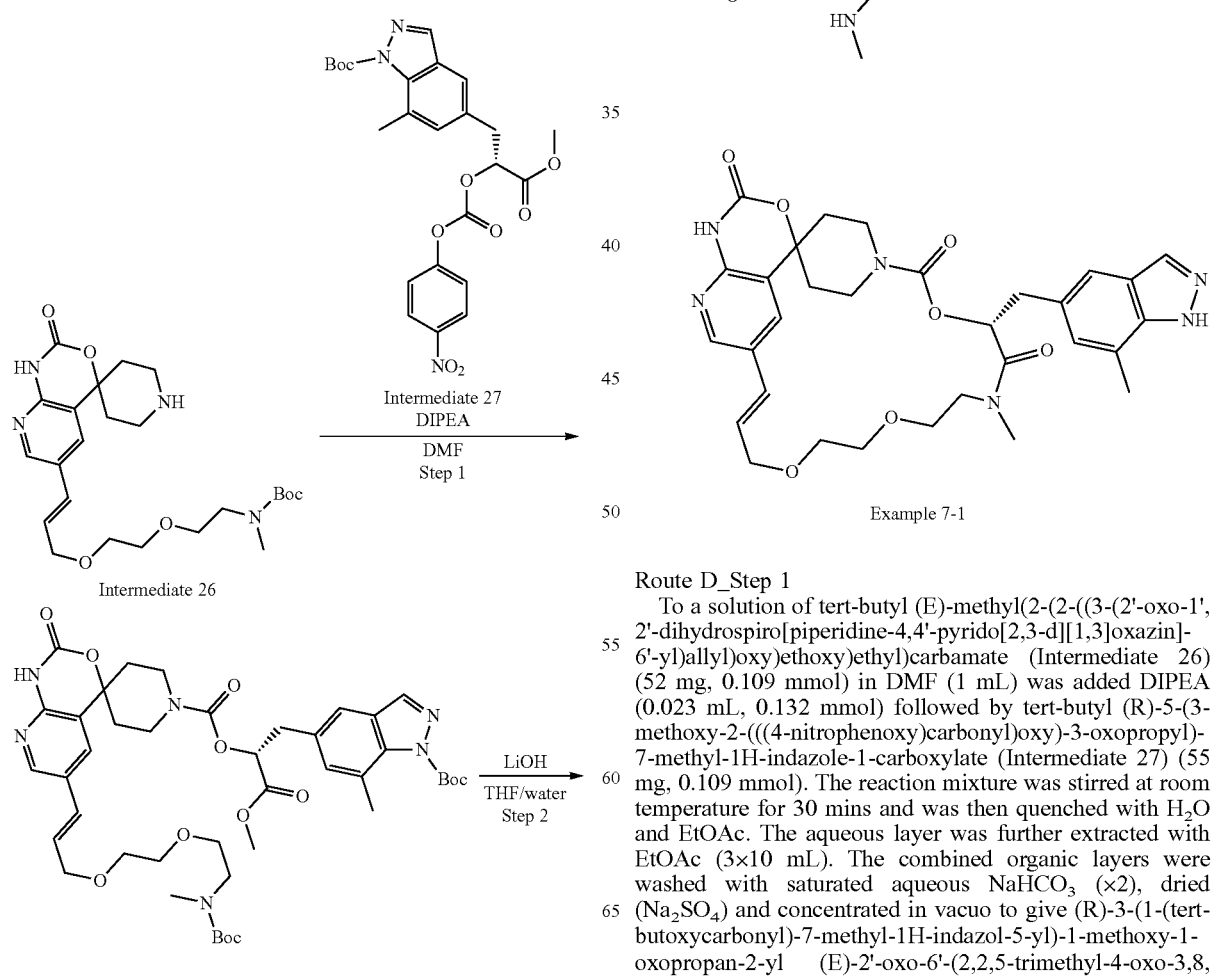

Example 7-1

Route D_Step 1

To a solution of tert-butyl (E)-methyl(2-(2-((3-(2'-oxo-1',2'-dihydrospiro[piperidine-4,4'-pyrido[2,3-d][1,3]oxazin]-6'-yl)allyl)oxy)ethoxy)ethyl)carbamate (Intermediate 26) (52 mg, 0.109 mmol) in DMF (1 mL) was added DIPEA (0.023 mL, 0.132 mmol) followed by tert-butyl (R)-5-(3-methoxy-2-(((4-nitrophenoxy)carbonyl)oxy)-3-oxopropyl)-7-methyl-1H-indazole-1-carboxylate (Intermediate 27) (55 mg, 0.109 mmol). The reaction mixture was stirred at room temperature for 30 mins and was then quenched with H₂O and EtOAc. The aqueous layer was further extracted with EtOAc (3×10 mL). The combined organic layers were washed with saturated aqueous NaHCO₃ (×2), dried (Na₂SO₄) and concentrated in vacuo to give (R)-3-(1-(tert-butoxycarbonyl)-7-methyl-1H-indazol-5-yl)-1-methoxy-1-oxopropan-2-yl (E)-2'-oxo-6'-(2,2,5-trimethyl-4-oxo-3,8, 11-trioxa-5-azatetradec-13-en-14-yl)-1',2'-dihydrospiro[piperidine-4,4'-pyrido[2,3-d][1,3]oxazine]-1-carboxylate (91 mg, 100%).

LC-MS (ESI+): 837.32 [M+H].

Route D_Step 2

To a solution of (R)-3-(1-(tert-butoxycarbonyl)-7-methyl-1H-indazol-5-yl)-1-methoxy-1-oxopropan-2-yl (E)-2'-oxo-6'-(2,2,5-trimethyl-4-oxo-3,8,11-trioxa-5-azatetradec-13-en-14-yi)-1',2'-dihydrospiro[piperidine-4,4'-pyrido[2,3-d][1,3]oxazine]-1-carboxylate (91 mg, 0.109 mmol) in THF (8 mL) and H$_2$O (2 mL) was added LiOH (10 mg, 0.436 mmol). The reaction mixture was stirred at room temperature for 3 h and then concentrated in vacuo. The resulting residue was diluted with H$_2$O (3 mL) and acidified to pH 5 by the dropwise addition of 0.2M HCl. The product was extracted with EtOAc, dried (Na$_2$SO$_4$) and concentrated in vacuo to give (R,E)-3-(7-methyl-1H-indazol-5-yl)-2-((2'-oxo-6'-(2,2,5-trimethyl-4-oxo-3,8,11-trioxa-5-azatetradec-13-en-14-yl)-1',2'-dihydrospiro[piperidine-4,4'-pyrido[2,3-d][1,3]oxazine]-1-carbonyl)oxy)propanoic acid (78 mg, 100%).

LC-MS (ESI+): 723.33 [M+H].

Route D_Step 3

A solution of (R,E)-3-(7-methyl-1H-indazol-5-yl)-2-((2'-oxo-6'-(2,2,5-trimethyl-4-oxo-3,8,11-trioxa-5-azatetradec-13-en-14-yl)-1',2'-dihydrospiro[piperidine-4,4'-pyrido[2,3-d][1,3]oxazine]-1-carbonyl)oxy)propanoic acid (78 mg, 0.109 mmol) in THF (10 mL) was cooled to 0° C. To this was then added 4M HCl in 1,4-dioxane (5 mL) and the reaction mixture was stirred until complete. The reaction mixture was then concentrated in vacuo to give (R,E)-3-(7-methyl-1H-indazol-5-yl)-2-((6'-(3-(2-(2-(methylamino)ethoxy)ethoxy)prop-1-en-1-yl)-2'-oxo-1',2'-dihydrospiro[piperidine-4,4'-pyrido[2,3-d][1,3]oxazine]-1-carbonyl)oxy)propanoic acid hydrochloride salt (84 mg, 100%).

LC-MS (ESI+): 623.26 [M+H].

Route D_Step 4

To a solution of PyAOP (164 mg, 0.109 mmol) and DIPEA (0.038 mL, 0.22 mmol) in DMF (18 mL) was added dropwise a solution of (R,E)-3-(7-methyl-1H-indazol-5-yl)-2-((6'-(3-(2-(2-(methylamino)ethoxy)ethoxy)prop-1-en-1-yl)-2'-oxo-1',2'-dihydrospiro[piperidine-4,4'-pyrido[2,3-d][1,3]oxazine]-1-carbonyl)oxy)propanoic acid hydrochloride salt (84 mg, 0.109 mmol) and DIPEA (0.076 mL, 0.440 mmol) in DMF (11 mL) over 20 mins. The reaction mixture was stirred for 20 mins then quenched with H$_2$O (250 mL) and EtOAc (100 mL). The aqueous layer was further extracted with EtOAc (3×60 mL). The combined organic layers were washed with saturated aqueous NaHCO$_3$, dried (Na$_2$SO$_4$) and concentrated in vacuo to give the crude product which was then purified using purification method E to give (7R,17E)-9-methyl-7-[(7-methyl-1H-indazol-5-yl)methyl]-6,12,15,25-tetraoxa-4,9,21,23-tetrazatetracyclo[17.6.2.2$^{1,4}$.0$^{22,26}$]nonacosa-17,19(27),20,22(26)-tetraene-5,8,24-trione (Example 7-1) (32 mg, 50%).

Characterisation data for Example 7-1 is shown in Table 3.

Route E

Exemplified by the Synthesis of Example 1-8, (1S, 10R)-12-methyl-10-[(7-methyl-1H-indazol-5-yl)methyl]-15,18-dioxa-5,9,12,24,26-pentazapentacyclo[20.5.2.1$^{1,4}$.1$^{3,7}$.0$^{25,28}$]hentriaconta-3,5,7(30),22(29),23,25(28)-hexaene-8,11,27-trione

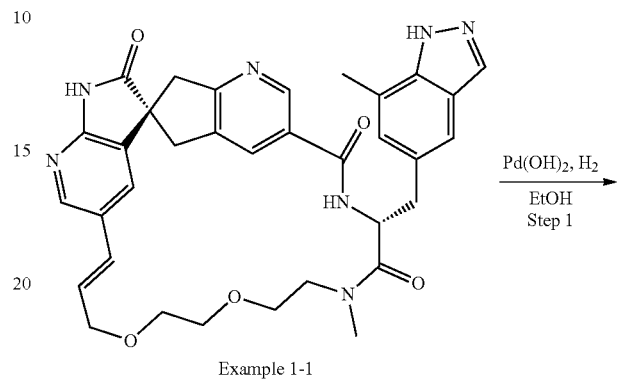

Example 1-1

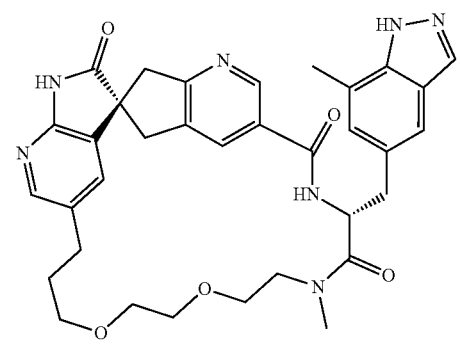

Example 1-8

Route E_Step 1

A solution (1S,10R,20E)-12-methyl-10-[(7-methyl-1H-indazol-5-yl)methyl]-15,18-dioxa-5,9,12,24,26-pentazapentacyclo[20.5.2.1$^{1,4}$.1$^{3,7}$.0$^{25,28}$]hentriaconta-3,5,7(30),20,22(29),23,25(28)-heptaene-8,11,27-trione (Example 1-1) (35 mg, 0.0563 mmol) in EtOH (6.0 mL) was purged with argon for 2 mins. To this was then added Pd(OH)$_2$/C (7.5 mg) and the reaction mixture was stirred at room temperature under a hydrogen atmosphere at atmospheric pressure overnight. The reaction mixture was filtered and concentrated in vacuo to give (1S,10R)-12-methyl-10-[(7-methyl-1H-indazol-5-yl)methyl]-15,18-dioxa-5,9,12,24,26-pentazapentacyclo[20.5.2.1$^{1,4}$.1$^{3,7}$.0$^{25,28}$]hentriaconta-3,5,7(30),22(29),23,25(28)-hexaene-8,11,27-trione (Example 1-8) (33.8 mg, 97%).

LC-MS (ESI+): 624.86 [M+H].

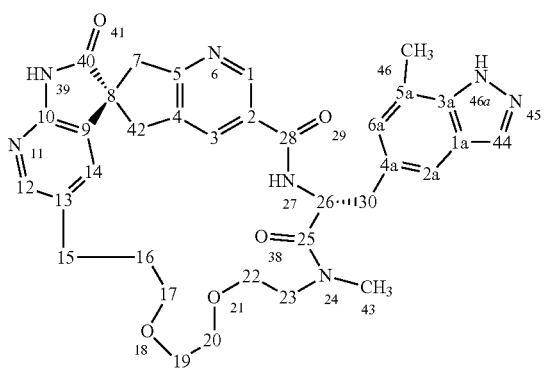

Route F

Exemplified by the Synthesis of Example 3-6, (1S,10R,20E)-12-methyl-10-[(7-methyl-1H-indazol-5-yl)methyl]-18-oxa-9,12,15,24,26-pentazapentacyclo[20.5.2.1¹,⁴.1³,⁷.0²⁵,²⁸]hentriaconta-3,5,7(30),20,22(29),23,25(28)-heptaene-8,11,27-trione

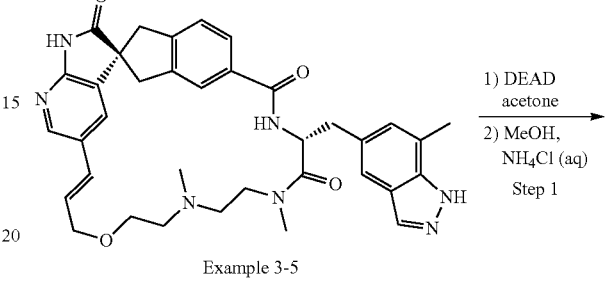

Example 3-5

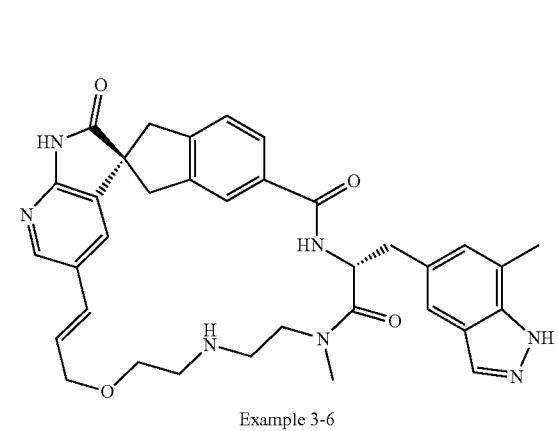

Example 3-6

Route F_Step 1

To a solution of (1S,10R,20E)-12,15-dimethyl-10-[(7-methyl-1H-indazol-5-yl)methyl]-18-oxa-9,12,15,24,26-pentazapentacyclo[20.5.2.1¹,⁴.1³,⁷.0²⁵,²⁸]hentriaconta-3,5,7(30),20,22(29),23,25(28)-heptaene-8,11,27-trione (Example 3-5) (45 mg, 0.078 mmol) in acetone (5 mL) was added dropwise DEAD (40% in toluene, 39 μL, 0.212 mmol). The reaction mixture was stirred at room temperature overnight. The reaction mixture was concentrated in vacuo and then dissolved in MeOH (5 mL) and saturated aqueous NH₄Cl (5 mL). The reaction mixture was heated at 60° C. for 1 h. The reaction mixture was then cooled and extracted with DCM. The aqueous layer was further extracted with DCM (3×4 mL). The combined organic layers were washed with saturated aqueous NaHCO₃, dried (Na₂SO₄), filtered and concentrated in vacuo to give crude product. The residue was purified using purification method L to give (1S,10R,20E)-12-methyl-10-[(7-methyl-1H-indazol-5-yl)methyl]-18-oxa-9,12,15,24,26-pentazapentacyclo[20.5.2.1¹,⁴.1³,⁷.0²⁵,²⁸]hentriaconta-3,5,7(30),20,22(29),23,25(28)-heptaene-8,11,27-trione (Example 3-6) (13 mg, 29%).

Characterisation data for Example 3-6 is shown in Table 3.

$^1$H NMR (500 MHz, DMSO-$d_6$): δ ppm 1.35-1.43 (m, 1H, 16<''>), 1.43-1.51 (m, 1H, 16<'>), 1.55-1.63 (m, 1H, 16<>), 1.64-1.73 (m, 1H, 16<>), 2.30-2.39 (m, 2H, 15<''>), 2.40-2.48 (m, 2H, 15<'>), 2.44 (s, 3H, 46), 2.45 (s, 3H, 46), 2.64 (ddd, J=13.9, 6.1, 3.5 Hz, 1H, 23<''>), 2.79 (s, 3H, 43), 2.92-2.98 (m, 4H, 30<''>, 7<''>, 23<''>), 2.93-3.05 (m, 4H, 17<''>, 19<''>, 19<'>), 2.99 (s, 3H, 43), 3.00-3.03 (m, 1H, 30<''>), 3.07-3.13 (m, 5H, 19<''>, 20, 42<''>), 3.14-3.18 (m, 2H, 17<>, 30<'>), 3.18-3.26 (m, 3H, 19<>, 17<>, 30<'>), 3.28-3.33 (m, 3H, 22<''>, 20), 3.37-3.43 (m, 1H, 22<'>), 3.44-3.51 (m, 3H, 22<''>, 42<'>), 3.51-3.58 (m, 3H, 22<>, 7<'>), 3.75-3.84 (m, 1H, 23<'>), 4.21 (ddd, J=14.0, 6.6, 3.8 Hz, 1H, 23<'>), 5.18 (q, J 9.0 Hz, 1H, 26), 5.23 (ddd, J=9.0, 8.0, 7.0 Hz, 1H, 26), 6.41 (d, J=1.8 Hz, 1H, 14), 6.47 (d, J=1.8 Hz, 1H, 14), 7.03 (s, 1H, 6a), 7.08 (s, 1H, 6a), 7.37 (s, 1H, 2a), 7.42 (s, 1H, 2a), 7.92 (d, J=1.5 Hz, 2H, 12), 7.94 (s, 1H, 44), 7.95 (s, 1H, 44), 8.28 (s, 1H, 3), 8.35 (s, 1H, 3), 8.73 (s, 1H, 1), 8.74 (s, 1H, 1), 8.92 (d, J=8.9 Hz, 1H, 27), 8.99 (d, J=9.2 Hz, 1H, 27), 11.21 (br. s., 2H, 39), 12.98 (br. s., 1H, 46a), 12.99 (br. s., 1H, 46a)

$^{13}$C NMR (126 MHz, DMSO-$d_6$): δ ppm 16.8 (46), 16.8 (46), 26.9 (15), 27.2 (15), 30.3 (16), 30.3 (16), 33.0 (43), 35.8 (43), 36.9 (30), 38.2 (30), 40.5 (42), 40.6 (42), 43.5 (7), 43.6 (7), 47.5 (23), 47.9 (23), 50.8 (26), 51.1 (26), 53.0 (8), 53.4 (8), 67.0 (17), 67.4 (22), 67.6 (17), 67.7 (22), 68.2 (19), 68.8 (19), 69.3 (20), 69.7 (20), 117.7 (2a), 118.7 (5a), 119.1 (5a), 122.7 (1a), 127.4 (2), 127.8 (2), 127.8 (6a), 127.9 (6a), 128.6 (14), 129.0 (14), 130.2 (4a), 130.2 (3), 130.6 (3), 130.7 (13), 133.4 (44), 133.5 (4), 133.8 (4), 139.1 (3a), 146.4 (12), 146.5 (12), 148.8 (1), 149.0 (1), 153.9 (10), 163.6 (28), 163.8 (28), 164.9 (5), 165.1 (5), 170.2 (25), 170.3 (25), 178.7 (40), 179.0 (40)

Characterisation data for Example 1-8 is also shown in Table 3.

Route G

Exemplified by the Synthesis of Example 3-10, (1R,10R)-12-methyl-10-[(7-methyl-1H-indazol-5-yl)methyl]-15,18-dioxa-9,12,24,26-tetrazapentacyclo[20.5.2.1¹,⁴.1³,⁷.0²⁵,²⁸]hentriaconta-3,5,7(30),22(29),23,25(28)-hexaene-8,11,27-trione

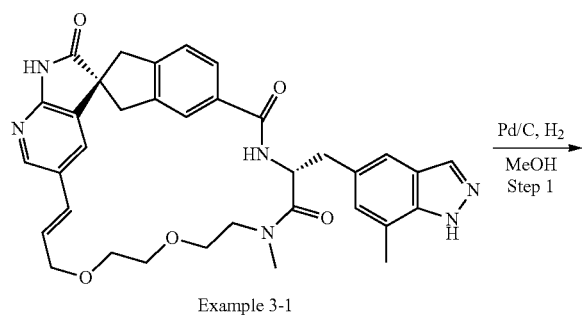

Example 3-1

Pd/C, H₂
MeOH
Step 1

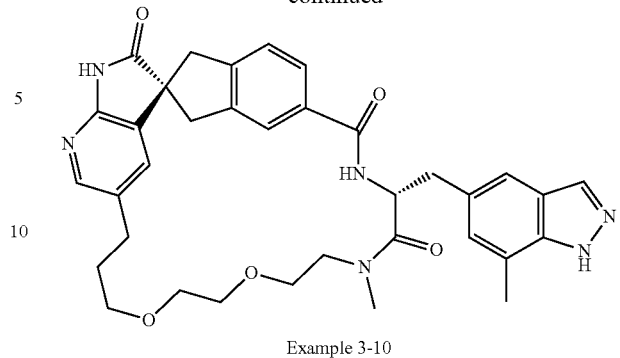

Example 3-10

Route G_Step 1

A solution (1R,10R,20E)-12-methyl-10-[(7-methyl-1H-indazol-5-yl)methyl]-15,18-dioxa-9,12,24,26-tetrazapentacyclo[20.5.2.1¹,⁴.1³,⁷.0²⁵,²⁸]hentriaconta-3,5,7(30),20,22(29),23,25(28)-heptaene-8,11,27-trione (Example 3-1) (2.04 mg, 0.003 mmol) in MeOH (5.0 mL) was treated with 10% Pd/C (dry, 0.04 mg, 0.0003 mmol). The reaction mixture was evacuated and purged with nitrogen and then stirred at room temperature under a hydrogen atmosphere at atmospheric pressure over the weekend. The reaction mixture was filtered and concentrated in vacuo to give (1R,10R)-12-methyl-10-[(7-methyl-1H-indazol-5-yl)methyl]-15,18-dioxa-9,12,24,26-tetrazapentacyclo[20.5.2.11,4.13,7.025,28]hentriaconta-3,5,7(30),22(29),23,25(28)-hexaene-8,11,27-trione (Example 3-10) (2.0 mg, 100%).

Characterisation for Example 3-10 is shown in Table 3.

TABLE 2

Intermediates
Table 2

| Intermediate Number | Name | Structure | Synthetic Route | Intermediates Used | LCMS Data |
|---|---|---|---|---|---|
| 1 | Ethyl (S,E)-2'-oxo-5'-(2,2,5-trimethyl-4-oxo-3,8,11-trioxa-5-azatetradec-13-en-14-yl)-1',2',5,7-tetrahydrospiro[cyclopenta[b]pyridine-6,3'-pyrrolo[2,3-b]pyridine]-3-carboxylate | 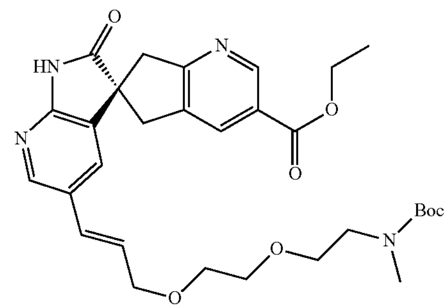 [SMILES: CCOC(=O)c1cnc2c(c1)C[C@@]1(C2)C(=O)Nc2ncc(/C=C/COCCOCCN(C)C(=O)OC(C)(C)C)cc21] | 1 | 32 and 33 | LC-MS (ESI+): 567.23 [M + H] |
| 2 | Methyl (R)-2-amino-3-(7-methyl-1H-indazol-5-yl)propanoate dihydrochloride | 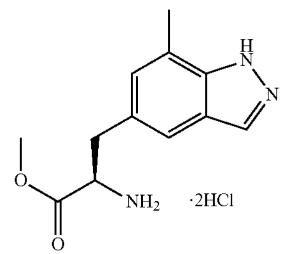 [SMILES: COC(=O)[C@H](N)Cc1cc(C)c2[nH]ncc2c1] | Commercially available, CAS: 1414976-14-9 | — | — |
| 3 | Methyl (S)-2-amino-3-(7-methyl-1H-indazol-5-yl)propanoate dihydrochloride | 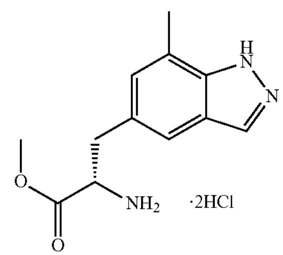 [SMILES: COC(=O)[C@@H](N)Cc1cc(C)c2[nH]ncc2c1] | 2 | 34 and 35 | LC-MS (ESI+): 233.99 [M + H] |

TABLE 2-continued

Intermediates Table 2

| Intermediate Number | Name | Structure | Synthetic Route | Intermediates Used | LCMS Data |
|---|---|---|---|---|---|
| 4 | Ethyl (S,E)-2'-oxo-5'-(2,2,5-trimethyl-4-oxo-3,8,11,14-tetraoxa-5-azaheptadec-16-en-17-yl)-1',2',5,7-tetrahydrospiro[cyclopenta[b]pyridine-6,3'-pyrrolo[2,3-b]pyridine]-3-carboxylate | 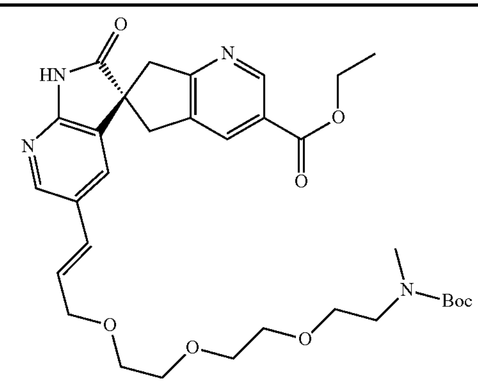 | 1 | 32 and 36 | LC-MS (ESI+): 611.92 [M + H] |
| 5 | Ethyl (S,E)-5'-(9-((tert-butoxycarbonyl)(methyl)amino)non-1-en-1-yl)-2'-oxo-1',2',5,7-tetrahydrospiro[cyclopenta[b]pyridine-6,3'-pyrrolo[2,3-b]pyridine]-3-carboxylate | 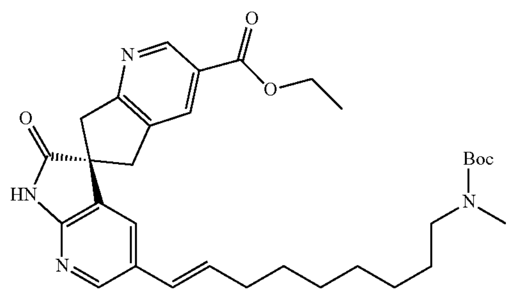 [SMILES: CCOC(=O)c1cnc2c(c1)C[C@@]1(C2)C(=O)Nc2ncc(/C=C/CCCCCCCN(C)C(=O)OC(C)(C)C)cc21] | 1 | 32 and 39 | LC-MS (ESI+): 564.06 [M + H] |

TABLE 2-continued

Intermediates
Table 2

| Intermediate Number | Name | Structure | Synthetic Route | Intermediates Used | LCMS Data |
|---|---|---|---|---|---|
| 6 | Methyl (S,E)-5'-(3-((tert-butoxycarbonyl)(methyl)amino)butoxy)prop-1-en-1-yl)-2'-oxo-1',2',5,7-tetrahydrospiro[cyclopenta[b]pyridine-6,3'-pyrrolo[2,3-b]pyridine]-3-carboxylate | 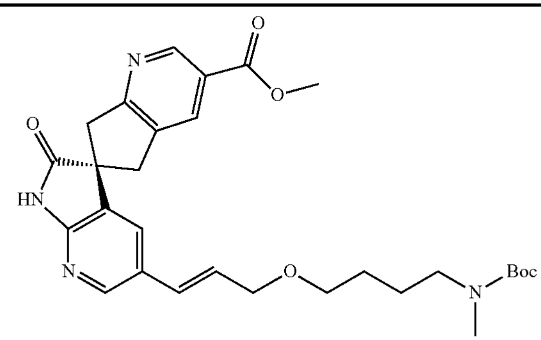 | 5 | 41, 42 and 43 | LC-MS (ESI+): 537.43 [M + H] |
| 7 | Ethyl (R,E)-2'-oxo-5'-(2,2,5-trimethyl-4-oxo-3,8,11-trioxa-5-azatetradec-13-en-14-yl)-1',2',5,7-tetrahydrospiro[cyclopenta[b]pyridine-6,3'-pyrrolo[2,3-b]pyridine]-3-carboxylate | 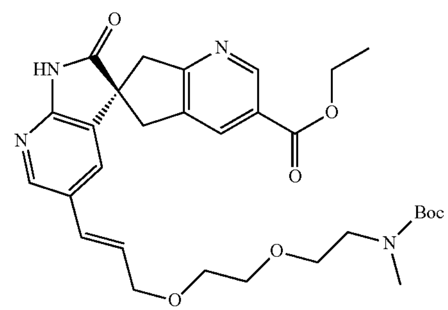 [SMILES: CCOC(=O)c1cnc2c(c1)C[C@]1(C2)C(=O)Nc2ncc(/C=C/COCCOCCN(C)C(=O)OC(C)(C)C)cc21] | 1 | 45 and 33 | LC-MS (ESI+): 567.35 [M + H] |

TABLE 2-continued

Intermediates Table 2

| Intermediate Number | Name | Structure | Synthetic Route | Intermediates Used | LCMS Data |
|---|---|---|---|---|---|
| 8 | Methyl (S,E)-5'-(3-(((tert-butoxycarbonyl)(methyl)amino)pentyl)oxy)prop-1-en-1-yl)-2'-oxo-1',2',5,7-tetrahydrospiro[cyclopenta[b]pyridine-6,3'-pyrrolo[2,3-b]pyridine]-3-carboxylate | 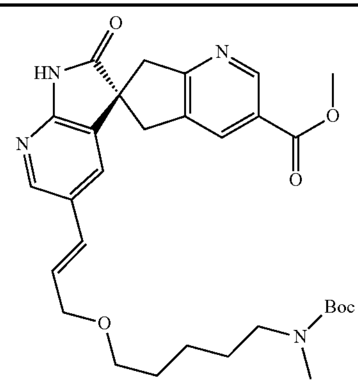 | 5 | 41, 42 and 46 | LC-MS (ESI+): 551.32 [M + H] |
| 9 | Isopropyl (S,E)-2'-oxo-5'-(2,2,5-trimethyl-4-oxo-3,8,11-trioxa-5-azatetradec-13-en-14-yl)-1',2',5,7-tetrahydrospiro[cyclopenta[c]pyridine-6,3'-pyrrolo[2,3-b]pyridine]-3-carboxylate | 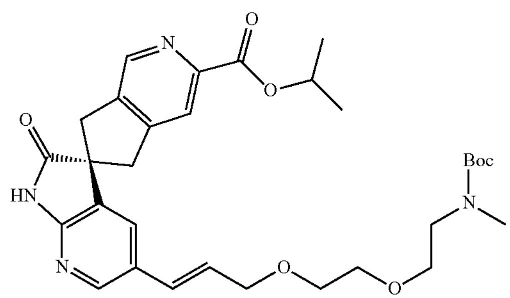 [SMILES: CC(C)OC(=O)c1cc2c(cn1)C[C@]1(C2)C(=O)Nc2ncc(/C=C/COCCOCCN(C)C(=O)OC(C)(C)C)cc21] | 9 | 49 and 33 | LC-MS (ESI+): 581.80 [M + H] |
| 10 | Isopropyl (R,E)-2'-oxo-5'-(2,2,5-trimethyl-4-oxo-3,8,11-trioxa-5-azatetradec-13-en-14-yl)-1',2',5,7-tetrahydrospiro[cyclopenta[c]pyridine-6,3'-pyrrolo[2,3-b]pyridine]-3-carboxylate | 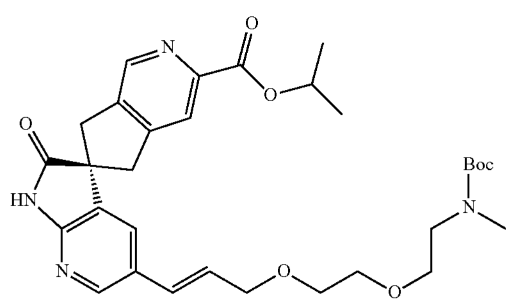 [SMILES: CC(C)OC(=O)c1cc2c(cn1)C[C@@]1(C2)C(=O)Nc2ncc(/C=C/COCCOCCN(C)C(=O)OC(C)(C)C)cc21] | 9 | 50 and 33 | LC-MS (ESI+): 581.41 [M + H] |

TABLE 2-continued

Intermediates Table 2

| Intermediate Number | Name | Structure | Synthetic Route | Intermediates Used | LCMS Data |
|---|---|---|---|---|---|
| 11 | Isopropyl (R,E)-5'-(3-((5-((tert-butoxycarbonyl)(methyl)amino)pentyl)(methyl)amino)prop-1-en-1-yl)-2'-oxo-1',2',5,7-tetrahydrospiro[cyclopenta[c]pyridine-6,3'-pyrrolo[2,3-b]pyridine]-3-carboxylate | 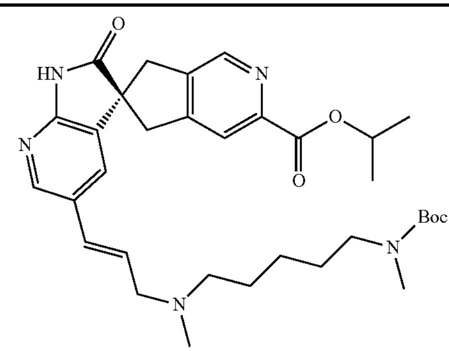 | 10 | 50, 52 and 53 | LC-MS (ESI+): 592.28 [M + H] |
| 12 | Methyl (R)-2-amino-3-(1,7-dimethyl-1H-indazol-5-yl)propanoate dihydrochloride | 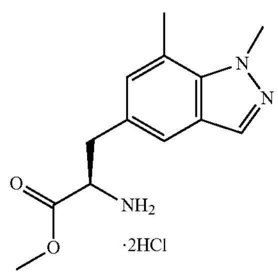 [SMILES: COC(=O)[C@H](N)Cc1cc(C)c2c(cnn2C)c1] | 7 | 2 | LC-MS (ESI+): 248.11 [M + H] |
| 13 | Isopropyl (R,E)-5'-(3-((5-((tert-butoxycarbonyl)(methyl)amino)pentyl)oxy)prop-1-en-1-yl)-2'-oxo-1',2',5,7-tetrahydrospiro[cyclopenta[c]pyridine-6,3'-pyrrolo[2,3-b]pyridine]-3-carboxylate | 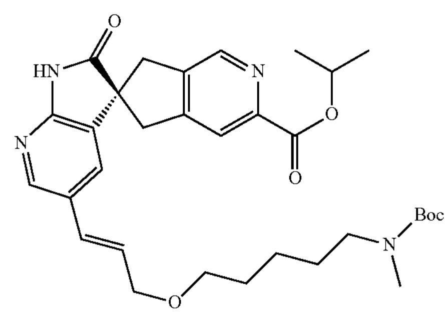 [SMILES: CC(C)OC(=O)c1cc2c(cn1)C[C@@]1(C2)C(=O)Nc2ncc(/C=C/COCCCCCN(C)C(=O)OC(C)(C)C)cc21] | 9 | 50 and 46 | LC-MS (ESI+): 579.58 [M + H] |

TABLE 2-continued

Intermediates Table 2

| Intermediate Number | Name | Structure | Synthetic Route | Intermediates Used | LCMS Data |
|---|---|---|---|---|---|
| 14 | Isopropyl (R,E)-5'-(3-(4-((tert-butoxycarbonyl)(methyl)amino)butoxy)prop-1-en-1-yl)-2'-oxo-1',2',5,7-tetrahydrospiro[cyclopenta[c]pyridine-6,3'-pyrrolo[2,3-b]pyridine]-3-carboxylate | 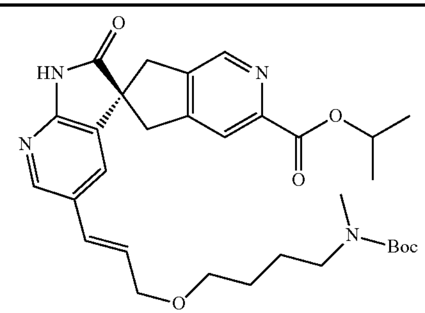 | 9 | 50 and 43 | LC-MS (ESI+): 565.50 [M + H] |
| 15 | Isopropyl (R,E)-2'-oxo-5'-(2,2,5,8-tetramethyl-4-oxo-3,11-dioxa-5,8-diazatetradec-13-en-14-yl)-1',2',5,7-tetrahydrospiro[cyclopenta[c]pyridine-6,3'-pyrrolo[2,3-b]pyridine]-3-carboxylate | 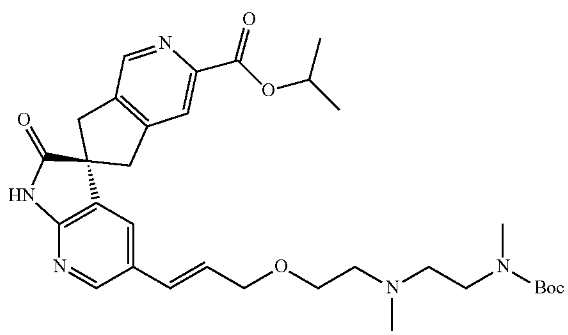 [SMILES: CC(C)OC(=O)c1cc2c(cn1)C[C@@]1(C2)C(=O)Nc2ncc(/C=C/COCCN(C)CCN(C)C(=O)OC(C)(C)C)cc21] | 13 | 50, 56 and 57 | LC-MS (ESI+): 594.25 [M + H] |
| 16 | Methyl (R,E)-2'-oxo-5'-(2,2,5-trimethyl-4-oxo-3,8,11-trioxa-5-azatetradec-13-en-14-yl)-1,1',2',3-tetrahydrospiro[indene-2,3'-pyrrolo[2,3-b]pyridine]-5-carboxylate | 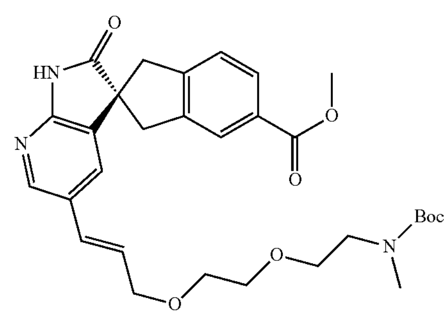 [SMILES: COC(=O)c1ccc2c(c1)C[C@@]1(C2)C(=O)Nc2ncc(/C=C/COCCOCCN(C)C(=O)OC(C)(C)C)cc21] | 16 | 60 and 33 | LC-MS (ESI+): 552.77 [M + H] |

TABLE 2-continued

Intermediates
Table 2

| Intermediate Number | Name | Structure | Synthetic Route | Intermediates Used | LCMS Data |
|---|---|---|---|---|---|
| 17 | Methyl (S,E)-2'-oxo-5'-(2,2,5-trimethyl-4-oxo-3,8,11-trioxa-5-azatetradec-13-en-14-yl)-1,1',2',3-tetrahydrospiro[indene-2,3'-pyrrolo[2,3-b]pyridine]-5-carboxylate | 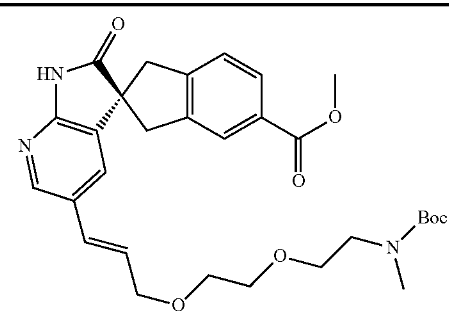 | 16 | 59 and 33 | LC-MS (ESI+): 552.77 [M + H] |
| 18 | Methyl (S,E)-5'-(3-(3-((tert-butoxycarbonyl)(methyl)amino)propoxy)prop-1-en-1-yl)-2'-oxo-1,1',2',3-tetrahydrospiro[indene-2,3'-pyrrolo[2,3-b]pyridine]-5-carboxylate | 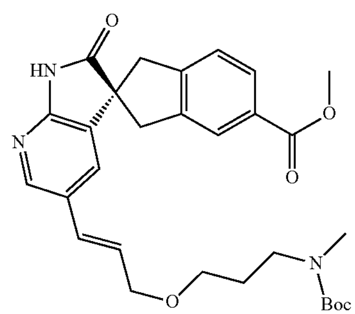 [SMILES: COC(=O)c1ccc2c(c1)C[C@]1(C2)C(=O)Nc2ncc(/C=C/COCCCN(C)C(=O)OC(C)(C)C)cc21] | 16 | 59 and 62 | LC-MS (ESI+): 522.80 [M + H] |
| 19 | Methyl (S,E)-5'-(3-(4-((tert-butoxycarbonyl)(methyl)amino)butoxy)prop-1-en-1-yl)-2'-oxo-1,1',2',3-tetrahydrospiro[indene-2,3'-pyrrolo[2,3-b]pyridine]-5-carboxylate | 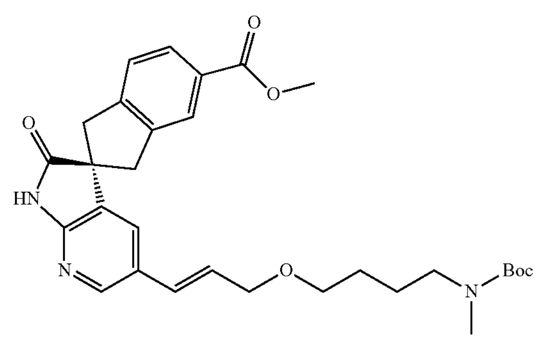 [SMILES: COC(=O)c1ccc2c(c1)C[C@]1(C2)C(=O)Nc2ncc(/C=C/COCCCCN(C)C(=O)OC(C)(C)C)cc21] | 16 | 59 and 43 | LC-MS (ESI+): 536.87 [M + H] |

TABLE 2-continued

Intermediates Table 2

| Intermediate Number | Name | Structure | Synthetic Route | Intermediates Used | LCMS Data |
|---|---|---|---|---|---|
| 20 | Methyl (S,E)-2'-oxo-5'-(2,2,5,8-tetramethyl-4-oxo-3,11-dioxa-5,8-diazatetradec-13-en-14-yl)-1,1',2',3'-tetrahydrospiro[indene-2,3'-pyrrolo[2,3-b]pyridine]-5-carboxylate | 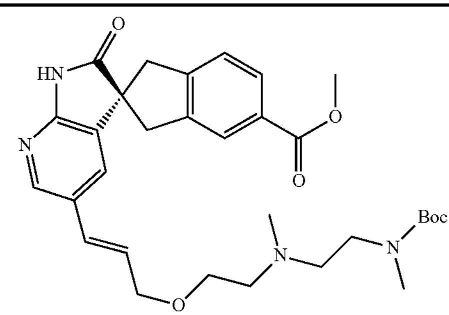 | 17 | 59, 56 and 57 | LC-MS (ESI+): 565.43 [M + H] |
| 21 | Methyl 2-amino-3-(7-chloro-1H-indazol-5-yl)propanoate | 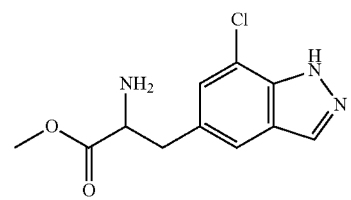 [SMILES: COC(=O)C(N)Cc1cc(Cl)c2[nH]ncc2c1] | Bioorganic & Medicinal Chemistry Letters, 23(6), 1870-1873; 2013 Commercially available, CAS: 635712-47-9 | — | — |
| 22 | Tert-butyl (R)-2-hydroxy-3-(7-methyl-1H-indazol-5-yl)propanoate | 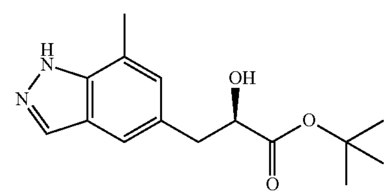 [SMILES: Cc1cc(C[C@@H](O)C(=O)OC(C)(C)C)cc2cn[nH]c12] | 18 | 64 | LC-MS (ESI+): 277.59 [M + H] |
| 23 | Tert-butyl (S)-2-hydroxy-3-(7-methyl-1H-indazol-5-yl)propanoate | 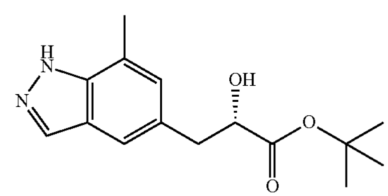 [SMILES: Cc1cc(C[C@H](O)C(=O)OC(C)(C)C)cc2cn[nH]c12] | 18 | 65 | LC-MS (ESI+): 277.59 [M + H] |

TABLE 2-continued

Intermediates Table 2

| Intermediate Number | Name | Structure | Synthetic Route | Intermediates Used | LCMS Data |
|---|---|---|---|---|---|
| 24 | Isomer 1: 2-chloro-1'-((2-(trimethylsilyl)ethoxy)methyl)-5,7-dihydrospiro[cyclopenta[b]pyridine-6,3'-pyrrolo[2,3-b]pyridin]-2'(1H)-one | 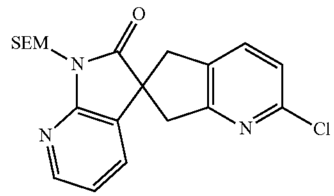 [SMILES: C[Si](C)(C)CCOCN1C(=O)C2(Cc3ccc(Cl)nc3C2)c2cccnc21] | 23 | 41 and 42 | LC-MS (ESI+): 402.1 [M + H] |
| 25 | Isomer 2: 2-chloro-1'-((2-(trimethylsilyl)ethoxy)methyl)-5,7-dihydrospiro[cyclopenta[b]pyridine-6,3'-pyrrolo[2,3-b]pyridin]-2'(1H)-one | 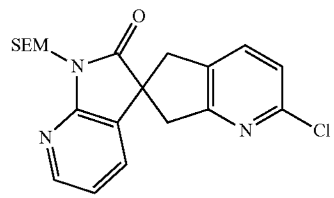 [SMILES: C[Si](C)(C)CCOCN1C(=O)C2(Cc3ccc(Cl)nc3C2)c2cccnc21] | 23 | 41 and 42 | LC-MS (ESI+): 402.1 [M + H] |
| 26 | Tert-butyl (E)-methyl(2-(2-((3-(2'-oxo-1',2'-dihydrospiro[piperidine-4,4'-pyrido[2,3-d][1,3]oxazin]-6'-yl)allyl)oxy)ethoxy)ethyl)carbamate | 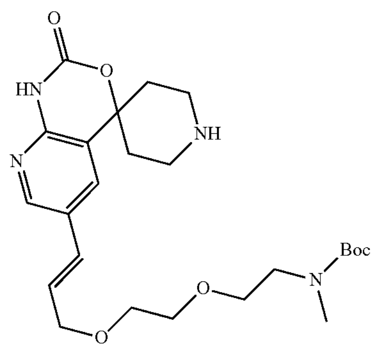 [SMILES: CN(CCOCCOC/C=C/c1cnc2c(c1)C1(CCNCC1)OC(=O)N2)C(=O)OC(C)(C)C] | 20 | 66 and 33 | LC-MS (ESI+): 477.17 [M + H] |

TABLE 2-continued

Intermediates
Table 2

| Intermediate Number | Name | Structure | Synthetic Route | Intermediates Used | LCMS Data |
|---|---|---|---|---|---|
| 27 | Tert-butyl (R)-5-(3-methoxy-2-(((4-nitrophenoxy)carbonyl)oxy)-3-oxopropyl)-7-methyl-1H-indazole-1-carboxylate | 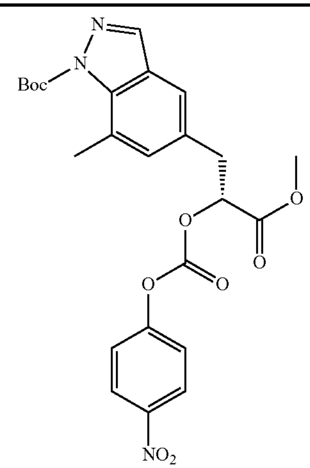 | 21 | 67 | LC-MS (ESI+): 400.00 [M + H − Boc] |
| 28 | Tert-butyl (E)-methyl(2-(2-(2-((3-(2'-oxo-1',2'-dihydrospiro[piperidine-4,4'-pyrido[2,3-d][1,3]oxazin]-6'-yl)allyl)oxy)ethoxy)ethoxy)ethyl)carbamate | 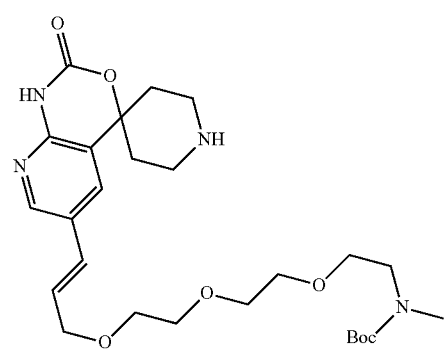 [SMILES: CN(CCOCCOCCOC/C=C/c1cnc2c(c1)C1(CCNCC1)OC(=O)N2)C(=O)OC(C)(C)C] | 20 | 66 and 36 | LC-MS (ESI+): 521.23 [M + H] |

TABLE 2-continued

Intermediates Table 2

| Intermediate Number | Name | Structure | Synthetic Route | Intermediates Used | LCMS Data |
|---|---|---|---|---|---|
| 29 | Tert-butyl (E)-methyl(5-((3-(2'-oxo-1',2'-dihydrospiro[piperidine-4,4'-pyrido[2,3-d][1,3]oxazin]-6'-yl)allyl)oxy)pentyl)carbamate | 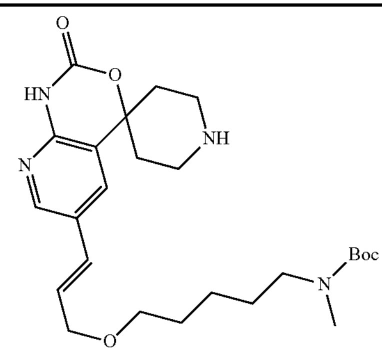 | 20 | 66 and 46 | LC-MS (ESI+): 475.28 [M + H] |
| 30 | Tert-butyl (E)-methyl(3-((3-(2'-oxo-1',2'-dihydrospiro[piperidine-4,4'-pyrido[2,3-d][1,3]oxazin]-6'-yl)allyl)oxy)ethoxy)propyl)carbamate | 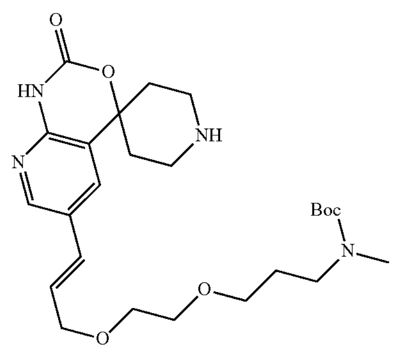 [SMILES: CN(CCCOCCOC/C=C/c1cnc2c(c1)C1(CCNCC1)OC(=O)N2)C(=O)OC(C)(C)C] | 20 | 66 and 68 | LC-MS (ESI+): 491.13 [M + H] |

TABLE 2-continued

Intermediates Table 2

| Intermediate Number | Name | Structure | Synthetic Route | Intermediates Used | LCMS Data |
|---|---|---|---|---|---|
| 31 | Isomer 1: Isopropyl (E)-2'-oxo-5'-(2,2,5-trimethyl-4-oxo-3,8,11-trioxa-5-azatetradec-13-en-14-yl)-1',2',5',7'-tetrahydrospiro[cyclopenta[b]pyridine-6,3'-pyrrolo[2,3-b]pyridine]-2-carboxylate | 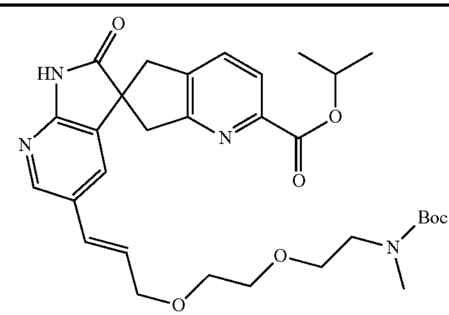 | 9 | 24 and 33 | LC-MS (ESI+): 581.80 [M + H] |
| 32 | (S)-2'-oxo-1',2',5',7'-tetrahydrospiro[cyclopenta[b]pyridine-6,3'-pyrrolo[2,3-b]pyridine]-3-carboxylic acid | 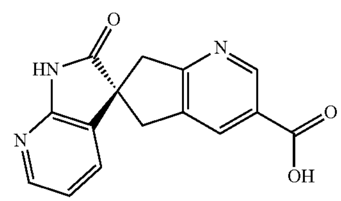 [SMILES: O=C(O)c1cnc2c(c1)C[C@@]1(C2)C(=O)Nc2ncccc21] | WO 2013169563 Commercially available, CAS: 1375541-21-1 | — | — |
| 33 | Tert-butyl (E)-methyl(2-(2-((3-(4,4,5,5-tetramethyl-1,3,2-dioxaborolan-2-yl)allyl)oxy)ethoxy)ethyl)carbamate | 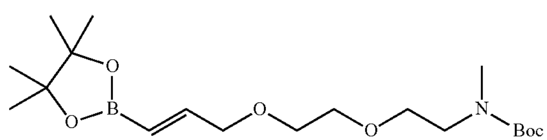 [SMILES: CN(CCOCCOC/C=C/B1OC(C)(C)C(C)(C)O1)C(=O)OC(C)(C)C] | 3 | 37 | LC-MS (ESI+): 408.70 [M + Na] |
| 34 | 5-Bromo-7-methyl-1H-indazole | 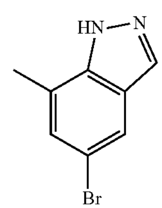 | Commercially available, CAS: 156454-43-2 | — | — |

TABLE 2-continued

Intermediates
Table 2

| Intermediate Number | Name | Structure | Synthetic Route | Intermediates Used | LCMS Data |
|---|---|---|---|---|---|
| 35 | Methyl (R)-2-((tert-butoxycarbonyl)amino)-3-iodopropanoate | 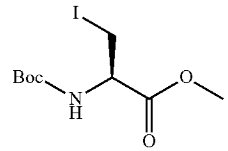 | Commercially available, CAS: 93267-04-0 | — | — |
| 36 | Tert-butyl (E)-methyl(2-(2-(2-((3-(4,4,5,5-tetramethyl-1,3,2-dioxaborolan-2-yl)allyl)oxy)ethoxy)ethyl)carbamate | 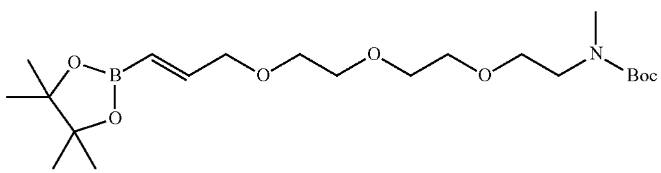 [SMILES: CN(CCOCCOCCOC/C=C/B1OC(C)(C)C(C)(C)O1)C(=O)OC(C)(C)C] | 3 | 38 | LC-MS (ESI+): 452.67 [M + Na] |
| 37 | 2-(2-Aminoethoxy)ethan-1-ol | 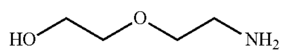 | Commercially available, CAS: 929-06-6 | — | — |
| 38 | 2-(2-(2-Aminoethoxy)ethoxy)ethan-1-ol | 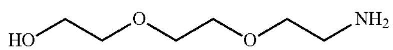 | Commercially available, CAS: 6338-55-2 | — | — |
| 39 | Tert-butyl (E)-methyl(9-(4,4,5,5-tetramethyl-1,3,2-dioxaborolan-2-yl)non-8-en-1-yl)carbamate | 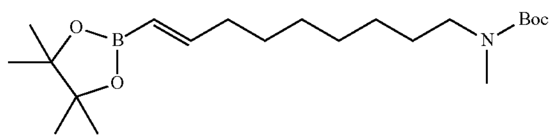 [SMILES: CN(CCCCCCC/C=C/B1OC(C)(C)C(C)(C)O1)C(=O)OC(C)(C)C] | 4 | 40 | LC-MS (ESI+): 404.87 [M + Na] |
| 40 | Non-8-yn-1-amine hydrochloride | 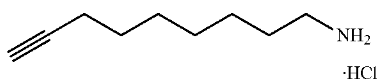 | Commercially available, CAS: 2108912-29-2 | — | — |
| 41 | Dimethyl pyridine-2,3-dicarboxylate | 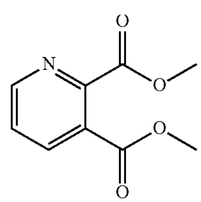 | Commercially available, CAS: 605-38-9 | — | — |

TABLE 2-continued

Intermediates Table 2

| Intermediate Number | Name | Structure | Synthetic Route | Intermediates Used | LCMS Data |
|---|---|---|---|---|---|
| 42 | 1-((2-(Trimethylsilyl)ethoxy)methyl)-1,3-dihydro-2H-pyrrolo[2,3-b]pyridin-2-one | 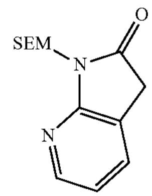 | See route 15 Commercially available, CAS: 879132-48-6 | 61 | LC-MS (ESI+): 265.1 [M + H] |
| 43 | Tert-butyl (E)-methyl(4-((3-(4,4,5,5-tetramethyl-1,3,2-dioxaborolan-2-yl)allyl)oxy)butyl)carbamate | 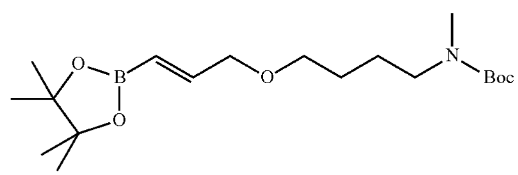 [SMILES: CN(CCCCOC/C=C/B1OC(C)(C)C(C)(C)O1)C(=O)OC(C)(C)C] | 6 | 44 | LC-MS (ESI+): 370.31 [M + H] |
| 44 | Tert-butyl (4-hydroxybutyl)(methyl)carbamate | 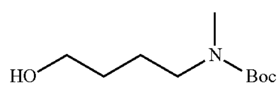 | Commercially available, CAS: 99207-32-6 | — | — |
| 45 | (R)-2'-oxo-1',2',5,7-tetrahydrospiro[cyclopenta[b]pyridine-6,3'-pyrrolo[2,3-b]pyridine]-3-carboxylic acid | 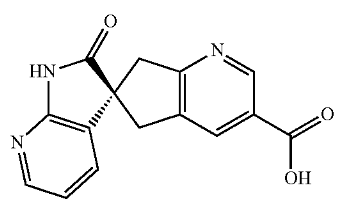 [SMILES: O=C(O)c1cnc2c(c1)C[C@]1(C2)C(=O)Nc2ncccc21] | WO 2013169563 | — | — |
| 46 | Tert-butyl (E)-methyl(5-((3-(4,4,5,5-tetramethyl-1,3,2-dioxaborolan-2-yl)allyl)oxy)pentyl)carbamate | 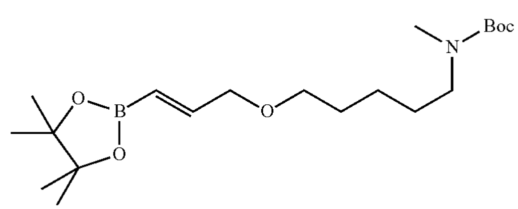 [SMILES: CN(CCCCCOC/C=C/B1OC(C)(C)C(C)(C)O1)C(=O)OC(C)(C)C] | 6 | 47 | LC-MS (ESI+): 284.28 [M + H − Boc] |

TABLE 2-continued

Intermediates Table 2

| Intermediate Number | Name | Structure | Synthetic Route | Intermediates Used | LCMS Data |
|---|---|---|---|---|---|
| 47 | Tert-butyl (5-hydroxypentyl)(methyl) carbamate | 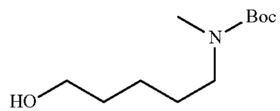 | Commercially available, CAS: 1373210-02-6 | — | — |
| 48 | Methyl 3,4-bis(bromomethyl) benzoate | 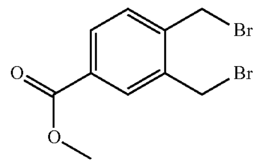 | Commercially available, CAS: 20896-23-5 | — | — |
| 49 | Isomer 1: (S)-3-chloro-1'-((2-(trimethylsilyl)ethoxy) methyl)-5,7-dihydrospiro[cyclopenta[c] pyridine-6,3'-pyrrolo[2,3-b]pyridin]-2'(1'H)-one | 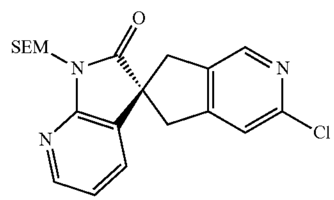 [SMILES: C[Si](C)(C)CCOCN1C(=O)[C@@]2(Cc3cnc(Cl)cc3C2)c2cccnc21] | 8 | 51 and 42 | LC-MS (ESI+): 402.1 [M + H] |
| 50 | Isomer 2: (R)-3-chloro-1'-((2-(trimethylsilyl)ethoxy) methyl)-5,7-dihydrospiro[cyclopenta[c] pyridine-6,3'-pyrrolo[2,3-b]pyridin]-2'(1'H)-one | 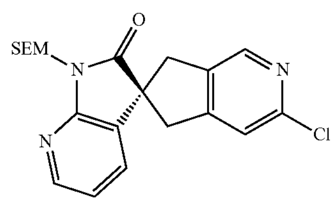 [SMILES: C[Si](C)(C)CCOCN1C(=O)[C@]2(Cc3cnc(Cl)cc3C2)c2cccnc21] | 8 | 51 and 42 | LC-MS (ESI+): 402.1 [M + H] |
| 51 | Pyridine-3,4-dicarboxylic acid | 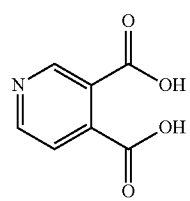 [SMILES: O=C(O)c1ccncc1C(=O)O] | Commercially available, CAS: 490-11-9 | — | — |

TABLE 2-continued

Intermediates Table 2

| Intermediate Number | Structure | Name | Synthetic Route | Intermediates Used | LCMS Data |
|---|---|---|---|---|---|
| 52 | 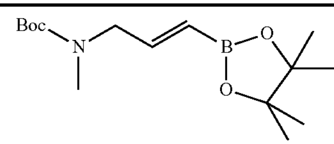 | Tert-butyl (E)-methyl(3-(4,4,5,5-tetramethyl-1,3,2-dioxaborolan-2-yl)allyl)carbamate | 11 | 54 | LC-MS (ESI+): 320.14 [M + Na] |
| 53 | 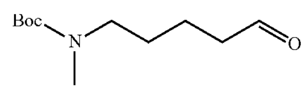 | Tert-butyl methyl(5-oxopentyl)carbamate | 12 | 55 | Not recorded |
| 54 | 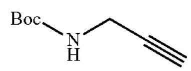 | Tert-butyl prop-2-yn-1-ylcarbamate | Commercially available, CAS: 92136-39-5 | — | — |
| 55 | 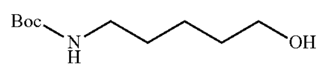 [SMILES: CC(C)(C)OC(=O)NCCCCCO] | Tert-butyl (5-hydroxypentyl)carbamate | Commercially available, CAS: 75178-90-4 | — | — |
| 56 | 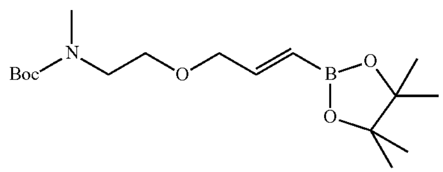 [SMILES: CN(CCOC/C=C/B1OC(C)(C)C(C)(C)O1)C(=O)OC(C)(C)C] | Tert-butyl (E)-methyl(2-((3-(4,4,5,5-tetramethyl-1,3,2-dioxaborolan-2-yl)allyl)oxy)ethyl)carbamate | 14 | 58 | LC-MS (ESI+): 364.16 [M + Na] |
| 57 | 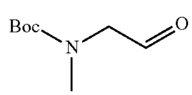 | Tert-butyl methyl(2-oxoethyl)carbamate | Commercially available, CAS: 123387-72-4 | — | — |
| 58 | 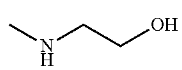 | 2-(methylamino)ethan-1-ol | Commercially available, CAS: 109-83-1 | — | — |
| 59 | 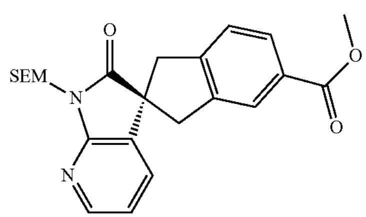 [SMILES: COC(=O)c1ccc2c(c1)C[C@]1(C2)C(=O)N(COCC[Si](C)(C)C)c2ncccc21] | Isomer 1: Methyl (S)-2'-oxo-1'-((2-(trimethylsilyl)ethoxy)methyl)-1,1',2',3-tetrahydrospiro[indene-2,3'-pyrrolo[2,3-b]pyridine]-5-carboxylate | 15 | 61 and 48 | LC-MS (ESI+): 425.1 [M + H] |

TABLE 2-continued

Intermediates Table 2

| Intermediate Number | Name | Structure | Synthetic Route | Intermediates Used | LCMS Data |
|---|---|---|---|---|---|
| 60 | Isomer 2: Methyl (R)-2'-oxo-1'-((2-(trimethylsilyl)ethoxy)methyl)-1,1',2',3-tetrahydrospiro[indene-2,3'-pyrrolo[2,3-b]pyridine]-5-carboxylate | 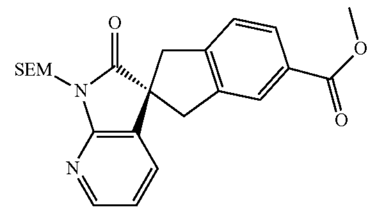 [SMILES: COC(=O)c1ccc2c(c1)C[C@@]1(C2)C(=O)N(COCC[Si](C)(C)C)c2ncccc21] | 15 | 61 and 48 | LC-MS (ESI+): 425.1 [M + H] |
| 61 | 1H-pyrrolo[2,3-b]pyridine | 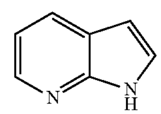 | Commercially available, CAS: 271-63-6 | — | — |
| 62 | Tert-butyl (E)-methyl(3-((3-(4,4,5,5-tetramethyl-1,3,2-dioxaborolan-2-yl)allyl)oxy)propyl)carbamate | 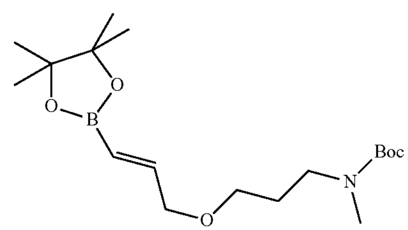 [SMILES: CN(CCCOC/C=C/B1OC(C)(C)C(C)(C)O1)C(=O)OC(C)(C)C] | 6 | 63 | LC-MS (ESI+): 256.70 [M + H − Boc] |
| 63 | Tert-butyl (3-hydroxypropyl)(methyl)carbamate | 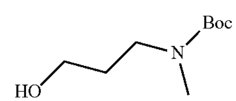 | Commercially available, CAS: 98642-44-5 | — | — |
| 64 | Methyl (R)-2-amino-3-(7-methyl-1H-indazol-5-yl)propanoate | 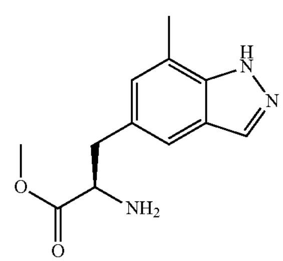 [SMILES: COC(=O)[C@H](N)Cc1cc(C)c2[nH]ncc2c1] | Commercially available, CAS: 890044-58-3 | — | — |

TABLE 2-continued

Intermediates Table 2

| Intermediate Number | Name | Structure | Synthetic Route | Intermediates Used | LCMS Data |
|---|---|---|---|---|---|
| 65 | Methyl (S)-2-amino-3-(7-methyl-1H-indazol-5-yl)propanoate | 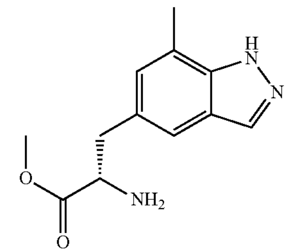 [SMILES: COC(=O)[C@@H](N)Cc1cc(C)c2[nH]ncc2c1] | 19 | 34 and 35 | LC-MS (ESI+): 234.56 [M + H] |
| 66 | 6'-Bromospiro[piperidine-4,4'-pyrido[2,3-d][1,3]oxazin]-2'(1'H)-one hydrochloride salt | 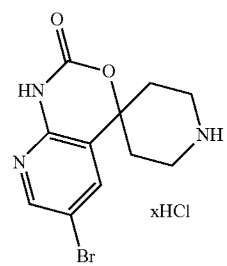 [SMILES: O=C1Nc2ncc(Br)cc2C2(CCNCC2)O1] | 24 | 72 | LC-MS (ESI+): 299.99 [M + H] |
| 67 | Methyl (R)-2-hydroxy-3-(7-methyl-1H-indazol-5-yl)propanoate | 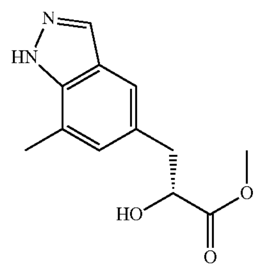 | 25 | 2 | LC-MS (ESI+): 235.55 [M + H] |
| 68 | Tert-butyl (E)-methyl(3-(2-((3-(4,4,5,5-tetramethyl-1,3,2-dioxaborolan-2-yl)allyl)oxy)ethoxy)propyl)carbamate | 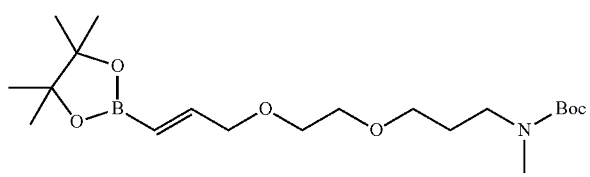 [SMILES: CN(CCCOCCOC/C=C/B1OC(C)(C)C(C)(C)O1)C(=O)OC(C)(C)C] | 22 | 69 and 70 | LC-MS (ESI+): 300.13 [M + H − Boc] |

TABLE 2-continued

Intermediates
Table 2

| Intermediate Number | Name | Structure | Synthetic Route | Intermediates Used | LCMS Data |
|---|---|---|---|---|---|
| 69 | 2-(Prop-2-yn-1-yloxy)ethan-1-ol | 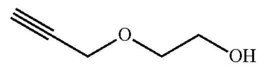 | Commercially available, CAS: 3973-18-0 | — | — |
| 70 | Tert-butyl (3-bromopropyl)carbamate | 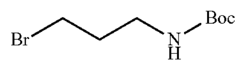 | Commercially available, CAS: 83948-53-2 | — | — |
| 71 | Isomer 2: Isopropyl (E)-2'-oxo-5'-(2,2,5-trimethyl-4-oxo-3,8,11-trioxa-5-azatetradec-13-en-14-yl)-1',2',5',7'-tetrahydrospiro[cyclopenta[b]pyridine-6,3'-pyrrolo[2,3-b]pyridine]-2-carboxylate | 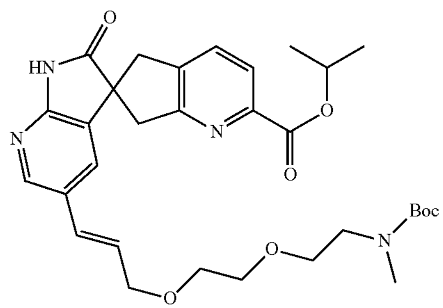 [SMILES: CC(C)OC(=O)c1ccc2c(n1)CC1(C2)C(=O)Nc2ncc(/C=C/COCCOCCN(C)C(=O)OC(C)(C)C)cc21] | 9 | 25 and 33 | LC-MS (ESI+): 581.80 [M + H] |
| 72 | Spiro[piperidine-4,4'-pyrido[2,3-d][1,3]oxazin]-2'(1'H)-one | 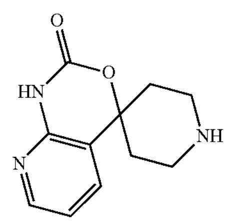 [SMILES: O=C1Nc2ncccc2C2(CCNCC2)O1] | Commercially available, CAS: 753440-87-8 | — | — |

TABLE 3

Example compounds Table 3

| Ex. No. | Name | Structure | Synthetic Method and Intermediates Used | Purification Method | ¹H NMR (two conformations are evident within ¹H NMR spectral data) | LCMS Method | LCMS data |
|---|---|---|---|---|---|---|---|
| 1-1 | (1S,10R,20E)-12-methyl-10-[(7-methyl-1H-indazol-5-yl)methyl]-15,18-dioxa-5,9,12,24,26-pentazapentacyclo[20.5.2.11,4.13,7.025,28]hentriaconta-3,5,7(30),20,22(29),23,25(28)-heptaene-8,11,27-trione | 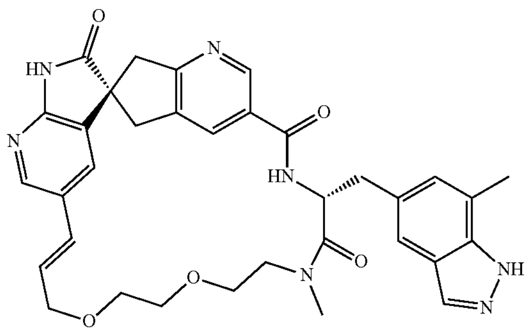 [SMILES: Cc1cc(C[C@H]2NC(=O)c3cnc4c(c3)C[C@@]3(C4)C(=O)Nc4ncc(cc43)/C=C/COCCOCCN(C)C2=O)cc2cn[nH]c12] | A (Step 2 HATU, DMA and Step 5 HATU, DMA) 1 and 2 | A | ¹H NMR (500 MHz, CD₃OD): δ ppm 2.55 (s, 6 H), 2.68-2.77 (m, 2 H), 2.94 (s, 3 H), 2.98 (s, 3 H), 3.07 (d, J = 16.5 Hz, 2 H), 3.14 (d, J = 15.6 Hz, 2 H), 3.14-3.20 (m, 2 H), 3.30 (d, J = 7.6 Hz, 2 H), 3.44-3.56 (m, 4 H), 3.56-3.63 (m, 4 H), 3.65 (t, J = 6.0 Hz, 4 H), 3.68 (d, J = 16.0 Hz, 2 H), 3.80 (d, J = 15.0 Hz, 2 H), 3.94-4.06 (m, 2 H), 4.06-4.14 (m, 2 H), 4.33 (dt, J = 14.2, 5.4 Hz, 2 H), 5.38 (d, J = 7.5 Hz, 1 H), 5.42 (t, J = 7.5 Hz, 1 H), 5.68-5.76 (m, 1 H), 5.77-5.86 (m, 1 H), 6.44 (d, J = 16.0 Hz, 1 H), 6.47 (d, J = 16.2 Hz, 1 H), 6.59 (d, J = 1.5 Hz, 1 H), 6.83 (d, J = 1.8 Hz, 1 H), 7.17 (s, 1 H), 7.20 (s, 1 H), 7.50 (s, 1 H), 7.54 (s, 1 H), 7.94 (d, J = 1.8 Hz, 1 H), 7.96 (d, J = 1.8 Hz, 1 H), 7.97 (s, 2 H), 8.18 (s, 1 H), 8.23 (s, 1 H), 8.83 (s, 1 H), 8.86 (s, 1 H) | Method 01_B | m/z 622.17 (M + H)⁺ (ES⁺), at 1.10 min |
| 1-2 | (1R,10R,20E)-12-methyl-10-[(7-methyl-1H-indazol-5-yl)methyl]-15,18-dioxa-5,9,12,24,26-pentazapentacyclo[20.5.2.11,4.13,7.025,28]hentriaconta-3,5,7(30),20,22(29),23,25(28)-heptaene-8,11,27-trione | 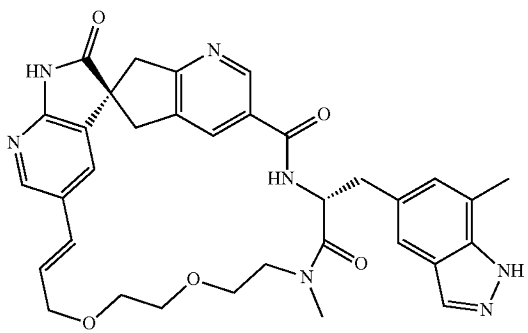 [SMILES: Cc1cc(C[C@H]2NC(=O)c3cnc4c(c3)C[C@]3(C4)C(=O)Nc4ncc(cc43)/C=C/COCCOCCN(C)C2=O)cc2cn[nH]c12] | A (Step 2 PyAOP, DMF and Step 5 PyAOP, DMF) 7 and 2 | B | | Method 01_A | m/z 622.37 (M + H)⁺ (ES⁺), at 3.72 min |

TABLE 3-continued

Example compounds Table 3

| Ex. No. | Name | Structure | Synthetic Method and Intermediates Used | Purification Method | $^1$H NMR (two conformations are evident within $^1$H NMR spectral data) | LCMS Method | LCMS data |
|---|---|---|---|---|---|---|---|
| 1-3 | (1S,10S,20E)-12-methyl-10-[(7-methyl-1H-indazol-5-yl)methyl]-15,18-dioxa-5,9,12,24,26-pentazapentacyclo[20.5.2.11,4.13,7.025,28]hentriaconta-3,5,7(30),20,22(29),23,25(28)-heptaene-8,11,27-trione | 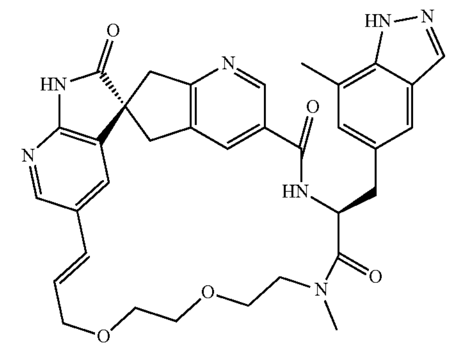 [SMILES: Cc1cc(C[C@@H]2NC(=O)c3cnc4c(c3)C[C@@]3(C4)C(=O)Nc4ncc(cc43)/C=C/COCCOCCN(C)C2=O)cc2cn[nH]c12] | A (Step 2 HATU, DMA and Step 5 HATU, DMA) 1 and 3 | A | | Method 01_A | m/z 622.05 (M + H)$^+$ (ES$^+$), at 3.70 min |
| 1-4 | (1S,10R,23E)-12-methyl-10-[(7-methyl-1H-indazol-5-yl)methyl]-15,18,21-trioxa-5,9,12,27,29-pentazapentacyclo[23.5.2.11,4.13,7.028,31]tetratriaconta-3,5,7(33),23,25(32),26,28(31)-heptaene-8,11,30-trione | 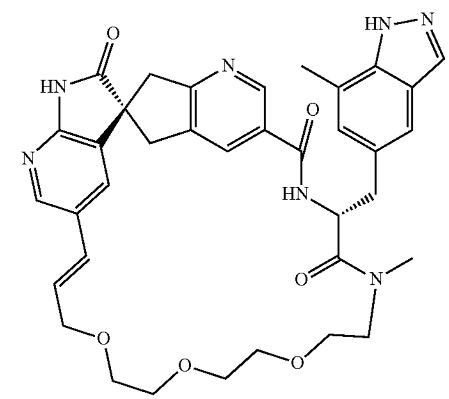 [SMILES: Cc1cc(C[C@H]2NC(=O)c3cnc4c(c3)C[C@@]3(C4)C(=O)Nc4ncc(cc43)/C=C/COCCOCCOCCN(C)C2=O)cc2cn[nH]c12] | A (Step 2 HATU, DMA and Step 5 HATU, DMA) 4 and 2 | A | $^1$H NMR (600 MHz DMSO-d$_6$): δ ppm 2.44 (s, 3 H), 2.44 (s, 3 H), 2.79 (ddd, J = 13.8, 6.7, 4.6 Hz, 1 H), 2.83 (s, 3 H), 2.93-3.02 (m, 2 H), 2.96 (s, 3 H), 3.03-3.08 (m, 2 H), 3.08-3.11 (m, 1 H), 3.11-3.18 (m, 4 H), 3.34-3.49 (m, 16 H), 3.43-3.48 (m, 2 H), 3.45-3.50 (m, 2 H), 3.50-3.57 (m, 4 H), 3.61 (dt, J = 14.9, 5.1 Hz, 1 H), 3.88-3.95 (m, 2 H), 3.96-4.04 (m, 3 H), 5.17-5.23 (m, 2 H), 5.85-5.92 (m, 1 H), 5.92-6.00 (m, 1 H), 6.39 (d, J = 16.0 Hz, 1 H), 6.43 (d, J = 16.1 Hz, 1 H), 6.77 (d, J = 2.0 Hz, 1 H), 6.94 (d, J = 2.0 Hz, 1 H), 7.03 (s, 1 H), 7.06 (s, 1 H), 7.38 (s, 1 H), 7.42 (s, 1 H), 7.94 (s, 1 H), 7.94 (s, 1 H), 8.04 (d, J = 2.0 Hz, 1 H), 8.07 (d, J = 2.0 Hz, 1 H), 8.22 (s, 1 H), 8.30 (s, 1 H), 8.70 (s, 1 H), 8.74 (s, 1 H), 8.93 (d, J = 8.6 Hz, 1 H), 9.02 (d, J = 9.0 Hz, 1 H), 11.37 (br. s., 2 H), 13.00 (br. s., 2 H) | Method 01_A | m/z 666.12 (M + H)$^+$ (ES$^+$), at 3.77 min |

TABLE 3-continued

Example compounds Table 3

| Ex. No. | Name | Structure | Synthetic Method and Intermediates Used | Purification Method | ¹H NMR (two conformations are evident within ¹H NMR spectral data) | LCMS Method | LCMS data |
|---|---|---|---|---|---|---|---|
| 1-5 | (1S,10R,20E)-12-methyl-10-[(7-methyl-1H-indazol-5-yl)methyl]-5,9,12,24,26-pentazapentacyclo[20.5.2.1¹,⁴.1³,⁷.0²⁵,²⁸]hentriaconta-3,5,7(30),20,22(29),23,25(28)-heptaene-8,11,27-trione | 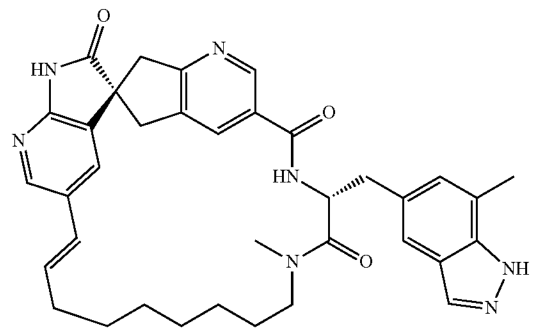 [SMILES: Cc1cc(C[C@H]2NC(=O)c3cnc4c(c3)C[C@@]3(C4)C(=O)Nc4ncc(cc43)/C=C/CCCCCCCN(C)C2=O)cc2cn[nH]c12] | A (Step 2 HATU, DMF and Step 5 HATU, DMF) 5 and 2 | A | ¹H NMR (600 MHz, DMSO-d₆): δ ppm 0.97-1.14 (m, 12 H), 1.15-1.27 (m, 3 H), 1.30-1.39 (m, 4 H), 1.49-1.55 (m, 2 H), 2.03-2.18 (m, 4 H), 2.44 (s, 3 H), 2.44-2.49 (m, 1 H), 2.46 (s, 3 H), 2.75 (s, 3 H), 2.76-2.80 (m, 1 H), 2.95 (s, 3 H), 2.96-3.02 (m, 3 H), 3.02-3.07 (m, 1 H), 3.08-3.18 (m, 4 H), 3.49 (d, J = 15.8 Hz, 2H), 3.56 (d, J = 16.0 Hz, 2 H), 3.55-3.63 (m, 1 H), 4.08-4.16 (m, 1 H), 5.14-5.22 (m, 1 H), 5.24-5.30 (m, 1 H), 5.56-5.62 (m, 1 H), 5.62-5.68 (m, 1 H), 6.29 (d, J = 15.6 Hz, 1 H), 6.30 (d, J = 16.0 Hz, 1 H), 6.51 (d, J = 2.0 Hz, 1 H), 6.62 (d, J = 1.8 Hz, 1 H), 7.01 (s, 1 H), 7.10 (s, 1 H), 7.37 (s, 1 H), 7.46 (s, 1 H),7.90 (d, J = 2.0 Hz, 1 H), 7.93 (d, J = 2.0 Hz, 1 H), 7.94(s, 1 H), 7.96 (s, 1 H), 8.26 (s, 1 H), 8.36 (s, 1 H),8.73 (br. s., 1 H), 8.74 (s, 1 H), 8.94 (d, J = 8.6 Hz, 1 H),9.01 (d, J = 9.0 Hz, 1 H), 11.33 (br. s., 1 H), 12.99 (br. s.,1 H), 13.00 (s, 1 H) | Method 01_A | m/z 619.10 (M + H)⁺ (ES⁺), at 5.13 min |
| 1-6 | (1S,10R,20E)-12-methyl-10-[(7-methyl-1H-indazol-5-yl)methyl]-18-oxa-5,9,12,24,26-pentazapentacyclo[20.5.2.1¹,⁴.1³,⁷.0²⁵,²⁸]hentriaconta-3,5,7(30),20,22(29),23,25(28)-heptaene-8,11,27-trione | 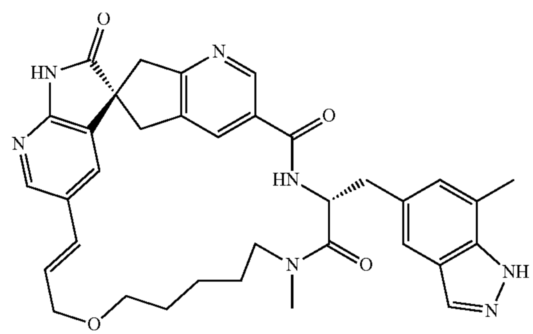 [SMILES: Cc1cc(C[C@H]2NC(=O)c3cnc4c(c3)C[C@@]3(C4)C(=O)Nc4ncc(cc43)/C=C/COCCCCCN(C)C2=O)cc2cn[nH]c12] | A_1 8 and 2 | P | ¹H NMR (600 MHz, DMSO-d6): δ ppm 0.85 (br. s., 1 H), 0.94-1.01 (m, 1 H), 1.06-1.14 (m, 1 H), 1.16-1.22 (m, 1 H), 1.23-1.33 (m, 2 H), 1.39 (br. s., 3 H), 1.44-1.56 (m, 3 H), 2.40-2.44 (m, 1 H), 2.45 (br. s., 3 H), 2.46 (s, 3 H), 2.76 (s, 3 H), 2.80-2.87 (m, 1 H), 2.93 (s, 3 H), 2.95-2.97 (m, 1 H), 2.99 (d, J = 16.1 Hz, 2 H), 3.02-3.05 (m, 1 H), 3.09 (d, J = 15.6 Hz, 2 H), 3.11-3.16 (m, 1 H), 3.18-3.28 (m, 5 H), 3.45-3.49 (m, 1 H), 3.50 (d, J = 15.0 Hz, 2 H), 3.58 (d, J = 16.0 Hz, 2 H), 3.57-3.64 (m, 1 H), 3.86-3.96 (m, 2 H), 3.96-4.03 (m, 2 H), 4.04-4.15 (m, 1 H), 5.16 (q, J = 7.9 Hz, 1 H), 5.20 (q, J = 8.4 Hz, 1 H), 5.58-5.66 (m, 1 H), 5.67-5.81 (m, 1 H), 6.41 (d, J = 15.6 Hz, 1 H), 6.43 (d, J = 16.0 Hz, 1 H), 6.48 (br. s., 1 H), 6.60 (s, 1 H), 7.03 (s, 1 H), 7.10 (s, 1 H), 7.38 (s, 1 H), 7.46 (s, 1 H), 7.89-8.04 (m, 4 H), 8.23 (br. s., 1 H), 8.30 (s, 1 H), 8.70 (s, 2 H), 8.95 (d, J = 8.6 Hz, 1 H), 9.09 (d, J = 9.0 Hz, 1 H), 11.39 (br. s., 2 H), 13.00 (br. s., 2 H) | Method 01_A | m/z 620.54 (M + H)⁺ (ES⁺), at 4.19 min |

TABLE 3-continued

Example compounds Table 3

| Ex. No. | Name | Structure | Synthetic Method and Intermediates Used | Purification Method | ¹H NMR (two conformations are evident within ¹H NMR spectral data) | LCMS Method | LCMS data |
|---|---|---|---|---|---|---|---|
| 1-7 | (1S,10R,19E)-12-methyl-10-[(7-methyl-1H-indazol-5-yl)methyl]-17-oxa-5,9,12,23,25-pentazapentacyclo [19.5.2.1⁴,¹³.0²⁴,²⁷]triaconta-3,5,7(29),19,21(28),22,24(27)-heptaene-8,11,26-trione | 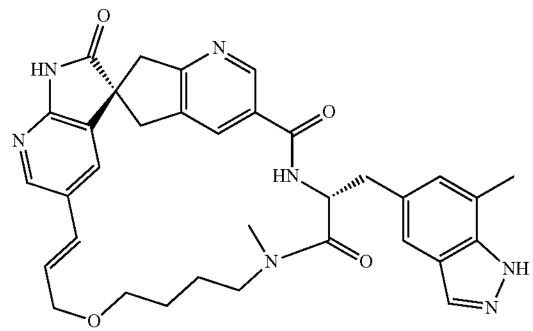 [SMILES: Cc1cc(C[C@H]2NC(=O)c3cnc4c(c3)C[C@@]3(C4)C(=O)Nc4ncc(cc43)/C=C/COCCCCN(C)C2=O)cc2cn[nH]c12] | A (Step 2 HATU, DMF and Step 5 HATU, DMF) 6 and 2 | A | | Method 01_A | m/z 606.42 (M + H)⁺ (ES⁺), at 2.98 min |
| 1-8 | (1S,10R)-12-methyl-10-[(7-methyl-1H-indazol-5-yl)methyl]-15,18-dioxa-5,9,12,24,26-pentazapentacyclo [20.5.2.1¹,¹³.0²⁵,²⁸]hentriaconta-3,5,7(30),22(29),23,25(28)-hexaene-8,11,27-trione | 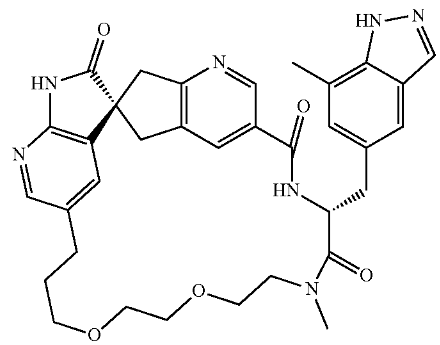 [SMILES: Cc1cc(C[C@H]2NC(=O)c3cnc4c(c3)C[C@@]3(C4)C(=O)Nc4ncc(cc43)CCCOCCOCCN(C)C2=O)cc2cn[nH]c12] | E Example 1-1 | N/A | ¹H NMR (500 MHz, DMSO-d₆): δ ppm 1.35-1.43 (m, 1 H), 1.43-1.51 (m, 1 H), 1.55-1.63 (m, 1 H), 1.64-1.73 (m, 1 H), 2.30-2.39 (m, 2 H), 2.40-2.48 (m, 2 H), 2.44 (s, 3 H), 2.45 (s, 3 H), 2.64 (ddd, J = 13.9, 6.1, 3.5 Hz, 1 H), 2.79 (s, 3 H), 2.92-2.98 (m, 4 H), 2.93-3.05 (m, 4 H), 2.99 (s, 3 H), 3.00-3.03 (m, 1 H), 3.07-3.13 (m, 5 H), 3.14-3.18 (m, 2 H), 3.18-3.26 (m, 3 H), 3.28-3.33 (m, 3 H), 3.37-3.43 (m, 1 H), 3.44-3.51 (m, 3 H), 3.51-3.58 (m, 3 H), 3.75-3.84 (m, 1 H), 4.21 (ddd, J = 14.0, 6.6, 3.8 Hz, 1 H), 5.18 (q, J 9.0 Hz, 1 H), 5.23 (ddd, J = 9.0, 8.0, 7.0 Hz, 1 H), 6.41 (d, J = 1.8 Hz, 1 H), 6.47 (d, J = 1.8 Hz, 1 H), 7.03 (s, 1 H), 7.08 (s, 1 H), 7.37 (s, 1 H), 7.42 (s, 1 H), 7.92 (d, J = 1.5 Hz, 2 H), 7.94 (s, 1 H), 7.95 (s, 1 H), 8.28 (s, 1 H), 8.35 (s, 1 H), 8.73 (s, 1 H), 8.74 (s, 1 H), 8.92 (d, J = 8.9 Hz, 1 H), 8.99 (d, J = 9.2 Hz, 1 H), 11.21 (br. s., 2 H), 12.98 (br. s., 1 H), 12.99 (br. s., 1 H) | Method 01_B | m/z 624.86 (M + H)⁺ (ES⁺), at 1.08 min |

TABLE 3-continued

Example compounds Table 3

| Ex. No. | Name | Structure | Synthetic Method and Intermediates Used | Purification Method | ¹H NMR (two conformations are evident within ¹H NMR spectral data) | LCMS Method | LCMS data |
|---|---|---|---|---|---|---|---|
| 2-1 | (1S,10R,20E)-12-methyl-10-[(7-methyl-1H-indazol-5-yl)methyl]-15,18-dioxa-6,9,12,24,26-pentazapentacyclo[20.5.2.1⁴,¹³.0²⁵,²⁸]hentriaconta-3,5,7(30),20,22(29),23,25(28)-heptaene-8,11,27-trione | 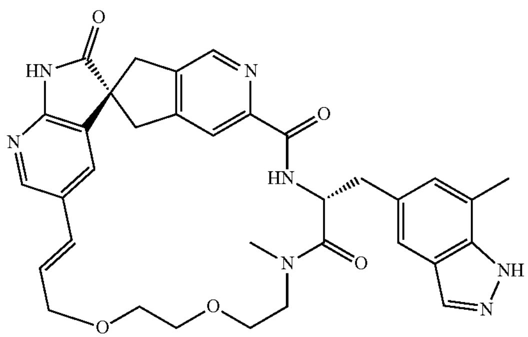 [SMILES: Cc1cc(C[C@H]2NC(=O)c3cc4c(cn3)C[C@]3(C4)C(=O)Nc4ncc(cc43)/C=C/COCCOCCN(C)C2=O)cc2cn[nH]c12] | A (Step 2 HATU, DMF and Step 5 HATU, DMF) 9 and 2 | A | | Method 01_A | m/z 622.14 (M + H)⁺ (ES⁺), at 3.67 min |
| 2-2 | (1R,10R,20E)-12-methyl-10-[(7-methyl-1H-indazol-5-yl)methyl]-15,18-dioxa-6,9,12,24,26-pentazapentacyclo[20.5.2.1⁴,¹³.0²⁵,²⁸]hentriaconta-3,5,7(30),20,22(29),23,25(28)-heptaene-8,11,27-trione | 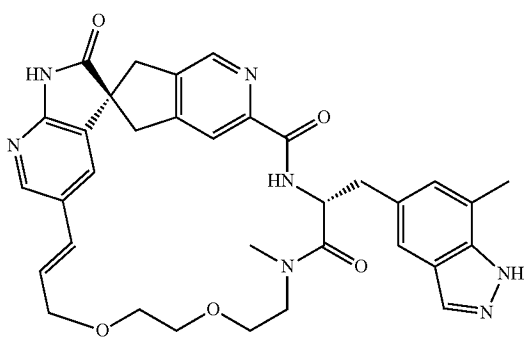 [SMILES: Cc1cc(C[C@H]2NC(=O)c3cc4c(cn3)C[C@@]3(C4)C(=O)Nc4ncc(cc43)/C=C/COCCOCCN(C)C2=O)cc2cn[nH]c12] | A (Step 2 HATU, DMF and Step 5 HATU, DMF) 10 and 2 | A | | Method 01_A | m/z 622.38 (M + H)⁺ (ES⁺), at 4.11 min |

TABLE 3-continued

Example compounds Table 3

| Ex. No. | Name | Structure | Synthetic Method and Intermediates Used | Purification Method | ¹H NMR (two conformations are evident within ¹H NMR spectral data) | LCMS Method | LCMS data |
|---|---|---|---|---|---|---|---|
| 2-3 | (1R,10R,20E)-12,18-dimethyl-10-[(7-methyl-1H-indazol-5-yl)methyl]-6,9,12,18,24,26-hexazapentacyclo[20.5.2.11,4.13,7.025,28]hentriaconta-3,5,7(30),20,22(29),23,25(28)-heptaene-8,11,27-trione | 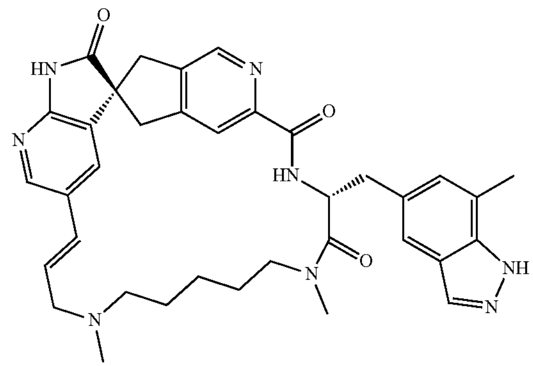 [SMILES: Cc1cc(C[C@H]2NC(=O)c3cc4c(cn3)C[C@@]3(C4)C(=O)Nc4ncc(cc43)/C=C/CN(C)CCCCCN(C)C2=O)cc2cn[nH]c12] | A (Step 2 HATU, DMF and Step 5 HATU, DMF) 11 and 2 | A | | Method 01_A | m/z 633.24 (M + H)+ (ES+), at 2.50 min |
| 2-4 | (1S,10R,20E)-10-[(1,7-dimethylindazol-5-yl)methyl]-12-methyl-15,18-dioxa-6,9,12,24,26-pentazapentacyclo[20.5.2.11,4.13,7.025,28]hentriaconta-3,5,7(30),20,22(29),23,25(28)-heptaene-8,11,27-trione | 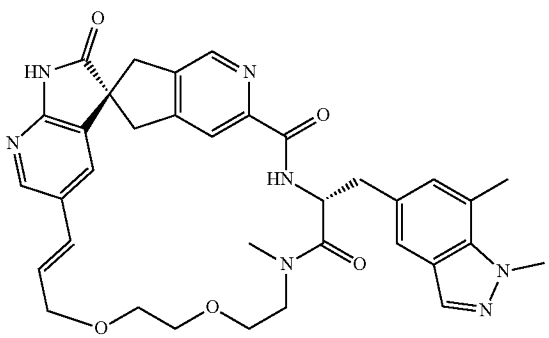 [SMILES: Cc1cc(C[C@H]2NC(=O)c3cc4c(cn3)C[C@]3(C4)C(=O)Nc4ncc(cc43)/C=C/COCCOCCN(C)C2=O)cc2cnn(C)c12] | A (Step 2 HATU, DMF and Step 5 HATU, DMF) 9 and 12 | A | | Method 01_A | m/z 636.35 (M + H)+ (ES+), at 4.03 min |

TABLE 3-continued

Example compounds Table 3

| Ex. No. | Name | Structure | Synthetic Method and Intermediates Used | Purification Method | $^1$H NMR (two conformations are evident within $^1$H NMR spectral data) | LCMS Method | LCMS data |
|---|---|---|---|---|---|---|---|
| 2-5 | (1R,10R,20E)-10-[(1,7-dimethylindazol-5-yl)methyl]-12-methyl-15,18-dioxa-6,9,12,24,26-pentazapentacyclo[20.5.2.11.4.13,7.025,28]hentriaconta-3,5,7(30),20,22(29),23,25(28)-heptaene-8,11,27-trione | 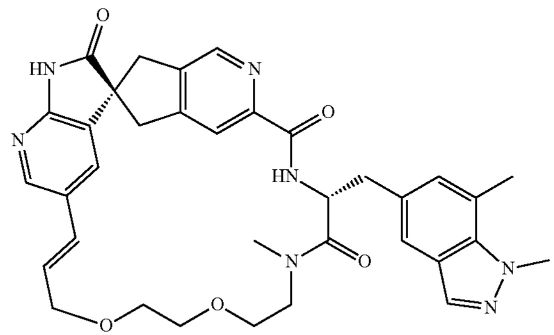 [SMILES: Cc1cc(C[C@H]2NC(=O)c3cc4c(cn3)C[C@@]3(C4)C(=O)Nc4ncc(cc43)/C=C/COCCOCCN(C)C2=O)cc2cnn(C)c12] | A (Step 2 HATU, DMF and Step 5 HATU, DMF) 10 and 12 | A | | Method 01_A | m/z 636.34 (M + H)$^+$ (ES$^+$), at 4.47 min |
| 2-6 | (1R,10R,20E)-10-[(1,7-dimethylindazol-5-yl)methyl]-12-methyl-18-oxa-6,9,12,24,26-pentazapentacyclo[20.5.2.11.4.13,7.025,28]hentriaconta-3,5,7(30),20,22(29),23,25(28)-heptaene-8,11,27-trione | 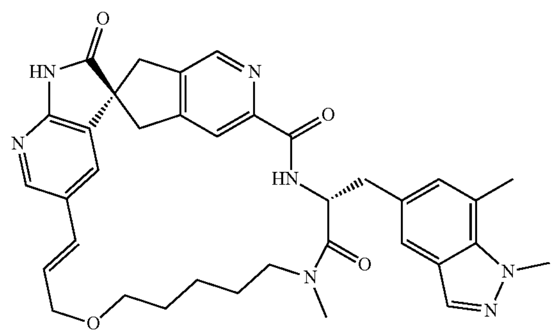 [SMILES: Cc1cc(C[C@H]2NC(=O)c3cc4c(cn3)C[C@@]3(C4)C(=O)Nc4ncc(cc43)/C=C/COCCCCCN(C)C2=O)cc2cnn(C)c12] | A (Step 2 HATU, DMF and Step 5 HATU, DMF) 13 and 12 | A | | Method 01_A | m/z 635.22 (M + H)$^+$ (ES$^+$), at 5.03 min |

TABLE 3-continued

Example compounds Table 3

| Ex. No. | Name | Structure | Synthetic Method and Intermediates Used | Purification Method | ¹H NMR (two conformations are evident within ¹H NMR spectral data) | LCMS Method | LCMS data |
|---|---|---|---|---|---|---|---|
| 2-7 | (1R,10R,19E)-10-[(1,7-dimethylindazol-5-yl)methyl]-12-methyl-17-oxa-6,9,12,23,25-pentazapentacyclo[19.5.2.11,4.13,7.024,27]triaconta-3,5,7(29),19,21(28),22,24(27)-heptaene-8,11,26-trione | 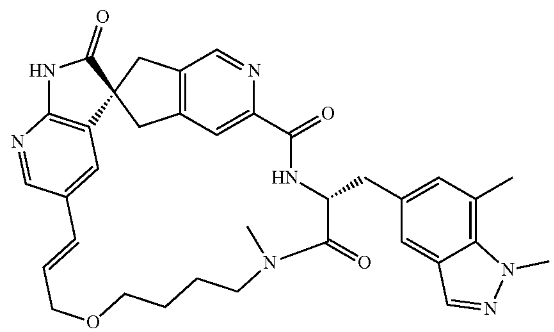 [SMILES: Cc1cc(C[C@H]2NC(=O)c3cc4c(cn3)C[C@@]3(C4)C(=O)Nc4ncc(cc43)/C=C/COCCCCN(C)C2=O)cc2cnn(C)c12] | A (Step 2 HATU, DMF and Step 5 HATU, DMF) 14 and 12 | A | | Method 01_A | m/z 621.14 (M + H)⁺ (ES⁺), at 3.94 min |
| 2-8 | (1R,10R,20E)-10-[(1,7-dimethylindazol-5-yl)methyl]-12,18-dimethyl-6,9,12,18,24,26-hexazapentacyclo[20.5.2.11,4.13,7.025,28]hentriaconta-3,5,7(30),20,22(29),23,25(28)-heptaene-8,11,27-trione | 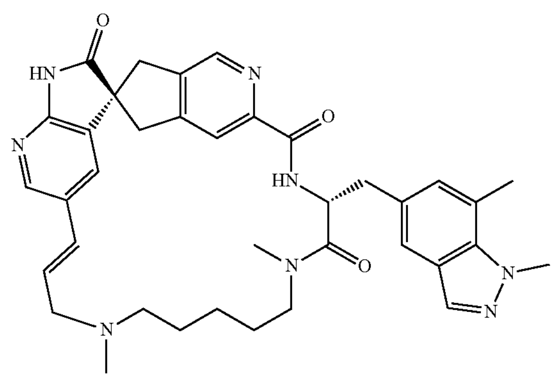 [SMILES: Cc1cc(C[C@H]2NC(=O)c3cc4c(cn3)C[C@@]3(C4)C(=O)Nc4ncc(cc43)/C=C/CN(C)CCCCCN(C)C2=O)cc2cnn(C)c12] | A (Step 2 HATU, DMF and Step 5 HATU, DMF) 11 and 12 | A | | Method 01_A | m/z 647.20 (M + H)⁺ (ES⁺), at 3.93 min |

TABLE 3-continued

Example compounds Table 3

| Ex. No. | Name | Structure | Synthetic Method and Intermediates Used | Purification Method | ¹H NMR (two conformations are evident within ¹H NMR spectral data) | LCMS Method | LCMS data |
|---|---|---|---|---|---|---|---|
| 2-9 | (1R,10R,20E)-10-[(1,7-dimethylindazol-5-yl)methyl]-12,15-dimethyl-18-oxa-6,9,12,15,24,26-hexazapentacyclo [20.5.2.11,4.13,7.025,28] hentriaconta-3,5,7(30),20,22(29),23,25(28)-heptaene-8,11,27-trione | 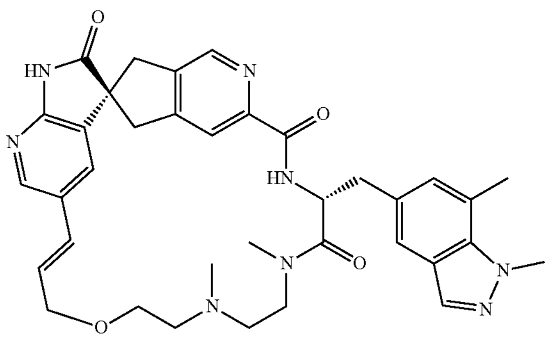 [SMILES: Cc1cc(C[C@H]2NC(=O)c3cc4c(cn3)C[C@@]3(C4)C(=O)Nc4ncc(cc43)/C=C/COCCN(C)CCN(C)C2=O)cc2cnn(C)c12] | A (Step 2 PyAOP, DMF and Step 5 HATU, DMF) 15 and 12 | N | | Method 01_A | m/z 649.10 (M + H)⁺ (ES⁺), at 3.84 min |
| 3-1 | (1R,10R,20E)-12-methyl-10-[(7-methyl-1H-indazol-5-yl)methyl]-15,18-dioxa-9,12,24,26-tetrazapentacyclo [20.5.2.11,4.13,7.025,28] hentriaconta-3,5,7(30),20,22(29),23,25(28)-heptaene-8,11,27-trione | 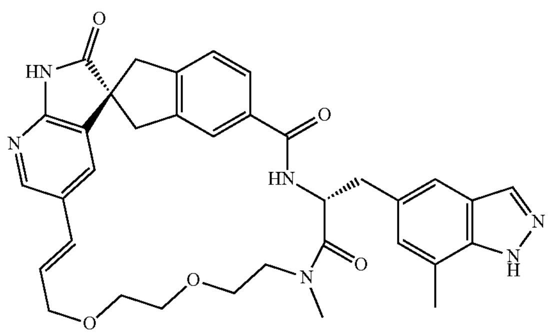 [SMILES: Cc1cc(C[C@H]2NC(=O)c3ccc4c(c3)C[C@@]3(C4)C(=O)Nc4ncc(cc43)/C=C/COCCOCCN(C)C2=O)cc2cn[nH]c12] | A (Step 1 heated to 50° C., Step 2 HATU, DMA and Step 5 HATU, DMA) 16 and 2 | G | ¹H NMR (500 MHz, CD₃OD): δ ppm 2.44 (s, 6 H), 2.62-2.70 (m, 1 H), 2.85 (s, 3 H), 2.92-2.95 (m, 1 H), 2.96 (s, 3 H), 2.96-3.04 (m, 5 H), 3.04-3.11 (m, 1 H), 3.12-3.19 (m, 1 H), 3.18-3.24 (m, 1 H), 3.35-3.43 (m, 4 H), 3.43-3.56 (m, 12 H), 3.60-3.68 (m, 1 H), 3.84-3.95 (m, 2 H), 3.98-4.08 (m, 2 H), 4.10-4.19 (m, 1 H), 5.11-5.17 (m, 1 H), 5.17-5.24 (m, 1 H), 5.49-5.62 (m, 2 H), 6.40 (d, J = 16.0 Hz, 1 H), 6.43 (d, J = 15.9 Hz, 1 H), 6.49 (d, J = 1.8 Hz, 1 H), 6.58 (d, J = 2.1 Hz, 1 H), 7.04 (s, 1 H), 7.09 (s, 1 H), 7.36 (d, J = 7.6 Hz, 1 H), 7.39 (d, J = 7.6 Hz, 1 H), 7.39 (s, 1 H), 7.44 (s, 1 H), 7.63 (d, J = 7.9 Hz, 1 H), 7.70 (d, J = 7.9 Hz, 1 H), 7.93 (br. s., 1 H), 7.94 (s, 2 H), 7.96 (d, J = 2.1 Hz, 1 H), 7.97 (d, J = 1.8 Hz, 1 H), 7.99 (s, 1 H), 8.79 (d, J = 8.9 Hz, 1 H), 8.89 (d, J = 8.9 Hz, 1 H), 11.32 (br. s., 1 H), 11.34 (s, 1 H), 12.98 (s, 2 H) | Method 01_B | m/z 621.02 (M + H)⁺ (ES⁺), at 1.23 min |

TABLE 3-continued

Example compounds Table 3

| Ex. No. | Name | Structure | Synthetic Method and Intermediates Used | Purification Method | $^1$H NMR (two conformations are evident within $^1$H NMR spectral data) | LCMS Method | LCMS data |
|---|---|---|---|---|---|---|---|
| 3-2 | (1S,10R,20E)-12-methyl-10-[(7-methyl-1H-indazol-5-yl)methyl]-15,18-dioxa-9,12,24-tetrazapentacyclo[20.5.2.11,4.13,7.025,28]hentriaconta-3,5,7(30),20,22(29),23,25(28)-heptaene-8,11,27-trione | 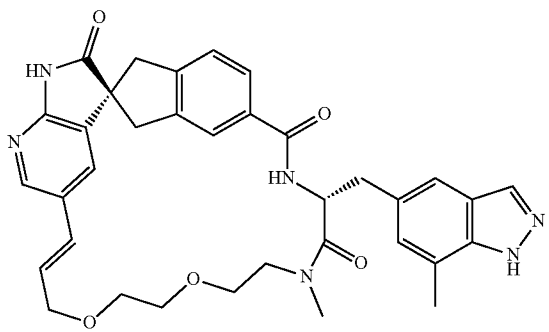 [SMILES: Cc1cc(C[C@H]2NC(=O)c3ccc4c(c3)C[C@]3(C4)C(=O)Nc4ncc(cc43)/C=C/COCCOCCN(C)C2=O)cc2cn[nH]c12] | A (Step 1 heated to 50° C., Step 2 HATU, DMA and Step 5 HATU, DMA) 17 and 2 | H | $^1$H NMR (500 MHz, CD$_3$OD): δ ppm 2.43 (s, 3 H), 2.44 (s, 3 H), 2.68 (dt, J = 13.9, 5.6 Hz, 1 H), 2.87 (s, 3 H), 2.94 (s, 3 H), 2.95-3.07 (m, 4 H), 2.96-3.01 (m, 1 H), 3.01-3.07 (m, 1 H), 3.07-3.14 (m, 1 H), 3.18 (dd, J = 13.4, 6.1 Hz, 1 H), 3.23 (dd, J = 13.4, 6.4 Hz, 1 H), 3.34-3.42 (m, 6 H), 3.42-3.54 (m, 10 H), 3.62-3.70 (m, 1 H), 3.85-3.93 (m, 2 H), 3.95-4.00 (m, 1 H), 4.02-4.08 (m, 1 H), 4.16 (dt, J = 13.7, 5.2 Hz, 1 H), 5.14-5.22 (m, 1 H), 5.21-5.28 (m, 1 H), 5.42-5.50 (m, 1 H), 5.50-5.57 (m, 1 H), 6.40 (d, J = 15.6 Hz, 1 H), 6.41 (d, J = 16.2 Hz, 1 H), 6.45 (d, J = 1.8 Hz, 2 H), 7.04 (s, 1 H), 7.09 (s, 1 H), 7.39 (s, 1 H), 7.42 (s, 1 H), 7.44 (s, 2 H), 7.72 (s, 1 H), 7.74 (s, 1 H), 7.88-8.00 (m, 5 H), 8.02 (d, J = 7.9 Hz, 1 H), 8.83 (d, J = 9.2 Hz, 1 H), 8.94 (d, J = 8.9 Hz, 1 H), 11.30 (s, 2 H), 12.97 (s, 2 H) | Method 01_B | m/z 621.07 (M + H)$^+$ (ES$^+$), at 1.19 min |
| 3-3 | (1S,10R,18E)-12-methyl-10-[(7-methyl-1H-indazol-5-yl)methyl]-16-oxa-9,12,22,24-tetrazapentacyclo[18.5.2.11,4.13,7.023,26]nonacosa-3,5,7(28),18,20(27),21,23(26)-heptaene-8,11,25-trione | 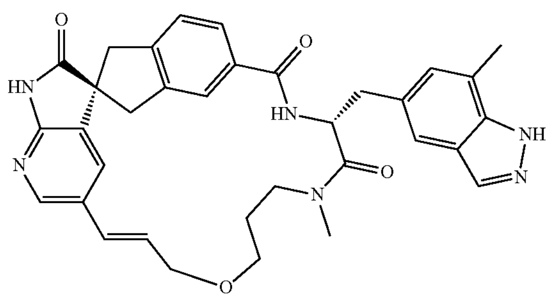 [SMILES: Cc1cc(C[C@H]2NC(=O)c3ccc4c(c3)C[C@]3(C4)C(=O)Nc4ncc(cc43)/C=C/COCCCN(C)C2=O)cc2cn[nH]c12] | A (Step 2 PyAOP, DMF and Step 5 PyAOP, DMF) 18 and 2 | E | $^1$H NMR (500 MHz, DMSO-d6): δ ppm 1.60-1.76 (m, 4 H), 2.43 (s, 3 H), 2.46 (s, 3 H), 2.52-2.58 (m, 2 H), 2.80 (s, 3 H), 2.88-2.96 (m, 4 H), 2.92 (s, 3 H), 3.03-3.10 (m, 2 H), 3.12-3.22 (m, 4 H), 3.23-3.30 (m, 2 H), 3.40 (d, J = 14.6 Hz, 2 H), 3.49 (q, J = 15.3 Hz, 2 H), 3.82-3.90 (m, 2 H), 4.01-4.13 (m, 4 H), 4.97 (br. s., 1 H), 5.18-5.26 (m, 1 H), 5.36-5.44 (m, 1 H), 5.52-5.61 (m, 1 H), 6.10 (br. s., 1 H), 6.18 (s, 1 H), 6.37 (d, J = 15.9 Hz, 2 H), 7.05 (s, 1 H), 7.11 (s, 1 H), 7.31 (d, J = 7.6 Hz, 1 H), 7.43 (d, J = 7.6 Hz, 1 H), 7.47 (s, 2 H), 7.67 (s, 1 H), 7.70 (br. s., 1 H), 7.87 (s, 1 H), 7.90 (s, 1 H), 7.94 (d, J = 7.6 Hz, 2 H), 7.96 (s, 2 H7), 8.80 (d, J = 9.2 Hz, 1 H), 9.05 (d, J = 8.5 Hz, 1 H), 11.25 (br. s., 1 H), 11.29 (s, 1 H), 12.97 (br. s., 1 H), 12.99 (br. s., 1 H) | Method 01_B | m/z 591.93 (M + H)$^+$ (ES$^+$), at 1.20 min |

TABLE 3-continued

Example compounds Table 3

| Ex. No. | Name | Structure | Synthetic Method and Intermediates Used | Purification Method | ¹H NMR (two conformations are evident within ¹H NMR spectral data) | LCMS Method | LCMS data |
|---|---|---|---|---|---|---|---|
| 3-4 | (1S,10R,19E)-12-methyl-10-[(7-methyl-1H-indazol-5-yl)methyl]-17-oxa-9,12,23,25-tetrazapentacyclo[19.5.2.11,4.13,7.024,27]triaconta-3,5,7(29),19,21(28),22,24(27)-heptaene-8,11,26-trione | 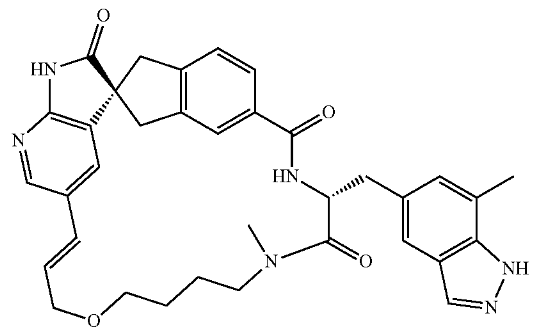 [SMILES: Cc1cc(C[C@H]2NC(=O)c3ccc4c(c3)C[C@]3(C4)C(=O)Nc4ncc(cc43)/C=C/COCCCCN(C)C2=O)cc2cn[nH]c12] | A (Step 1 heated to 60° C., Step 2 HATU, DMF and Step 5 HATU, DMF) 19 and 2 | A | | Method 01_A | m/z 605.97 (M + H)⁺ (ES⁺), at 4.32 min |
| 3-5 | (1S,10R,20E)-12,15-dimethyl-10-[(7-methyl-1H-indazol-5-yl)methyl]-18-oxa-9,12,15,24,26-pentazapentacyclo[20.5.2.11,4.13,7.025,28]hentriaconta-3,5,7(30),20,22(29),23,25(28)-heptaene-8,11,27-trione | 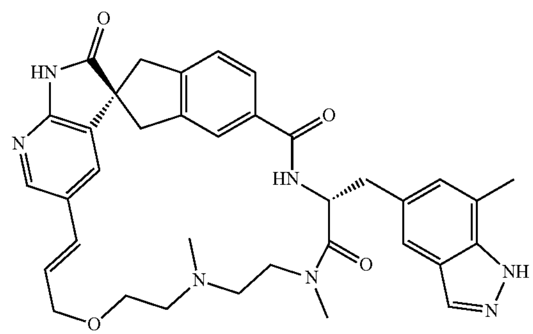 [SMILES: Cc1cc(C[C@H]2NC(=O)c3ccc4c(c3)C[C@]3(C4)C(=O)Nc4ncc(cc43)/C=C/COCCN(C)CCN(C)C2=O)cc2cn[nH]c12] | A (Step 2 PyAOP, DMF and Step 5 PyAOP, DMF) 20 and 2 | K | | Method 01_B | m/z 634.38 (M + H)⁺ (ES⁺), at 0.90 min |

TABLE 3-continued

Example compounds Table 3

| Ex. No. | Name | Structure | Synthetic Method and Intermediates Used | Purification Method | $^1$H NMR (two conformations are evident within $^1$H NMR spectral data) | LCMS Method | LCMS data |
|---|---|---|---|---|---|---|---|
| 3-6 | (1S,10R,20E)-12-methyl-10-[(7-methyl-1H-indazol-5-yl)methyl]-18-oxa-9,12,15,24,26-pentazapentacyclo[20.5.2.11,4.13,7.025,28]hentriaconta-3,5,7(30)20,22(29)23,25(28)-heptaene-8,11,27-trione | 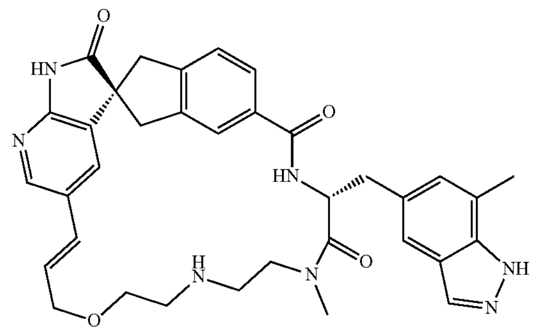 [SMILES: Cc1cc(C[C@H]2NC(=O)c3ccc4c(c3)C[C@]3(C4)C(=O)Nc4ncc(cc43)/C=C/COCCNCCN(C)C2=O)cc2cn[nH]c12] | F Example 3-5 | L | | Method 01_B | m/z 620.38 (M + H)+ (ES+), at 1.11 min |
| 3-7 | (1R,10R,20E)-10-[(1,7-dimethylindazol-5-yl)methyl]-12-methyl-15,18-dioxa-9,12,24,26-tetrazapentacyclo[20.5.2.11,4.13,7.025,28]hentriaconta-3,5,7(30)20,22(29)23,25(28)-heptaene-8,11,27-trione | 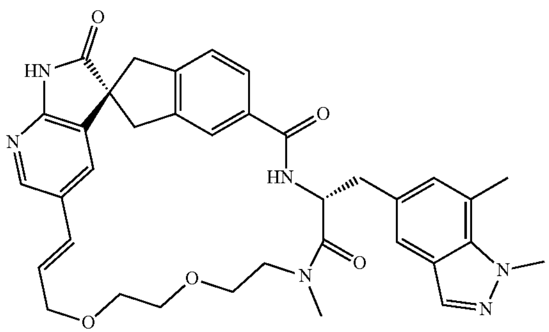 [SMILES: Cc1cc(C[C@H]2NC(=O)c3ccc4c(c3)C[C@@]3(C4)C(=O)Nc4ncc(cc43)/C=C/COCCOCCN(C)C2=O)cc2cnn(C)c12] | A (Step 1 heated to 50° C., Step 2 HATU, DMF and Step 5 HATU, DMF) 16 and 12 | J | $^1$H NMR (500 MHz, DMSO-d6): δ ppm 2.62-2.66 (m, 1 H), 2.67 (br. s., 6 H), 2.85 (s, 3 H), 2.89-2.95 (m, 2 H), 2.93-3.03 (m, 4 H), 2.97 (br. s., 3 H), 3.04-3.08 (m, 1 H), 3.13 (dd, J = 13.3, 6.3 Hz, 1 H), 3.16-3.23 (m, 1 H), 3.35-3.41 (m, 4 H), 3.43-3.56 (m, 12 H), 3.60-3.71 (m, 1 H), 3.85-3.95 (m, 2 H>), 3.97-4.06 (m, 2 H), 4.09-4.17 (m, 1 H), 4.20 (br. s., 6 H), 5.10-5.16 (m, 1 H), 5.16-5.24 (m, 1 H), 5.52-5.64 (m, 2 H), 6.40 (d, J = 16.0 Hz, 1 H), 6.43 (d, J = 15.9 Hz, 1 H), 6.49 (br. s., 1 H), 6.58 (br. s., 1 H), 7.02 (br. s., 1 H), 7.07 (br. s., 1 H), 7.31-7.44 (m, 2 H), 7.35 (br. s., 1 H), 7.41 (br. s., 1 H), 7.64 (d, J = 7.9 Hz, 1 H), 7.71 (d, J = 7.0 Hz, 1 H), 7.85 (br. s., 2 H), 7.91-8.03 (m, 4 H), 8.79 (d, J = 8.9 Hz, 1 H), 8.90 (d, J = 8.5 Hz, 1 H), 11.33 (br. s., 2 H) | Method 01_A | m/z 636.06 (M + H)+ (ES+), at 3.49 min |

TABLE 3-continued

Example compounds Table 3

| Ex. No. | Name | Structure | Synthetic Method and Intermediates Used | Purification Method | 1H NMR (two conformations are evident within 1H NMR spectral data) | LCMS Method | LCMS data |
|---|---|---|---|---|---|---|---|
| 3-8 | (1S,10R,20E)-10-[(1,7-dimethylindazol-5-yl)methyl]-12-methyl-15,18-dioxa-9,12,24,26-tetrazapentacyclo[20.5.2.11,4.13,7.025,28]hentriaconta-3,5,7(30),20,22(29),23,25(28)-heptaene-8,11,27-trione | 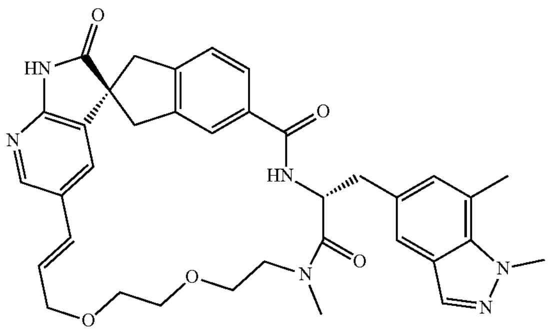 | A (Step 1 heated to 50° C., Step 2 HATU, DMF and Step 5 HATU, DMF) 17 and 12 | M | 1H NMR (500 MHz, DMSO-d6): δ ppm 2.67 (s, 6 H), 2.68-2.74 (m, 2 H), 2.87 (s, 3 H), 2.95 (s, 3 H), 2.96-3.06 (m, 6 H), 3.16 (dd, J = 14.0, 6.4 Hz, 1 H), 3.21 (dd, J = 13.4, 6.7 Hz, 1 H), 3.36-3.42 (m, 6 H), 3.43-3.54 (m, 10 H), 3.86-3.99 (m, 2 H), 3.98-4.08 (m, 2 H), 4.11-4.18 (m, 2 H), 4.20 (s, 6 H), 5.19 (q, J = 7.3 Hz, 1 H), 5.21-5.28 (m, 1 H), 5.42-5.51 (m, 1 H), 5.50-5.57 (m, 1 H), 6.40 (d, J = 15.9 Hz, 1 H), 6.41 (d, J = 16.2 Hz, 1 H), 6.46 (s, 2 H), 7.02 (s, 1 H), 7.07 (s, 1 H), 7.37 (s, 1 H), 7.42 (s, 2 H), 7.44 (br. s, 1 H), 7.73 (s, 1 H), 7.75 (s, 1 H), 7.79-7.86 (m, 2 H), 7.94 (s, 2 H), 7.95-7.98 (m, 1 H), 8.02 (d, J = 7.9 Hz, 1 H), 8.83 (d, J = 9.2 Hz, 1 H), 8.94 (d, J = 8.9 Hz, 1 H), 11.30 (s, 2 H) | Method 01_A | m/z 636.07 (M + H)+ (ES+), at 3.40 min |
| 3-9 | (1R,20E)-10-[(7-chloro-1H-indazol-5-yl)methyl]-12-methyl-15,18-dioxa-9,12,24,26-tetrazapentacyclo[20.5.2.11,4.13,7.025,28]hentriaconta-3,5,7(30),20,22(29),23,25(28)-heptaene-8,11,27-trione (diastereomeric mixture) | 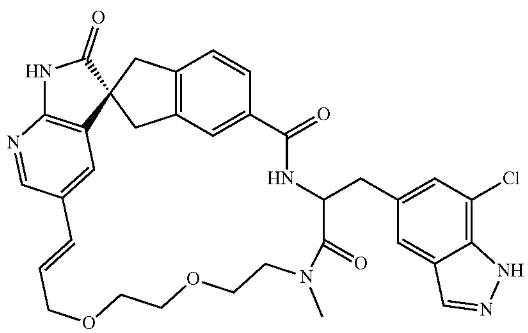 [SMILES: CN1CCOCCOC/C=C/c2cnc3c(c2)[C@]2(Cc4ccc(cc4C2)C(=O)NC(Cc2cc(Cl)c4[nH]ncc4c2)C1=O)C(=O)N3] | A (Step 1 heated to 60° C., Step 2 HATU, DMF and Step 5 PyAOP, DMF) 16 and 21 | J | 1H NMR (600 MHz, DMSO-d6): δ ppm 2.65-2.79 (m, 2 H), 2.87 (s, 3 H), 2.90 (s, 3 H), 2.93-3.02 (m, 8 H), 2.98 (s, 3 H), 2.99 (s, 3 H), 3.02-3.13 (m, 4 H), 3.12-3.16 (m, 2 H), 3.16-3.28 (m, 3 H), 3.30-3.49 (m, 24 H), 3.49-3.55 (m, 8 H), 3.68 (dt, J = 14.5, 5.0 Hz, 2 H), 3.86-3.95 (m, 4 H), 3.96-4.07 (m, 4 H), 4.12-4.23 (m, 2 H), 5.13-5.29 (m, 4 H), 5.43-5.50 (m, 1 H), 5.50-5.55 (m, 1 H), 5.58 (ddd, J = 16.1, 8.1, 4.6 Hz, 2 H), 6.37-6.47 (m, 4 H), 6.46 (d, J = 2.0 Hz, 1 H), 6.46-6.47 (m, 1 H), 6.50 (d, J = 1.7 Hz, 1 H), 6.60 (d, J = 2.0 Hz, 1 H), 7.35 (d, J = 7.9 Hz, 1 H), 7.38 (d, J = 7.7 Hz, 1 H), 7.39 (s, 2 H), 7.42 (d, J = 7.7 Hz, 1 H), 7.43 (d, J = 7.7 Hz, 1 H), 7.45 (s, 2 H), 7.57 (s, 2 H), 7.60 (d, J = 8.1 Hz, 1 H), 7.63 (s, 2 H), 7.66 (d, J = 8.4 Hz, 1 H), 7.67-7.70 (m, 2 H), 7.92-7.96 (m, 3 H), 7.96-7.98 (m, 4 H), 8.00 (d, J = 7.5 Hz, 1 H), 8.05-8.13 (m, 4 H), 8.82 (d, J = 9.4 Hz, 1 H), 8.85 (d, J = 9.4 Hz, 1 H), 8.93 (d, J = 9.4 Hz, 1 H), 8.97 (d, J = 9.0 Hz, 1 H), 11.30 (br. s., 2 H), 11.32 (br. s., 1 H), 11.34 (s, 1 H), 13.42 (br. s, 4 H) | Method 01_A | m/z 641.29, 643.28 (M + H)+ (ES+), at 3.21, 3.29 min |

TABLE 3-continued

Example compounds Table 3

| Ex. No. | Name | Structure | Synthetic Method and Intermediates Used | Purification Method | ¹H NMR (two conformations are evident within ¹H NMR spectral data) | LCMS Method | LCMS data |
|---|---|---|---|---|---|---|---|
| 3-10 | (1R,10R)-12-methyl-10-[(7-methyl-1H-indazol-5-yl)methyl]-15,18-dioxa-9,12,24,26-tetrazapentacyclo[20.5.2.1¹,⁴.1³,⁷.0²⁵,²⁸]hentriaconta-3,5,7(30),22(29),23,25(28)-hexaene-8,11,27-trione | 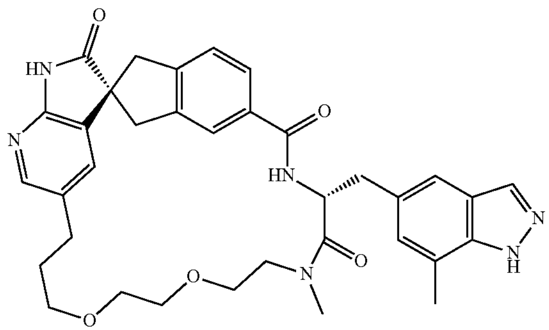 [SMILES: Cc1cc(C[C@H]2NC(=O)c3ccc4c(c3)C[C@@]3(C4)C(=O)Nc4ncc(cc43)CCCOCCOCCN(C)C2=O)cc2cn[nH]c12] | G Example 3-1 | N/A | | Method 03_A | m/z 623.30 (M + H)⁺ (ES⁺), at 3.38 min |
| 3-11 | (1S,10R)-12-methyl-10-[(7-methyl-1H-indazol-5-yl)methyl]-15,18-dioxa-9,12,24,26-tetrazapentacyclo[20.5.2.1¹,⁴.1³,⁷.0²⁵,²⁸]hentriaconta-3,5,7(30),22(29),23,25(28)-hexaene-8,11,27-trione | 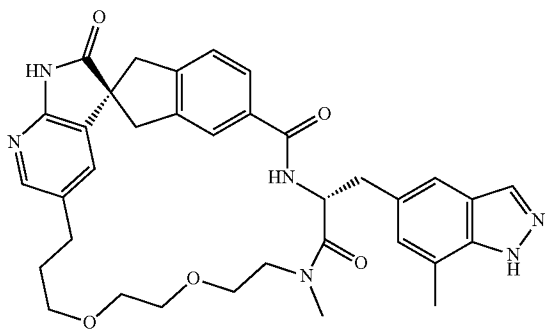 [SMILES: Cc1cc(C[C@H]2NC(=O)c3ccc4c(c3)C[C@]3(C4)C(=O)Nc4ncc(cc43)CCCOCCOCCN(C)C2=O)cc2cn[nH]c12] | G Example 3-2 | N/A | | Method 03_A | m/z 623.30 (M + H)⁺ (ES⁺), at 3.25 min |

TABLE 3-continued

Example compounds Table 3

| Ex. No. | Name | Structure | Synthetic Method and Intermediates Used | Purification Method | ¹H NMR (two conformations are evident within ¹H NMR spectral data) | LCMS Method | LCMS data |
|---|---|---|---|---|---|---|---|
| 4-1 | (1S,10R,20E)-12-methyl-10-[(7-methyl-1H-indazol-5-yl)methyl]-9,15,18-trioxa-5,12,24,26-tetrazapentacyclo[20.5.2.1¹,¹³.0⁷,²⁵.0²,²⁸]hentriaconta-3,5,7(30),20,22(29),23,25(28)-heptaene-8,11,27-trione | 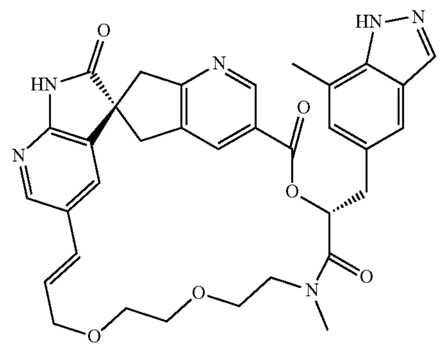 [SMILES: Cc1cc(C[C@H]2OC(=O)c3cnc4c(c3)C[C@@]3(C4)C(=O)Nc4ncc(cc43)/C=C/COCCOCCN(C)C2=O)cc2cn[nH]c12] | C (Step 2 Purification Method C) 1 and 22 | C | ¹H NMR (600 MHz, DMSO-d6): δ ppm 2.42 (s, 3 H),2.86 (s, 3 H), 2.95 (s, 3 H), 2.96-3.01 (m, 2 H), 3.04 (d, J = 16.7 Hz, 1 H), 3.06 (d, J = 16.5 Hz, 1 H), 3.19 (d, J = 15.4 Hz, 2 H), 3.22-3.29 (m, 4 H), 3.34-3.40 (m, 4 H), 3.43-3.45 (m, 2 H), 3.47 (d, J = 5.0 Hz, 4 H), 3.49 (s, 2 H), 3.50-3.53 (m, 2 H), 3.62 (d, J = 16.1 Hz, 1 H), 3.63 (d, J = 16.3 Hz, 1 H), 3.78-3.85 (m, 2 H), 3.89 (dd, J = 13.4, 8.3 Hz, 1 H), 3.92 (dd, J = 13.9, 7.3 Hz, 1 H), 4.01 (ddd, J = 12.4, 4.5, 1.6 Hz, 1 H), 4.05 (ddd, J = 13.6, 5.1, 1.5 Hz, 1 H), 5.62 (ddd, J = 16.1, 8.2, 4.7 Hz, 1 H), 5.71 (dd, J = 16.0, 7.5, 5.0 Hz, 1 H), 5.86 (dd, J = 8.3, 5.8 Hz, 1 H), 5.89 (t, J = 7.0 Hz, 1 H), 6.41 (d, J = 16.3 Hz, 1 H), 6.43 (d, J = 16.1 Hz, 1 H), 6.53 (d, J = 2.0 Hz, 1 H), 6.57 (d, J = 2.0 Hz, 1 H), 7.08 (s, 1 H), 7.12 (s, 1 H), 7.44 (s, 1 H), 7.49 (s, 1 H), 7.94 (s, 1 H), 7.95 (s, 1 H), 7.98 (d, J = 2.0 Hz, 1 H), 7.99 (d, J = 2.0 Hz, 1 H), 8.21-8.27 (m, 1 H), 8.32 (s, 1 H), 8.85 (s, 2 H), 11.38 (br. s., 1 H), 11.40 (s, 1 H), 13.02 (br. s., 2 H) | Method 01_C | m/z 623.78 (M + H)⁺ (ES⁺), at 0.82 min |
| 4-2 | (1S,10S,20E)-12-methyl-10-[(7-methyl-1H-indazol-5-yl)methyl]-9,15,18-trioxa-5,12,24,26-tetrazapentacyclo[20.5.2.1¹,¹³.0⁷,²⁵.0²,²⁸]hentriaconta-3,5,7(30),20,22(29),23,25(28)-heptaene-8,11,27-trione | 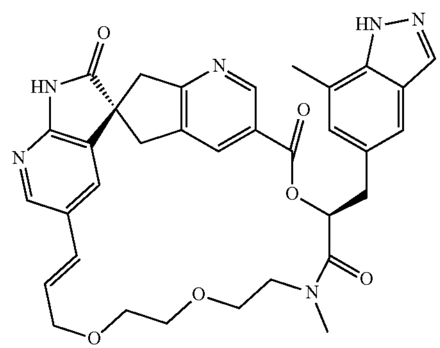 [SMILES: Cc1cc(C[C@@H]2OC(=O)c3cnc4c(c3)C[C@@]3(C4)C(=O)Nc4ncc(cc43)/C=C/COCCOCCN(C)C2=O)cc2cn[nH]c12] | C (Step 2 heated to 105° C. and Purification Method C, Step 3 1,4-dioxane/MeOH) 1 and 23 | C | ¹H NMR (500 MHz, DMSO-d6): δ ppm 2.43 (s, 3 H), 2.46 (s, 3 H), 2.90 (s, 3 H), 2.99 (s, 3 H), 2.99-3.01 (m, 2 H), 3.03-3.06 (m, 2 H), 3.07-3.12 (m, 2 H), 3.29 (d, J = 7.0 Hz, 4 H), 3.38-3.41 (m, 4 H), 3.41-3.48 (m, 6 H), 3.49-3.56 (m, 4 H), 3.59-3.64 (m, 2 H), 3.80-3.88 (m, 2 H), 3.89-3.96 (m, 2 H), 3.96-4.07 (m, 2 H), 5.57 (ddd, J = 16.0, 6.5, 5.0 Hz, 1 H), 5.69 (dt, J = 16.0, 6.2 Hz, 1 H), 5.88-5.94 (m, 1 H), 5.92 (t, J = 7.0 Hz, 1 H), 6.41 (d, J = 15.9 Hz, 1 H), 6.43 (d, J = 16.2 Hz, 1 H), 6.45 (d, J = 1.8 Hz, 1 H), 6.51 (d, J = 1.5 Hz, 1 H), 7.11 (s, 1 H), 7.15 (s, 1 H), 7.49 (s, 1 H), 7.53 (s, 1 H), 7.93-8.01 (m, 4 H), 8.11 (s, 1 H), 8.13 (s, 1 H), 9.02 (s, 1 H), 9.06 (s, 1 H), 11.38 (s, 2 H), 13.05 (br. s., 2 H) | Method 01_C | m/z 623.76 (M + H)⁺ (ES⁺), at 0.78 min |

TABLE 3-continued

Example compounds Table 3

| Ex. No. | Name | Structure | Synthetic Method and Intermediates Used | Purification Method | ¹H NMR (two conformations are evident within ¹H NMR spectral data) | LCMS Method | LCMS data |
|---|---|---|---|---|---|---|---|
| 5-1 | (1S,10R,20E)-12-methyl-10-[(7-methyl-1H-indazol-5-yl)methyl]-9,15,18-trioxa-12,24,26-triazapentacyclo[20.5.2.11,4.13,7.025,28]hentriaconta-3,5,7(30),20,22(29),23,25(28)-heptaene-8,11,27-trione | 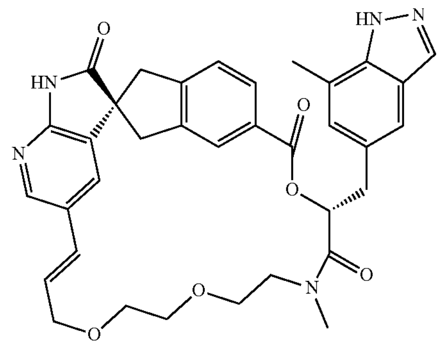 [SMILES: Cc1cc(C[C@H]2OC(=O)c3ccc4c(c3)C[C@]3(C4)C(=O)Nc4ncc(cc43)/C=C/COCCOCCN(C)C2=O)cc2cn[nH]c12] | C (Step 1 heated to 60° C., Step 2 heated to 107-130° C. and Purification Method O, Step 3 1,4-dioxane/THF) 17 and 22 | I | ¹H NMR (500 MHz, DMSO-d6): δ ppm 2.45 and 2.43 (s, 3 H), 2.86-3.08 (m, 4 H), 3.23-3.28 (m, 4 H), 3.35-3.55 (m, 8 H), 3.83-4.04 (m, 3 H), 5.53-5.56, and 5.42-5.50 (m, 1 H), 5.86-5.94 (m, 1 H), 6.37-6.49 (m, 2 H), 7.13 and 7.08 (s, 1 H), 7.43-7.55 (m, 2 H), 7.81 (s, 1 H), 7.93-8.01 (m, 3H), 11.32 (br. s., 1 H), 13.04 (br. s., 1 H) | Method 01_C | m/z 622.85 (M + H)⁺ (ES⁺), at 0.88 min |
| 5-2 | (1R,10R,20E)-12-methyl-10-[(7-methyl-1H-indazol-5-yl)methyl]-9,15,18-trioxa-12,24,26-triazapentacyclo[20.5.2.11,4.13,7.025,28]hentriaconta-3,5,7(30),20,22(29),23,25(28)-heptaene-8,11,27-trione | 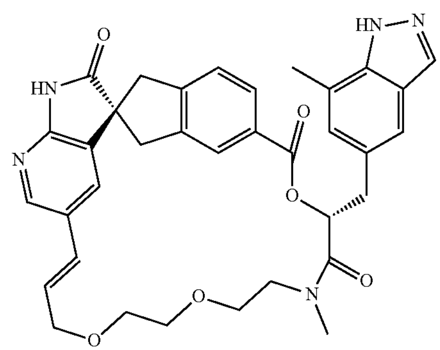 [SMILES: Cc1cc(C[C@H]2OC(=O)c3ccc4c(c3)C[C@@]3(C4)C(=O)Nc4ncc(cc43)/C=C/COCCOCCN(C)C2=O)cc2cn[nH]c12] | C (Step 1 heated to 60° C., 2 Step heated to 107-130° C. and Purification Method E, Step 3 1,4-dioxane/THF) 16 and 22 | I | ¹H NMR (500 MHz, DMSO-d6): δ ppm 2.43 (s, 3 H), 2.45 (s, 3 H), 2.85 (s, 3 H), 2.95 (s, 3 H), 2.97-3.04 (m, 1 H), 2.97-3.14 (m, 4 H), 3.20-3.31 (m, 5 H), 3.34-3.40 (m, 4 H), 3.40-3.56 (m, 4 H), 3.41-3.44 (m, 2 H), 3.45 (s, 4 H), 3.46-3.47 (m, 1 H), 3.49-3.52 (m, 2 H), 3.74-3.83 (m, 1 H), 3.84-3.94 (m, 2 H), 4.01 (dd, J = 13.1, 4.6 Hz, 1 H), 4.07 (dd, J = 13.7, 3.1 Hz, 1 H), 5.45-5.54 (m, 1 H), 5.56-5.64 (m, 1 H), 5.81 (t, J = 7.0 Hz, 1 H), 5.86 (t, J = 7.0 Hz, 1 H), 6.41 (d, J = 16.2 Hz, 1 H), 6.43 (d, J = 15.9 Hz, 1 H), 6.48 (d, J = 1.8 Hz, 1 H), 6.52 (d, J = 1.8 Hz, 1 H), 7.08 (s, 1 H), 7.13 (s, 1 H), 7.44 (s, 1 H), 7.47 (d, J = 7.9 Hz, 2 H), 7.49 (s, 1 H), 7.82 (d, J = 7.3 Hz, 1 H), 7.81-7.85 (m, 1 H), 7.92 (s, 1 H), 7.95 (br. s., 1 H), 7.96 (s, 1 H), 7.97 (d, J = 1.8 Hz, 1 H), 7.99 (d, J = 1.8 Hz, 1 H), 8.01 (s, 1 H), 11.35 (br. s, 2 H), 13.03 (br. s., 2 H) | Method 01_C | m/z 622.85 (M + H)⁺ (ES⁺), at 0.89 min |

TABLE 3-continued

Example compounds Table 3

| Ex. No. | Name | Structure | Synthetic Method and Intermediates Used | Purification Method | ¹H NMR (two conformations are evident within ¹H NMR spectral data) | LCMS Method | LCMS data |
|---|---|---|---|---|---|---|---|
| 6-1 | (7R,17E)-9-methyl-7-[(7-methyl-1H-indazol-5-yl)methyl]-12,15,25-trioxa-4,6,9,21,23-pentazatetracyclo[17.6.2.2¹,⁴.0²²,²⁶]nonacosa-17,19(27),20,22(26)-tetraene-5,8,24-trione | 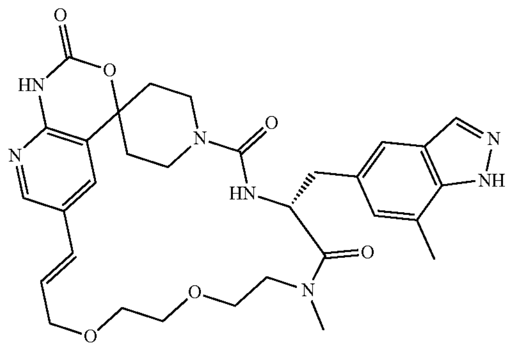 [SMILES: Cc1cc(C[C@H]2NC(=O)N3CCC4(CC3)OC(=O)Nc3ncc(cc34)/C=C/COCCOCCN(C)C2=O)cc2cn[nH]c12] | B 26 and 2 | D | | Method 01_A | m/z 604.24 (M + H)⁺ (ES⁺), at 2.69 min |
| 7-1 | (7R,17E)-9-methyl-7-[(7-methyl-1H-indazol-5-yl)methyl]-6,12,15,25-tetraoxa-4,9,21,23-tetrazatetracyclo[17.6.2.2¹,⁴.0²²,²⁶]nonacosa-17,19(27),20,22(26)-tetraene-5,8,24-trione | 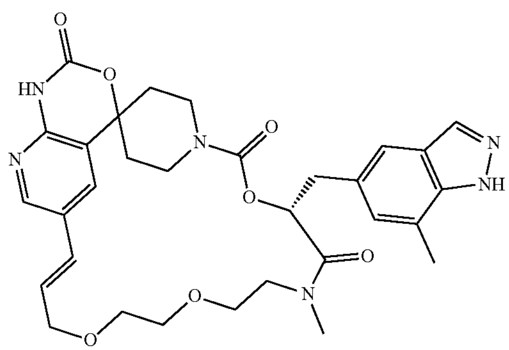 | D 26 and 27 | E | | Method 01_B | m/z 605.36 (M + H)⁺ (ES⁺), at 1.26 min |

TABLE 3-continued

Example compounds Table 3

| Ex. No. | Name | Structure | Synthetic Method and Intermediates Used | Purification Method | ¹H NMR (two conformations are evident within ¹H NMR spectral data) | LCMS Method | LCMS data |
|---|---|---|---|---|---|---|---|
| 7-2 | (7R,20E)-9-methyl-7-[(7-methyl-1H-indazol-5-yl)methyl]-6,12,15,18,28-pentaoxa-4,9,24,26-tetrazatetracyclo[20.6.2.2¹,⁴.0²⁵,²⁹]dotriaconta-20,22(30),23,25(29)-tetraene-5,8,27-trione | 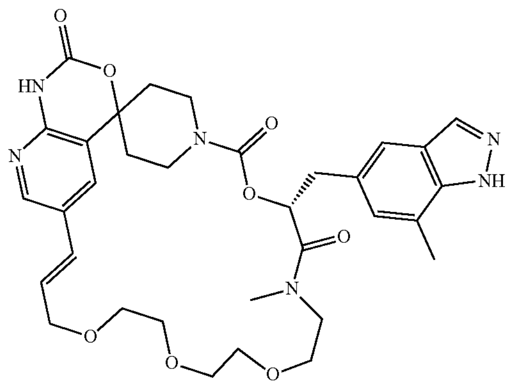 [SMILES: Cc1cc(C[C@H]2OC(=O)N3CCC4(CC3)OC(=O)Nc3ncc(cc34)/C=C/COCCOCCOCCN(C)C2=O)cc2cn[nH]c12] | D 28 and 27 | F | | Method 01_A | m/z 649.33 (M + H)⁺ (ES⁺), at 3.18 min |
| 7-3 | (7R,17E)-9-methyl-7-[(7-methyl-1H-indazol-5-yl)methyl]-6,15,25-trioxa-4,9,21,23-tetrazatetracyclo[17.6.2.2¹,⁴.0²²,²⁶]nonacosa-17,19(27),20,22(26)-tetraene-5,8,24-trione | 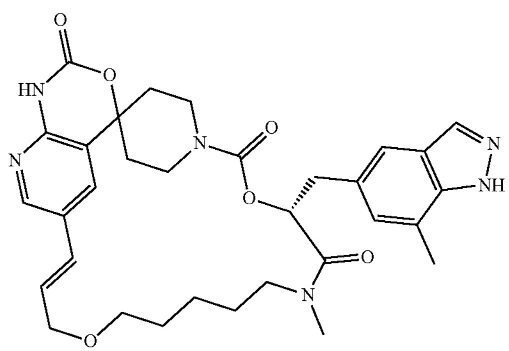 [SMILES: Cc1cc(C[C@H]2OC(=O)N3CCC4(CC3)OC(=O)Nc3ncc(cc34)/C=C/COCCCCCN(C)C2=O)cc2cn[nH]c12] | D 29 and 27 | F | | Method 01_A | m/z 603.26 (M + H)⁺ (ES⁺), at 3.80 min |

TABLE 3-continued

Example compounds Table 3

| Ex. No. | Name | Structure | Synthetic Method and Intermediates Used | Purification Method | ¹H NMR (two conformations are evident within ¹H NMR spectral data) | LCMS Method | LCMS data |
|---|---|---|---|---|---|---|---|
| 7-4 | (7R,18E)-9-methyl-7-[(7-methyl-1H-indazol-5-yl)methyl]-6,13,16,26-tetraoxa-4,9,22,24-tetrazatetracyclo[18.6.2.21,4.023,27]triaconta-18,20(28),21,23(27)-tetraene-5,8,25-trione | 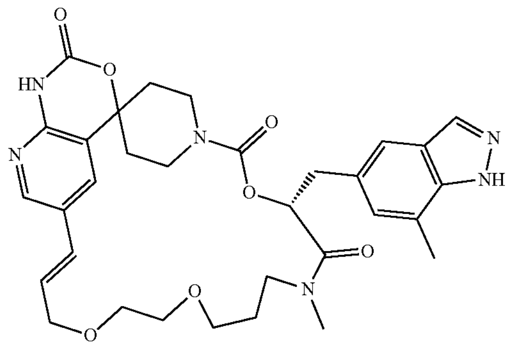 | D<br>30 and 27 | C | | Method 01_A | m/z 619.17 (M + H)+ (ES+), at 3.33 min |
| 7-5 | (7R)-9-methyl-7-[(7-methyl-1H-indazol-5-yl)methyl]-6,12,15,18,28-pentaoxa-4,9,24,26-tetrazatetracyclo[20.6.2.21,4.025,29]dotriaconta-22(30),23,25(29)-triene-5,8,27-trione | 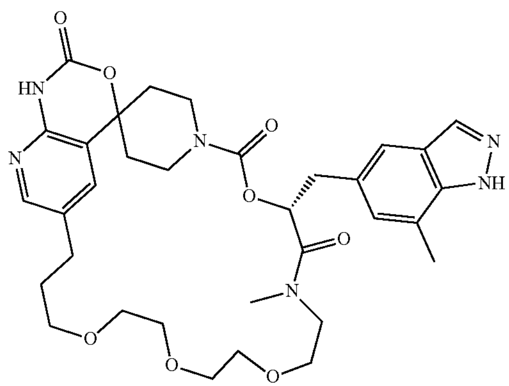 [SMILES: Cc1cc(C[C@H]2OC(=O)N3CCC4(CC3)OC(=O)Nc3ncc(cc34)CCCOCCOCCOCCN(C)C2=O)cc2cn[nH]c12] | E<br>Example 7-2 | N/A | | Method 02_A | m/z 651.17 (M + H)+ (ES+), at 3.12 min |

TABLE 3-continued

Example compounds Table 3

| Ex. No. | Name | Structure | Synthetic Method and Intermediates Used | Purification Method | ¹H NMR (two conformations are evident within ¹H NMR spectral data) | LCMS Method | LCMS data |
|---|---|---|---|---|---|---|---|
| 7-6 | (7R)-9-methyl-7-[(7-methyl-1H-indazol-5-yl)methyl]-6,15,25-trioxa-4,9,21,23-tetrazatetracyclo [17.6.2.2¹,⁴.0²²,²⁶] nonacosa-19(27),20,22(26)-triene-5,8,24-trione | 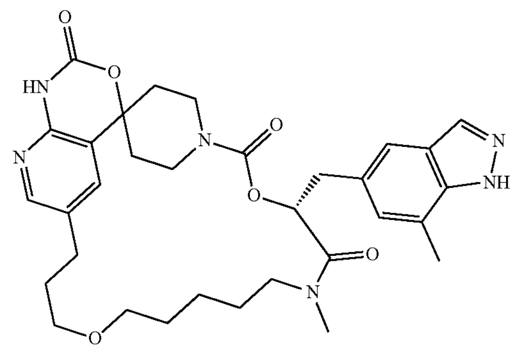 [SMILES: Cc1cc(C[C@H]2OC(=O)N3CCC4(CC3)OC(=O)Nc3ncc(cc34)CCCOCCCCCN(C)C2=O)cc2cn[nH]c12] | E Example 7-3 | N/A | | Method 01_A | m/z 605.16 (M + H)⁺ (ES⁺), at 3.71 min |
| 7-7 | (7R)-9-methyl-7-[(7-methyl-1H-indazol-5-yl)methyl]-6,13,16,26-tetraoxa-4,9,22,24-tetrazatetracyclo [18.6.2.2¹,⁴.0²³,²⁷] triaconta-20(28),21,23(27)-triene-5,8,25-trione | 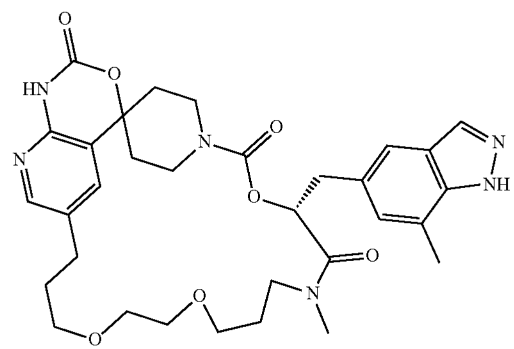 [SMILES: Cc1cc(C[C@H]2OC(=O)N3CCC4(CC3)OC(=O)Nc3ncc(cc34)CCCOCCOCCCN(C)C2=O)cc2cn[nH]c12] | E Example 7-4 | A | | Method 02_A | m/z 621.17 (M + H)⁺ (ES⁺), at 3.27 min |

TABLE 3-continued

Example compounds Table 3

| Ex. No. | Name | Structure | Synthetic Method and Intermediates Used | Purification Method | ¹H NMR (two conformations are evident within ¹H NMR spectral data) | LCMS Method | LCMS data |
|---|---|---|---|---|---|---|---|
| 8-1 | Isomer 2: (10R,20E)-12-methyl-10-[(7-methyl-1H-indazol-5-yl)methyl]-15,18-dioxa-9,12,24,26,30-pentazapentacyclo[20.5.2.11,4.13,7.02,5.28]hentriaconta-3,5,7(30),20,22,24,28-heptaene-8,11,27-trione | 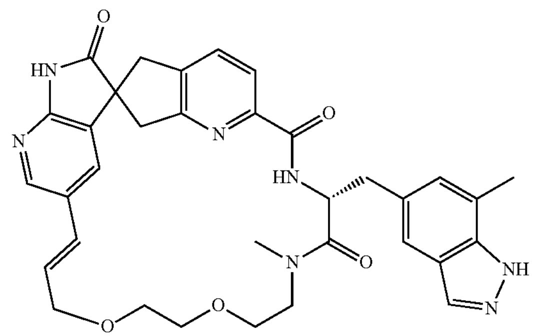 [SMILES: Cc1cc(C[C@H]2NC(=O)c3ccc4c(n3)CC3(C4)C(=O)Nc4ncc(cc43)/C=C/COCCOCCN(C)C2=O)cc2cn[nH]c12] | A (Step 2 PyAOP, DMF, Step 4 1,4-dioxane/THF and Step 5 PyAOP, DMF) 71 and 2 | E | | Method 01_B | m/z 622.87 (M + H)⁺ (ES⁺), at 1.21 min |
| 8-2 | Isomer 1: (10R,20E)-12-methyl-10-[(7-methyl-1H-indazol-5-yl)methyl]-15,18-dioxa-9,12,24,26,30-pentazapentacyclo[20.5.2.11,4.13,7.02,5.28]hentriaconta-3,5,7(30),20,22,24,28-heptaene-8,11,27-trione | 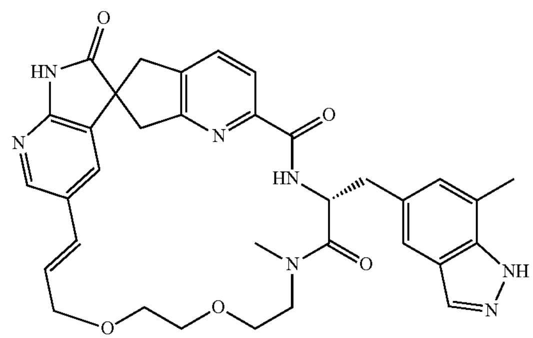 [SMILES: Cc1cc(C[C@H]2NC(=O)c3ccc4c(n3)CC3(C4)C(=O)Nc4ncc(cc43)/C=C/COCCOCCN(C)C2=O)cc2cn[nH]c12] | A (Step 2 HATU, DMF and Step 5 HATU, DMF) 31 and 2 | A | | Method 01_A | m/z 622.15 (M + H)⁺ (ES⁺), at 3.65 min |

Biological Activity cAMP Functional Assay cAMP production following receptor activation was determined using the Homogeneous Time-Resolved Fluorescence (HTRF) cAMP dynamic-2 assay (Cisbio, France). The human neuroblastoma cell line SK-N-MC endogenously expressing the human CGRP receptor was seeded at a density of 12,500 cells/well in solid walled 96 well half area plates (Costar, Catalog Number 3688, Corning Life Sciences, Germany). After 16 h incubation at 37° C. media was removed and cells were incubated at 37° C. for 30 min in serum free media containing 500 μM IBMX (Tocris, Abingdon, UK, Catalog Number 2845) and increasing concentrations of test antagonist. Following this cells were challenged with an $EC_{80}$ concentration of human CGRP (0.3 nM) for a further 30 min at 37° C. and then cAMP production was determined as manufacturer's instructions before plates were read on a PheraStar fluorescence plate reader (BMG LabTech, Germany). $IC_{50}$ values were derived from the inhibition curve. The $pIC_{50}$ values (where $pIC_{50}=-\log_{10} IC_{50}$) were converted to a functional $pK_b$ value using a modified Cheng-Prussoff equation where $K_d$=agonist $EC_{50}$ and L hot=agonist challenge concentration. The $pK_b$ values of certain compounds of the invention are detailed in Table 4.

TABLE 4

CGRP $pK_b$ values

| Example | CGRP $pK_b$ |
|---|---|
| 1-1 | 9.6 |
| 1-2 | 6.7 |
| 1-3 | 8.0 |
| 1-4 | 9.6 |
| 1-5 | 10.9 |
| 1-6 | 10.9 |
| 1-7 | 10.2 |
| 1-8 | 8.9 |
| 2-1 | 8.6 |
| 2-2 | 9.1 |
| 2-3 | 8.9 |
| 2-4 | 7.6 |
| 2-5 | 9.3 |
| 2-6 | 9.1 |
| 2-7 | 9 |
| 2-8 | 8.7 |
| 2-9 | 8.9 |
| 3-1 | 8.9 |
| 3-2 | 9.2 |
| 3-3 | 9.1 |
| 3-4 | 9.5 |
| 3-5 | 9.4 |
| 3-6 | 9.3 |
| 3-7 | 7.9 |
| 3-8 | 9.4 |
| 3-9 | 8.9 |
| 3-10 | 8.1 |
| 3-11 | 8.7 |
| 4-1 | 9.7 |
| 4-2 | 8.5 |
| 5-1 | 9.3 |
| 5-2 | 9.4 |
| 6-1 | 9.3 |
| 7-1 | 8.9 |
| 7-2 | 8.7 |
| 7-3 | 8.9 |
| 7-4 | 8.9 |
| 7-5 | 8.8 |
| 7-6 | 9.6 |
| 7-7 | 8.4 |
| 8-1 | 7.7 |
| 8-2 | 7.5 |

The invention claimed is:

1. A compound of Formula (1):

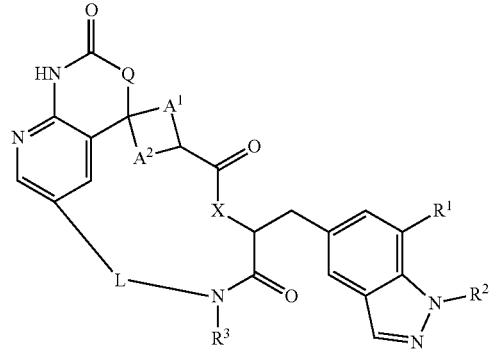

or a salt thereof, wherein;

$A^1$, $A^2$ and the atoms to which they are attached together represent an optionally substituted bicyclic or monocyclic ring system;

Q is a bond or O;

X is O or NH;

$R^1$ is H, $C_{1-3}$ alkyl or halo;

$R^2$ is H or $C_{1-3}$ alkyl;

$R^3$ is H or $C_{1-3}$ alkyl;

and L is a $C_{4-15}$ linker group, wherein one, two or three, but not all, of the carbon atoms of the linker group may be optionally replaced by a heteroatom selected from O and N.

2. The compound according to claim 1, which is a compound of Formula (2a), (2b), (2c) or (2d):

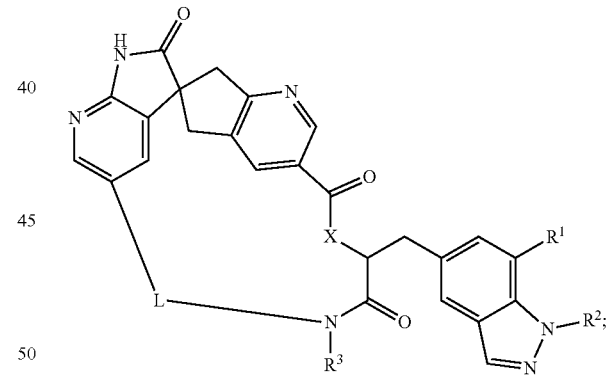

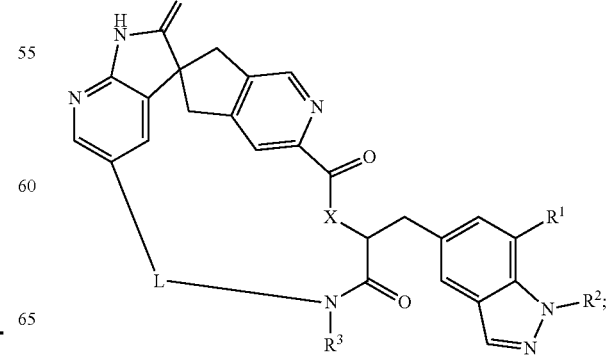

(2c)
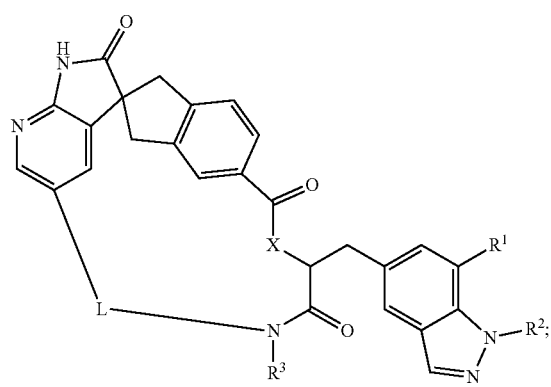
(2d)
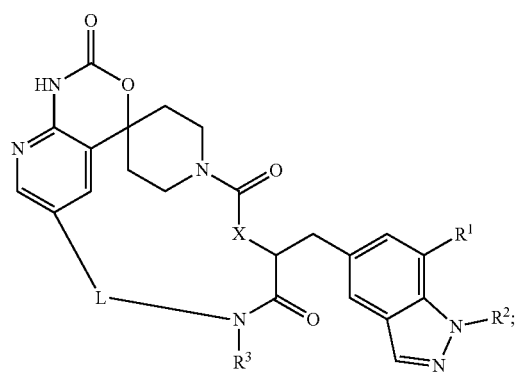
or a salt thereof.
3. The compound according to claim 1, which is a compound of Formula (3a), (3b), (3c), (4a), (4b), or (4c):
(3a)
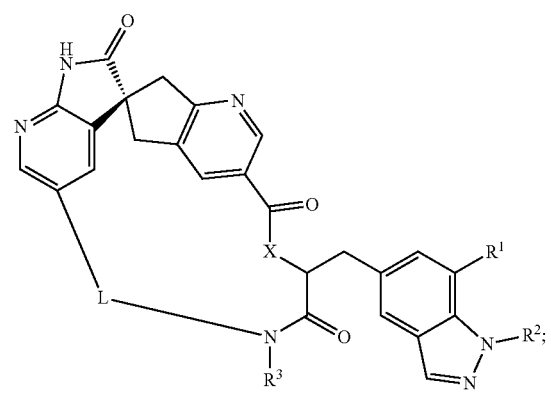
(3b)
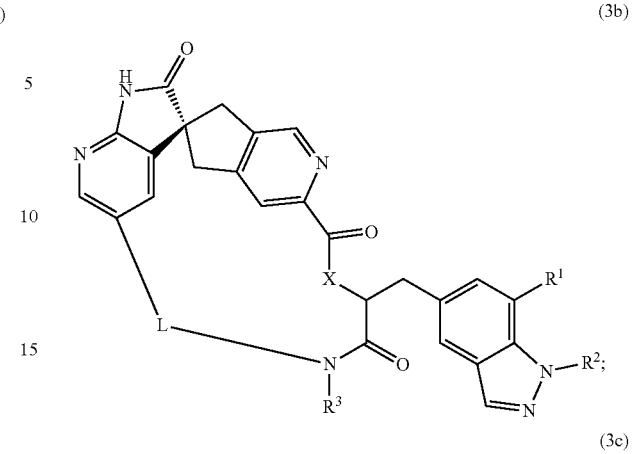
(3c)
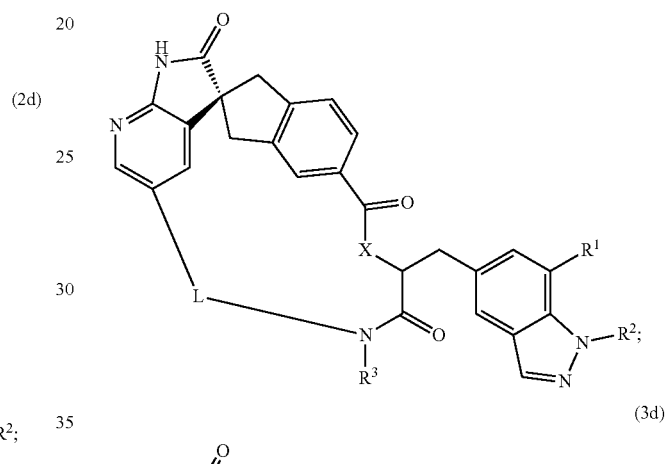
(3d)
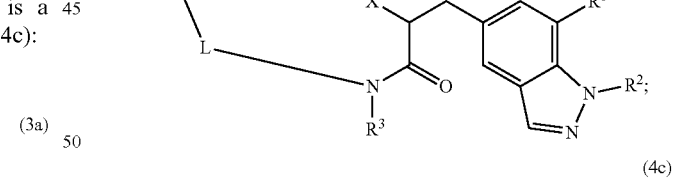
(4c)
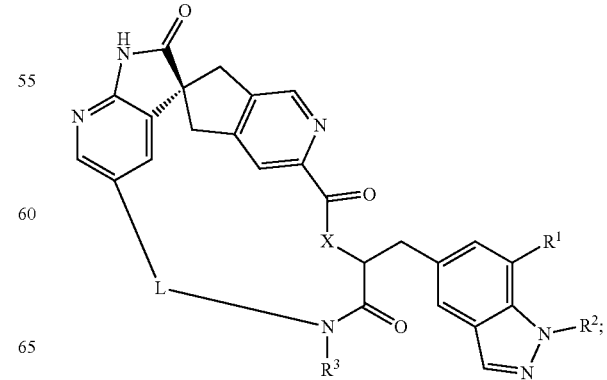

-continued (4d)

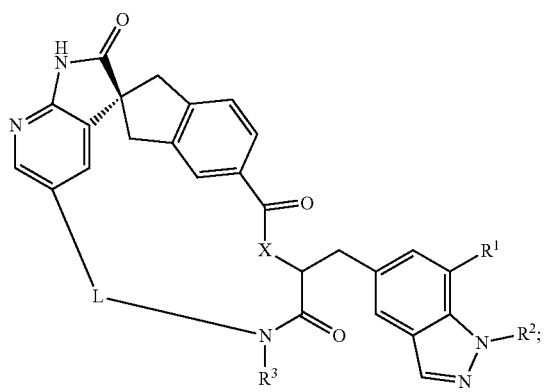

or a salt thereof.

4. The compound according to claim 1, which is a compound of Formula (5):

(5)

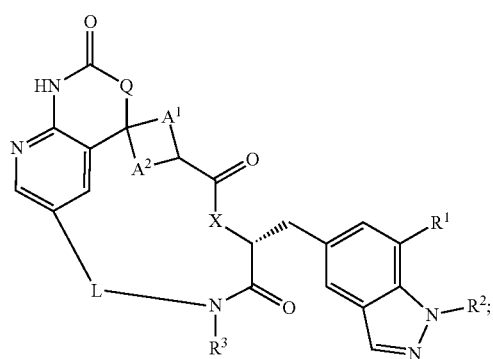

or a salt thereof.

5. The compound according to claim 1, or a salt thereof, wherein $A^1$, $A^2$ and the atoms to which they are attached together represent a ring system selected from the group consisting of:

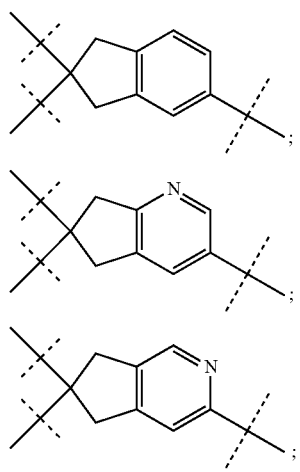

-continued

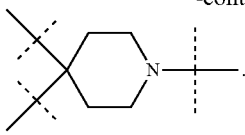

6. The compound according to claim 1, or a salt thereof, wherein Q is a bond.
7. The compound according to claim 1, or a salt thereof, wherein Q is O.
8. The compound according to claim 1, or a salt thereof, wherein X is NH.
9. The compound according to claim 1, or a salt thereof, wherein X is O.
10. The compound according to claim 1, or a salt thereof, wherein $R^1$ is methyl.
11. The compound according to claim 1, or a salt thereof, wherein $R^2$ is H or methyl.
12. The compound according to claim 1, or a salt thereof, wherein $R^2$ is H.
13. The compound according to claim 1, or a salt thereof, wherein $R^3$ is methyl.
14. The compound according to claim 1, or a salt thereof, wherein L is a linker group of the formula:

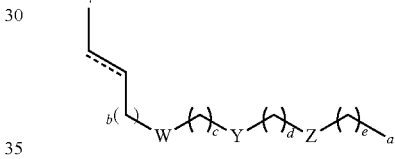

wherein "r" indicates the point of attachment to the ring and "a" indicates the point of attachment to the amide group; W, Y and Z are independently selected from a bond, O, $CH_2$, NH and NMe; b, c, d and e are independently 1, 2 or 3 and the dotted line indicates that the bond may be a single or double bond.

15. The compound according to claim 1, or a salt thereof, wherein L is selected from the group consisting of:
—$CHCHCH_2OCH_2CH_2OCH_2CH_2$—;
—$CHCHCH_2OCH_2CH_2OCH_2CH_2OCH_2CH_2$—;
—$CH_2CH_2CH_2OCH_2CH_2OCH_2CH_2$—;
—$CHCHCH_2CH_2CH_2CH_2CH_2CH_2CH_2$—;
—$CHCHCH_2OCH_2CH_2CH_2CH_2CH_2$—;
—$CHCHCH_2OCH_2CH_2CH_2CH_2$—;
—$CHCHCH_2OCH_2CH_2CH_2$—;
—$CHCHCH_2OCH_2CH_2N(CH_3)CH_2CH_2$—;
—$CHCHCH_2OCH_2CH_2NHCH_2CH_2$—;
—$CHCHCH_2N(CH_3)CH_2CH_2CH_2CH_2CH_2$—;
—$CH_2CH_2CH_2OCH_2CH_2OCH_2CH_2OCH_2CH_2$—;
—$CH_2CH_2CH_2OCH_2CH_2CH_2CH_2CH_2$—;
—$CH_2CH_2CH_2OCH_2CH_2OCH_2CH_2CH_2$—;
and
—$CHCHCH_2OCH_2CH_2OCH_2CH_2CH_2$—.

16. The compound according to claim 5, or a salt thereof, wherein L is:
—$CHCHCH_2OCH_2CH_2OCH_2CH_2$—
or
$CHCHCH_2OCH_2CH_2CH_2CH_2CH_2$—.

17. The compound according to claim 1 which is selected from the group consisting of:

(1S,10R,20E)-12-methyl-10-[(7-methyl-1H-indazol-5-yl)
methyl]-15,18-dioxa-5,9,12,24,26-pentazapentacyclo
[20.5.2.1¹,⁴.1³,⁷.0²⁵,²⁸]hentriaconta-3,5,7(30),20,22
(29),23,25(28)-heptaene-8,11,27-trione;

(1R,10R,20E)-12-methyl-10-[(7-methyl-1H-indazol-5-
yl)methyl]-15,18-dioxa-5,9,12,24,26-pentazapentacy-
clo[20.5.2.1¹,⁴.1³,⁷.0²⁵,²⁸]hentriaconta-3,5,7(30),20,
22(29),23,25(28)-heptaene-8,11,27-trione;

(1S,10S,20E)-12-methyl-10-[(7-methyl-1H-indazol-5-yl)
methyl]-15,18-dioxa-5,9,12,24,26-pentazapentacyclo
[20.5.2.1¹,⁴.1³,⁷.0²⁵,²⁸]hentriaconta-3,5,7(30),20,22
(29),23,25(28)-heptaene-8,11,27-trione;

(1S,10R,23E)-12-methyl-10-[(7-methyl-1H-indazol-5-yl)
methyl]-15,18,21-trioxa-5,9,12,27,29-pentazapentacy-
clo[23.5.2.1¹,⁴.1³,⁷.0²⁸,³¹]tetratriaconta-3,5,7(33),
23,25(32),26,28(31)-heptaene-8,11,30-trione;

(1S,10R,20E)-12-methyl-10-[(7-methyl-1H-indazol-5-yl)
methyl]-5,9,12,24,26-pentazapentacyclo[20.5.2.1¹,
4.1³,⁷.0²⁵,²⁸]hentriaconta-3,5,7(30),20,22(29),23,25
(28)-heptaene-8,11,27-trione;

(1S,10R,20E)-12-methyl-10-[(7-methyl-1H-indazol-5-yl)
methyl]-18-oxa-5,9,12,24,26-pentazapentacyclo
[20.5.2.1¹,⁴.1³,⁷.0²⁵,²⁸]hentriaconta-3,5,7(30),20,22
(29),23,25(28)-heptaene-8,11,27-trione;

(1S,10R,19E)-12-methyl-10-[(7-methyl-1H-indazol-5-yl)
methyl]-17-oxa-5,9,12,23,25-pentazapentacyclo
[19.5.2.1¹,⁴.1³,⁷.0²⁴,²⁷]triaconta-3,5,7(29),19,21
(28),22,24(27)-heptaene-8,11,26-trione;

(1S,10R)-12-methyl-10-[(7-methyl-1H-indazol-5-yl)
methyl]-15,18-dioxa-5,9,12,24,26-pentazapentacyclo
[20.5.2.1¹,⁴.1³,⁷.0²⁵,²⁸]hentriaconta-3,5,7(30),22
(29),23,25(28)-hexaene-8,11,27-trione;

(1S,10R,20E)-12-methyl-10-[(7-methyl-1H-indazol-5-yl)
methyl]-15,18-dioxa-6,9,12,24,26-pentazapentacyclo
[20.5.2.1¹,⁴.1³,⁷.0²⁵,²⁸]hentriaconta-3,5,7(30),20,22
(29),23,25(28)-heptaene-8,11,27-trione;

(1R,10R,20E)-12-methyl-10-[(7-methyl-1H-indazol-5-
yl)methyl]-15,18-dioxa-6,9,12,24,26-pentazapentacy-
clo[20.5.2.1¹,⁴.1³,⁷.0²⁵,²⁸]hentriaconta-3,5,7(30),20,
22(29),23,25(28)-heptaene-8,11,27-trione;

(1R,10R,20E)-12,18-dimethyl-10-[(7-methyl-1H-inda-
zol-5-yl)methyl]-6,9,12,18,24,26-hexazapentacyclo
[20.5.2.1¹,⁴.1³,⁷.0²⁵,²⁸]hentriaconta-3,5,7(30),20,22
(29),23,25(28)-heptaene-8,11,27-trione;

(1S,10R,20E)-10-[(1,7-dimethylindazol-5-yl)methyl]-12-
methyl-15,18-dioxa-6,9,12,24,26-pentazapentacyclo
[20.5.2.1¹,⁴.1³,⁷.0²⁵,²⁸]hentriaconta-3,5,7(30),20,22
(29),23,25(28)-heptaene-8,11,27-trione;

(1R,10R,20E)-10-[(1,7-dimethylindazol-5-yl)methyl]-
12-methyl-15,18-dioxa-6,9,12,24,26-pentazapentacy-
clo[20.5.2.1¹,⁴.1³,⁷.0²⁵,²⁸]hentriaconta-3,5,7(30),20,
22(29),23,25(28)-heptaene-8,11,27-trione;

(1R,10R,20E)-10-[(1,7-dimethylindazol-5-yl)methyl]-
12-methyl-18-oxa-6,9,12,24,26-pentazapentacyclo
[20.5.2.1¹,⁴.1³,⁷.0²⁵,²⁸]hentriaconta-3,5,7(30),20,22
(29),23,25(28)-heptaene-8,11,27-trione;

(1R,10R,19E)-10-[(1,7-dimethylindazol-5-yl)methyl]-
12-methyl-17-oxa-6,9,12,23,25-pentazapentacyclo
[19.5.2.1¹,⁴.1³,⁷.0²⁴,²⁷]triaconta-3, 5,7(29),19,21
(28),22,24(27)-heptaene-8,11,26-trione;

(1R,10R,20E)-10-[(1,7-dimethylindazol-5-yl)methyl]-12,
18-dimethyl-6,9,12,18,24,26-hexazapentacyclo
[20.5.2.1¹,⁴.1³,⁷.0²⁵,²⁸]hentriaconta-3,5,7(30),20,22
(29),23,25(28)-heptaene-8,11,27-trione;

(1R,10R,20E)-10-[(1,7-dimethylindazol-5-yl)methyl]-12,
15-dimethyl-18-oxa-6,9,12,15,24,26-hexazapentacy-
clo[20.5.2.1¹,⁴.1³,⁷.0²⁵,²⁸]hentriaconta-3,5,7(30),20,
22(29),23,25(28)-heptaene-8,11,27-trione;

(1R,10R,20E)-12-methyl-10-[(7-methyl-1H-indazol-5-
yl)methyl]-15,18-dioxa-9,12,24,26-tetrazapentacyclo
[20.5.2.1¹,⁴.1³,⁷.0²⁵,²⁸]hentriaconta-3,5,7(30),20,22
(29),23,25(28)-heptaene-8,11,27-trione;

(1S,10R,20E)-12-methyl-10-[(7-methyl-1H-indazol-5-yl)
methyl]-15,18-dioxa-9,12,24,26-tetrazapentacyclo
[20.5.2.1¹,⁴.1³,⁷.0²⁵,²⁸]hentriaconta-3,5,7(30),20,22
(29),23,25(28)-heptaene-8,11,27-trione;

(1S,10R,18E)-12-methyl-10-[(7-methyl-1H-indazol-5-yl)
methyl]-16-oxa-9,12,22,24-tetrazapentacyclo
[18.5.2.1¹,⁴.1³,⁷.0²³,²⁶]nonacosa-3,5,7(28),18,20
(27),21,23(26)-heptaene-8,11,25-trione;

(1S,10R,19E)-12-methyl-10-[(7-methyl-1H-indazol-5-yl)
methyl]-17-oxa-9,12,23,25-tetrazapentacyclo
[19.5.2.1¹,⁴.1³,⁷.0²⁴,²⁷]triaconta-3,5,7(29),19,21
(28),22,24(27)-heptaene-8,11,26-trione;

(1S,10R,20E)-12,15-dimethyl-10-[(7-methyl-1H-inda-
zol-5-yl)methyl]-18-oxa-9,12,15,24,26-pentazapenta-
cyclo[20.5.2.1¹,⁴.1³,⁷.0²⁵,²⁸]hentriaconta-3,5,7(30),
20,22(29),23,25(28)-heptaene-8,11,27-trione;

(1S,10R,20E)-12-methyl-10-[(7-methyl-1H-indazol-5-yl)
methyl]-18-oxa-9,12,15,24,26-pentazapentacyclo
[20.5.2.1¹,⁴.1³,⁷.0²⁵,²⁸]hentriaconta-3,5,7(30),20,22
(29),23,25(28)-heptaene-8,11,27-trione;

(1R,10R,20E)-10-[(1,7-dimethylindazol-5-yl)methyl]-
12-methyl-15,18-dioxa-9,12,24,26-tetrazapentacyclo
[20.5.2.1¹,⁴.1³,⁷.0²⁵,²⁸]hentriaconta-3,5,7(30),20,22
(29),23,25(28)-heptaene-8,11,27-trione;

(1S,10R,20E)-10-[(1,7-dimethylindazol-5-yl)methyl]-12-
methyl-15,18-dioxa-9,12,24,26-tetrazapentacyclo
[20.5.2.1¹,⁴.1³,⁷.0²⁵,²⁸]hentriaconta-3,5,7(30),20,22
(29),23,25(28)-heptaene-8,11,27-trione;

(1R,20E)-10-[(7-chloro-1H-indazol-5-yl)methyl]-12-
methyl-15,18-dioxa-9,12,24,26-tetrazapentacyclo
[20.5.2.1¹,⁴.1³,⁷.0²⁵,²⁸]hentriaconta-3,5,7(30),20,22
(29),23,25(28)-heptaene-8,11,27-trione;

(1R,10R)-12-methyl-10-[(7-methyl-1H-indazol-5-yl)
methyl]-15,18-dioxa-9,12,24,26-tetrazapentacyclo
[20.5.2.1¹,⁴.1³,⁷.0²⁵,²⁸]hentriaconta-3,5,7(30),22
(29),23,25(28)-hexaene-8,11,27-trione;

(1S,10R)-12-methyl-10-[(7-methyl-1H-indazol-5-yl)
methyl]-15,18-dioxa-9,12,24,26-tetrazapentacyclo
[20.5.2.1¹,⁴.1³,⁷.0²⁵,²⁸]hentriaconta-3,5,7(30),22
(29),23,25(28)-hexaene-8,11,27-trione;

(1S,10R,20E)-12-methyl-10-[(7-methyl-1H-indazol-5-yl)
methyl]-9,15,18-trioxa-5,12,24,26-tetrazapentacyclo
[20.5.2.1¹,⁴.1³,⁷.0²⁵,²⁸]hentriaconta-3,5,7(30),20,22
(29),23,25(28)-heptaene-8,11,27-trione;

(1S,10S,20E)-12-methyl-10-[(7-methyl-1H-indazol-5-yl)
methyl]-9,15,18-trioxa-5,12,24,26-tetrazapentacyclo
[20.5.2.1¹,⁴.1³,⁷.0²⁵,²⁸]hentriaconta-3,5,7(30),20,22
(29),23,25(28)-heptaene-8,11,27-trione;

(1S,10R,20E)-12-methyl-10-[(7-methyl-1H-indazol-5-yl)
methyl]-9,15,18-trioxa-12,24,26-triazapentacyclo
[20.5.2.1¹,⁴.1³,⁷.0²⁵,²⁸]hentriaconta-3,5,7(30),20,22
(29),23,25(28)-heptaene-8,11,27-trione;

(1R,10R,20E)-12-methyl-10-[(7-methyl-1H-indazol-5-
yl)methyl]-9,15,18-trioxa-12,24,26-triazapentacyclo
[20.5.2.1¹,⁴.1³,⁷.0²⁵,²⁸]hentriaconta-3,5,7(30),20,22
(29),23,25(28)-heptaene-8,11,27-trione;

(7R,17E)-9-methyl-7-[(7-methyl-1H-indazol-5-yl)
methyl]-12,15,25-trioxa-4,6,9,21,23-pentazatetracyclo
[17.6.2.2²,⁵.0²²,²⁶]nonacosa-17,19(27),20,22(26)-tet-
raene-5,8,24-trione;

(7R,17E)-9-methyl-7-[(7-methyl-1H-indazol-5-yl)methyl]-6,12,15,25-tetraoxa-4,9,21,23-tetrazatetracyclo[17.6.2.2¹,⁴.0²²,²⁶]nonacosa-17,19(27),20,22(26)-tetraene-5,8,24-trione;

(7R,20E)-9-methyl-7-[(7-methyl-1H-indazol-5-yl)methyl]-6,12,15,18,28-pentaoxa-4,9,24,26-tetrazatetracyclo[20.6.2.2¹,⁴.0²⁵,²⁹]dotriaconta-20,22(30),23,25(29)-tetraene-5,8,27-trione;

(7R,17E)-9-methyl-7-[(7-methyl-1H-indazol-5-yl)methyl]-6,15,25-trioxa-4,9,21,23-tetrazatetracyclo[17.6.2.2¹,⁴.0²²,²⁶]nonacosa-17,19(27),20,22(26)-tetraene-5,8,24-trione;

(7R,18E)-9-methyl-7-[(7-methyl-1H-indazol-5-yl)methyl]-6,13,16,26-tetraoxa-4,9,22,24-tetrazatetracyclo[18.6.2.2¹,⁴.0²³,²⁷]triaconta-18,20(28),21,23(27)-tetraene-5,8,25-trione;

(7R)-9-methyl-7-[(7-methyl-1H-indazol-5-yl)methyl]-6,12,15,18,28-pentaoxa-4,9,24,26-tetrazatetracyclo[20.6.2.2¹,⁴.0²⁵,²⁹]dotriaconta-22(30),23,25(29)-triene-5,8,27-trione;

(7R)-9-methyl-7-[(7-methyl-1H-indazol-5-yl)methyl]-6,15,25-trioxa-4,9,21,23-tetrazatetracyclo[17.6.2.2¹,⁴.0²²,²⁶]nonacosa-19(27),20,22(26)-triene-5,8,24-trione;

(7R)-9-methyl-7-[(7-methyl-1H-indazol-5-yl)methyl]-6,13,16,26-tetraoxa-4,9,22,24-tetrazatetracyclo[18.6.2.2¹,⁴.0²³,²⁷]triaconta-20(28),21,23(27)-triene-5,8,25-trione;

(10R,20E)-12-methyl-10-[(7-methyl-1H-indazol-5-yl)methyl]-15,18-dioxa-9,12,24,26,30-pentazapentacyclo[20.5.2.1¹,⁴.1³,⁷.0²⁵,²⁸]hentriaconta-3,5,7(30),20,22,24,28-heptaene-8,11,27-trione;

and salts thereof.

18. A pharmaceutical composition comprising a compound according to claim 1, or a pharmaceutically acceptable salt, and a pharmaceutically acceptable excipient.

19. A method of treating migraine, comprising administering an effective amount of a compound according to claim 1, or a pharmaceutically acceptable salt, to a subject in need thereof.

20. The method according to claim 19, wherein the migraine is chronic migraine.

21. The method according to claim 19, wherein the migraine is pure menstrual migraine.

22. The method according to claim 19, wherein the migraine is frequent episodic migraine.

23. The method according to claim 19, wherein the migraine is menstrually-related migraine.

24. The method according to claim 19, wherein the migraine is migraine with aura.

25. The method according to claim 19, wherein the migraine is migraine without aura.

26. The method according to claim 19, wherein the migraine is familial hemiplegic migraine.

27. The method according to claim 19, wherein the migraine is sporadic hemiplegic migraine.

28. The method according to claim 19, wherein the migraine is basilar-type migraine.

29. The method according to claim 19, wherein the migraine is abdominal migraine.

30. The method according to claim 19, wherein the migraine is retinal migraine.

31. The method according to claim 19, wherein the migraine is status migrainosus.

* * * * *